US012703865B2

(12) United States Patent
Zhang et al.

(10) Patent No.: US 12,703,865 B2
(45) Date of Patent: Aug. 11, 2026

(54) SMALL INTERFERING RNA TARGETING C3 AND USES THEREOF

(71) Applicant: Sanegene Bio USA Inc., Woburn, MA (US)

(72) Inventors: Chunyang Zhang, Burlington, MA (US); Xin Geng, Belmont, MA (US); Shiyu Wang, Belmont, MA (US); Weimin Wang, Winchester, MA (US)

(73) Assignee: Sanegene Bio USA Inc., Woburn, MA (US)

( * ) Notice: Subject to any disclaimer, the term of this patent is extended or adjusted under 35 U.S.C. 154(b) by 0 days.

(21) Appl. No.: 18/650,710

(22) Filed: Apr. 30, 2024

(65) Prior Publication Data

US 2024/0301421 A1 Sep. 12, 2024

Related U.S. Application Data

(63) Continuation of application No. 18/487,663, filed on Oct. 16, 2023.

(60) Provisional application No. 63/416,070, filed on Oct. 14, 2022.

(51) Int. Cl.
*C12N 15/113* (2010.01)
*A61P 37/06* (2006.01)

(52) U.S. Cl.
CPC ............ *C12N 15/113* (2013.01); *A61P 37/06* (2018.01); *C12N 2310/11* (2013.01); *C12N 2310/315* (2013.01); *C12N 2310/321* (2013.01); *C12N 2310/322* (2013.01)

(58) Field of Classification Search
CPC .............. C12N 15/113; C12N 2310/11; C12N 2310/321; C12N 2310/322; C12N 2310/14; C12N 2310/351; C12N 2310/31; C12N 2310/3521
See application file for complete search history.

(56) References Cited

U.S. PATENT DOCUMENTS

| | | | |
|---|---|---|---|
| 4,522,811 A | 6/1985 | Eppstein et al. | |
| 8,012,473 B2 | 9/2011 | Campagne | |
| 8,192,742 B2 | 6/2012 | Bansal | |
| 8,703,136 B2 | 4/2014 | Baas et al. | |
| 10,155,983 B2 | 12/2018 | Ero et al. | |
| 10,465,194 B2 | 11/2019 | Borodovsky et al. | |
| 12,365,896 B2 | 7/2025 | Keating et al. | |
| 2005/0214308 A1 | 9/2005 | Ashkenazi et al. | |
| 2005/0244851 A1 | 11/2005 | Blume et al. | |
| 2005/0244858 A1 | 11/2005 | Rossi et al. | |
| 2009/0023673 A1 | 1/2009 | Manoharan et al. | |
| 2009/0239814 A1 | 9/2009 | Manoharan et al. | |
| 2009/0247608 A1 | 10/2009 | Manoharan et al. | |
| 2010/0028848 A1 | 2/2010 | Parker et al. | |
| 2011/0293727 A1 | 12/2011 | De Los Rios et al. | |
| 2012/0136042 A1 | 5/2012 | Manoharan et al. | |
| 2013/0158824 A1 | 6/2013 | Nassouri et al. | |
| 2015/0196655 A1* | 7/2015 | Nair ..................... | A61K 47/549 536/17.4 |
| 2015/0337377 A1 | 11/2015 | Ero et al. | |
| 2016/0298124 A1 | 10/2016 | Borodovsky et al. | |
| 2020/0263183 A1 | 8/2020 | Borodovsky et al. | |
| 2020/0339998 A1 | 10/2020 | Borodovsky et al. | |
| 2022/0364088 A1* | 11/2022 | Keating ................. | C12N 15/66 |
| 2023/0138928 A1* | 5/2023 | Wang .................. | C12N 15/113 514/44 A |
| 2024/0344063 A1 | 10/2024 | Brown et al. | |
| 2024/0352463 A1 | 10/2024 | Khan et al. | |
| 2025/0002910 A1 | 1/2025 | Scheibler | |
| 2025/0283071 A1 | 9/2025 | Schlegel et al. | |

FOREIGN PATENT DOCUMENTS

| | | |
|---|---|---|
| CN | 116854754 * | 10/2023 |
| WO | WO-8902439 A1 | 3/1989 |
| WO | WO-9506731 A2 | 3/1995 |
| WO | WO-9511910 A1 | 5/1995 |
| WO | WO-9914226 A2 | 3/1999 |
| WO | WO-0056746 A2 | 9/2000 |
| WO | WO-0056748 A1 | 9/2000 |
| WO | WO-0066604 A2 | 11/2000 |
| WO | WO-2007064846 A2 | 6/2007 |
| WO | WO2008118711 A2 | 10/2008 |
| WO | WO2008154251 A2 | 12/2008 |
| WO | WO-2009082607 A2 | 7/2009 |
| WO | WO-2010042755 A2 | 4/2010 |
| WO | WO-2012089352 A1 | 7/2012 |
| WO | WO-2015006740 A2 | 1/2015 |
| WO | WO-2015089368 A2 | 6/2015 |
| WO | WO-2016100401 A1 | 6/2016 |

(Continued)

OTHER PUBLICATIONS

Chernikov et al. Current Development of siRNA Bioconjugates: From Research to the Clinic, 2019, Frontiers in Pharmacology, 10, p. 1-25. (Year: 2019).*

(Continued)

*Primary Examiner* — Jennifer Dunston
*Assistant Examiner* — Keyur A Vyas
(74) *Attorney, Agent, or Firm* — Fenwick & West LLP; Chen Chen; Robert E. Powers

(57) ABSTRACT

This disclosure relates to isolated oligonucleotides comprising duplex regions targeting human complement C3 mRNA, and delivery systems, kits and compositions comprising the same, and methods of using the same for inhibiting or downregulating C3 gene expression.

9 Claims, 7 Drawing Sheets

Specification includes a Sequence Listing.

(56) References Cited

FOREIGN PATENT DOCUMENTS

| | | | |
|---|---|---|---|
| WO | WO-2016201272 | A1 | 12/2016 |
| WO | WO-2017214112 | A1 | 12/2017 |
| WO | WO-2018039364 | A1 | 3/2018 |
| WO | WO-2018045317 | A1 | 3/2018 |
| WO | WO-2019089922 | A1 | 5/2019 |
| WO | WO-2020022802 | A1 | 1/2020 |
| WO | WO-2020123410 | A1 | 6/2020 |
| WO | WO-2021081026 | A1 | 4/2021 |
| WO | WO-2021119034 | A1 | 6/2021 |
| WO | WO-2021178607 | A1 | 9/2021 |
| WO | WO-2022136673 | A1 | 6/2022 |
| WO | WO-2022159158 | A1 | 7/2022 |
| WO | WO-2022251484 | A1 | 12/2022 |
| WO | WO2023014938 | A1 | 2/2023 |
| WO | WO-2023044370 | A2 | 3/2023 |
| WO | WO2023164464 | A1 | 8/2023 |
| WO | WO2024015796 | A1 | 1/2024 |
| WO | WO-2024081954 | A2 | 4/2024 |
| WO | WO-2024189348 | A1 | 9/2024 |

OTHER PUBLICATIONS

Martin-Nieves et al., Oligonucleotides Containing 1-Aminomethyl or 1-Mercaptomethyl- 2-deoxy-D-ribofuranoses: Synthesis, Purification, Characterization, and Conjugation with Fluorophores and Lipids Feb. 5, 2021, Bioconjugate Chem., 32, 350-366 (Year: 2021).*
Matsuda et al., siRNA Conjugates Carrying Sequentially Assembled Trivalent N-Acetylgalactosamine Linked Through Nucleosides Elicit Robust Gene Silencing In Vivo in Hepatocytes, 2015, ACS Chemical Biology, 10, 1181-1187. (Year: 2015).*
Kamola et al., The siRNA Non-seed Region and Its Target Sequences Are Auxiliary Determinants of Off Target Effects, 2017, PLoS Computational Biology, 11: e1004656, p. 1-17. (Year: 2017).*
Fakhr et al.,Precise and efficient siRNA design: a key point in competent gene silencing, 2016, Cancer Gene Ther., 23, 73-82. (Year: 2016).*
CN116854754, pub. Oct. 10, 2023, a WIPO machine translation of CN116854754, Gengshen et al. (Year: 2023).*
Albazli et al., "Complement Inhibitor Therapy for Myasthenia Gravis", Front. Immunol., Sec. Autoimmune and Autoinflammatory Disorders, Jun. 2, 2020, 11(917): pp. 1-11.
Altschul et al. "Basic local alignment search tool" Journal of molecular biology (1990); 215(3):403-410.
Altschul et al. "Gapped BLAST and PSI-BLAST: a new generation of protein database search programs" Nucleic acids research (1997); 25(17):3389-3402.
Beecher et al. "Therapies Directed Against B-Cells and Downstream Effectors in Generalized Autoimmune Myasthenia Gravis: Current Status", Drugs, 2019, 79: 353-364.
Beltrame et al. "The lectin pathway of complement and rheumatic heart disease". Front. Pediatr., Sec. Pediatric Cardiology, Jan. 21, 2015, 2(148): pp. 1-14.
Brodsky et al. "Multicenter phase 3 study of the complement inhibitor eculizumab for the treatment of patients with paroxysmal nocturnal hemoglobinuria", Blood, Clinical Trials & Observations, Feb. 15, 2008, 111(4): pp. 1840-1847.
Carrillo et al. "The multiple sequence alignment problem in biology" SIAM Journal on Applied Mathematics (1988); 48(5):1073-1082.
Cload et al. "Polyether tethered oligonucleotide probes" Journal of the American Chemical Society (1991); 113(16):6324-6326.
Co-pending U.S. Appl. No. 18/487,663, inventors Zhang; Chunyang et al., filed on Oct. 16, 2023.
Dhillon "Moxetumomab pasudotox: first global approval." Drugs 78.16 (2018): 1763-1767.
Ferentz et al. "Disulfide-crosslinked oligonucleotides" Journal of the American Chemical Society (1991); 113(10):4000-4002.
Garred et al. "Therapeutic Targeting of the Complement System: From Rare Diseases to Pandemics", Pharmacological Reviews, Apr. 2021, 73(2): pp. 792-827.
Howard et al., "Clinical Effects of the Self-administered Subcutaneous Complement Inhibitor Zilucoplan in Patients With Moderate to Severe Generalized Myasthenia Gravis Results of a Phase 2 Randomized, Double-Blind, Placebo-Controlled, Multicenter Clinical Trial", JAMA Neurology, Original Investigation, 2020; 77(5):582-592.
Jaschke et al. "Automated incorporation of polyethylene glycol into synthetic oligonucleotides" Tetrahedron Letters (1993); 34(2):301-304.
Karlin et al. "Applications and statistics for multiple high-scoring segments in molecular sequences" Proceedings of the National Academy of Sciences (1993); 90(12):5873-5877.
Keshari et al. "Inhibition of complement C5 protects against organ failure and reduces mortality in a baboon model of *Escherichia coli* sepsis", PNAS, Jul. 18, 2017: pp. E6390-E6399.
Kulasekararaj et al., "Ravulizumab (ALXN1210) vs eculizumab in C5-inhibitor-experienced adult patients with PNH: the 302 study", Blood, Clinical Trials & Observations, 2019, 133(6): pp. 540-549.
Lee et al. "Ravulizumab (ALXN1210) vs eculizumab in adult patients with PNH naive to complement inhibitors: the 301 study", Blood, Clinical Trials & Observations, 2019, 133(6): pp. 530-539.
Lee et al. "Ravulizumab for the treatment of paroxysmal nocturnal hemoglobinuria", Expert Opinion on Biological Therapy, Feb. 14, 2020, 20:3, 227-237.
Loirat et al. An international consensus approach to the management of atypical hemolytic uremic syndrome in children. Pediatr Nephrol, Apr. 11, 2015, 31: pp. 15-39.
Mckeage, "Ravulizumab: First Global Approval", Drugs, 2019, 79: pp. 347-352.
Parker, "Eculizumab for paroxysmal nocturnal haemoglobinuria", New Drug Class, Feb. 28, 2009, 373(9665): pp. 759-767.
Seela et al. "Oligodeoxyribonucleotides containing 1, 3-propanediol as nucleoside substitute" Nucleic Acids Research (1987); 15(7):3113-3129.
Selmaj, et al. "Novel emerging treatments for NMOSD", Neurol Neurochir Pol 2019;53(5): pp. 317-326.
Stern, et al. "Ravulizumab: a novel C5 inhibitor for the treatment of paroxysmal nocturnal hemoglobinuria", Therapeutic Advances in Hematology, Dec. 2019, 10: pp. 1-11.
Tschumi et al. "Eculizumab in atypical hemolytic uremic syndrome: long-term clinical course and histological findings", Pediatric Nephrology, Brief Report, 2011, 26:pp. 2085-2088.
Winkler "Oligonucleotide conjugates for therapeutic applications" Therapeutic Delivery (2013); 4(7):791-809.
Ricklin et al. "Complement component C3—The "Swiss Army Knife" of innate immunity and host defense" Immunological reviews (2016); 274(1):33-58.
Zheng X et al. "Preventing renal ischemiareperfusion injury using small interfering RNA by targeting complement 3 gene" American Journal of Transplantation (2006); 6(9):2099-2108.
Foster et al. "Advanced siRNA Designs Further Improve In Vivo Performance of GalNAc-siRNA Conjugates", Mol Ther., Mar. 7, 2018; vol. 26, Issue 3, pp. 708-717. doi: 10.1016/j.ymthe.2017.12.02.
Ray et al. "Inclisiran in Patients at High Cardiovascular Risk with Elevated LDL Cholesterol", N Engl J Med. Apr. 13, 2017; vol. 376, Issue 15, pp. 1430-1440. doi: 10.1056/NEJMoa1615758.

* cited by examiner

SEQUENCE LISTING

```
Sequence total quantity: 463
SEQ ID NO: 1           moltype = RNA  length = 5231
FEATURE                Location/Qualifiers
source                 1..5231
                       mol_type = mRNA
                       organism = Homo sapiens
SEQUENCE: 1
actcctcccc atcctctccc tctgtccctc tgtccctctg accctgcact gtcccagcac  60
catgggaccc acctcaggtc ccagcctgct gctcctgcta ctaacccacc tcccccctggc  120
tctggggagt cccatgtact ctatcatcac ccccaacatc ttgcggctgg agagcgagga  180
gaccatggtg ctggaggccc acgacgcgca aggggatgtt ccagtcactg ttactgtcca  240
cgacttccca ggcaaaaaac tagtgctgtc cagtgagaag actgtgctga cccctgccac  300
caaccacatg ggcaacgtca ccttcacgat cccagccaac agggagttca agtcagaaaa  360
ggggcgcaac aagttcgtga ccgtgcaggc caccttcggg acccaagtgg tggagaaggt  420
ggtgctggtc agcctgcaga gcgggtacct cttcatccag acagacaaga ccatctacac  480
ccctggctcc acagttctct atcggatctt caccgtcaac cacaagctgc tacccgtggg  540
ccggacggtc atggtcaaca ttgagaaccc ggaaggcatc ccggtcaagc aggactcctt  600
gtcttctcag aaccagcttg gcgtcttgcc cttgtcttgg gacattccgg aactcgtcaa  660
catgggccag tggaagatcc gagcctacta tgaaaactca ccacagcagg tcttctccac  720
tgagtttgag gtgaaggagt acgtgctgcc cagtttcgag gtcatagtgg agcctacaga  780
gaaattctac tacatctata acgagaaggg cctggaggtc accatcaccg ccaggttcct  840
ctacgggaag aaagtggagg gaactgcctt tgtcatcttc gggatccagg atggcgaaca  900
gaggatttcc ctgcctgaat ccctcaagcg cattccgatt gaggatggct cgggggaggt  960
tgtgctgagc cggaaggtac tgctggacgg ggtgcagaac ccccgagcag aagacctggt  1020
ggggaagtct ttgtacgtgt ctgccaccgt catcttgcac tcaggcagtg acatggtgca  1080
```

-continued

```
ggcagagcgc agcgggatcc ccatcgtgac ctctccctac cagatccact tcaccaagac  1140
acccaagtac ttcaaaccag gaatgccctt tgacctcatg gtgttcgtga cgaaccctga  1200
tggctctcca gcctaccgag tccccgtggc agtccagggc gaggacactg tgcagtctct  1260
aacccaggga gatggcgtgg ccaaactcag catcaacaca caccccagcc agaagccctt  1320
gagcatcacg gtgcgcacga agaagcagga gctctcggag gcagagcagg ctaccaggac  1380
catgcaggct ctgccctaca gcaccgtggg caactccaac aattacctgc atctctcagt  1440
gctacgtaca gagctcagac ccggggagac cctcaacgtc aacttcctcc tgcgaatgga  1500
ccgcgcccac gaggccaaga tccgctacta cacctacctg atcatgaaca agggcaggct  1560
gttgaaggcg ggacgccagg tgcgagagcc cggccaggac ctggtggtgc tgcccctgtc  1620
catcaccacc gacttcatcc cttccttccg cctggtggcg tactacacgc tgatcggtgc  1680
cagcggccag agggaggtgg tggccgactc cgtgtgggtg gacgtcaagg actcctgcgt  1740
gggctcgctg gtggtaaaaa gcggccagtc agaagaccgg cagcctgtac ctgggcagca  1800
gatgaccctg aagatagagg gtgaccacgg ggcccgggtg gtactggtgg ccgtggacaa  1860
gggcgtgttc gtgctgaata agaagaacaa actgacgcag agtaagatct gggacgtggt  1920
ggagaaggca gacatcggct gcaccccggg cagtgggaag gattacgccg gtgtcttctc  1980
cgacgcaggg ctgaccttca cgagcagcag tggccagcag accgcccaga gggcagaact  2040
tcagtgcccg cagccagccg cccgccgacg ccgttccgtg cagctcacgg agaagcgaat  2100
ggacaaagtc ggcaagtacc ccaaggagct gcgcaagtgc tgcgaggacg gcatgcggga  2160
gaaccccatg aggttctcgt gccagcgccg gacccgtttc atctccctgg gcgaggcgtg  2220
caagaaggtc ttcctggact gctgcaacta catcacagag ctgcggcggc agcacgcgcg  2280
ggccagccac ctgggcctgg ccaggagtaa cctggatgag gacatcattg cagaagagaa  2340
catcgtttcc cgaagtgagt tcccagagag ctggctgtgg aacgttgagg acttgaaaga  2400
gccaccgaaa aatggaatct ctacgaagct catgaatata tttttgaaag actccatcac  2460
cacgtgggag attctggctg tgagcatgtc ggacaagaaa gggatctgtg tggcagaccc  2520
cttcgaggtc acagtaatgc aggacttctt catcgacctg cggctaccct actctgttgt  2580
tcgaaacgag caggtggaaa tccgagccgt tctctacaat taccggcaga accaagagct  2640
caaggtgagg gtggaactac tccacaatcc agccttctgc agcctggcca ccaccaagag  2700
gcgtcaccag cagaccgtaa ccatcccccc caagtcctcg ttgtccgttc catatgtcat  2760
cgtgccgcta aagaccggcc tgcaggaagt ggaagtcaag gctgctgtct accatcattt  2820
catcagtgac ggtgtcagga agtccctgaa ggtcgtgccg gaaggaatca gaatgaacaa  2880
aactgtggct gttcgcaccc tggatccaga acgcctgggc cgtgaaggag tgcagaaaga  2940
ggacatccca cctgcagacc tcagtgacca agtcccggac accgagtctg agaccagaat  3000
tctcctgcaa gggaccccag tggcccagat gacagaggat gccgtcgacg cggaacggct  3060
gaagcacctc attgtgaccc cctcgggctg cggggaacag aacatgatcg gcatgacgcc  3120
cacggtcatc gctgtgcatt acctggatga aacggagcag tgggagaagt tcggcctaga  3180
gaagcggcag gggccttgg agctcatcaa gaaggggtac acccagcagc tggccttcag  3240
acaacccagc tctgcctttg cggccttcgt gaaacgggca cccagcacct ggctgaccgc  3300
ctacgtggtc aaggtcttct ctctggctgt caacctcatc gccatcgact cccaagtcct  3360
ctgcggggct gttaaatggc tgatcctgga gaagcagaag cccgacgggg tcttccagga  3420
ggatgcgccc gtgatacacc aagaaatgat tggtggatta cggaacaaca acgagaaaga  3480
catggccctc acggcctttg ttctcatctc gctgcaggag gctaaagata tttgcgagga  3540
gcaggtcaac agcctgccag gcagcatcac taaagcagga gacttccttg aagccaacta  3600
catgaaccta cagagatcct acactgtggc cattgctggc tatgctctgg cccagatggg  3660
caggctgaag gggcctcttc ttaacaaatt tctgaccaca gccaaagata agaaccgctg  3720
ggaggaccct ggtaagcagc tctacaacgt ggaggccaca tcctatgccc tcttggccct  3780
actgcagcta aaagactttg actttgtgcc tcccgtcgtg cgttggctca atgaacagag  3840
atactacggt ggtggctatg gctctaccca ggccaccttc atggtgttcc aagccttggc  3900
tcaataccaa aaggacgccc ctgaccacca ggaactgaac cttgatgtgt ccctccaact  3960
gcccagccgc agctccaaga tcacccaccg tatccactgg gaatctgcca gcctcctgcg  4020
atcagaagag accaaggaaa atgagggttt cacagtcaca gctgaaggaa aaggccaagg  4080
caccttgtcg gtggtgacaa tgtaccatgc taaggccaaa gatcaactca cctgtaataa  4140
attcgacctc aaggtcacca taaaaccagc accggaaaca gaaaagaggc ctcaggatgc  4200
caagaacact atgatccttg agatctgtac caggtaccgg ggagaccagg atgccactat  4260
gtctatattg gacatatcca tgatgactgg ctttgctcca gacacagatg acctgaagca  4320
gctggccaat ggtgttgaca gatacatctc caagtatgag ctggacaaag ccttctccga  4380
taggaacacc ctcatcatct acctggacaa ggtctcacac tctgaggatg actgtctagc  4440
tttcaaagtt caccaatact ttaatgtaga gcttatccag cctggagcag tcaaggtcta  4500
cgcctattac aacctggagg aaagctgtac ccggttctac catccggaaa aggaggatgg  4560
aaagctgaac aagctctgcc gtgatgaact gtgccgctgt gctgaggaga attgcttcat  4620
acaaaagtcg gatgacaagg tcaccctgga agaacggctg gacaaggcct gtgagccagg  4680
agtggactat gtgtacaaga cccgactggt caaggttcag ctgtccaatg actttgacga  4740
gtacatcatg gccattgagc agaccatcaa gtcaggctcg gatgaggtgc aggttggaca  4800
gcagcgcacg ttcatcagcc ccatcaagtg cagagaagcc ctgaagctgg aggagaagaa  4860
acactacctc atgtggggtc tctcctccga tttctgggga gagaagccca acctcagcta  4920
catcatcggg aaggacactt gggtggagca ctggcccgag gaggacgaat gccaagacga  4980
agagaaccag aaacaatgcc aggacctcgg cgccttcacc gagagcatgg ttgtctttgg  5040
gtgccccaac tgaccacacc cccattcccc cactccagat aaagcttcag ttatatctca  5100
cgtgtctgga gttctttgcc aagagggaga ggctgaaatc cccagccgcc tcacctgcag  5160
ctcagctcca tcctacttga aacctcacct gttcccaccg cattttctcc tggcgttcgc  5220
ctgctagtgt g                                                      5231

SEQ ID NO: 2           moltype = RNA  length = 22
FEATURE                Location/Qualifiers
source                 1..22
                       mol_type = other RNA
                       organism = synthetic construct
SEQUENCE: 2
tgagaagaca aggagtcctg ct                                          22
```

-continued

```
SEQ ID NO: 3            moltype = RNA  length = 22
FEATURE                 Location/Qualifiers
source                  1..22
                        mol_type = other RNA
                        organism = synthetic construct
SEQUENCE: 3
ttagtagaat ttctctgtag gc                                              22

SEQ ID NO: 4            moltype = RNA  length = 22
FEATURE                 Location/Qualifiers
source                  1..22
                        mol_type = other RNA
                        organism = synthetic construct
SEQUENCE: 4
tgtagtagaa tttctctgta gg                                              22

SEQ ID NO: 5            moltype = RNA  length = 22
FEATURE                 Location/Qualifiers
source                  1..22
                        mol_type = other RNA
                        organism = synthetic construct
SEQUENCE: 5
tatgtagtag aatttctctg ta                                              22

SEQ ID NO: 6            moltype = RNA  length = 22
FEATURE                 Location/Qualifiers
source                  1..22
                        mol_type = other RNA
                        organism = synthetic construct
SEQUENCE: 6
tgatgtagta gaatttctct gt                                              22

SEQ ID NO: 7            moltype = RNA  length = 22
FEATURE                 Location/Qualifiers
source                  1..22
                        mol_type = other RNA
                        organism = synthetic construct
SEQUENCE: 7
tatagatgta gtagaatttc tc                                              22

SEQ ID NO: 8            moltype = RNA  length = 22
FEATURE                 Location/Qualifiers
source                  1..22
                        mol_type = other RNA
                        organism = synthetic construct
SEQUENCE: 8
ttatagatgt agtagaattt ct                                              22

SEQ ID NO: 9            moltype = RNA  length = 22
FEATURE                 Location/Qualifiers
source                  1..22
                        mol_type = other RNA
                        organism = synthetic construct
SEQUENCE: 9
tttatagatg tagtagaatt tc                                              22

SEQ ID NO: 10           moltype = RNA  length = 22
FEATURE                 Location/Qualifiers
source                  1..22
                        mol_type = other RNA
                        organism = synthetic construct
SEQUENCE: 10
tgtgtgttga tgctgagttt gg                                              22

SEQ ID NO: 11           moltype = RNA  length = 22
FEATURE                 Location/Qualifiers
source                  1..22
                        mol_type = other RNA
                        organism = synthetic construct
SEQUENCE: 11
tctatcttca gggtcatctg ct                                              22

SEQ ID NO: 12           moltype = RNA  length = 22
FEATURE                 Location/Qualifiers
source                  1..22
                        mol_type = other RNA
                        organism = synthetic construct
SEQUENCE: 12
taaaatatat tcatgagctt cg                                              22
```

```
SEQ ID NO: 13          moltype = RNA  length = 22
FEATURE                Location/Qualifiers
source                 1..22
                       mol_type = other RNA
                       organism = synthetic construct
SEQUENCE: 13
tatgaagaag tcctgcatta ct                                           22

SEQ ID NO: 14          moltype = RNA  length = 22
FEATURE                Location/Qualifiers
source                 1..22
                       mol_type = other RNA
                       organism = synthetic construct
SEQUENCE: 14
tttcgaacaa cagagtaggg ta                                           22

SEQ ID NO: 15          moltype = RNA  length = 22
FEATURE                Location/Qualifiers
source                 1..22
                       mol_type = other RNA
                       organism = synthetic construct
SEQUENCE: 15
tttttgttca ttctgattcc tt                                           22

SEQ ID NO: 16          moltype = RNA  length = 22
FEATURE                Location/Qualifiers
source                 1..22
                       mol_type = other RNA
                       organism = synthetic construct
SEQUENCE: 16
taagtctttt agctgcagta gg                                           22

SEQ ID NO: 17          moltype = RNA  length = 22
FEATURE                Location/Qualifiers
source                 1..22
                       mol_type = other RNA
                       organism = synthetic construct
SEQUENCE: 17
taagtcaaag tcttttagct gc                                           22

SEQ ID NO: 18          moltype = RNA  length = 22
FEATURE                Location/Qualifiers
source                 1..22
                       mol_type = other RNA
                       organism = synthetic construct
SEQUENCE: 18
taaagtcaaa gtcttttagc tg                                           22

SEQ ID NO: 19          moltype = RNA  length = 22
FEATURE                Location/Qualifiers
source                 1..22
                       mol_type = other RNA
                       organism = synthetic construct
SEQUENCE: 19
tgttcattga gccaacgcac ga                                           22

SEQ ID NO: 20          moltype = RNA  length = 22
FEATURE                Location/Qualifiers
source                 1..22
                       mol_type = other RNA
                       organism = synthetic construct
SEQUENCE: 20
taatttatta caggtgagtt ga                                           22

SEQ ID NO: 21          moltype = RNA  length = 22
FEATURE                Location/Qualifiers
source                 1..22
                       mol_type = other RNA
                       organism = synthetic construct
SEQUENCE: 21
tctggtttta tggtgacctt ga                                           22

SEQ ID NO: 22          moltype = RNA  length = 22
FEATURE                Location/Qualifiers
source                 1..22
                       mol_type = other RNA
                       organism = synthetic construct
SEQUENCE: 22
```

```
tgagtgtgag accttgtcca gg                                          22

SEQ ID NO: 23          moltype = RNA  length = 22
FEATURE                Location/Qualifiers
source                 1..22
                       mol_type = other RNA
                       organism = synthetic construct
SEQUENCE: 23
tcagagtgtg agaccttgtc ca                                          22

SEQ ID NO: 24          moltype = RNA  length = 22
FEATURE                Location/Qualifiers
source                 1..22
                       mol_type = other RNA
                       organism = synthetic construct
SEQUENCE: 24
ttattggtga actttgaaag ct                                          22

SEQ ID NO: 25          moltype = RNA  length = 22
FEATURE                Location/Qualifiers
source                 1..22
                       mol_type = other RNA
                       organism = synthetic construct
SEQUENCE: 25
ttaataggcg tagaccttga ct                                          22

SEQ ID NO: 26          moltype = RNA  length = 22
FEATURE                Location/Qualifiers
source                 1..22
                       mol_type = other RNA
                       organism = synthetic construct
SEQUENCE: 26
tttgtaatag gcgtagacct tg                                          22

SEQ ID NO: 27          moltype = RNA  length = 22
FEATURE                Location/Qualifiers
source                 1..22
                       mol_type = other RNA
                       organism = synthetic construct
SEQUENCE: 27
tgtagaaccg ggtacagctt tc                                          22

SEQ ID NO: 28          moltype = RNA  length = 22
FEATURE                Location/Qualifiers
source                 1..22
                       mol_type = other RNA
                       organism = synthetic construct
SEQUENCE: 28
tcagagcttg ttcagctttc ca                                          22

SEQ ID NO: 29          moltype = RNA  length = 22
FEATURE                Location/Qualifiers
source                 1..22
                       mol_type = other RNA
                       organism = synthetic construct
SEQUENCE: 29
tatgaagcaa ttctcctcag ca                                          22

SEQ ID NO: 30          moltype = RNA  length = 22
FEATURE                Location/Qualifiers
source                 1..22
                       mol_type = other RNA
                       organism = synthetic construct
SEQUENCE: 30
ttatgaagca attctcctca gc                                          22

SEQ ID NO: 31          moltype = RNA  length = 22
FEATURE                Location/Qualifiers
source                 1..22
                       mol_type = other RNA
                       organism = synthetic construct
SEQUENCE: 31
ttttgtatga agcaattctc ct                                          22

SEQ ID NO: 32          moltype = RNA  length = 20
FEATURE                Location/Qualifiers
source                 1..20
                       mol_type = other RNA
                       organism = synthetic construct
```

-continued

```
SEQUENCE: 32
caggactcct tgtcttctca                                              20

SEQ ID NO: 33           moltype = RNA  length = 20
FEATURE                 Location/Qualifiers
source                  1..20
                        mol_type = other RNA
                        organism = synthetic construct
SEQUENCE: 33
ctacagagaa attctactaa                                              20

SEQ ID NO: 34           moltype = RNA  length = 20
FEATURE                 Location/Qualifiers
source                  1..20
                        mol_type = other RNA
                        organism = synthetic construct
SEQUENCE: 34
tacagagaaa ttctactaca                                              20

SEQ ID NO: 35           moltype = RNA  length = 20
FEATURE                 Location/Qualifiers
source                  1..20
                        mol_type = other RNA
                        organism = synthetic construct
SEQUENCE: 35
cagagaaatt ctactacata                                              20

SEQ ID NO: 36           moltype = RNA  length = 20
FEATURE                 Location/Qualifiers
source                  1..20
                        mol_type = other RNA
                        organism = synthetic construct
SEQUENCE: 36
agagaaattc tactacatca                                              20

SEQ ID NO: 37           moltype = RNA  length = 20
FEATURE                 Location/Qualifiers
source                  1..20
                        mol_type = other RNA
                        organism = synthetic construct
SEQUENCE: 37
gaaattctac tacatctata                                              20

SEQ ID NO: 38           moltype = RNA  length = 20
FEATURE                 Location/Qualifiers
source                  1..20
                        mol_type = other RNA
                        organism = synthetic construct
SEQUENCE: 38
aaattctact acatctataa                                              20

SEQ ID NO: 39           moltype = RNA  length = 20
FEATURE                 Location/Qualifiers
source                  1..20
                        mol_type = other RNA
                        organism = synthetic construct
SEQUENCE: 39
aattctacta catctataaa                                              20

SEQ ID NO: 40           moltype = RNA  length = 20
FEATURE                 Location/Qualifiers
source                  1..20
                        mol_type = other RNA
                        organism = synthetic construct
SEQUENCE: 40
aaactcagca tcaacacaca                                              20

SEQ ID NO: 41           moltype = RNA  length = 20
FEATURE                 Location/Qualifiers
source                  1..20
                        mol_type = other RNA
                        organism = synthetic construct
SEQUENCE: 41
cagatgaccc tgaagataga                                              20

SEQ ID NO: 42           moltype = RNA  length = 20
FEATURE                 Location/Qualifiers
source                  1..20
                        mol_type = other RNA
```

-continued

```
                      organism = synthetic construct
SEQUENCE: 42
aagctcatga atatatttta                                                    20

SEQ ID NO: 43         moltype = RNA  length = 20
FEATURE               Location/Qualifiers
source                1..20
                      mol_type = other RNA
                      organism = synthetic construct
SEQUENCE: 43
taatgcagga cttcttcata                                                    20

SEQ ID NO: 44         moltype = RNA  length = 20
FEATURE               Location/Qualifiers
source                1..20
                      mol_type = other RNA
                      organism = synthetic construct
SEQUENCE: 44
ccctactctg ttgttcgaaa                                                    20

SEQ ID NO: 45         moltype = RNA  length = 20
FEATURE               Location/Qualifiers
source                1..20
                      mol_type = other RNA
                      organism = synthetic construct
SEQUENCE: 45
ggaatcagaa tgaacaaaaa                                                    20

SEQ ID NO: 46         moltype = RNA  length = 20
FEATURE               Location/Qualifiers
source                1..20
                      mol_type = other RNA
                      organism = synthetic construct
SEQUENCE: 46
tactgcagct aaaagactta                                                    20

SEQ ID NO: 47         moltype = RNA  length = 20
FEATURE               Location/Qualifiers
source                1..20
                      mol_type = other RNA
                      organism = synthetic construct
SEQUENCE: 47
agctaaaaga ctttgactta                                                    20

SEQ ID NO: 48         moltype = RNA  length = 20
FEATURE               Location/Qualifiers
source                1..20
                      mol_type = other RNA
                      organism = synthetic construct
SEQUENCE: 48
gctaaaagac tttgacttta                                                    20

SEQ ID NO: 49         moltype = RNA  length = 20
FEATURE               Location/Qualifiers
source                1..20
                      mol_type = other RNA
                      organism = synthetic construct
SEQUENCE: 49
gtgcgttggc tcaatgaaca                                                    20

SEQ ID NO: 50         moltype = RNA  length = 20
FEATURE               Location/Qualifiers
source                1..20
                      mol_type = other RNA
                      organism = synthetic construct
SEQUENCE: 50
aactcacctg taataaatta                                                    20

SEQ ID NO: 51         moltype = RNA  length = 20
FEATURE               Location/Qualifiers
source                1..20
                      mol_type = other RNA
                      organism = synthetic construct
SEQUENCE: 51
aaggtcacca taaaaccaga                                                    20

SEQ ID NO: 52         moltype = RNA  length = 20
FEATURE               Location/Qualifiers
source                1..20
```

-continued

```
                        mol_type = other RNA
                        organism = synthetic construct
SEQUENCE: 52
tggacaaggt ctcacactca                                                20

SEQ ID NO: 53           moltype = RNA  length = 20
FEATURE                 Location/Qualifiers
source                  1..20
                        mol_type = other RNA
                        organism = synthetic construct
SEQUENCE: 53
gacaaggtct cacactctga                                                20

SEQ ID NO: 54           moltype = RNA  length = 20
FEATURE                 Location/Qualifiers
source                  1..20
                        mol_type = other RNA
                        organism = synthetic construct
SEQUENCE: 54
ctttcaaagt tcaccaataa                                                20

SEQ ID NO: 55           moltype = RNA  length = 20
FEATURE                 Location/Qualifiers
source                  1..20
                        mol_type = other RNA
                        organism = synthetic construct
SEQUENCE: 55
tcaaggtcta cgcctattaa                                                20

SEQ ID NO: 56           moltype = RNA  length = 20
FEATURE                 Location/Qualifiers
source                  1..20
                        mol_type = other RNA
                        organism = synthetic construct
SEQUENCE: 56
aggtctacgc ctattacaaa                                                20

SEQ ID NO: 57           moltype = RNA  length = 20
FEATURE                 Location/Qualifiers
source                  1..20
                        mol_type = other RNA
                        organism = synthetic construct
SEQUENCE: 57
aagctgtacc cggttctaca                                                20

SEQ ID NO: 58           moltype = RNA  length = 20
FEATURE                 Location/Qualifiers
source                  1..20
                        mol_type = other RNA
                        organism = synthetic construct
SEQUENCE: 58
gaaagctgaa caagctctga                                                20

SEQ ID NO: 59           moltype = RNA  length = 20
FEATURE                 Location/Qualifiers
source                  1..20
                        mol_type = other RNA
                        organism = synthetic construct
SEQUENCE: 59
ctgaggagaa ttgcttcata                                                20

SEQ ID NO: 60           moltype = RNA  length = 20
FEATURE                 Location/Qualifiers
source                  1..20
                        mol_type = other RNA
                        organism = synthetic construct
SEQUENCE: 60
tgaggagaat tgcttcataa                                                20

SEQ ID NO: 61           moltype = RNA  length = 20
FEATURE                 Location/Qualifiers
source                  1..20
                        mol_type = other RNA
                        organism = synthetic construct
SEQUENCE: 61
gagaattgct tcatacaaaa                                                20

SEQ ID NO: 62           moltype = RNA  length = 22
FEATURE                 Location/Qualifiers
```

```
source                  1..22
                        mol_type = other RNA
                        organism = synthetic construct
SEQUENCE: 62
tgacagtgca gggtcagagg ga                                          22

SEQ ID NO: 63           moltype = RNA  length = 22
FEATURE                 Location/Qualifiers
source                  1..22
                        mol_type = other RNA
                        organism = synthetic construct
SEQUENCE: 63
tttttgcctg ggaagtcgtg ga                                          22

SEQ ID NO: 64           moltype = RNA  length = 22
FEATURE                 Location/Qualifiers
source                  1..22
                        mol_type = other RNA
                        organism = synthetic construct
SEQUENCE: 64
ttttttgcct gggaagtcgt gg                                          22

SEQ ID NO: 65           moltype = RNA  length = 22
FEATURE                 Location/Qualifiers
source                  1..22
                        mol_type = other RNA
                        organism = synthetic construct
SEQUENCE: 65
tttttttgcc tgggaagtcg tg                                          22

SEQ ID NO: 66           moltype = RNA  length = 22
FEATURE                 Location/Qualifiers
source                  1..22
                        mol_type = other RNA
                        organism = synthetic construct
SEQUENCE: 66
tgtttttgc ctgggaagtc gt                                           22

SEQ ID NO: 67           moltype = RNA  length = 22
FEATURE                 Location/Qualifiers
source                  1..22
                        mol_type = other RNA
                        organism = synthetic construct
SEQUENCE: 67
tctgtctgga tgaagaggta cc                                          22

SEQ ID NO: 68           moltype = RNA  length = 22
FEATURE                 Location/Qualifiers
source                  1..22
                        mol_type = other RNA
                        organism = synthetic construct
SEQUENCE: 68
tgtctgtctg gatgaagagg ta                                          22

SEQ ID NO: 69           moltype = RNA  length = 22
FEATURE                 Location/Qualifiers
source                  1..22
                        mol_type = other RNA
                        organism = synthetic construct
SEQUENCE: 69
tttgtctgtc tggatgaaga gg                                          22

SEQ ID NO: 70           moltype = RNA  length = 22
FEATURE                 Location/Qualifiers
source                  1..22
                        mol_type = other RNA
                        organism = synthetic construct
SEQUENCE: 70
ttagatggtc ttgtctgtct gg                                          22

SEQ ID NO: 71           moltype = RNA  length = 22
FEATURE                 Location/Qualifiers
source                  1..22
                        mol_type = other RNA
                        organism = synthetic construct
SEQUENCE: 71
tgtagatggt cttgtctgtc tg                                          22

SEQ ID NO: 72           moltype = RNA  length = 22
```

```
FEATURE                Location/Qualifiers
source                 1..22
                       mol_type = other RNA
                       organism = synthetic construct
SEQUENCE: 72
ttgtagatgg tcttgtctgt ct                                            22

SEQ ID NO: 73          moltype = RNA  length = 22
FEATURE                Location/Qualifiers
source                 1..22
                       mol_type = other RNA
                       organism = synthetic construct
SEQUENCE: 73
tgtgtagatg gtcttgtctg tc                                            22

SEQ ID NO: 74          moltype = RNA  length = 22
FEATURE                Location/Qualifiers
source                 1..22
                       mol_type = other RNA
                       organism = synthetic construct
SEQUENCE: 74
tgacaaggag tcctgcttga cc                                            22

SEQ ID NO: 75          moltype = RNA  length = 22
FEATURE                Location/Qualifiers
source                 1..22
                       mol_type = other RNA
                       organism = synthetic construct
SEQUENCE: 75
taagacaagg agtcctgctt ga                                            22

SEQ ID NO: 76          moltype = RNA  length = 22
FEATURE                Location/Qualifiers
source                 1..22
                       mol_type = other RNA
                       organism = synthetic construct
SEQUENCE: 76
tttctgagaa gacaaggagt cc                                            22

SEQ ID NO: 77          moltype = RNA  length = 22
FEATURE                Location/Qualifiers
source                 1..22
                       mol_type = other RNA
                       organism = synthetic construct
SEQUENCE: 77
tgacgagttc cggaatgtcc ca                                            22

SEQ ID NO: 78          moltype = RNA  length = 22
FEATURE                Location/Qualifiers
source                 1..22
                       mol_type = other RNA
                       organism = synthetic construct
SEQUENCE: 78
tttgacgagt tccggaatgt cc                                            22

SEQ ID NO: 79          moltype = RNA  length = 22
FEATURE                Location/Qualifiers
source                 1..22
                       mol_type = other RNA
                       organism = synthetic construct
SEQUENCE: 79
tgttgacgag ttccggaatg tc                                            22

SEQ ID NO: 80          moltype = RNA  length = 22
FEATURE                Location/Qualifiers
source                 1..22
                       mol_type = other RNA
                       organism = synthetic construct
SEQUENCE: 80
tcttccactg gcccatgttg ac                                            22

SEQ ID NO: 81          moltype = RNA  length = 22
FEATURE                Location/Qualifiers
source                 1..22
                       mol_type = other RNA
                       organism = synthetic construct
SEQUENCE: 81
tcatagtagg ctcggatctt cc                                            22
```

```
SEQ ID NO: 82          moltype = RNA  length = 22
FEATURE                Location/Qualifiers
source                 1..22
                       mol_type = other RNA
                       organism = synthetic construct
SEQUENCE: 82
tttcatagta ggctcggatc tt                                           22

SEQ ID NO: 83          moltype = RNA  length = 22
FEATURE                Location/Qualifiers
source                 1..22
                       mol_type = other RNA
                       organism = synthetic construct
SEQUENCE: 83
ttttcatagt aggctcggat ct                                           22

SEQ ID NO: 84          moltype = RNA  length = 22
FEATURE                Location/Qualifiers
source                 1..22
                       mol_type = other RNA
                       organism = synthetic construct
SEQUENCE: 84
tcaaactcag tggagaagac ct                                           22

SEQ ID NO: 85          moltype = RNA  length = 22
FEATURE                Location/Qualifiers
source                 1..22
                       mol_type = other RNA
                       organism = synthetic construct
SEQUENCE: 85
tctccttcac ctcaaactca gt                                           22

SEQ ID NO: 86          moltype = RNA  length = 22
FEATURE                Location/Qualifiers
source                 1..22
                       mol_type = other RNA
                       organism = synthetic construct
SEQUENCE: 86
ttactccttc acctcaaact ca                                           22

SEQ ID NO: 87          moltype = RNA  length = 22
FEATURE                Location/Qualifiers
source                 1..22
                       mol_type = other RNA
                       organism = synthetic construct
SEQUENCE: 87
tgtactcctt cacctcaaac tc                                           22

SEQ ID NO: 88          moltype = RNA  length = 22
FEATURE                Location/Qualifiers
source                 1..22
                       mol_type = other RNA
                       organism = synthetic construct
SEQUENCE: 88
tgaaactggg cagcacgtac tc                                           22

SEQ ID NO: 89          moltype = RNA  length = 22
FEATURE                Location/Qualifiers
source                 1..22
                       mol_type = other RNA
                       organism = synthetic construct
SEQUENCE: 89
tctatgacct cgaaactggg ca                                           22

SEQ ID NO: 90          moltype = RNA  length = 22
FEATURE                Location/Qualifiers
source                 1..22
                       mol_type = other RNA
                       organism = synthetic construct
SEQUENCE: 90
tcactatgac ctcgaaactg gg                                           22

SEQ ID NO: 91          moltype = RNA  length = 22
FEATURE                Location/Qualifiers
source                 1..22
                       mol_type = other RNA
                       organism = synthetic construct
SEQUENCE: 91
tctctgtagg ctccactatg ac                                           22
```

```
SEQ ID NO: 92          moltype = RNA  length = 22
FEATURE                Location/Qualifiers
source                 1..22
                       mol_type = other RNA
                       organism = synthetic construct
SEQUENCE: 92
tttctctgta ggctccacta tg                                              22

SEQ ID NO: 93          moltype = RNA  length = 22
FEATURE                Location/Qualifiers
source                 1..22
                       mol_type = other RNA
                       organism = synthetic construct
SEQUENCE: 93
tagtagaatt tctctgtagg ct                                              22

SEQ ID NO: 94          moltype = RNA  length = 22
FEATURE                Location/Qualifiers
source                 1..22
                       mol_type = other RNA
                       organism = synthetic construct
SEQUENCE: 94
ttagatgtag tagaatttct ct                                              22

SEQ ID NO: 95          moltype = RNA  length = 22
FEATURE                Location/Qualifiers
source                 1..22
                       mol_type = other RNA
                       organism = synthetic construct
SEQUENCE: 95
tgttatagat gtagtagaat tt                                              22

SEQ ID NO: 96          moltype = RNA  length = 22
FEATURE                Location/Qualifiers
source                 1..22
                       mol_type = other RNA
                       organism = synthetic construct
SEQUENCE: 96
tagatgacaa aggcagttcc ct                                              22

SEQ ID NO: 97          moltype = RNA  length = 22
FEATURE                Location/Qualifiers
source                 1..22
                       mol_type = other RNA
                       organism = synthetic construct
SEQUENCE: 97
taagatgaca aaggcagttc cc                                              22

SEQ ID NO: 98          moltype = RNA  length = 22
FEATURE                Location/Qualifiers
source                 1..22
                       mol_type = other RNA
                       organism = synthetic construct
SEQUENCE: 98
tcttggtgaa gtggatctgg ta                                              22

SEQ ID NO: 99          moltype = RNA  length = 22
FEATURE                Location/Qualifiers
source                 1..22
                       mol_type = other RNA
                       organism = synthetic construct
SEQUENCE: 99
tgtcttggtg aagtggatct gg                                              22

SEQ ID NO: 100         moltype = RNA  length = 22
FEATURE                Location/Qualifiers
source                 1..22
                       mol_type = other RNA
                       organism = synthetic construct
SEQUENCE: 100
tgaggtcaaa gggcattcct gg                                              22

SEQ ID NO: 101         moltype = RNA  length = 22
FEATURE                Location/Qualifiers
source                 1..22
                       mol_type = other RNA
                       organism = synthetic construct
SEQUENCE: 101
```

-continued

```
taacaccatg aggtcaaagg gc                                            22

SEQ ID NO: 102          moltype = RNA  length = 22
FEATURE                 Location/Qualifiers
source                  1..22
                        mol_type = other RNA
                        organism = synthetic construct
SEQUENCE: 102
tgactcggta ggctggagag cc                                            22

SEQ ID NO: 103          moltype = RNA  length = 22
FEATURE                 Location/Qualifiers
source                  1..22
                        mol_type = other RNA
                        organism = synthetic construct
SEQUENCE: 103
ttgttgatgc tgagtttggc ca                                            22

SEQ ID NO: 104          moltype = RNA  length = 22
FEATURE                 Location/Qualifiers
source                  1..22
                        mol_type = other RNA
                        organism = synthetic construct
SEQUENCE: 104
tgtgttgatg ctgagtttgg cc                                            22

SEQ ID NO: 105          moltype = RNA  length = 22
FEATURE                 Location/Qualifiers
source                  1..22
                        mol_type = other RNA
                        organism = synthetic construct
SEQUENCE: 105
tgatgctcaa gggcttctgg ct                                            22

SEQ ID NO: 106          moltype = RNA  length = 22
FEATURE                 Location/Qualifiers
source                  1..22
                        mol_type = other RNA
                        organism = synthetic construct
SEQUENCE: 106
ttgatgctca agggcttctg gc                                            22

SEQ ID NO: 107          moltype = RNA  length = 22
FEATURE                 Location/Qualifiers
source                  1..22
                        mol_type = other RNA
                        organism = synthetic construct
SEQUENCE: 107
tcaggtaatt gttggagttg cc                                            22

SEQ ID NO: 108          moltype = RNA  length = 22
FEATURE                 Location/Qualifiers
source                  1..22
                        mol_type = other RNA
                        organism = synthetic construct
SEQUENCE: 108
tgagatgcag gtaattgttg ga                                            22

SEQ ID NO: 109          moltype = RNA  length = 22
FEATURE                 Location/Qualifiers
source                  1..22
                        mol_type = other RNA
                        organism = synthetic construct
SEQUENCE: 109
tctgagagat gcaggtaatt gt                                            22

SEQ ID NO: 110          moltype = RNA  length = 22
FEATURE                 Location/Qualifiers
source                  1..22
                        mol_type = other RNA
                        organism = synthetic construct
SEQUENCE: 110
tgaggaagtt gacgttgagg gt                                            22

SEQ ID NO: 111          moltype = RNA  length = 22
FEATURE                 Location/Qualifiers
source                  1..22
                        mol_type = other RNA
                        organism = synthetic construct
```

```
SEQUENCE: 111
tcattcgcag gaggaagttg ac                                        22

SEQ ID NO: 112          moltype = RNA  length = 22
FEATURE                 Location/Qualifiers
source                  1..22
                        mol_type = other RNA
                        organism = synthetic construct
SEQUENCE: 112
tgtgtagtag cggatcttgg cc                                        22

SEQ ID NO: 113          moltype = RNA  length = 22
FEATURE                 Location/Qualifiers
source                  1..22
                        mol_type = other RNA
                        organism = synthetic construct
SEQUENCE: 113
tatcaggtag gtgtagtagc gg                                        22

SEQ ID NO: 114          moltype = RNA  length = 22
FEATURE                 Location/Qualifiers
source                  1..22
                        mol_type = other RNA
                        organism = synthetic construct
SEQUENCE: 114
tgatgaagtc ggtggtgatg ga                                        22

SEQ ID NO: 115          moltype = RNA  length = 22
FEATURE                 Location/Qualifiers
source                  1..22
                        mol_type = other RNA
                        organism = synthetic construct
SEQUENCE: 115
tgaaggaagg gatgaagtcg gt                                        22

SEQ ID NO: 116          moltype = RNA  length = 22
FEATURE                 Location/Qualifiers
source                  1..22
                        mol_type = other RNA
                        organism = synthetic construct
SEQUENCE: 116
tttctgactg gccgcttttt ac                                        22

SEQ ID NO: 117          moltype = RNA  length = 22
FEATURE                 Location/Qualifiers
source                  1..22
                        mol_type = other RNA
                        organism = synthetic construct
SEQUENCE: 117
tatcttcagg gtcatctgct gc                                        22

SEQ ID NO: 118          moltype = RNA  length = 22
FEATURE                 Location/Qualifiers
source                  1..22
                        mol_type = other RNA
                        organism = synthetic construct
SEQUENCE: 118
ttatcttcag ggtcatctgc tg                                        22

SEQ ID NO: 119          moltype = RNA  length = 22
FEATURE                 Location/Qualifiers
source                  1..22
                        mol_type = other RNA
                        organism = synthetic construct
SEQUENCE: 119
tatgtagttg cagcagtcca gg                                        22

SEQ ID NO: 120          moltype = RNA  length = 22
FEATURE                 Location/Qualifiers
source                  1..22
                        mol_type = other RNA
                        organism = synthetic construct
SEQUENCE: 120
tgtgatgtag ttgcagcagt cc                                        22

SEQ ID NO: 121          moltype = RNA  length = 22
FEATURE                 Location/Qualifiers
source                  1..22
                        mol_type = other RNA
```

-continued

```
                       organism = synthetic construct
SEQUENCE: 121
tcaaaaatat attcatgagc tt                                          22

SEQ ID NO: 122         moltype = RNA  length = 22
FEATURE                Location/Qualifiers
source                 1..22
                       mol_type = other RNA
                       organism = synthetic construct
SEQUENCE: 122
tttcaaaaat atattcatga gc                                          22

SEQ ID NO: 123         moltype = RNA  length = 22
FEATURE                Location/Qualifiers
source                 1..22
                       mol_type = other RNA
                       organism = synthetic construct
SEQUENCE: 123
ttttcaaaaa tatattcatg ag                                          22

SEQ ID NO: 124         moltype = RNA  length = 22
FEATURE                Location/Qualifiers
source                 1..22
                       mol_type = other RNA
                       organism = synthetic construct
SEQUENCE: 124
tctttcaaaa atatattcat ga                                          22

SEQ ID NO: 125         moltype = RNA  length = 22
FEATURE                Location/Qualifiers
source                 1..22
                       mol_type = other RNA
                       organism = synthetic construct
SEQUENCE: 125
tgtctttcaa aaatatattc at                                          22

SEQ ID NO: 126         moltype = RNA  length = 22
FEATURE                Location/Qualifiers
source                 1..22
                       mol_type = other RNA
                       organism = synthetic construct
SEQUENCE: 126
tattactgtg acctcgaagg gg                                          22

SEQ ID NO: 127         moltype = RNA  length = 22
FEATURE                Location/Qualifiers
source                 1..22
                       mol_type = other RNA
                       organism = synthetic construct
SEQUENCE: 127
tcattactgt gacctcgaag gg                                          22

SEQ ID NO: 128         moltype = RNA  length = 22
FEATURE                Location/Qualifiers
source                 1..22
                       mol_type = other RNA
                       organism = synthetic construct
SEQUENCE: 128
tgaagtcctg cattactgtg ac                                          22

SEQ ID NO: 129         moltype = RNA  length = 22
FEATURE                Location/Qualifiers
source                 1..22
                       mol_type = other RNA
                       organism = synthetic construct
SEQUENCE: 129
tgaagaagtc ctgcattact gt                                          22

SEQ ID NO: 130         moltype = RNA  length = 22
FEATURE                Location/Qualifiers
source                 1..22
                       mol_type = other RNA
                       organism = synthetic construct
SEQUENCE: 130
tgatgaagaa gtcctgcatt ac                                          22

SEQ ID NO: 131         moltype = RNA  length = 22
FEATURE                Location/Qualifiers
source                 1..22
```

```
                        mol_type = other RNA
                        organism = synthetic construct
SEQUENCE: 131
tgaacaacag agtagggtag cc                                              22

SEQ ID NO: 132          moltype = RNA  length = 22
FEATURE                 Location/Qualifiers
source                  1..22
                        mol_type = other RNA
                        organism = synthetic construct
SEQUENCE: 132
ttttcgaaca acagagtagg gt                                              22

SEQ ID NO: 133          moltype = RNA  length = 22
FEATURE                 Location/Qualifiers
source                  1..22
                        mol_type = other RNA
                        organism = synthetic construct
SEQUENCE: 133
tgtttcgaac aacagagtag gg                                              22

SEQ ID NO: 134          moltype = RNA  length = 22
FEATURE                 Location/Qualifiers
source                  1..22
                        mol_type = other RNA
                        organism = synthetic construct
SEQUENCE: 134
tgatttccac ctgctcgttt cg                                              22

SEQ ID NO: 135          moltype = RNA  length = 22
FEATURE                 Location/Qualifiers
source                  1..22
                        mol_type = other RNA
                        organism = synthetic construct
SEQUENCE: 135
tttggttctg ccggtaattg ta                                              22

SEQ ID NO: 136          moltype = RNA  length = 22
FEATURE                 Location/Qualifiers
source                  1..22
                        mol_type = other RNA
                        organism = synthetic construct
SEQUENCE: 136
tcttggttct gccggtaatt gt                                              22

SEQ ID NO: 137          moltype = RNA  length = 22
FEATURE                 Location/Qualifiers
source                  1..22
                        mol_type = other RNA
                        organism = synthetic construct
SEQUENCE: 137
tgtagttcca ccctcacctt ga                                              22

SEQ ID NO: 138          moltype = RNA  length = 22
FEATURE                 Location/Qualifiers
source                  1..22
                        mol_type = other RNA
                        organism = synthetic construct
SEQUENCE: 138
tgattgtgga gtagttccac cc                                              22

SEQ ID NO: 139          moltype = RNA  length = 22
FEATURE                 Location/Qualifiers
source                  1..22
                        mol_type = other RNA
                        organism = synthetic construct
SEQUENCE: 139
tggattgtgg agtagttcca cc                                              22

SEQ ID NO: 140          moltype = RNA  length = 22
FEATURE                 Location/Qualifiers
source                  1..22
                        mol_type = other RNA
                        organism = synthetic construct
SEQUENCE: 140
tctggattgt ggagtagttc ca                                              22

SEQ ID NO: 141          moltype = RNA  length = 22
FEATURE                 Location/Qualifiers
```

```
source                  1..22
                        mol_type = other RNA
                        organism = synthetic construct
SEQUENCE: 141
tctgcagaag gctggattgt gg                                              22

SEQ ID NO: 142          moltype = RNA  length = 22
FEATURE                 Location/Qualifiers
source                  1..22
                        mol_type = other RNA
                        organism = synthetic construct
SEQUENCE: 142
tggatggtta cggtctgctg gt                                              22

SEQ ID NO: 143          moltype = RNA  length = 22
FEATURE                 Location/Qualifiers
source                  1..22
                        mol_type = other RNA
                        organism = synthetic construct
SEQUENCE: 143
tttgttcatt ctgattcctt cc                                              22

SEQ ID NO: 144          moltype = RNA  length = 22
FEATURE                 Location/Qualifiers
source                  1..22
                        mol_type = other RNA
                        organism = synthetic construct
SEQUENCE: 144
tgttttgttc attctgattc ct                                              22

SEQ ID NO: 145          moltype = RNA  length = 22
FEATURE                 Location/Qualifiers
source                  1..22
                        mol_type = other RNA
                        organism = synthetic construct
SEQUENCE: 145
taattctggt ctcagactcg gt                                              22

SEQ ID NO: 146          moltype = RNA  length = 22
FEATURE                 Location/Qualifiers
source                  1..22
                        mol_type = other RNA
                        organism = synthetic construct
SEQUENCE: 146
tgaattctgg tctcagactc gg                                              22

SEQ ID NO: 147          moltype = RNA  length = 22
FEATURE                 Location/Qualifiers
source                  1..22
                        mol_type = other RNA
                        organism = synthetic construct
SEQUENCE: 147
tggcatcctc tgtcatctgg gc                                              22

SEQ ID NO: 148          moltype = RNA  length = 22
FEATURE                 Location/Qualifiers
source                  1..22
                        mol_type = other RNA
                        organism = synthetic construct
SEQUENCE: 148
tcaggtaatg cacagcgatg ac                                              22

SEQ ID NO: 149          moltype = RNA  length = 22
FEATURE                 Location/Qualifiers
source                  1..22
                        mol_type = other RNA
                        organism = synthetic construct
SEQUENCE: 149
tttcatccag gtaatgcaca gc                                              22

SEQ ID NO: 150          moltype = RNA  length = 22
FEATURE                 Location/Qualifiers
source                  1..22
                        mol_type = other RNA
                        organism = synthetic construct
SEQUENCE: 150
tgtttcatcc aggtaatgca ca                                              22

SEQ ID NO: 151          moltype = RNA  length = 22
```

```
FEATURE                Location/Qualifiers
source                 1..22
                       mol_type = other RNA
                       organism = synthetic construct
SEQUENCE: 151
tttcttgatg agctccaagg cc                                           22

SEQ ID NO: 152         moltype = RNA  length = 22
FEATURE                Location/Qualifiers
source                 1..22
                       mol_type = other RNA
                       organism = synthetic construct
SEQUENCE: 152
tcttcttgat gagctccaag gc                                           22

SEQ ID NO: 153         moltype = RNA  length = 22
FEATURE                Location/Qualifiers
source                 1..22
                       mol_type = other RNA
                       organism = synthetic construct
SEQUENCE: 153
ttgaaggcca gctgctgggt gt                                           22

SEQ ID NO: 154         moltype = RNA  length = 22
FEATURE                Location/Qualifiers
source                 1..22
                       mol_type = other RNA
                       organism = synthetic construct
SEQUENCE: 154
taagaccttg accacgtagg cg                                           22

SEQ ID NO: 155         moltype = RNA  length = 22
FEATURE                Location/Qualifiers
source                 1..22
                       mol_type = other RNA
                       organism = synthetic construct
SEQUENCE: 155
tgagagaaga ccttgaccac gt                                           22

SEQ ID NO: 156         moltype = RNA  length = 22
FEATURE                Location/Qualifiers
source                 1..22
                       mol_type = other RNA
                       organism = synthetic construct
SEQUENCE: 156
tcaggatcag ccatttaaca gc                                           22

SEQ ID NO: 157         moltype = RNA  length = 22
FEATURE                Location/Qualifiers
source                 1..22
                       mol_type = other RNA
                       organism = synthetic construct
SEQUENCE: 157
tgtatcacgg gcgcatcctc ct                                           22

SEQ ID NO: 158         moltype = RNA  length = 22
FEATURE                Location/Qualifiers
source                 1..22
                       mol_type = other RNA
                       organism = synthetic construct
SEQUENCE: 158
tggaagtctc ctgctttagt ga                                           22

SEQ ID NO: 159         moltype = RNA  length = 22
FEATURE                Location/Qualifiers
source                 1..22
                       mol_type = other RNA
                       organism = synthetic construct
SEQUENCE: 159
taaggaagtc tcctgcttta gt                                           22

SEQ ID NO: 160         moltype = RNA  length = 22
FEATURE                Location/Qualifiers
source                 1..22
                       mol_type = other RNA
                       organism = synthetic construct
SEQUENCE: 160
tttcatgtag ttggcttcaa gg                                           22
```

```
SEQ ID NO: 161          moltype = RNA  length = 22
FEATURE                 Location/Qualifiers
source                  1..22
                        mol_type = other RNA
                        organism = synthetic construct
SEQUENCE: 161
ttgtaggttc atgtagttgg ct                                              22

SEQ ID NO: 162          moltype = RNA  length = 22
FEATURE                 Location/Qualifiers
source                  1..22
                        mol_type = other RNA
                        organism = synthetic construct
SEQUENCE: 162
tatctctgta ggttcatgta gt                                              22

SEQ ID NO: 163          moltype = RNA  length = 22
FEATURE                 Location/Qualifiers
source                  1..22
                        mol_type = other RNA
                        organism = synthetic construct
SEQUENCE: 163
tcagtgtagg atctctgtag gt                                              22

SEQ ID NO: 164          moltype = RNA  length = 22
FEATURE                 Location/Qualifiers
source                  1..22
                        mol_type = other RNA
                        organism = synthetic construct
SEQUENCE: 164
tcagcaatgg ccacagtgta gg                                              22

SEQ ID NO: 165          moltype = RNA  length = 22
FEATURE                 Location/Qualifiers
source                  1..22
                        mol_type = other RNA
                        organism = synthetic construct
SEQUENCE: 165
tctgcagtag ggccaagagg gc                                              22

SEQ ID NO: 166          moltype = RNA  length = 22
FEATURE                 Location/Qualifiers
source                  1..22
                        mol_type = other RNA
                        organism = synthetic construct
SEQUENCE: 166
ttcttttagc tgcagtaggg cc                                              22

SEQ ID NO: 167          moltype = RNA  length = 22
FEATURE                 Location/Qualifiers
source                  1..22
                        mol_type = other RNA
                        organism = synthetic construct
SEQUENCE: 167
tgtcttttag ctgcagtagg gc                                              22

SEQ ID NO: 168          moltype = RNA  length = 22
FEATURE                 Location/Qualifiers
source                  1..22
                        mol_type = other RNA
                        organism = synthetic construct
SEQUENCE: 168
tcaaagtcaa agtcttttag ct                                              22

SEQ ID NO: 169          moltype = RNA  length = 22
FEATURE                 Location/Qualifiers
source                  1..22
                        mol_type = other RNA
                        organism = synthetic construct
SEQUENCE: 169
tcacaaagtc aaagtctttt ag                                              22

SEQ ID NO: 170          moltype = RNA  length = 22
FEATURE                 Location/Qualifiers
source                  1..22
                        mol_type = other RNA
                        organism = synthetic construct
SEQUENCE: 170
tgtatctctg ttcattgagc ca                                              22
```

```
SEQ ID NO: 171          moltype = RNA  length = 22
FEATURE                 Location/Qualifiers
source                  1..22
                        mol_type = other RNA
                        organism = synthetic construct
SEQUENCE: 171
tagtatctct gttcattgag cc                                           22

SEQ ID NO: 172          moltype = RNA  length = 22
FEATURE                 Location/Qualifiers
source                  1..22
                        mol_type = other RNA
                        organism = synthetic construct
SEQUENCE: 172
ttagtatctc tgttcattga gc                                           22

SEQ ID NO: 173          moltype = RNA  length = 22
FEATURE                 Location/Qualifiers
source                  1..22
                        mol_type = other RNA
                        organism = synthetic construct
SEQUENCE: 173
tcttttggta ttgagccaag gc                                           22

SEQ ID NO: 174          moltype = RNA  length = 22
FEATURE                 Location/Qualifiers
source                  1..22
                        mol_type = other RNA
                        organism = synthetic construct
SEQUENCE: 174
tgattcccag tggatacggt gg                                           22

SEQ ID NO: 175          moltype = RNA  length = 22
FEATURE                 Location/Qualifiers
source                  1..22
                        mol_type = other RNA
                        organism = synthetic construct
SEQUENCE: 175
tcagattccc agtggatacg gt                                           22

SEQ ID NO: 176          moltype = RNA  length = 22
FEATURE                 Location/Qualifiers
source                  1..22
                        mol_type = other RNA
                        organism = synthetic construct
SEQUENCE: 176
tttttccttg gtctcttctg at                                           22

SEQ ID NO: 177          moltype = RNA  length = 22
FEATURE                 Location/Qualifiers
source                  1..22
                        mol_type = other RNA
                        organism = synthetic construct
SEQUENCE: 177
tattttcctt ggtctcttct ga                                           22

SEQ ID NO: 178          moltype = RNA  length = 22
FEATURE                 Location/Qualifiers
source                  1..22
                        mol_type = other RNA
                        organism = synthetic construct
SEQUENCE: 178
tcattttcct tggtctcttc tg                                           22

SEQ ID NO: 179          moltype = RNA  length = 22
FEATURE                 Location/Qualifiers
source                  1..22
                        mol_type = other RNA
                        organism = synthetic construct
SEQUENCE: 179
tctgtgaaac cctcattttc ct                                           22

SEQ ID NO: 180          moltype = RNA  length = 22
FEATURE                 Location/Qualifiers
source                  1..22
                        mol_type = other RNA
                        organism = synthetic construct
SEQUENCE: 180
```

```
tttcagctgt gactgtgaaa cc                                          22

SEQ ID NO: 181          moltype = RNA  length = 22
FEATURE                 Location/Qualifiers
source                  1..22
                        mol_type = other RNA
                        organism = synthetic construct
SEQUENCE: 181
tttccttcag ctgtgactgt ga                                          22

SEQ ID NO: 182          moltype = RNA  length = 22
FEATURE                 Location/Qualifiers
source                  1..22
                        mol_type = other RNA
                        organism = synthetic construct
SEQUENCE: 182
tttttccttc agctgtgact gt                                          22

SEQ ID NO: 183          moltype = RNA  length = 22
FEATURE                 Location/Qualifiers
source                  1..22
                        mol_type = other RNA
                        organism = synthetic construct
SEQUENCE: 183
tcttttcctt cagctgtgac tg                                          22

SEQ ID NO: 184          moltype = RNA  length = 22
FEATURE                 Location/Qualifiers
source                  1..22
                        mol_type = other RNA
                        organism = synthetic construct
SEQUENCE: 184
tcttagcatg gtacattgtc ac                                          22

SEQ ID NO: 185          moltype = RNA  length = 22
FEATURE                 Location/Qualifiers
source                  1..22
                        mol_type = other RNA
                        organism = synthetic construct
SEQUENCE: 185
tgaggtcgaa tttattacag gt                                          22

SEQ ID NO: 186          moltype = RNA  length = 22
FEATURE                 Location/Qualifiers
source                  1..22
                        mol_type = other RNA
                        organism = synthetic construct
SEQUENCE: 186
ttttatggtg accttgaggt cg                                          22

SEQ ID NO: 187          moltype = RNA  length = 22
FEATURE                 Location/Qualifiers
source                  1..22
                        mol_type = other RNA
                        organism = synthetic construct
SEQUENCE: 187
tttttatggt gaccttgagg tc                                          22

SEQ ID NO: 188          moltype = RNA  length = 22
FEATURE                 Location/Qualifiers
source                  1..22
                        mol_type = other RNA
                        organism = synthetic construct
SEQUENCE: 188
tgttttatgg tgaccttgag gt                                          22

SEQ ID NO: 189          moltype = RNA  length = 22
FEATURE                 Location/Qualifiers
source                  1..22
                        mol_type = other RNA
                        organism = synthetic construct
SEQUENCE: 189
tctgtttccg gtgctggttt ta                                          22

SEQ ID NO: 190          moltype = RNA  length = 22
FEATURE                 Location/Qualifiers
source                  1..22
                        mol_type = other RNA
                        organism = synthetic construct
```

```
SEQUENCE: 190
tgtgttcttg gcatcctgag gc                                            22

SEQ ID NO: 191          moltype = RNA  length = 22
FEATURE                 Location/Qualifiers
source                  1..22
                        mol_type = other RNA
                        organism = synthetic construct
SEQUENCE: 191
tatcatagtg ttcttggcat cc                                            22

SEQ ID NO: 192          moltype = RNA  length = 22
FEATURE                 Location/Qualifiers
source                  1..22
                        mol_type = other RNA
                        organism = synthetic construct
SEQUENCE: 192
taaggatcat agtgttcttg gc                                            22

SEQ ID NO: 193          moltype = RNA  length = 22
FEATURE                 Location/Qualifiers
source                  1..22
                        mol_type = other RNA
                        organism = synthetic construct
SEQUENCE: 193
tcaaggatca tagtgttctt gg                                            22

SEQ ID NO: 194          moltype = RNA  length = 22
FEATURE                 Location/Qualifiers
source                  1..22
                        mol_type = other RNA
                        organism = synthetic construct
SEQUENCE: 194
ttagacatag tggcatcctg gt                                            22

SEQ ID NO: 195          moltype = RNA  length = 22
FEATURE                 Location/Qualifiers
source                  1..22
                        mol_type = other RNA
                        organism = synthetic construct
SEQUENCE: 195
tcagtcatca tggatatgtc ca                                            22

SEQ ID NO: 196          moltype = RNA  length = 22
FEATURE                 Location/Qualifiers
source                  1..22
                        mol_type = other RNA
                        organism = synthetic construct
SEQUENCE: 196
ttacttggag atgtatctgt ca                                            22

SEQ ID NO: 197          moltype = RNA  length = 22
FEATURE                 Location/Qualifiers
source                  1..22
                        mol_type = other RNA
                        organism = synthetic construct
SEQUENCE: 197
tatacttgga gatgtatctg tc                                            22

SEQ ID NO: 198          moltype = RNA  length = 22
FEATURE                 Location/Qualifiers
source                  1..22
                        mol_type = other RNA
                        organism = synthetic construct
SEQUENCE: 198
tcatacttgg agatgtatct gt                                            22

SEQ ID NO: 199          moltype = RNA  length = 22
FEATURE                 Location/Qualifiers
source                  1..22
                        mol_type = other RNA
                        organism = synthetic construct
SEQUENCE: 199
tctcatactt ggagatgtat ct                                            22

SEQ ID NO: 200          moltype = RNA  length = 22
FEATURE                 Location/Qualifiers
source                  1..22
                        mol_type = other RNA
```

```
                         organism = synthetic construct
SEQUENCE: 200
ttttgtccag ctcatacttg ga                                          22

SEQ ID NO: 201           moltype = RNA  length = 22
FEATURE                  Location/Qualifiers
source                   1..22
                         mol_type = other RNA
                         organism = synthetic construct
SEQUENCE: 201
tctttgtcca gctcatactt gg                                          22

SEQ ID NO: 202           moltype = RNA  length = 22
FEATURE                  Location/Qualifiers
source                   1..22
                         mol_type = other RNA
                         organism = synthetic construct
SEQUENCE: 202
tctatcggag aaggctttgt cc                                          22

SEQ ID NO: 203           moltype = RNA  length = 22
FEATURE                  Location/Qualifiers
source                   1..22
                         mol_type = other RNA
                         organism = synthetic construct
SEQUENCE: 203
tttcctatcg gagaaggctt tg                                          22

SEQ ID NO: 204           moltype = RNA  length = 22
FEATURE                  Location/Qualifiers
source                   1..22
                         mol_type = other RNA
                         organism = synthetic construct
SEQUENCE: 204
tgtgttccta tcggagaagg ct                                          22

SEQ ID NO: 205           moltype = RNA  length = 22
FEATURE                  Location/Qualifiers
source                   1..22
                         mol_type = other RNA
                         organism = synthetic construct
SEQUENCE: 205
tatgatgagg gtgttcctat cg                                          22

SEQ ID NO: 206           moltype = RNA  length = 22
FEATURE                  Location/Qualifiers
source                   1..22
                         mol_type = other RNA
                         organism = synthetic construct
SEQUENCE: 206
tgatgatgag ggtgttccta tc                                          22

SEQ ID NO: 207           moltype = RNA  length = 22
FEATURE                  Location/Qualifiers
source                   1..22
                         mol_type = other RNA
                         organism = synthetic construct
SEQUENCE: 207
tgtagatgat gagggtgttc ct                                          22

SEQ ID NO: 208           moltype = RNA  length = 22
FEATURE                  Location/Qualifiers
source                   1..22
                         mol_type = other RNA
                         organism = synthetic construct
SEQUENCE: 208
tcttgtccag gtagatgatg ag                                          22

SEQ ID NO: 209           moltype = RNA  length = 22
FEATURE                  Location/Qualifiers
source                   1..22
                         mol_type = other RNA
                         organism = synthetic construct
SEQUENCE: 209
tgaccttgtc caggtagatg at                                          22

SEQ ID NO: 210           moltype = RNA  length = 22
FEATURE                  Location/Qualifiers
source                   1..22
```

-continued

```
                      mol_type = other RNA
                      organism = synthetic construct
SEQUENCE: 210
tctcagagtg tgagaccttg tc                                          22

SEQ ID NO: 211        moltype = RNA  length = 22
FEATURE               Location/Qualifiers
source                1..22
                      mol_type = other RNA
                      organism = synthetic construct
SEQUENCE: 211
tcatcctcag agtgtgagac ct                                          22

SEQ ID NO: 212        moltype = RNA  length = 22
FEATURE               Location/Qualifiers
source                1..22
                      mol_type = other RNA
                      organism = synthetic construct
SEQUENCE: 212
tgtaataggc gtagaccttg ac                                          22

SEQ ID NO: 213        moltype = RNA  length = 22
FEATURE               Location/Qualifiers
source                1..22
                      mol_type = other RNA
                      organism = synthetic construct
SEQUENCE: 213
tgttgtaata ggcgtagacc tt                                          22

SEQ ID NO: 214        moltype = RNA  length = 22
FEATURE               Location/Qualifiers
source                1..22
                      mol_type = other RNA
                      organism = synthetic construct
SEQUENCE: 214
tggttgtaat aggcgtagac ct                                          22

SEQ ID NO: 215        moltype = RNA  length = 22
FEATURE               Location/Qualifiers
source                1..22
                      mol_type = other RNA
                      organism = synthetic construct
SEQUENCE: 215
ttgttcagct ttccatcctc ct                                          22

SEQ ID NO: 216        moltype = RNA  length = 22
FEATURE               Location/Qualifiers
source                1..22
                      mol_type = other RNA
                      organism = synthetic construct
SEQUENCE: 216
tgaagcaatt ctcctcagca ca                                          22

SEQ ID NO: 217        moltype = RNA  length = 22
FEATURE               Location/Qualifiers
source                1..22
                      mol_type = other RNA
                      organism = synthetic construct
SEQUENCE: 217
tttgtatgaa gcaattctcc tc                                          22

SEQ ID NO: 218        moltype = RNA  length = 22
FEATURE               Location/Qualifiers
source                1..22
                      mol_type = other RNA
                      organism = synthetic construct
SEQUENCE: 218
tttttgtatg aagcaattct cc                                          22

SEQ ID NO: 219        moltype = RNA  length = 22
FEATURE               Location/Qualifiers
source                1..22
                      mol_type = other RNA
                      organism = synthetic construct
SEQUENCE: 219
ttacacatag tccactcctg gc                                          22

SEQ ID NO: 220        moltype = RNA  length = 22
FEATURE               Location/Qualifiers
```

-continued

```
source                  1..22
                        mol_type = other RNA
                        organism = synthetic construct
SEQUENCE: 220
tgtacacata gtccactcct gg                                           22

SEQ ID NO: 221          moltype = RNA  length = 22
FEATURE                 Location/Qualifiers
source                  1..22
                        mol_type = other RNA
                        organism = synthetic construct
SEQUENCE: 221
tgtcttgtac acatagtcca ct                                           22

SEQ ID NO: 222          moltype = RNA  length = 22
FEATURE                 Location/Qualifiers
source                  1..22
                        mol_type = other RNA
                        organism = synthetic construct
SEQUENCE: 222
tgtactcgtc aaagtcattg ga                                           22

SEQ ID NO: 223          moltype = RNA  length = 22
FEATURE                 Location/Qualifiers
source                  1..22
                        mol_type = other RNA
                        organism = synthetic construct
SEQUENCE: 223
tatgatgtac tcgtcaaagt ca                                           22

SEQ ID NO: 224          moltype = RNA  length = 22
FEATURE                 Location/Qualifiers
source                  1..22
                        mol_type = other RNA
                        organism = synthetic construct
SEQUENCE: 224
tctcatccga gcctgacttg at                                           22

SEQ ID NO: 225          moltype = RNA  length = 22
FEATURE                 Location/Qualifiers
source                  1..22
                        mol_type = other RNA
                        organism = synthetic construct
SEQUENCE: 225
tgtccaacct gcacctcatc cg                                           22

SEQ ID NO: 226          moltype = RNA  length = 22
FEATURE                 Location/Qualifiers
source                  1..22
                        mol_type = other RNA
                        organism = synthetic construct
SEQUENCE: 226
tgtcagttgg ggcacccaaa ga                                           22

SEQ ID NO: 227          moltype = RNA  length = 20
FEATURE                 Location/Qualifiers
source                  1..20
                        mol_type = other RNA
                        organism = synthetic construct
SEQUENCE: 227
cctctgaccc tgcactgtca                                              20

SEQ ID NO: 228          moltype = RNA  length = 20
FEATURE                 Location/Qualifiers
source                  1..20
                        mol_type = other RNA
                        organism = synthetic construct
SEQUENCE: 228
cacgacttcc caggcaaaaa                                              20

SEQ ID NO: 229          moltype = RNA  length = 20
FEATURE                 Location/Qualifiers
source                  1..20
                        mol_type = other RNA
                        organism = synthetic construct
SEQUENCE: 229
acgacttccc aggcaaaaaa                                              20

SEQ ID NO: 230          moltype = RNA  length = 20
```

-continued

```
FEATURE                Location/Qualifiers
source                 1..20
                       mol_type = other RNA
                       organism = synthetic construct
SEQUENCE: 230
cgacttccca ggcaaaaaaa                                                    20

SEQ ID NO: 231         moltype = RNA  length = 20
FEATURE                Location/Qualifiers
source                 1..20
                       mol_type = other RNA
                       organism = synthetic construct
SEQUENCE: 231
gacttcccag gcaaaaaaca                                                    20

SEQ ID NO: 232         moltype = RNA  length = 20
FEATURE                Location/Qualifiers
source                 1..20
                       mol_type = other RNA
                       organism = synthetic construct
SEQUENCE: 232
tacctcttca tccagacaga                                                    20

SEQ ID NO: 233         moltype = RNA  length = 20
FEATURE                Location/Qualifiers
source                 1..20
                       mol_type = other RNA
                       organism = synthetic construct
SEQUENCE: 233
cctcttcatc cagacagaca                                                    20

SEQ ID NO: 234         moltype = RNA  length = 20
FEATURE                Location/Qualifiers
source                 1..20
                       mol_type = other RNA
                       organism = synthetic construct
SEQUENCE: 234
tcttcatcca gacagacaaa                                                    20

SEQ ID NO: 235         moltype = RNA  length = 20
FEATURE                Location/Qualifiers
source                 1..20
                       mol_type = other RNA
                       organism = synthetic construct
SEQUENCE: 235
agacagacaa gaccatctaa                                                    20

SEQ ID NO: 236         moltype = RNA  length = 20
FEATURE                Location/Qualifiers
source                 1..20
                       mol_type = other RNA
                       organism = synthetic construct
SEQUENCE: 236
gacagacaag accatctaca                                                    20

SEQ ID NO: 237         moltype = RNA  length = 20
FEATURE                Location/Qualifiers
source                 1..20
                       mol_type = other RNA
                       organism = synthetic construct
SEQUENCE: 237
acagacaaga ccatctacaa                                                    20

SEQ ID NO: 238         moltype = RNA  length = 20
FEATURE                Location/Qualifiers
source                 1..20
                       mol_type = other RNA
                       organism = synthetic construct
SEQUENCE: 238
cagacaagac catctacaca                                                    20

SEQ ID NO: 239         moltype = RNA  length = 20
FEATURE                Location/Qualifiers
source                 1..20
                       mol_type = other RNA
                       organism = synthetic construct
SEQUENCE: 239
tcaagcagga ctccttgtca                                                    20
```

-continued

```
SEQ ID NO: 240          moltype = RNA  length = 20
FEATURE                 Location/Qualifiers
source                  1..20
                        mol_type = other RNA
                        organism = synthetic construct
SEQUENCE: 240
aagcaggact ccttgtctta                                              20

SEQ ID NO: 241          moltype = RNA  length = 20
FEATURE                 Location/Qualifiers
source                  1..20
                        mol_type = other RNA
                        organism = synthetic construct
SEQUENCE: 241
actccttgtc ttctcagaaa                                              20

SEQ ID NO: 242          moltype = RNA  length = 20
FEATURE                 Location/Qualifiers
source                  1..20
                        mol_type = other RNA
                        organism = synthetic construct
SEQUENCE: 242
ggacattccg gaactcgtca                                              20

SEQ ID NO: 243          moltype = RNA  length = 20
FEATURE                 Location/Qualifiers
source                  1..20
                        mol_type = other RNA
                        organism = synthetic construct
SEQUENCE: 243
acattccgga actcgtcaaa                                              20

SEQ ID NO: 244          moltype = RNA  length = 20
FEATURE                 Location/Qualifiers
source                  1..20
                        mol_type = other RNA
                        organism = synthetic construct
SEQUENCE: 244
cattccggaa ctcgtcaaca                                              20

SEQ ID NO: 245          moltype = RNA  length = 20
FEATURE                 Location/Qualifiers
source                  1..20
                        mol_type = other RNA
                        organism = synthetic construct
SEQUENCE: 245
caacatgggc cagtggaaga                                              20

SEQ ID NO: 246          moltype = RNA  length = 20
FEATURE                 Location/Qualifiers
source                  1..20
                        mol_type = other RNA
                        organism = synthetic construct
SEQUENCE: 246
aagatccgag cctactatga                                              20

SEQ ID NO: 247          moltype = RNA  length = 20
FEATURE                 Location/Qualifiers
source                  1..20
                        mol_type = other RNA
                        organism = synthetic construct
SEQUENCE: 247
gatccgagcc tactatgaaa                                              20

SEQ ID NO: 248          moltype = RNA  length = 20
FEATURE                 Location/Qualifiers
source                  1..20
                        mol_type = other RNA
                        organism = synthetic construct
SEQUENCE: 248
atccgagcct actatgaaaa                                              20

SEQ ID NO: 249          moltype = RNA  length = 20
FEATURE                 Location/Qualifiers
source                  1..20
                        mol_type = other RNA
                        organism = synthetic construct
SEQUENCE: 249
gtcttctcca ctgagtttga                                              20
```

```
SEQ ID NO: 250          moltype = RNA  length = 20
FEATURE                 Location/Qualifiers
source                  1..20
                        mol_type = other RNA
                        organism = synthetic construct
SEQUENCE: 250
tgagtttgag gtgaaggaga                                               20

SEQ ID NO: 251          moltype = RNA  length = 20
FEATURE                 Location/Qualifiers
source                  1..20
                        mol_type = other RNA
                        organism = synthetic construct
SEQUENCE: 251
agtttgaggt gaaggagtaa                                               20

SEQ ID NO: 252          moltype = RNA  length = 20
FEATURE                 Location/Qualifiers
source                  1..20
                        mol_type = other RNA
                        organism = synthetic construct
SEQUENCE: 252
gtttgaggtg aaggagtaca                                               20

SEQ ID NO: 253          moltype = RNA  length = 20
FEATURE                 Location/Qualifiers
source                  1..20
                        mol_type = other RNA
                        organism = synthetic construct
SEQUENCE: 253
gtacgtgctg cccagtttca                                               20

SEQ ID NO: 254          moltype = RNA  length = 20
FEATURE                 Location/Qualifiers
source                  1..20
                        mol_type = other RNA
                        organism = synthetic construct
SEQUENCE: 254
cccagtttcg aggtcataga                                               20

SEQ ID NO: 255          moltype = RNA  length = 20
FEATURE                 Location/Qualifiers
source                  1..20
                        mol_type = other RNA
                        organism = synthetic construct
SEQUENCE: 255
cagtttcgag gtcatagtga                                               20

SEQ ID NO: 256          moltype = RNA  length = 20
FEATURE                 Location/Qualifiers
source                  1..20
                        mol_type = other RNA
                        organism = synthetic construct
SEQUENCE: 256
catagtggag cctacagaga                                               20

SEQ ID NO: 257          moltype = RNA  length = 20
FEATURE                 Location/Qualifiers
source                  1..20
                        mol_type = other RNA
                        organism = synthetic construct
SEQUENCE: 257
tagtggagcc tacagagaaa                                               20

SEQ ID NO: 258          moltype = RNA  length = 20
FEATURE                 Location/Qualifiers
source                  1..20
                        mol_type = other RNA
                        organism = synthetic construct
SEQUENCE: 258
cctacagaga aattctacta                                               20

SEQ ID NO: 259          moltype = RNA  length = 20
FEATURE                 Location/Qualifiers
source                  1..20
                        mol_type = other RNA
                        organism = synthetic construct
SEQUENCE: 259
```

```
agaaattcta ctacatctaa                                              20

SEQ ID NO: 260          moltype = RNA  length = 20
FEATURE                 Location/Qualifiers
source                  1..20
                        mol_type = other RNA
                        organism = synthetic construct
SEQUENCE: 260
attctactac atctataaca                                              20

SEQ ID NO: 261          moltype = RNA  length = 20
FEATURE                 Location/Qualifiers
source                  1..20
                        mol_type = other RNA
                        organism = synthetic construct
SEQUENCE: 261
ggaactgcct ttgtcatcta                                              20

SEQ ID NO: 262          moltype = RNA  length = 20
FEATURE                 Location/Qualifiers
source                  1..20
                        mol_type = other RNA
                        organism = synthetic construct
SEQUENCE: 262
gaactgcctt tgtcatctta                                              20

SEQ ID NO: 263          moltype = RNA  length = 20
FEATURE                 Location/Qualifiers
source                  1..20
                        mol_type = other RNA
                        organism = synthetic construct
SEQUENCE: 263
ccagatccac ttcaccaaga                                              20

SEQ ID NO: 264          moltype = RNA  length = 20
FEATURE                 Location/Qualifiers
source                  1..20
                        mol_type = other RNA
                        organism = synthetic construct
SEQUENCE: 264
agatccactt caccaagaca                                              20

SEQ ID NO: 265          moltype = RNA  length = 20
FEATURE                 Location/Qualifiers
source                  1..20
                        mol_type = other RNA
                        organism = synthetic construct
SEQUENCE: 265
aggaatgccc tttgacctca                                              20

SEQ ID NO: 266          moltype = RNA  length = 20
FEATURE                 Location/Qualifiers
source                  1..20
                        mol_type = other RNA
                        organism = synthetic construct
SEQUENCE: 266
cctttgacct catggtgtta                                              20

SEQ ID NO: 267          moltype = RNA  length = 20
FEATURE                 Location/Qualifiers
source                  1..20
                        mol_type = other RNA
                        organism = synthetic construct
SEQUENCE: 267
ctctccagcc taccgagtca                                              20

SEQ ID NO: 268          moltype = RNA  length = 20
FEATURE                 Location/Qualifiers
source                  1..20
                        mol_type = other RNA
                        organism = synthetic construct
SEQUENCE: 268
gccaaactca gcatcaacaa                                              20

SEQ ID NO: 269          moltype = RNA  length = 20
FEATURE                 Location/Qualifiers
source                  1..20
                        mol_type = other RNA
                        organism = synthetic construct
```

-continued

```
SEQUENCE: 269
ccaaactcag catcaacaca                                                20

SEQ ID NO: 270          moltype = RNA  length = 20
FEATURE                 Location/Qualifiers
source                  1..20
                        mol_type = other RNA
                        organism = synthetic construct
SEQUENCE: 270
ccagaagccc ttgagcatca                                                20

SEQ ID NO: 271          moltype = RNA  length = 20
FEATURE                 Location/Qualifiers
source                  1..20
                        mol_type = other RNA
                        organism = synthetic construct
SEQUENCE: 271
cagaagccct tgagcatcaa                                                20

SEQ ID NO: 272          moltype = RNA  length = 20
FEATURE                 Location/Qualifiers
source                  1..20
                        mol_type = other RNA
                        organism = synthetic construct
SEQUENCE: 272
caactccaac aattacctga                                                20

SEQ ID NO: 273          moltype = RNA  length = 20
FEATURE                 Location/Qualifiers
source                  1..20
                        mol_type = other RNA
                        organism = synthetic construct
SEQUENCE: 273
caacaattac ctgcatctca                                                20

SEQ ID NO: 274          moltype = RNA  length = 20
FEATURE                 Location/Qualifiers
source                  1..20
                        mol_type = other RNA
                        organism = synthetic construct
SEQUENCE: 274
aattacctgc atctctcaga                                                20

SEQ ID NO: 275          moltype = RNA  length = 20
FEATURE                 Location/Qualifiers
source                  1..20
                        mol_type = other RNA
                        organism = synthetic construct
SEQUENCE: 275
cctcaacgtc aacttcctca                                                20

SEQ ID NO: 276          moltype = RNA  length = 20
FEATURE                 Location/Qualifiers
source                  1..20
                        mol_type = other RNA
                        organism = synthetic construct
SEQUENCE: 276
caacttcctc ctgcgaatga                                                20

SEQ ID NO: 277          moltype = RNA  length = 20
FEATURE                 Location/Qualifiers
source                  1..20
                        mol_type = other RNA
                        organism = synthetic construct
SEQUENCE: 277
ccaagatccg ctactacaca                                                20

SEQ ID NO: 278          moltype = RNA  length = 20
FEATURE                 Location/Qualifiers
source                  1..20
                        mol_type = other RNA
                        organism = synthetic construct
SEQUENCE: 278
gctactacac ctacctgata                                                20

SEQ ID NO: 279          moltype = RNA  length = 20
FEATURE                 Location/Qualifiers
source                  1..20
                        mol_type = other RNA
```

```
                        organism = synthetic construct
SEQUENCE: 279
catcaccacc gacttcatca                                              20

SEQ ID NO: 280          moltype = RNA  length = 20
FEATURE                 Location/Qualifiers
source                  1..20
                        mol_type = other RNA
                        organism = synthetic construct
SEQUENCE: 280
cgacttcatc ccttccttca                                              20

SEQ ID NO: 281          moltype = RNA  length = 20
FEATURE                 Location/Qualifiers
source                  1..20
                        mol_type = other RNA
                        organism = synthetic construct
SEQUENCE: 281
aaaaagcggc cagtcagaaa                                              20

SEQ ID NO: 282          moltype = RNA  length = 20
FEATURE                 Location/Qualifiers
source                  1..20
                        mol_type = other RNA
                        organism = synthetic construct
SEQUENCE: 282
agcagatgac cctgaagata                                              20

SEQ ID NO: 283          moltype = RNA  length = 20
FEATURE                 Location/Qualifiers
source                  1..20
                        mol_type = other RNA
                        organism = synthetic construct
SEQUENCE: 283
gcagatgacc ctgaagataa                                              20

SEQ ID NO: 284          moltype = RNA  length = 20
FEATURE                 Location/Qualifiers
source                  1..20
                        mol_type = other RNA
                        organism = synthetic construct
SEQUENCE: 284
tggactgctg caactacata                                              20

SEQ ID NO: 285          moltype = RNA  length = 20
FEATURE                 Location/Qualifiers
source                  1..20
                        mol_type = other RNA
                        organism = synthetic construct
SEQUENCE: 285
actgctgcaa ctacatcaca                                              20

SEQ ID NO: 286          moltype = RNA  length = 20
FEATURE                 Location/Qualifiers
source                  1..20
                        mol_type = other RNA
                        organism = synthetic construct
SEQUENCE: 286
gctcatgaat atatttttga                                              20

SEQ ID NO: 287          moltype = RNA  length = 20
FEATURE                 Location/Qualifiers
source                  1..20
                        mol_type = other RNA
                        organism = synthetic construct
SEQUENCE: 287
tcatgaatat atttttgaaa                                              20

SEQ ID NO: 288          moltype = RNA  length = 20
FEATURE                 Location/Qualifiers
source                  1..20
                        mol_type = other RNA
                        organism = synthetic construct
SEQUENCE: 288
catgaatata tttttgaaaa                                              20

SEQ ID NO: 289          moltype = RNA  length = 20
FEATURE                 Location/Qualifiers
source                  1..20
```

```
                        mol_type = other RNA
                        organism = synthetic construct
SEQUENCE: 289
atgaatatat ttttgaaaga                                              20

SEQ ID NO: 290          moltype = RNA  length = 20
FEATURE                 Location/Qualifiers
source                  1..20
                        mol_type = other RNA
                        organism = synthetic construct
SEQUENCE: 290
gaatatattt ttgaaagaca                                              20

SEQ ID NO: 291          moltype = RNA  length = 20
FEATURE                 Location/Qualifiers
source                  1..20
                        mol_type = other RNA
                        organism = synthetic construct
SEQUENCE: 291
ccttcgaggt cacagtaata                                              20

SEQ ID NO: 292          moltype = RNA  length = 20
FEATURE                 Location/Qualifiers
source                  1..20
                        mol_type = other RNA
                        organism = synthetic construct
SEQUENCE: 292
cttcgaggtc acagtaatga                                              20

SEQ ID NO: 293          moltype = RNA  length = 20
FEATURE                 Location/Qualifiers
source                  1..20
                        mol_type = other RNA
                        organism = synthetic construct
SEQUENCE: 293
cacagtaatg caggacttca                                              20

SEQ ID NO: 294          moltype = RNA  length = 20
FEATURE                 Location/Qualifiers
source                  1..20
                        mol_type = other RNA
                        organism = synthetic construct
SEQUENCE: 294
agtaatgcag gacttcttca                                              20

SEQ ID NO: 295          moltype = RNA  length = 20
FEATURE                 Location/Qualifiers
source                  1..20
                        mol_type = other RNA
                        organism = synthetic construct
SEQUENCE: 295
aatgcaggac ttcttcatca                                              20

SEQ ID NO: 296          moltype = RNA  length = 20
FEATURE                 Location/Qualifiers
source                  1..20
                        mol_type = other RNA
                        organism = synthetic construct
SEQUENCE: 296
ctaccctact ctgttgttca                                              20

SEQ ID NO: 297          moltype = RNA  length = 20
FEATURE                 Location/Qualifiers
source                  1..20
                        mol_type = other RNA
                        organism = synthetic construct
SEQUENCE: 297
cctactctgt tgttcgaaaa                                              20

SEQ ID NO: 298          moltype = RNA  length = 20
FEATURE                 Location/Qualifiers
source                  1..20
                        mol_type = other RNA
                        organism = synthetic construct
SEQUENCE: 298
ctactctgtt gttcgaaaca                                              20

SEQ ID NO: 299          moltype = RNA  length = 20
FEATURE                 Location/Qualifiers
```

```
source                  1..20
                        mol_type = other RNA
                        organism = synthetic construct
SEQUENCE: 299
aaacgagcag gtggaaatca                                              20

SEQ ID NO: 300          moltype = RNA  length = 20
FEATURE                 Location/Qualifiers
source                  1..20
                        mol_type = other RNA
                        organism = synthetic construct
SEQUENCE: 300
caattaccgg cagaaccaaa                                              20

SEQ ID NO: 301          moltype = RNA  length = 20
FEATURE                 Location/Qualifiers
source                  1..20
                        mol_type = other RNA
                        organism = synthetic construct
SEQUENCE: 301
aattaccggc agaaccaaga                                              20

SEQ ID NO: 302          moltype = RNA  length = 20
FEATURE                 Location/Qualifiers
source                  1..20
                        mol_type = other RNA
                        organism = synthetic construct
SEQUENCE: 302
aaggtgaggg tggaactaca                                              20

SEQ ID NO: 303          moltype = RNA  length = 20
FEATURE                 Location/Qualifiers
source                  1..20
                        mol_type = other RNA
                        organism = synthetic construct
SEQUENCE: 303
gtggaactac tccacaatca                                              20

SEQ ID NO: 304          moltype = RNA  length = 20
FEATURE                 Location/Qualifiers
source                  1..20
                        mol_type = other RNA
                        organism = synthetic construct
SEQUENCE: 304
tggaactact ccacaatcca                                              20

SEQ ID NO: 305          moltype = RNA  length = 20
FEATURE                 Location/Qualifiers
source                  1..20
                        mol_type = other RNA
                        organism = synthetic construct
SEQUENCE: 305
gaactactcc acaatccaga                                              20

SEQ ID NO: 306          moltype = RNA  length = 20
FEATURE                 Location/Qualifiers
source                  1..20
                        mol_type = other RNA
                        organism = synthetic construct
SEQUENCE: 306
acaatccagc cttctgcaga                                              20

SEQ ID NO: 307          moltype = RNA  length = 20
FEATURE                 Location/Qualifiers
source                  1..20
                        mol_type = other RNA
                        organism = synthetic construct
SEQUENCE: 307
cagcagaccg taaccatcca                                              20

SEQ ID NO: 308          moltype = RNA  length = 20
FEATURE                 Location/Qualifiers
source                  1..20
                        mol_type = other RNA
                        organism = synthetic construct
SEQUENCE: 308
aaggaatcag aatgaacaaa                                              20

SEQ ID NO: 309          moltype = RNA  length = 20
```

```
FEATURE                Location/Qualifiers
source                 1..20
                       mol_type = other RNA
                       organism = synthetic construct
SEQUENCE: 309
gaatcagaat gaacaaaaca                                                  20

SEQ ID NO: 310         moltype = RNA  length = 20
FEATURE                Location/Qualifiers
source                 1..20
                       mol_type = other RNA
                       organism = synthetic construct
SEQUENCE: 310
cgagtctgag accagaatta                                                  20

SEQ ID NO: 311         moltype = RNA  length = 20
FEATURE                Location/Qualifiers
source                 1..20
                       mol_type = other RNA
                       organism = synthetic construct
SEQUENCE: 311
gagtctgaga ccagaattca                                                  20

SEQ ID NO: 312         moltype = RNA  length = 20
FEATURE                Location/Qualifiers
source                 1..20
                       mol_type = other RNA
                       organism = synthetic construct
SEQUENCE: 312
ccagatgaca gaggatgcca                                                  20

SEQ ID NO: 313         moltype = RNA  length = 20
FEATURE                Location/Qualifiers
source                 1..20
                       mol_type = other RNA
                       organism = synthetic construct
SEQUENCE: 313
catcgctgtg cattacctga                                                  20

SEQ ID NO: 314         moltype = RNA  length = 20
FEATURE                Location/Qualifiers
source                 1..20
                       mol_type = other RNA
                       organism = synthetic construct
SEQUENCE: 314
tgtgcattac ctggatgaaa                                                  20

SEQ ID NO: 315         moltype = RNA  length = 20
FEATURE                Location/Qualifiers
source                 1..20
                       mol_type = other RNA
                       organism = synthetic construct
SEQUENCE: 315
tgcattacct ggatgaaaca                                                  20

SEQ ID NO: 316         moltype = RNA  length = 20
FEATURE                Location/Qualifiers
source                 1..20
                       mol_type = other RNA
                       organism = synthetic construct
SEQUENCE: 316
ccttggagct catcaagaaa                                                  20

SEQ ID NO: 317         moltype = RNA  length = 20
FEATURE                Location/Qualifiers
source                 1..20
                       mol_type = other RNA
                       organism = synthetic construct
SEQUENCE: 317
cttggagctc atcaagaaga                                                  20

SEQ ID NO: 318         moltype = RNA  length = 20
FEATURE                Location/Qualifiers
source                 1..20
                       mol_type = other RNA
                       organism = synthetic construct
SEQUENCE: 318
acccagcagc tggccttcaa                                                  20
```

-continued

```
SEQ ID NO: 319          moltype = RNA  length = 20
FEATURE                 Location/Qualifiers
source                  1..20
                        mol_type = other RNA
                        organism = synthetic construct
SEQUENCE: 319
cctacgtggt caaggtctta                                              20

SEQ ID NO: 320          moltype = RNA  length = 20
FEATURE                 Location/Qualifiers
source                  1..20
                        mol_type = other RNA
                        organism = synthetic construct
SEQUENCE: 320
gtggtcaagg tcttctctca                                              20

SEQ ID NO: 321          moltype = RNA  length = 20
FEATURE                 Location/Qualifiers
source                  1..20
                        mol_type = other RNA
                        organism = synthetic construct
SEQUENCE: 321
tgttaaatgg ctgatcctga                                              20

SEQ ID NO: 322          moltype = RNA  length = 20
FEATURE                 Location/Qualifiers
source                  1..20
                        mol_type = other RNA
                        organism = synthetic construct
SEQUENCE: 322
gaggatgcgc ccgtgataca                                              20

SEQ ID NO: 323          moltype = RNA  length = 20
FEATURE                 Location/Qualifiers
source                  1..20
                        mol_type = other RNA
                        organism = synthetic construct
SEQUENCE: 323
actaaagcag gagacttcca                                              20

SEQ ID NO: 324          moltype = RNA  length = 20
FEATURE                 Location/Qualifiers
source                  1..20
                        mol_type = other RNA
                        organism = synthetic construct
SEQUENCE: 324
taaagcagga gacttcctta                                              20

SEQ ID NO: 325          moltype = RNA  length = 20
FEATURE                 Location/Qualifiers
source                  1..20
                        mol_type = other RNA
                        organism = synthetic construct
SEQUENCE: 325
ttgaagccaa ctacatgaaa                                              20

SEQ ID NO: 326          moltype = RNA  length = 20
FEATURE                 Location/Qualifiers
source                  1..20
                        mol_type = other RNA
                        organism = synthetic construct
SEQUENCE: 326
ccaactacat gaacctacaa                                              20

SEQ ID NO: 327          moltype = RNA  length = 20
FEATURE                 Location/Qualifiers
source                  1..20
                        mol_type = other RNA
                        organism = synthetic construct
SEQUENCE: 327
tacatgaacc tacagagata                                              20

SEQ ID NO: 328          moltype = RNA  length = 20
FEATURE                 Location/Qualifiers
source                  1..20
                        mol_type = other RNA
                        organism = synthetic construct
SEQUENCE: 328
ctacagagat cctacactga                                              20
```

```
SEQ ID NO: 329          moltype = RNA  length = 20
FEATURE                 Location/Qualifiers
source                  1..20
                        mol_type = other RNA
                        organism = synthetic construct
SEQUENCE: 329
tacactgtgg ccattgctga                                              20

SEQ ID NO: 330          moltype = RNA  length = 20
FEATURE                 Location/Qualifiers
source                  1..20
                        mol_type = other RNA
                        organism = synthetic construct
SEQUENCE: 330
cctcttggcc ctactgcaga                                              20

SEQ ID NO: 331          moltype = RNA  length = 20
FEATURE                 Location/Qualifiers
source                  1..20
                        mol_type = other RNA
                        organism = synthetic construct
SEQUENCE: 331
ccctactgca gctaaaagaa                                              20

SEQ ID NO: 332          moltype = RNA  length = 20
FEATURE                 Location/Qualifiers
source                  1..20
                        mol_type = other RNA
                        organism = synthetic construct
SEQUENCE: 332
cctactgcag ctaaaagaca                                              20

SEQ ID NO: 333          moltype = RNA  length = 20
FEATURE                 Location/Qualifiers
source                  1..20
                        mol_type = other RNA
                        organism = synthetic construct
SEQUENCE: 333
ctaaaagact ttgactttga                                              20

SEQ ID NO: 334          moltype = RNA  length = 20
FEATURE                 Location/Qualifiers
source                  1..20
                        mol_type = other RNA
                        organism = synthetic construct
SEQUENCE: 334
aaaagacttt gactttgtga                                              20

SEQ ID NO: 335          moltype = RNA  length = 20
FEATURE                 Location/Qualifiers
source                  1..20
                        mol_type = other RNA
                        organism = synthetic construct
SEQUENCE: 335
gctcaatgaa cagagataca                                              20

SEQ ID NO: 336          moltype = RNA  length = 20
FEATURE                 Location/Qualifiers
source                  1..20
                        mol_type = other RNA
                        organism = synthetic construct
SEQUENCE: 336
ctcaatgaac agagatacta                                              20

SEQ ID NO: 337          moltype = RNA  length = 20
FEATURE                 Location/Qualifiers
source                  1..20
                        mol_type = other RNA
                        organism = synthetic construct
SEQUENCE: 337
tcaatgaaca gagatactaa                                              20

SEQ ID NO: 338          moltype = RNA  length = 20
FEATURE                 Location/Qualifiers
source                  1..20
                        mol_type = other RNA
                        organism = synthetic construct
SEQUENCE: 338
```

-continued

```
cttggctcaa taccaaaaga                                          20

SEQ ID NO: 339          moltype = RNA  length = 20
FEATURE                 Location/Qualifiers
source                  1..20
                        mol_type = other RNA
                        organism = synthetic construct
SEQUENCE: 339
accgtatcca ctgggaatca                                          20

SEQ ID NO: 340          moltype = RNA  length = 20
FEATURE                 Location/Qualifiers
source                  1..20
                        mol_type = other RNA
                        organism = synthetic construct
SEQUENCE: 340
cgtatccact gggaatctga                                          20

SEQ ID NO: 341          moltype = RNA  length = 20
FEATURE                 Location/Qualifiers
source                  1..20
                        mol_type = other RNA
                        organism = synthetic construct
SEQUENCE: 341
cagaagagac caaggaaaaa                                          20

SEQ ID NO: 342          moltype = RNA  length = 20
FEATURE                 Location/Qualifiers
source                  1..20
                        mol_type = other RNA
                        organism = synthetic construct
SEQUENCE: 342
agaagagacc aaggaaaata                                          20

SEQ ID NO: 343          moltype = RNA  length = 20
FEATURE                 Location/Qualifiers
source                  1..20
                        mol_type = other RNA
                        organism = synthetic construct
SEQUENCE: 343
gaagagacca aggaaaatga                                          20

SEQ ID NO: 344          moltype = RNA  length = 20
FEATURE                 Location/Qualifiers
source                  1..20
                        mol_type = other RNA
                        organism = synthetic construct
SEQUENCE: 344
gaaaatgagg gtttcacaga                                          20

SEQ ID NO: 345          moltype = RNA  length = 20
FEATURE                 Location/Qualifiers
source                  1..20
                        mol_type = other RNA
                        organism = synthetic construct
SEQUENCE: 345
tttcacagtc acagctgaaa                                          20

SEQ ID NO: 346          moltype = RNA  length = 20
FEATURE                 Location/Qualifiers
source                  1..20
                        mol_type = other RNA
                        organism = synthetic construct
SEQUENCE: 346
acagtcacag ctgaaggaaa                                          20

SEQ ID NO: 347          moltype = RNA  length = 20
FEATURE                 Location/Qualifiers
source                  1..20
                        mol_type = other RNA
                        organism = synthetic construct
SEQUENCE: 347
agtcacagct gaaggaaaaa                                          20

SEQ ID NO: 348          moltype = RNA  length = 20
FEATURE                 Location/Qualifiers
source                  1..20
                        mol_type = other RNA
                        organism = synthetic construct
```

```
SEQUENCE: 348
gtcacagctg aaggaaaaga                                             20

SEQ ID NO: 349          moltype = RNA  length = 20
FEATURE                 Location/Qualifiers
source                  1..20
                        mol_type = other RNA
                        organism = synthetic construct
SEQUENCE: 349
gacaatgtac catgctaaga                                             20

SEQ ID NO: 350          moltype = RNA  length = 20
FEATURE                 Location/Qualifiers
source                  1..20
                        mol_type = other RNA
                        organism = synthetic construct
SEQUENCE: 350
ctgtaataaa ttcgacctca                                             20

SEQ ID NO: 351          moltype = RNA  length = 20
FEATURE                 Location/Qualifiers
source                  1..20
                        mol_type = other RNA
                        organism = synthetic construct
SEQUENCE: 351
acctcaaggt caccataaaa                                             20

SEQ ID NO: 352          moltype = RNA  length = 20
FEATURE                 Location/Qualifiers
source                  1..20
                        mol_type = other RNA
                        organism = synthetic construct
SEQUENCE: 352
cctcaaggtc accataaaaa                                             20

SEQ ID NO: 353          moltype = RNA  length = 20
FEATURE                 Location/Qualifiers
source                  1..20
                        mol_type = other RNA
                        organism = synthetic construct
SEQUENCE: 353
ctcaaggtca ccataaaaca                                             20

SEQ ID NO: 354          moltype = RNA  length = 20
FEATURE                 Location/Qualifiers
source                  1..20
                        mol_type = other RNA
                        organism = synthetic construct
SEQUENCE: 354
aaaccagcac cggaaacaga                                             20

SEQ ID NO: 355          moltype = RNA  length = 20
FEATURE                 Location/Qualifiers
source                  1..20
                        mol_type = other RNA
                        organism = synthetic construct
SEQUENCE: 355
ctcaggatgc caagaacaca                                             20

SEQ ID NO: 356          moltype = RNA  length = 20
FEATURE                 Location/Qualifiers
source                  1..20
                        mol_type = other RNA
                        organism = synthetic construct
SEQUENCE: 356
atgccaagaa cactatgata                                             20

SEQ ID NO: 357          moltype = RNA  length = 20
FEATURE                 Location/Qualifiers
source                  1..20
                        mol_type = other RNA
                        organism = synthetic construct
SEQUENCE: 357
caagaacact atgatcctta                                             20

SEQ ID NO: 358          moltype = RNA  length = 20
FEATURE                 Location/Qualifiers
source                  1..20
                        mol_type = other RNA
```

```
                         organism = synthetic construct
SEQUENCE: 358
aagaacacta tgatccttga                                                 20

SEQ ID NO: 359           moltype = RNA  length = 20
FEATURE                  Location/Qualifiers
source                   1..20
                         mol_type = other RNA
                         organism = synthetic construct
SEQUENCE: 359
caggatgcca ctatgtctaa                                                 20

SEQ ID NO: 360           moltype = RNA  length = 20
FEATURE                  Location/Qualifiers
source                   1..20
                         mol_type = other RNA
                         organism = synthetic construct
SEQUENCE: 360
gacatatcca tgatgactga                                                 20

SEQ ID NO: 361           moltype = RNA  length = 20
FEATURE                  Location/Qualifiers
source                   1..20
                         mol_type = other RNA
                         organism = synthetic construct
SEQUENCE: 361
acagatacat ctccaagtaa                                                 20

SEQ ID NO: 362           moltype = RNA  length = 20
FEATURE                  Location/Qualifiers
source                   1..20
                         mol_type = other RNA
                         organism = synthetic construct
SEQUENCE: 362
cagatacatc tccaagtata                                                 20

SEQ ID NO: 363           moltype = RNA  length = 20
FEATURE                  Location/Qualifiers
source                   1..20
                         mol_type = other RNA
                         organism = synthetic construct
SEQUENCE: 363
agatacatct ccaagtatga                                                 20

SEQ ID NO: 364           moltype = RNA  length = 20
FEATURE                  Location/Qualifiers
source                   1..20
                         mol_type = other RNA
                         organism = synthetic construct
SEQUENCE: 364
atacatctcc aagtatgaga                                                 20

SEQ ID NO: 365           moltype = RNA  length = 20
FEATURE                  Location/Qualifiers
source                   1..20
                         mol_type = other RNA
                         organism = synthetic construct
SEQUENCE: 365
caagtatgag ctggacaaaa                                                 20

SEQ ID NO: 366           moltype = RNA  length = 20
FEATURE                  Location/Qualifiers
source                   1..20
                         mol_type = other RNA
                         organism = synthetic construct
SEQUENCE: 366
aagtatgagc tggacaaaga                                                 20

SEQ ID NO: 367           moltype = RNA  length = 20
FEATURE                  Location/Qualifiers
source                   1..20
                         mol_type = other RNA
                         organism = synthetic construct
SEQUENCE: 367
acaaagcctt ctccgataga                                                 20

SEQ ID NO: 368           moltype = RNA  length = 20
FEATURE                  Location/Qualifiers
source                   1..20
```

```
                        mol_type = other RNA
                        organism = synthetic construct
SEQUENCE: 368
aagccttctc cgataggaaa                                              20

SEQ ID NO: 369          moltype = RNA  length = 20
FEATURE                 Location/Qualifiers
source                  1..20
                        mol_type = other RNA
                        organism = synthetic construct
SEQUENCE: 369
ccttctccga taggaacaca                                              20

SEQ ID NO: 370          moltype = RNA  length = 20
FEATURE                 Location/Qualifiers
source                  1..20
                        mol_type = other RNA
                        organism = synthetic construct
SEQUENCE: 370
ataggaacac cctcatcata                                              20

SEQ ID NO: 371          moltype = RNA  length = 20
FEATURE                 Location/Qualifiers
source                  1..20
                        mol_type = other RNA
                        organism = synthetic construct
SEQUENCE: 371
taggaacacc ctcatcatca                                              20

SEQ ID NO: 372          moltype = RNA  length = 20
FEATURE                 Location/Qualifiers
source                  1..20
                        mol_type = other RNA
                        organism = synthetic construct
SEQUENCE: 372
gaacaccctc atcatctaca                                              20

SEQ ID NO: 373          moltype = RNA  length = 20
FEATURE                 Location/Qualifiers
source                  1..20
                        mol_type = other RNA
                        organism = synthetic construct
SEQUENCE: 373
catcatctac ctggacaaga                                              20

SEQ ID NO: 374          moltype = RNA  length = 20
FEATURE                 Location/Qualifiers
source                  1..20
                        mol_type = other RNA
                        organism = synthetic construct
SEQUENCE: 374
catctacctg gacaaggtca                                              20

SEQ ID NO: 375          moltype = RNA  length = 20
FEATURE                 Location/Qualifiers
source                  1..20
                        mol_type = other RNA
                        organism = synthetic construct
SEQUENCE: 375
caaggtctca cactctgaga                                              20

SEQ ID NO: 376          moltype = RNA  length = 20
FEATURE                 Location/Qualifiers
source                  1..20
                        mol_type = other RNA
                        organism = synthetic construct
SEQUENCE: 376
gtctcacact ctgaggatga                                              20

SEQ ID NO: 377          moltype = RNA  length = 20
FEATURE                 Location/Qualifiers
source                  1..20
                        mol_type = other RNA
                        organism = synthetic construct
SEQUENCE: 377
caaggtctac gcctattaca                                              20

SEQ ID NO: 378          moltype = RNA  length = 20
FEATURE                 Location/Qualifiers
```

-continued

```
source                1..20
                      mol_type = other RNA
                      organism = synthetic construct
SEQUENCE: 378
ggtctacgcc tattacaaca                                              20

SEQ ID NO: 379        moltype = RNA  length = 20
FEATURE               Location/Qualifiers
source                1..20
                      mol_type = other RNA
                      organism = synthetic construct
SEQUENCE: 379
gtctacgcct attacaacca                                              20

SEQ ID NO: 380        moltype = RNA  length = 20
FEATURE               Location/Qualifiers
source                1..20
                      mol_type = other RNA
                      organism = synthetic construct
SEQUENCE: 380
gaggatggaa agctgaacaa                                              20

SEQ ID NO: 381        moltype = RNA  length = 20
FEATURE               Location/Qualifiers
source                1..20
                      mol_type = other RNA
                      organism = synthetic construct
SEQUENCE: 381
tgctgaggag aattgcttca                                              20

SEQ ID NO: 382        moltype = RNA  length = 20
FEATURE               Location/Qualifiers
source                1..20
                      mol_type = other RNA
                      organism = synthetic construct
SEQUENCE: 382
ggagaattgc ttcatacaaa                                              20

SEQ ID NO: 383        moltype = RNA  length = 20
FEATURE               Location/Qualifiers
source                1..20
                      mol_type = other RNA
                      organism = synthetic construct
SEQUENCE: 383
agaattgctt catacaaaaa                                              20

SEQ ID NO: 384        moltype = RNA  length = 20
FEATURE               Location/Qualifiers
source                1..20
                      mol_type = other RNA
                      organism = synthetic construct
SEQUENCE: 384
caggagtgga ctatgtgtaa                                              20

SEQ ID NO: 385        moltype = RNA  length = 20
FEATURE               Location/Qualifiers
source                1..20
                      mol_type = other RNA
                      organism = synthetic construct
SEQUENCE: 385
aggagtggac tatgtgtaca                                              20

SEQ ID NO: 386        moltype = RNA  length = 20
FEATURE               Location/Qualifiers
source                1..20
                      mol_type = other RNA
                      organism = synthetic construct
SEQUENCE: 386
tggactatgt gtacaagaca                                              20

SEQ ID NO: 387        moltype = RNA  length = 20
FEATURE               Location/Qualifiers
source                1..20
                      mol_type = other RNA
                      organism = synthetic construct
SEQUENCE: 387
caatgacttt gacgagtaca                                              20

SEQ ID NO: 388        moltype = RNA  length = 20
```

```
FEATURE                Location/Qualifiers
source                 1..20
                       mol_type = other RNA
                       organism = synthetic construct
SEQUENCE: 388
actttgacga gtacatcata                                      20

SEQ ID NO: 389         moltype = RNA  length = 20
FEATURE                Location/Qualifiers
source                 1..20
                       mol_type = other RNA
                       organism = synthetic construct
SEQUENCE: 389
caagtcaggc tcggatgaga                                      20

SEQ ID NO: 390         moltype = RNA  length = 20
FEATURE                Location/Qualifiers
source                 1..20
                       mol_type = other RNA
                       organism = synthetic construct
SEQUENCE: 390
gatgaggtgc aggttggaca                                      20

SEQ ID NO: 391         moltype = RNA  length = 20
FEATURE                Location/Qualifiers
source                 1..20
                       mol_type = other RNA
                       organism = synthetic construct
SEQUENCE: 391
tttgggtgcc ccaactgaca                                      20

SEQ ID NO: 392         moltype = RNA  length = 22
FEATURE                Location/Qualifiers
source                 1..22
                       mol_type = other RNA
                       organism = synthetic construct
SEQUENCE: 392
tctccactat gacctcgaaa ct                                   22

SEQ ID NO: 393         moltype = RNA  length = 22
FEATURE                Location/Qualifiers
source                 1..22
                       mol_type = other RNA
                       organism = synthetic construct
SEQUENCE: 393
tggaatgtcc caagacaagg gc                                   22

SEQ ID NO: 394         moltype = RNA  length = 22
FEATURE                Location/Qualifiers
source                 1..22
                       mol_type = other RNA
                       organism = synthetic construct
SEQUENCE: 394
taaatatatt catgagcttc gt                                   22

SEQ ID NO: 395         moltype = RNA  length = 22
FEATURE                Location/Qualifiers
source                 1..22
                       mol_type = other RNA
                       organism = synthetic construct
SEQUENCE: 395
tgatctcaag gatcatagtg tt                                   22

SEQ ID NO: 396         moltype = RNA  length = 22
FEATURE                Location/Qualifiers
source                 1..22
                       mol_type = other RNA
                       organism = synthetic construct
SEQUENCE: 396
tcttttgtat gaagcaattc tc                                   22

SEQ ID NO: 397         moltype = RNA  length = 22
FEATURE                Location/Qualifiers
source                 1..22
                       mol_type = other RNA
                       organism = synthetic construct
SEQUENCE: 397
tttctgcttc tccaggatca gc                                   22
```

```
SEQ ID NO: 398          moltype = RNA  length = 22
FEATURE                 Location/Qualifiers
source                  1..22
                        mol_type = other RNA
                        organism = synthetic construct
SEQUENCE: 398
tctgcttctc caggatcagc ca                                              22

SEQ ID NO: 399          moltype = RNA  length = 22
FEATURE                 Location/Qualifiers
source                  1..22
                        mol_type = other RNA
                        organism = synthetic construct
SEQUENCE: 399
tctcaatggc catgatgtac tc                                              22

SEQ ID NO: 400          moltype = RNA  length = 22
FEATURE                 Location/Qualifiers
source                  1..22
                        mol_type = other RNA
                        organism = synthetic construct
SEQUENCE: 400
ttgtagttgc agcagtccag ga                                              22

SEQ ID NO: 401          moltype = RNA  length = 22
FEATURE                 Location/Qualifiers
source                  1..22
                        mol_type = other RNA
                        organism = synthetic construct
SEQUENCE: 401
tcttggaaca ccatgaaggt gg                                              22

SEQ ID NO: 402          moltype = RNA  length = 22
FEATURE                 Location/Qualifiers
source                  1..22
                        mol_type = other RNA
                        organism = synthetic construct
SEQUENCE: 402
tctcatccag gttactcctg gc                                              22

SEQ ID NO: 403          moltype = RNA  length = 22
FEATURE                 Location/Qualifiers
source                  1..22
                        mol_type = other RNA
                        organism = synthetic construct
SEQUENCE: 403
tgtcctcatc caggttactc ct                                              22

SEQ ID NO: 404          moltype = RNA  length = 22
FEATURE                 Location/Qualifiers
source                  1..22
                        mol_type = other RNA
                        organism = synthetic construct
SEQUENCE: 404
tcagaaatcg gaggagagac cc                                              22

SEQ ID NO: 405          moltype = RNA  length = 22
FEATURE                 Location/Qualifiers
source                  1..22
                        mol_type = other RNA
                        organism = synthetic construct
SEQUENCE: 405
tcttgaccag tcgggtcttg ta                                              22

SEQ ID NO: 406          moltype = RNA  length = 22
FEATURE                 Location/Qualifiers
source                  1..22
                        mol_type = other RNA
                        organism = synthetic construct
SEQUENCE: 406
tctgtaggtt catgtagttg gc                                              22

SEQ ID NO: 407          moltype = RNA  length = 22
FEATURE                 Location/Qualifiers
source                  1..22
                        mol_type = other RNA
                        organism = synthetic construct
SEQUENCE: 407
tgaagacctt gaccacgtag gc                                              22
```

```
SEQ ID NO: 408          moltype = RNA  length = 22
FEATURE                 Location/Qualifiers
source                  1..22
                        mol_type = other RNA
                        organism = synthetic construct
SEQUENCE: 408
tgaacctcat ggggttctcc cg                                              22

SEQ ID NO: 409          moltype = RNA  length = 22
FEATURE                 Location/Qualifiers
source                  1..22
                        mol_type = other RNA
                        organism = synthetic construct
SEQUENCE: 409
tctctatctt cagggtcatc tg                                              22

SEQ ID NO: 410          moltype = RNA  length = 22
FEATURE                 Location/Qualifiers
source                  1..22
                        mol_type = other RNA
                        organism = synthetic construct
SEQUENCE: 410
tagaacctca tggggttctc cc                                              22

SEQ ID NO: 411          moltype = RNA  length = 22
FEATURE                 Location/Qualifiers
source                  1..22
                        mol_type = other RNA
                        organism = synthetic construct
SEQUENCE: 411
tgtggttgac ggtgaagatc cg                                              22

SEQ ID NO: 412          moltype = RNA  length = 22
FEATURE                 Location/Qualifiers
source                  1..22
                        mol_type = other RNA
                        organism = synthetic construct
SEQUENCE: 412
tctctgggaa ctcacttcgg ga                                              22

SEQ ID NO: 413          moltype = RNA  length = 22
FEATURE                 Location/Qualifiers
source                  1..22
                        mol_type = other RNA
                        organism = synthetic construct
SEQUENCE: 413
tcttgtggtt gacggtgaag at                                              22

SEQ ID NO: 414          moltype = RNA  length = 22
FEATURE                 Location/Qualifiers
source                  1..22
                        mol_type = other RNA
                        organism = synthetic construct
SEQUENCE: 414
tctcaaggat catagtgttc tt                                              22

SEQ ID NO: 415          moltype = RNA  length = 22
FEATURE                 Location/Qualifiers
source                  1..22
                        mol_type = other RNA
                        organism = synthetic construct
SEQUENCE: 415
tttggaacac catgaaggtg gc                                              22

SEQ ID NO: 416          moltype = RNA  length = 22
FEATURE                 Location/Qualifiers
source                  1..22
                        mol_type = other RNA
                        organism = synthetic construct
SEQUENCE: 416
tcttctgctt ctccaggatc ag                                              22

SEQ ID NO: 417          moltype = RNA  length = 22
FEATURE                 Location/Qualifiers
source                  1..22
                        mol_type = other RNA
                        organism = synthetic construct
SEQUENCE: 417
```

-continued

```
tctcaaactc agtggagaag ac                                              22

SEQ ID NO: 418          moltype = RNA  length = 20
FEATURE                 Location/Qualifiers
source                  1..20
                        mol_type = other RNA
                        organism = synthetic construct
SEQUENCE: 418
tttcgaggtc atagtggaga                                                 20

SEQ ID NO: 419          moltype = RNA  length = 20
FEATURE                 Location/Qualifiers
source                  1..20
                        mol_type = other RNA
                        organism = synthetic construct
SEQUENCE: 419
ccttgtcttg ggacattcca                                                 20

SEQ ID NO: 420          moltype = RNA  length = 20
FEATURE                 Location/Qualifiers
source                  1..20
                        mol_type = other RNA
                        organism = synthetic construct
SEQUENCE: 420
gaagctcatg aatatattta                                                 20

SEQ ID NO: 421          moltype = RNA  length = 20
FEATURE                 Location/Qualifiers
source                  1..20
                        mol_type = other RNA
                        organism = synthetic construct
SEQUENCE: 421
cactatgatc cttgagatca                                                 20

SEQ ID NO: 422          moltype = RNA  length = 20
FEATURE                 Location/Qualifiers
source                  1..20
                        mol_type = other RNA
                        organism = synthetic construct
SEQUENCE: 422
gaattgcttc atacaaaaga                                                 20

SEQ ID NO: 423          moltype = RNA  length = 20
FEATURE                 Location/Qualifiers
source                  1..20
                        mol_type = other RNA
                        organism = synthetic construct
SEQUENCE: 423
tgatcctgga gaagcagaaa                                                 20

SEQ ID NO: 424          moltype = RNA  length = 20
FEATURE                 Location/Qualifiers
source                  1..20
                        mol_type = other RNA
                        organism = synthetic construct
SEQUENCE: 424
gctgatcctg gagaagcaga                                                 20

SEQ ID NO: 425          moltype = RNA  length = 20
FEATURE                 Location/Qualifiers
source                  1..20
                        mol_type = other RNA
                        organism = synthetic construct
SEQUENCE: 425
gtacatcatg gccattgaga                                                 20

SEQ ID NO: 426          moltype = RNA  length = 20
FEATURE                 Location/Qualifiers
source                  1..20
                        mol_type = other RNA
                        organism = synthetic construct
SEQUENCE: 426
ctggactgct gcaactacaa                                                 20

SEQ ID NO: 427          moltype = RNA  length = 20
FEATURE                 Location/Qualifiers
source                  1..20
                        mol_type = other RNA
                        organism = synthetic construct
```

```
SEQUENCE: 427
accttcatgg tgttccaaga                                              20

SEQ ID NO: 428          moltype = RNA  length = 20
FEATURE                 Location/Qualifiers
source                  1..20
                        mol_type = other RNA
                        organism = synthetic construct
SEQUENCE: 428
caggagtaac ctggatgaga                                              20

SEQ ID NO: 429          moltype = RNA  length = 20
FEATURE                 Location/Qualifiers
source                  1..20
                        mol_type = other RNA
                        organism = synthetic construct
SEQUENCE: 429
gagtaacctg gatgaggaca                                              20

SEQ ID NO: 430          moltype = RNA  length = 20
FEATURE                 Location/Qualifiers
source                  1..20
                        mol_type = other RNA
                        organism = synthetic construct
SEQUENCE: 430
gtctctcctc cgatttctga                                              20

SEQ ID NO: 431          moltype = RNA  length = 20
FEATURE                 Location/Qualifiers
source                  1..20
                        mol_type = other RNA
                        organism = synthetic construct
SEQUENCE: 431
caagacccga ctggtcaaga                                              20

SEQ ID NO: 432          moltype = RNA  length = 20
FEATURE                 Location/Qualifiers
source                  1..20
                        mol_type = other RNA
                        organism = synthetic construct
SEQUENCE: 432
caactacatg aacctacaga                                              20

SEQ ID NO: 433          moltype = RNA  length = 20
FEATURE                 Location/Qualifiers
source                  1..20
                        mol_type = other RNA
                        organism = synthetic construct
SEQUENCE: 433
ctacgtggtc aaggtcttca                                              20

SEQ ID NO: 434          moltype = RNA  length = 20
FEATURE                 Location/Qualifiers
source                  1..20
                        mol_type = other RNA
                        organism = synthetic construct
SEQUENCE: 434
ggagaacccc atgaggttca                                              20

SEQ ID NO: 435          moltype = RNA  length = 20
FEATURE                 Location/Qualifiers
source                  1..20
                        mol_type = other RNA
                        organism = synthetic construct
SEQUENCE: 435
gatgaccctg aagatagaga                                              20

SEQ ID NO: 436          moltype = RNA  length = 20
FEATURE                 Location/Qualifiers
source                  1..20
                        mol_type = other RNA
                        organism = synthetic construct
SEQUENCE: 436
gagaacccca tgaggttcta                                              20

SEQ ID NO: 437          moltype = RNA  length = 20
FEATURE                 Location/Qualifiers
source                  1..20
                        mol_type = other RNA
```

-continued

```
                        organism = synthetic construct
SEQUENCE: 437
gatcttcacc gtcaaccaca                                                20

SEQ ID NO: 438          moltype = RNA  length = 20
FEATURE                 Location/Qualifiers
source                  1..20
                        mol_type = other RNA
                        organism = synthetic construct
SEQUENCE: 438
ccgaagtgag ttcccagaga                                                20

SEQ ID NO: 439          moltype = RNA  length = 20
FEATURE                 Location/Qualifiers
source                  1..20
                        mol_type = other RNA
                        organism = synthetic construct
SEQUENCE: 439
cttcaccgtc aaccacaaga                                                20

SEQ ID NO: 440          moltype = RNA  length = 20
FEATURE                 Location/Qualifiers
source                  1..20
                        mol_type = other RNA
                        organism = synthetic construct
SEQUENCE: 440
gaacactatg atccttgaga                                                20

SEQ ID NO: 441          moltype = RNA  length = 20
FEATURE                 Location/Qualifiers
source                  1..20
                        mol_type = other RNA
                        organism = synthetic construct
SEQUENCE: 441
caccttcatg gtgttccaaa                                                20

SEQ ID NO: 442          moltype = RNA  length = 20
FEATURE                 Location/Qualifiers
source                  1..20
                        mol_type = other RNA
                        organism = synthetic construct
SEQUENCE: 442
gatcctggag aagcagaaga                                                20

SEQ ID NO: 443          moltype = RNA  length = 20
FEATURE                 Location/Qualifiers
source                  1..20
                        mol_type = other RNA
                        organism = synthetic construct
SEQUENCE: 443
cttctccact gagtttgaga                                                20

SEQ ID NO: 444          moltype = RNA  length = 20
FEATURE                 Location/Qualifiers
modified_base           1..3
                        mod_base = OTHER
                        note = linked via phosphorothioate bond
modified_base           1
                        mod_base = cm
modified_base           2
                        mod_base = um
modified_base           3
                        mod_base = OTHER
                        note = 2'-O-methyl-adenosine
modified_base           4
                        mod_base = cm
modified_base           5
                        mod_base = OTHER
                        note = 2'-O-methyl-adenosine
modified_base           6
                        mod_base = OTHER
                        note = 2'-fluoro-guanosine
modified_base           7
                        mod_base = OTHER
                        note = 2'-O-methyl-adenosine
modified_base           8
                        mod_base = OTHER
                        note = 2'-fluoro-guanosine
modified_base           9
```

```
                         mod_base = OTHER
                         note = 2'-fluoro-adenosine
modified_base            10
                         mod_base = OTHER
                         note = 2'-fluoro-adenosine
modified_base            11
                         mod_base = OTHER
                         note = 2'-fluoro-adenosine
modified_base            12
                         mod_base = um
modified_base            13
                         mod_base = um
modified_base            14
                         mod_base = cm
modified_base            15
                         mod_base = um
modified_base            16
                         mod_base = OTHER
                         note = 2'-O-methyl-adenosine
modified_base            17
                         mod_base = cm
modified_base            18..20
                         mod_base = OTHER
                         note = linked via phosphorothioate bond
modified_base            18
                         mod_base = um
modified_base            19
                         mod_base = OTHER
                         note = 2'-O-methyl-adenosine
modified_base            20
                         mod_base = OTHER
                         note = 2'-O-methyl-adenosine
modified_base            20
                         mod_base = OTHER
                         note = conjugated to 3 iterations of
                          (2R,3R,4R,5S)-5-(3-(5-(((2R,3R,4R,5R,6R)-
                          3-acetamido-4,5-dihydroxy-6-(hydroxymethyl)tetrahydro-2H-py
                          ran-2-yl)oxy)
                          pentanamido)propyl)-2-((hydroxyl)methyl)-4-methoxytetrahydr
                          ofuran-3-oxyl
source                   1..20
                         mol_type = other RNA
                         organism = synthetic construct
SEQUENCE: 444
ctacagagaa attctactaa                                                20

SEQ ID NO: 445           moltype = RNA  length = 20
FEATURE                  Location/Qualifiers
modified_base            1..3
                         mod_base = OTHER
                         note = linked via phosphorothioate bond
modified_base            1
                         mod_base = um
modified_base            2
                         mod_base = OTHER
                         note = 2'-O-methyl-adenosine
modified_base            3
                         mod_base = cm
modified_base            4
                         mod_base = OTHER
                         note = 2'-O-methyl-adenosine
modified_base            5
                         mod_base = gm
modified_base            6
                         mod_base = OTHER
                         note = 2'-fluoro-adenosine
modified_base            7
                         mod_base = gm
modified_base            8
                         mod_base = OTHER
                         note = 2'-fluoro-adenosine
modified_base            9
                         mod_base = OTHER
                         note = 2'-fluoro-adenosine
modified_base            10
                         mod_base = OTHER
                         note = 2'-fluoro-adenosine
modified_base            11
                         mod_base = OTHER
```

```
                         note = 2'-fluoro-uridine
modified_base            12
                         mod_base = um
modified_base            13
                         mod_base = cm
modified_base            14
                         mod_base = um
modified_base            15
                         mod_base = OTHER
                         note = 2'-O-methyl-adenosine
modified_base            16
                         mod_base = cm
modified_base            17
                         mod_base = um
modified_base            18..20
                         mod_base = OTHER
                         note = linked via phosphorothioate bond
modified_base            18
                         mod_base = OTHER
                         note = 2'-O-methyl-adenosine
modified_base            19
                         mod_base = cm
modified_base            20
                         mod_base = OTHER
                         note = 2'-O-methyl-adenosine
modified_base            20
                         mod_base = OTHER
                         note = conjugated to 3 iterations of
                          (2R,3R,4R,5S)-5-(3-(5-(((2R,3R,4R,5R,6R)-
                          3-acetamido-4,5-dihydroxy-6-(hydroxymethyl)tetrahydro-2H-py
                          ran-2-yl)oxy)
                          pentanamido)propyl)-2-((hydroxyl)methyl)-4-methoxytetrahydr
                          ofuran-3-oxyl
source                   1..20
                         mol_type = other RNA
                         organism = synthetic construct
SEQUENCE: 445
tacagagaaa ttctactaca                                                20

SEQ ID NO: 446           moltype = RNA  length = 20
FEATURE                  Location/Qualifiers
modified_base            1..3
                         mod_base = OTHER
                         note = linked via phosphorothioate bond
modified_base            1
                         mod_base = cm
modified_base            2
                         mod_base = OTHER
                         note = 2'-O-methyl-adenosine
modified_base            3
                         mod_base = gm
modified_base            4
                         mod_base = OTHER
                         note = 2'-O-methyl-adenosine
modified_base            5
                         mod_base = gm
modified_base            6
                         mod_base = OTHER
                         note = 2'-fluoro-adenosine
modified_base            7
                         mod_base = OTHER
                         note = 2'-O-methyl-adenosine
modified_base            8
                         mod_base = OTHER
                         note = 2'-fluoro-adenosine
modified_base            9
                         mod_base = OTHER
                         note = 2'-fluoro-uridine
modified_base            10
                         mod_base = OTHER
                         note = 2'-fluoro-uridine
modified_base            11
                         mod_base = OTHER
                         note = 2'-fluoro-cytidine
modified_base            12
                         mod_base = um
modified_base            13
                         mod_base = OTHER
                         note = 2'-O-methyl-adenosine
```

```
modified_base          14
                       mod_base = cm
modified_base          15
                       mod_base = um
modified_base          16
                       mod_base = OTHER
                       note = 2'-O-methyl-adenosine
modified_base          17
                       mod_base = cm
modified_base          18..20
                       mod_base = OTHER
                       note = linked via phosphorothioate bond
modified_base          18
                       mod_base = OTHER
                       note = 2'-O-methyl-adenosine
modified_base          19
                       mod_base = um
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-
                        3-acetamido-4,5-dihydroxy-6-(hydroxymethyl)tetrahydro-2H-py
                        ran-2-yl)oxy)
                        pentanamido)propyl)-2-((hydroxyl)methyl)-4-methoxytetrahydr
                        ofuran-3-oxyl
source                 1..20
                       mol_type = other RNA
                       organism = synthetic construct
SEQUENCE: 446
cagagaaatt ctactacata                                                20

SEQ ID NO: 447         moltype = RNA  length = 20
FEATURE                Location/Qualifiers
modified_base          1..3
                       mod_base = OTHER
                       note = linked via phosphorothioate bond
modified_base          1
                       mod_base = gm
modified_base          2
                       mod_base = OTHER
                       note = 2'-O-methyl-adenosine
modified_base          3
                       mod_base = OTHER
                       note = 2'-O-methyl-adenosine
modified_base          4
                       mod_base = OTHER
                       note = 2'-O-methyl-adenosine
modified_base          5
                       mod_base = um
modified_base          6
                       mod_base = OTHER
                       note = 2'-fluoro-uridine
modified_base          7
                       mod_base = cm
modified_base          8
                       mod_base = OTHER
                       note = 2'-fluoro-uridine
modified_base          9
                       mod_base = OTHER
                       note = 2'-fluoro-adenosine
modified_base          10
                       mod_base = OTHER
                       note = 2'-fluoro-cytidine
modified_base          11
                       mod_base = OTHER
                       note = 2'-fluoro-uridine
modified_base          12
                       mod_base = OTHER
                       note = 2'-O-methyl-adenosine
modified_base          13
                       mod_base = cm
modified_base          14
                       mod_base = OTHER
                       note = 2'-O-methyl-adenosine
modified_base          15
                       mod_base = um
```

-continued

```
modified_base          16
                       mod_base = cm
modified_base          17
                       mod_base = um
modified_base          18..20
                       mod_base = OTHER
                       note = linked via phosphorothioate bond
modified_base          18
                       mod_base = OTHER
                       note = 2'-O-methyl-adenosine
modified_base          19
                       mod_base = um
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-
                        3-acetamido-4,5-dihydroxy-6-(hydroxymethyl)tetrahydro-2H-py
                        ran-2-yl)oxy)
                        pentanamido)propyl)-2-((hydroxyl)methyl)-4-methoxytetrahydr
                        ofuran-3-oxyl
source                 1..20
                       mol_type = other RNA
                       organism = synthetic construct
SEQUENCE: 447
gaaattctac tacatctata                                                20

SEQ ID NO: 448         moltype = RNA  length = 20
FEATURE                Location/Qualifiers
modified_base          1..3
                       mod_base = OTHER
                       note = linked via phosphorothioate bond
modified_base          1
                       mod_base = cm
modified_base          2
                       mod_base = um
modified_base          3
                       mod_base = gm
modified_base          4
                       mod_base = OTHER
                       note = 2'-O-methyl-adenosine
modified_base          5
                       mod_base = gm
modified_base          6
                       mod_base = OTHER
                       note = 2'-fluoro-guanosine
modified_base          7
                       mod_base = OTHER
                       note = 2'-O-methyl-adenosine
modified_base          8
                       mod_base = OTHER
                       note = 2'-fluoro-guanosine
modified_base          9
                       mod_base = OTHER
                       note = 2'-fluoro-adenosine
modified_base          10
                       mod_base = OTHER
                       note = 2'-fluoro-adenosine
modified_base          11
                       mod_base = OTHER
                       note = 2'-fluoro-uridine
modified_base          12
                       mod_base = um
modified_base          13
                       mod_base = gm
modified_base          14
                       mod_base = cm
modified_base          15
                       mod_base = um
modified_base          16
                       mod_base = um
modified_base          17
                       mod_base = cm
modified_base          18..20
                       mod_base = OTHER
                       note = linked via phosphorothioate bond
modified_base          18
```

```
                        mod_base = OTHER
                        note = 2'-O-methyl-adenosine
modified_base           19
                        mod_base = um
modified_base           20
                        mod_base = OTHER
                        note = 2'-O-methyl-adenosine
modified_base           20
                        mod_base = OTHER
                        note = conjugated to 3 iterations of
                         (2R,3R,4R,5S)-5-(3-(5-(((2R,3R,4R,5R,6R)-
                         3-acetamido-4,5-dihydroxy-6-(hydroxymethyl)tetrahydro-2H-py
                         ran-2-yl)oxy)
                         pentanamido)propyl)-2-((hydroxyl)methyl)-4-methoxytetrahydr
                         ofuran-3-oxyl
source                  1..20
                        mol_type = other RNA
                        organism = synthetic construct
SEQUENCE: 448
ctgaggagaa ttgcttcata                                                20

SEQ ID NO: 449          moltype = RNA  length = 20
FEATURE                 Location/Qualifiers
modified_base           1..3
                        mod_base = OTHER
                        note = linked via phosphorothioate bond
modified_base           1
                        mod_base = gm
modified_base           2
                        mod_base = OTHER
                        note = 2'-O-methyl-adenosine
modified_base           3
                        mod_base = gm
modified_base           4
                        mod_base = OTHER
                        note = 2'-O-methyl-adenosine
modified_base           5
                        mod_base = OTHER
                        note = 2'-O-methyl-adenosine
modified_base           6
                        mod_base = OTHER
                        note = 2'-fluoro-uridine
modified_base           7
                        mod_base = um
modified_base           8
                        mod_base = OTHER
                        note = 2'-fluoro-guanosine
modified_base           9
                        mod_base = OTHER
                        note = 2'-fluoro-cytidine
modified_base           10
                        mod_base = OTHER
                        note = 2'-fluoro-uridine
modified_base           11
                        mod_base = OTHER
                        note = 2'-fluoro-uridine
modified_base           12
                        mod_base = cm
modified_base           13
                        mod_base = OTHER
                        note = 2'-O-methyl-adenosine
modified_base           14
                        mod_base = um
modified_base           15
                        mod_base = OTHER
                        note = 2'-O-methyl-adenosine
modified_base           16
                        mod_base = cm
modified_base           17
                        mod_base = OTHER
                        note = 2'-O-methyl-adenosine
modified_base           18..20
                        mod_base = OTHER
                        note = linked via phosphorothioate bond
modified_base           18
                        mod_base = OTHER
                        note = 2'-O-methyl-adenosine
modified_base           19
                        mod_base = OTHER
```

```
                        note = 2'-O-methyl-adenosine
modified_base           20
                        mod_base = OTHER
                        note = 2'-O-methyl-adenosine
modified_base           20
                        mod_base = OTHER
                        note = conjugated to 3 iterations of
                         (2R,3R,4R,5S)-5-(3-(5-(((2R,3R,4R,5R,6R)-
                         3-acetamido-4,5-dihydroxy-6-(hydroxymethyl)tetrahydro-2H-py
                         ran-2-yl)oxy)
                         pentanamido)propyl)-2-((hydroxyl)methyl)-4-methoxytetrahydr
                         ofuran-3-oxyl
source                  1..20
                        mol_type = other RNA
                        organism = synthetic construct
SEQUENCE: 449
gagaattgct tcatacaaaa                                                      20

SEQ ID NO: 450          moltype =   length =
SEQUENCE: 450
000

SEQ ID NO: 451          moltype = RNA  length = 22
FEATURE                 Location/Qualifiers
modified_base           1..3
                        mod_base = OTHER
                        note = linked via phosphorothioate bond
modified_base           1
                        mod_base = um
modified_base           2
                        mod_base = OTHER
                        note = 2'-fluoro-uridine
modified_base           3
                        mod_base = OTHER
                        note = 2'-fluoro-adenosine
modified_base           4
                        mod_base = gm
modified_base           5
                        mod_base = OTHER
                        note = 2'-fluoro-uridine
modified_base           6
                        mod_base = OTHER
                        note = 2'-O-methyl-adenosine
modified_base           7
                        mod_base = OTHER
                        note = 2'-fluoro-guanosine
modified_base           8
                        mod_base = OTHER
                        note = 2'-O-methyl-adenosine
modified_base           9
                        mod_base = OTHER
                        note = 2'-O-methyl-adenosine
modified_base           10
                        mod_base = OTHER
                        note = 2'-fluoro-uridine
modified_base           11
                        mod_base = um
modified_base           12
                        mod_base = um
modified_base           13
                        mod_base = cm
modified_base           14
                        mod_base = OTHER
                        note = 2'-fluoro-uridine
modified_base           15
                        mod_base = cm
modified_base           16
                        mod_base = OTHER
                        note = 2'-fluoro-uridine
modified_base           17
                        mod_base = gm
modified_base           18
                        mod_base = um
modified_base           19
                        mod_base = OTHER
                        note = 2'-O-methyl-adenosine
modified_base           20..22
                        mod_base = OTHER
                        note = linked via phosphorothioate bond
```

-continued

```
modified_base         20
                      mod_base = gm
modified_base         21
                      mod_base = gm
modified_base         22
                      mod_base = cm
source                1..22
                      mol_type = other RNA
                      organism = synthetic construct
SEQUENCE: 451
ttagtagaat ttctctgtag gc                                          22

SEQ ID NO: 452        moltype = RNA  length = 22
FEATURE               Location/Qualifiers
modified_base         1..3
                      mod_base = OTHER
                      note = linked via phosphorothioate bond
modified_base         1
                      mod_base = um
modified_base         2
                      mod_base = OTHER
                      note = 2'-fluoro-guanosine
modified_base         3
                      mod_base = OTHER
                      note = 2'-fluoro-uridine
modified_base         4
                      mod_base = OTHER
                      note = 2'-O-methyl-adenosine
modified_base         5
                      mod_base = OTHER
                      note = 2'-fluoro-guanosine
modified_base         6
                      mod_base = um
modified_base         7
                      mod_base = OTHER
                      note = 2'-fluoro-adenosine
modified_base         8
                      mod_base = gm
modified_base         9
                      mod_base = OTHER
                      note = 2'-O-methyl-adenosine
modified_base         10
                      mod_base = OTHER
                      note = 2'-fluoro-adenosine
modified_base         11
                      mod_base = um
modified_base         12
                      mod_base = um
modified_base         13
                      mod_base = um
modified_base         14
                      mod_base = OTHER
                      note = 2'-fluoro-cytidine
modified_base         15
                      mod_base = um
modified_base         16
                      mod_base = OTHER
                      note = 2'-fluoro-cytidine
modified_base         17
                      mod_base = um
modified_base         18
                      mod_base = gm
modified_base         19
                      mod_base = um
modified_base         20..22
                      mod_base = OTHER
                      note = linked via phosphorothioate bond
modified_base         20
                      mod_base = OTHER
                      note = 2'-O-methyl-adenosine
modified_base         21
                      mod_base = gm
modified_base         22
                      mod_base = gm
source                1..22
                      mol_type = other RNA
                      organism = synthetic construct
SEQUENCE: 452
tgtagtagaa tttctctgta gg                                          22
```

```
SEQ ID NO: 453          moltype = RNA  length = 22
FEATURE                 Location/Qualifiers
modified_base           1..3
                        mod_base = OTHER
                        note = linked via phosphorothioate bond
modified_base           1
                        mod_base = um
modified_base           2
                        mod_base = OTHER
                        note = 2'-fluoro-adenosine
modified_base           3
                        mod_base = OTHER
                        note = 2'-fluoro-uridine
modified_base           4
                        mod_base = gm
modified_base           5
                        mod_base = OTHER
                        note = 2'-fluoro-uridine
modified_base           6
                        mod_base = OTHER
                        note = 2'-O-methyl-adenosine
modified_base           7
                        mod_base = OTHER
                        note = 2'-fluoro-guanosine
modified_base           8
                        mod_base = um
modified_base           9
                        mod_base = OTHER
                        note = 2'-O-methyl-adenosine
modified_base           10
                        mod_base = OTHER
                        note = 2'-fluoro-guanosine
modified_base           11
                        mod_base = OTHER
                        note = 2'-O-methyl-adenosine
modified_base           12
                        mod_base = OTHER
                        note = 2'-O-methyl-adenosine
modified_base           13
                        mod_base = um
modified_base           14
                        mod_base = OTHER
                        note = 2'-fluoro-uridine
modified_base           15
                        mod_base = um
modified_base           16
                        mod_base = OTHER
                        note = 2'-fluoro-cytidine
modified_base           17
                        mod_base = um
modified_base           18
                        mod_base = cm
modified_base           19
                        mod_base = um
modified_base           20..22
                        mod_base = OTHER
                        note = linked via phosphorothioate bond
modified_base           20
                        mod_base = gm
modified_base           21
                        mod_base = um
modified_base           22
                        mod_base = OTHER
                        note = 2'-O-methyl-adenosine
source                  1..22
                        mol_type = other RNA
                        organism = synthetic construct
SEQUENCE: 453
tatgtagtag aatttctctg ta                                            22

SEQ ID NO: 454          moltype = RNA  length = 22
FEATURE                 Location/Qualifiers
modified_base           1..3
                        mod_base = OTHER
                        note = linked via phosphorothioate bond
modified_base           1
                        mod_base = um
modified_base           2
```

-continued

```
                        mod_base = OTHER
                        note = 2'-fluoro-adenosine
modified_base           3
                        mod_base = OTHER
                        note = 2'-fluoro-uridine
modified_base           4
                        mod_base = OTHER
                        note = 2'-O-methyl-adenosine
modified_base           5
                        mod_base = OTHER
                        note = 2'-fluoro-guanosine
modified_base           6
                        mod_base = OTHER
                        note = 2'-O-methyl-adenosine
modified_base           7
                        mod_base = OTHER
                        note = 2'-fluoro-uridine
modified_base           8
                        mod_base = gm
modified_base           9
                        mod_base = um
modified_base           10
                        mod_base = OTHER
                        note = 2'-fluoro-adenosine
modified_base           11
                        mod_base = gm
modified_base           12
                        mod_base = um
modified_base           13
                        mod_base = OTHER
                        note = 2'-O-methyl-adenosine
modified_base           14
                        mod_base = OTHER
                        note = 2'-fluoro-guanosine
modified_base           15
                        mod_base = OTHER
                        note = 2'-O-methyl-adenosine
modified_base           16
                        mod_base = OTHER
                        note = 2'-fluoro-adenosine
modified_base           17
                        mod_base = um
modified_base           18
                        mod_base = um
modified_base           19
                        mod_base = um
modified_base           20..22
                        mod_base = OTHER
                        note = linked via phosphorothioate bond
modified_base           20
                        mod_base = cm
modified_base           21
                        mod_base = um
modified_base           22
                        mod_base = cm
source                  1..22
                        mol_type = other RNA
                        organism = synthetic construct
SEQUENCE: 454
tatagatgta gtagaatttc tc                                              22

SEQ ID NO: 455          moltype = RNA  length = 22
FEATURE                 Location/Qualifiers
modified_base           1..3
                        mod_base = OTHER
                        note = linked via phosphorothioate bond
modified_base           1
                        mod_base = um
modified_base           2
                        mod_base = OTHER
                        note = 2'-fluoro-adenosine
modified_base           3
                        mod_base = OTHER
                        note = 2'-fluoro-uridine
modified_base           4
                        mod_base = gm
modified_base           5
                        mod_base = OTHER
                        note = 2'-fluoro-adenosine
```

```
modified_base          6
                       mod_base = OTHER
                       note = 2'-O-methyl-adenosine
modified_base          7
                       mod_base = OTHER
                       note = 2'-fluoro-guanosine
modified_base          8
                       mod_base = cm
modified_base          9
                       mod_base = OTHER
                       note = 2'-O-methyl-adenosine
modified_base          10
                       mod_base = OTHER
                       note = 2'-fluoro-adenosine
modified_base          11
                       mod_base = um
modified_base          12
                       mod_base = um
modified_base          13
                       mod_base = cm
modified_base          14
                       mod_base = OTHER
                       note = 2'-fluoro-uridine
modified_base          15
                       mod_base = cm
modified_base          16
                       mod_base = OTHER
                       note = 2'-fluoro-cytidine
modified_base          17
                       mod_base = um
modified_base          18
                       mod_base = cm
modified_base          19
                       mod_base = OTHER
                       note = 2'-O-methyl-adenosine
modified_base          20..22
                       mod_base = OTHER
                       note = linked via phosphorothioate bond
modified_base          20
                       mod_base = gm
modified_base          21
                       mod_base = cm
modified_base          22
                       mod_base = OTHER
                       note = 2'-O-methyl-adenosine
source                 1..22
                       mol_type = other RNA
                       organism = synthetic construct
SEQUENCE: 455
tatgaagcaa ttctcctcag ca                                              22

SEQ ID NO: 456         moltype = RNA  length = 22
FEATURE                Location/Qualifiers
modified_base          1..3
                       mod_base = OTHER
                       note = linked via phosphorothioate bond
modified_base          1
                       mod_base = um
modified_base          2
                       mod_base = OTHER
                       note = 2'-fluoro-uridine
modified_base          3
                       mod_base = OTHER
                       note = 2'-fluoro-uridine
modified_base          4
                       mod_base = um
modified_base          5
                       mod_base = OTHER
                       note = 2'-fluoro-guanosine
modified_base          6
                       mod_base = um
modified_base          7
                       mod_base = OTHER
                       note = 2'-fluoro-adenosine
modified_base          8
                       mod_base = um
modified_base          9
                       mod_base = gm
modified_base          10
```

-continued

```
                          mod_base = OTHER
                          note = 2'-fluoro-adenosine
modified_base             11
                          mod_base = OTHER
                          note = 2'-O-methyl-adenosine
modified_base             12
                          mod_base = gm
modified_base             13
                          mod_base = cm
modified_base             14
                          mod_base = OTHER
                          note = 2'-fluoro-adenosine
modified_base             15
                          mod_base = OTHER
                          note = 2'-O-methyl-adenosine
modified_base             16
                          mod_base = OTHER
                          note = 2'-fluoro-uridine
modified_base             17
                          mod_base = um
modified_base             18
                          mod_base = cm
modified_base             19
                          mod_base = um
modified_base             20..22
                          mod_base = OTHER
                          note = linked via phosphorothioate bond
modified_base             20
                          mod_base = cm
modified_base             21
                          mod_base = cm
modified_base             22
                          mod_base = um
source                    1..22
                          mol_type = other RNA
                          organism = synthetic construct
SEQUENCE: 456
ttttgtatga agcaattctc ct                                              22

SEQ ID NO: 457            moltype = RNA  length = 22
FEATURE                   Location/Qualifiers
modified_base             1..3
                          mod_base = OTHER
                          note = linked via phosphorothioate bond
modified_base             1
                          mod_base = OTHER
                          note = mono methyl protected phosphate mimic linked uridine
modified_base             2
                          mod_base = OTHER
                          note = 2'-fluoro-uridine
modified_base             3
                          mod_base = OTHER
                          note = 2'-fluoro-adenosine
modified_base             4
                          mod_base = gm
modified_base             5
                          mod_base = OTHER
                          note = 2'-fluoro-uridine
modified_base             6
                          mod_base = OTHER
                          note = 2'-O-methyl-adenosine
modified_base             7
                          mod_base = OTHER
                          note = 2'-fluoro-guanosine
modified_base             8
                          mod_base = OTHER
                          note = 2'-O-methyl-adenosine
modified_base             9
                          mod_base = OTHER
                          note = 2'-O-methyl-adenosine
modified_base             10
                          mod_base = OTHER
                          note = 2'-fluoro-uridine
modified_base             11
                          mod_base = um
modified_base             12
                          mod_base = um
modified_base             13
                          mod_base = cm
```

```
modified_base          14
                       mod_base = OTHER
                       note = 2'-fluoro-uridine
modified_base          15
                       mod_base = cm
modified_base          16
                       mod_base = OTHER
                       note = 2'-fluoro-uridine
modified_base          17
                       mod_base = gm
modified_base          18
                       mod_base = um
modified_base          19
                       mod_base = OTHER
                       note = 2'-O-methyl-adenosine
modified_base          20..22
                       mod_base = OTHER
                       note = linked via phosphorothioate bond
modified_base          20
                       mod_base = gm
modified_base          21
                       mod_base = gm
modified_base          22
                       mod_base = cm
source                 1..22
                       mol_type = other RNA
                       organism = synthetic construct
SEQUENCE: 457
ttagtagaat ttctctgtag gc                                             22

SEQ ID NO: 458         moltype = RNA  length = 22
FEATURE                Location/Qualifiers
modified_base          1..3
                       mod_base = OTHER
                       note = linked via phosphorothioate bond
modified_base          1
                       mod_base = OTHER
                       note = mono methyl protected phosphate mimic linked uridine
modified_base          2
                       mod_base = OTHER
                       note = 2'-fluoro-guanosine
modified_base          3
                       mod_base = OTHER
                       note = 2'-fluoro-uridine
modified_base          4
                       mod_base = OTHER
                       note = 2'-O-methyl-adenosine
modified_base          5
                       mod_base = OTHER
                       note = 2'-fluoro-guanosine
modified_base          6
                       mod_base = um
modified_base          7
                       mod_base = OTHER
                       note = 2'-fluoro-adenosine
modified_base          8
                       mod_base = gm
modified_base          9
                       mod_base = OTHER
                       note = 2'-O-methyl-adenosine
modified_base          10
                       mod_base = OTHER
                       note = 2'-fluoro-adenosine
modified_base          11
                       mod_base = um
modified_base          12
                       mod_base = um
modified_base          13
                       mod_base = um
modified_base          14
                       mod_base = OTHER
                       note = 2'-fluoro-cytidine
modified_base          15
                       mod_base = um
modified_base          16
                       mod_base = OTHER
                       note = 2'-fluoro-cytidine
modified_base          17
                       mod_base = um
```

-continued

```
modified_base          18
                       mod_base = gm
modified_base          19
                       mod_base = um
modified_base          20..22
                       mod_base = OTHER
                       note = linked via phosphorothioate bond
modified_base          20
                       mod_base = OTHER
                       note = 2'-O-methyl-adenosine
modified_base          21
                       mod_base = gm
modified_base          22
                       mod_base = gm
source                 1..22
                       mol_type = other RNA
                       organism = synthetic construct
SEQUENCE: 458
tgtagtagaa tttctctgta gg                                            22

SEQ ID NO: 459         moltype = RNA  length = 22
FEATURE                Location/Qualifiers
modified_base          1..3
                       mod_base = OTHER
                       note = linked via phosphorothioate bond
modified_base          1
                       mod_base = OTHER
                       note = mono methyl protected phosphate mimic linked uridine
modified_base          2
                       mod_base = OTHER
                       note = 2'-fluoro-adenosine
modified_base          3
                       mod_base = OTHER
                       note = 2'-fluoro-uridine
modified_base          4
                       mod_base = gm
modified_base          5
                       mod_base = OTHER
                       note = 2'-fluoro-uridine
modified_base          6
                       mod_base = OTHER
                       note = 2'-O-methyl-adenosine
modified_base          7
                       mod_base = OTHER
                       note = 2'-fluoro-guanosine
modified_base          8
                       mod_base = um
modified_base          9
                       mod_base = OTHER
                       note = 2'-O-methyl-adenosine
modified_base          10
                       mod_base = OTHER
                       note = 2'-fluoro-guanosine
modified_base          11
                       mod_base = OTHER
                       note = 2'-O-methyl-adenosine
modified_base          12
                       mod_base = OTHER
                       note = 2'-O-methyl-adenosine
modified_base          13
                       mod_base = um
modified_base          14
                       mod_base = OTHER
                       note = 2'-fluoro-uridine
modified_base          15
                       mod_base = um
modified_base          16
                       mod_base = OTHER
                       note = 2'-fluoro-cytidine
modified_base          17
                       mod_base = um
modified_base          18
                       mod_base = cm
modified_base          19
                       mod_base = um
modified_base          20..22
                       mod_base = OTHER
                       note = linked via phosphorothioate bond
modified_base          20
```

```
                         mod_base = gm
modified_base            21
                         mod_base = um
modified_base            22
                         mod_base = OTHER
                         note = 2'-O-methyl-adenosine
source                   1..22
                         mol_type = other RNA
                         organism = synthetic construct
SEQUENCE: 459
tatgtagtag aatttctctg ta                                            22

SEQ ID NO: 460           moltype = RNA  length = 23
FEATURE                  Location/Qualifiers
modified_base            1..3
                         mod_base = OTHER
                         note = linked via phosphorothioate bond
modified_base            1
                         mod_base = OTHER
                         note = 2'-O-methyl-adenosine
modified_base            2
                         mod_base = OTHER
                         note = 2'-fluoro-guanosine
modified_base            3
                         mod_base = um
modified_base            4
                         mod_base = OTHER
                         note = 2'-O-methyl-adenosine
modified_base            5
                         mod_base = OTHER
                         note = 2'-O-methyl-adenosine
modified_base            6
                         mod_base = OTHER
                         note = 2'-fluoro-uridine
modified_base            7
                         mod_base = um
modified_base            8
                         mod_base = OTHER
                         note = 2'-fluoro-guanosine
modified_base            9
                         mod_base = OTHER
                         note = 2'-fluoro-uridine
modified_base            10
                         mod_base = OTHER
                         note = 2'-O-methyl-adenosine
modified_base            11
                         mod_base = gm
modified_base            12
                         mod_base = OTHER
                         note = 2'-O-methyl-adenosine
modified_base            13
                         mod_base = gm
modified_base            14
                         mod_base = OTHER
                         note = 2'-fluoro-adenosine
modified_base            15
                         mod_base = OTHER
                         note = 2'-O-methyl-adenosine
modified_base            16
                         mod_base = OTHER
                         note = 2'-fluoro-cytidine
modified_base            17
                         mod_base = gm
modified_base            18
                         mod_base = gm
modified_base            19
                         mod_base = cm
modified_base            20
                         mod_base = um
modified_base            21..23
                         mod_base = OTHER
                         note = linked via phosphorothioate bond
modified_base            21
                         mod_base = cm
modified_base            22
                         mod_base = gm
modified_base            23
                         mod_base = gm
source                   1..23
```

```
                         mol_type = other RNA
                         organism = synthetic construct
SEQUENCE: 460
agtaattgta gagaacggct cgg                                          23

SEQ ID NO: 461           moltype = RNA  length = 23
FEATURE                  Location/Qualifiers
source                   1..23
                         mol_type = other RNA
                         organism = synthetic construct
SEQUENCE: 461
agtaattgta gagaacggct cgg                                          23

SEQ ID NO: 462           moltype = RNA  length = 21
FEATURE                  Location/Qualifiers
source                   1..21
                         mol_type = other RNA
                         organism = synthetic construct
SEQUENCE: 462
gagccgttct ctacaattac t                                            21

SEQ ID NO: 463           moltype = RNA  length = 20
FEATURE                  Location/Qualifiers
modified_base            1..3
                         mod_base = OTHER
                         note = linked via phosphorothioate bond
modified_base            1
                         mod_base = cm
modified_base            2
                         mod_base = um
modified_base            3
                         mod_base = OTHER
                         note = 2'-O-methyl-adenosine
modified_base            4
                         mod_base = cm
modified_base            5
                         mod_base = OTHER
                         note = 2'-O-methyl-adenosine
modified_base            6
                         mod_base = OTHER
                         note = 2'-fluoro-guanosine
modified_base            7
                         mod_base = OTHER
                         note = 2'-O-methyl-adenosine
modified_base            8
                         mod_base = OTHER
                         note = 2'-fluoro-guanosine
modified_base            9
                         mod_base = OTHER
                         note = 2'-fluoro-adenosine
modified_base            10
                         mod_base = OTHER
                         note = 2'-fluoro-adenosine
modified_base            11
                         mod_base = OTHER
                         note = 2'-fluoro-adenosine
modified_base            12
                         mod_base = um
modified_base            13
                         mod_base = um
modified_base            14
                         mod_base = cm
modified_base            15
                         mod_base = um
modified_base            16
                         mod_base = OTHER
                         note = 2'-O-methyl-adenosine
modified_base            17
                         mod_base = cm
modified_base            18..20
                         mod_base = OTHER
                         note = linked via phosphorothioate bond
modified_base            18
                         mod_base = um
modified_base            19
                         mod_base = OTHER
                         note = 2'-O-methyl-adenosine
modified_base            20
                         mod_base = OTHER
```

-continued

```
                        note = 2'-O-methyl-adenosine
source                  1..20
                        mol_type = other RNA
                        organism = synthetic construct
SEQUENCE: 463
ctacagagaa attctactaa                                   20
```

SMALL INTERFERING RNA TARGETING C3 AND USES THEREOF

RELATED APPLICATIONS

This application is a continuation of U.S. application Ser. No. 18/487,663, filed Oct. 16, 2023, which claims priority to, and the benefit of, U.S. Provisional Application No. 63/416,070, filed Oct. 14, 2022, the entire contents of each of which are incorporated herein by reference.

REFERENCE TO AN ELECTRONIC SEQUENCE LISTING

The contents of the electronic sequence listing (SANB_016_001US_SeqList_ST26.xml; Size: 604,034 bytes; and Date of Creation: Aug. 7, 2025) are herein incorporated by reference in its entirety.

BACKGROUND

The complement system is a part of the innate immune system consisting of multiple soluble proteins that are present in the serum as inactive precursors. Upon activation, these complement components form an amplifying cascade that leads to the generation of bioactive effector compounds. This cascade plays a central role in maintaining cellular integrity and tissue homeostasis via the removal of damaged or dying cells, immune complexes, and cell debris. It also plays a role in immunomodulation, metabolism, inflammation, and host defense against pathogens. The complement system has three activation pathways, all of which revolve around the proteolytic cleavage of C3, a central component that serves as a convergence point for downstream effector function. The central role of C3 in the complement cascade makes it an ideal target for complement modulation.

Deficiencies or loss-of-function mutations of the ordinary complement components may lead to dysregulation of normal complement system function and possible overproduction of complement components. Excessive production and/or dysregulation is linked to an increasing number of ailments, for example, but not limited, to neurological, hematological, eye, kidney, and autoimmune diseases and/or disorders, and infections. Accordingly, there is a need for therapies for subject having diseases, disorders and symptoms associated with elevated complement C3 expression levels. The present disclosure provides compositions targeting C3 and methods of reducing C3 expression for treatment of subjects having a complement-associated disease, disorder or symptom.

SUMMARY

The present disclosure provides an isolated oligonucleotide comprising a sense strand and an antisense strand, wherein: the sense strand comprises a nucleotide sequence that is substantially identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region.

In some embodiments of the isolated oligonucleotide of the present disclosure, the sense strand comprises a nucleotide sequence that is at least 70%, at least 80%, at least 90%, at least 95%, or at least 99% identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

In some embodiments of the isolated oligonucleotide of the present disclosure, the sense strand comprises a nucleotide sequence that is identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

In some embodiments of the isolated oligonucleotide of the present disclosure, the sense strand comprises a nucleotide sequence that is substantially identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, the sense strand comprises a nucleotide sequence that is at least 70%, at least 80%, at least 90%, at least 95%, or at least 99% identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, the sense strand comprises a nucleotide sequence that is identical to a region between any one of the nucleotide positions selected from: a) 1281 to 1301; b) 1797 to 1817; c) 2862 to 2882; d) 4402 to 4424; and e) 4520 to 4540 from the 5' end of a human complement C3 mRNA sequence according to SEQ ID NO: 1.

In some embodiments of the isolated oligonucleotide of the present disclosure, the sense strand comprises a nucleotide sequence that is substantially identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a nucleotide sequence that is at least 70%, at least 80%, at least 90%, at least 95%, or at least 99% identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a nucleotide sequence that is identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a sequence that is substantially identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the sense strand comprises a sequence that is at least 70%, at least 80%, at least 90%, at least 95%, or at least 99% identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the sense strand comprises a sequence that is identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the isolated oligonucleotide is capable of inducing degradation of the C3 mRNA.

In some embodiments of the isolated oligonucleotide of the present disclosure, the sense strand is a single stranded RNA molecule. In some embodiments of the isolated oligonucleotide of the present disclosure, the antisense strand is a single stranded RNA molecule. In some embodiments of the isolated oligonucleotide of the present disclosure, both the sense strand and the antisense strand are single stranded RNA molecules.

In some embodiments of the isolated oligonucleotide of the present disclosure, the single stranded RNA molecule of the sense strand comprises a 3' overhang. In some embodiments, in the single stranded RNA molecule of the sense strand, the 3' overhang comprises at least one nucleotide. In some embodiments, in the single stranded RNA molecule of the sense strand, the 3' overhang comprises two nucleotides.

In some embodiments of the isolated oligonucleotide of the present disclosure, the single stranded RNA molecule of the antisense strand comprises a 3' overhang. In some embodiments, in the single stranded RNA molecule of the antisense strand, the 3' overhang comprises at least one nucleotide. In some embodiments, in the single stranded RNA molecule of the antisense strand, the 3' overhang comprises two nucleotides.

In some embodiments of the isolated oligonucleotide of the present disclosure, the 3' overhang comprises any one of thymidine-thymidine (dTdT), Adenine-Adenine (AA), Cysteine-Cysteine (CC), Guanine-Guanine (GG) or Uracil-Uracil (UU).

In some embodiments of the isolated oligonucleotide of the present disclosure, the sense strand comprises an RNA sequence of at least 20 nucleotides in length. In some embodiments of the isolated oligonucleotide of the present disclosure, the sense strand comprises an RNA sequence of 20 nucleotides in length.

In some embodiments of the isolated oligonucleotide of the present disclosure, the antisense strand comprises an RNA sequence of at least 22 nucleotides in length. In some embodiments of the isolated oligonucleotide of the present disclosure, the antisense strand comprises an RNA sequence of 22 nucleotides in length.

In some embodiments of the isolated oligonucleotide of the present disclosure, the double stranded region is between 19 and 21 nucleotides in length. In some embodiments of the present disclosure, the double stranded region is 20 nucleotides in length.

In some embodiments of the isolated oligonucleotide of the present disclosure, the double stranded region comprises an antisense strand and a sense strand, according to any one of the pairs of antisense strand and sense strand sequences in Table 1, as described in herein.

In some embodiments of the isolated oligonucleotide of the present disclosure, the antisense strand comprises a nucleotide sequence according to any one of: SEQ ID NOs: 2-31.

In some embodiments of the isolated oligonucleotide of the present disclosure, the sense strand comprises a nucleotide sequence according to any one of: SEQ ID NOs: 32-61.

In some embodiments of the isolated oligonucleotide of the present disclosure, the antisense strand comprises a nucleotide sequence according to any one of: SEQ ID NOs: 2-31; and the sense strand comprises a nucleotide sequence according to any one of: SEQ ID NOs: 32-61, wherein the antisense strand and the sense strand sequences have sufficient complementarity to allow formation of a double stranded region between the antisense and the sense strands.

In some embodiments of the isolated oligonucleotide of the present disclosure, the sense strand comprises a nucleotide sequence that is identical to a region between any one of the nucleotide positions selected from a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.1 nM.

In some embodiments of the isolated oligonucleotide of the present disclosure, the sense strand comprises a nucleotide sequence that is identical to a region between any one of the nucleotide positions selected from a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%), at a dose of 0.01 nM.

In some embodiments of the isolated oligonucleotide of the present disclosure, the sense strand comprises a nucleotide sequence that is identical to a region between any one of the nucleotide positions selected from a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.01 nM.

The present disclosure also provides an isolated oligonucleotide comprising a sense strand and an antisense strand, wherein the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%) at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%) at a dose of 0.01 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.01 nM.

The present disclosure also provides an isolated oligonucleotide comprising a sense strand and an antisense strand, wherein the sense strand or the antisense strand or both comprise one or more modified nucleotide(s).

In some embodiments of the isolated oligonucleotide comprising a sense strand and an antisense strand, the antisense strand comprises a mono methyl protected phosphate mimic (5'-MeEP).

In some embodiments of the isolated oligonucleotide comprising a sense strand and an antisense strand, the sense strand or the antisense strand or both, a terminal or internal nucleotide is linked to a targeting ligand. In some embodiments, the targeting ligand comprises at least one GalNAc G1b moiety.

In some embodiments of the isolated oligonucleotide comprising a sense strand and an antisense strand, the antisense strand comprises nucleotides modified with 2'-F modification, and nucleotides modified with 2'-O-methyl modification, according to the formula: $3'(M)_0(F)_0(M)_6(F)_1(M)_1(F)_1(M)_3(F)_1(M)_2(F)_1(M)_1(F)_1(M)_1(F)_2(M)_1$ 5'.

In some embodiments of the isolated oligonucleotide comprising a sense strand and an antisense strand, the sense strand comprises nucleotides modified with 2'-F modification, and nucleotides modified with 2'-O-methyl modification, according to the formula: $5'(M)_0(F)_0(M)_5(F)_1(M)_1(F)_4(M)_9$ 3'.

In some embodiments of the isolated oligonucleotide comprising a sense strand and an antisense strand, the antisense strand comprises any one of: i) an antisense strand of nucleic acid sequence according to SEQ ID NO: 451 (5' [mUs][fUs][fA][mG][fU][mA][fG][mA][mA][fU][mU][mU][mC][fU][mC][fU][mG][mU][mA][mGs][mGs][mC] 3'); ii) an antisense strand of nucleic acid sequence according to SEQ ID NO: 452 (5' [mUs][fGs][fU][mA][fG][mU][fA][mG][mA][fA][mU][mU][mU][fC][mU][fC][mU][mG][mU][mAs][mGs][mG] 3'); iii) an antisense strand of nucleic acid sequence according to SEQ ID NO: 453 (5' [mUs][fAs][fU][mG][fU][mA][fG][mU][mA][fG][mA][mA][mU][fU][mU][fC][mU][mC][mU][mGs][mUs][mA] 3'), iv) an antisense strand of nucleic acid sequence according to SEQ ID NO: 454 (5' [mUs][fAs][fU][mA][fG][mA][fU][mG][mU][fA][mG][mU][mA][fG][mA][fA][mU][mU][mU][mCs][mUs][mC] 3'); v) an antisense strand of nucleic acid sequence according to SEQ ID NO: 455 (5' [mUs][fAs][fU][mG][fA][mA][fG][mC][mA][fA][mU][mU][mC][fU][mC][fC][mU][mC][mA][mGs][mCs][mA] 3'); vi) an antisense strand of nucleic acid sequence according to SEQ ID NO: 456 (5' [mUs][fUs][fU][mU][fG][mU][fA][mU][mG][fA][mA][mG][mC][fA][mA][fU][mU][mC][mU][mCs][mCs][mU] 3'), vii) an antisense strand of nucleic acid sequence according to SEQ ID NO: 457 (5' [MeEPmUs][fUs][fA][mG][fU][mA][fG][mA][mA][fU][mU][mU][mC][fU][mC][fU][mG][mU][mA][mGs][mGs][mC] 3'); viii) an antisense strand of nucleic acid sequence according to SEQ ID NO: 458 (5' [MeEPmUs][fGs][fU][mA][fG][mU][fA][mG][mA][fA][mU][mU][mU][fC][mU][fC][mU][mG][mU][mAs][mGs][mG] 3'); or ix) an antisense strand of nucleic acid sequence according to SEQ ID NO: 459 (5' [MeEPmUs][fAs][fU][mG][fU][mA][fG][mU][mA][fG][mA][mA][mU][fU][mU][fC][mU][mC][mU][mGs][mUs][mA] 3'), wherein "m" is a 2'-O-methyl modified nucleotide, "f" is a 2'-F modified nucleotide, "s" is a phosphorothioate internucleotide linkage, "MeEP" is a mono methyl protected phosphate mimic.

In some embodiments of the isolated oligonucleotide comprising a sense strand and an antisense strand, the sense strand comprises any one of: i) a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3'); ii) a sense strand of nucleic acid sequence according to SEQ ID NO: 445 (5' [mUs][mAs][mC][mA][mG][fA][mG][fA][fA][fA][fU][mU][mC][mU][mA][mC][mU][mAs][mCs][mA][G1b][G1b][G1b] 3'); iii) a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3'), iv) a sense strand of nucleic acid sequence according to SEQ ID NO: 447 (5' [mGs][mAs][mA][mA][mU][fU][mC][fU][fA][fC][fU][mA][mC][mA][mU][mC][mU][mAs][mUs][mA][G1b][G1b][G1b] 3'); v) a sense strand of nucleic acid sequence according to SEQ ID NO: 448 (5' [mCs][mUs][mG][mA][mG][fG][mA][fG][fA][fA][fU][mU][mG][mC][mU][mU][mC][mAs][mUs][mA][G1b][G1b][G1b] 3'); or vi) a sense strand of nucleic acid sequence according to SEQ ID NO: 449 (5' [mGs][mAs][mG][mA][mA][fU][mU][fG][fC][fU][fU][mC][mA][mU][mA][mC][mA][mAs][mAs][mA][G1b][G1b][G1b] 3'), wherein "m" is a 2'-O-methyl modified nucleotide, "f" is a 2'-F modified nucleotide, "s" is a phosphorothioate internucleotide linkage, and "G1b" is a GalNac G1b moiety.

In some embodiments of the isolated oligonucleotide comprising a sense strand and an antisense strand, the double stranded region comprises: i) an antisense strand of nucleic acid sequence according to SEQ ID NO: 451 (5' [mUs][fUs][fA][mG][fU][mA][fG][mA][mA][fU][mU][mU][mC][fU][mC][fU][mG][mU][mA][mGs][mGs][mC] 3'), and a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3'); ii) an antisense strand of nucleic acid sequence according to SEQ ID NO: 453 (5' [mUs][fAs][fU][mG][fU][mA][fG][mU][mA][fG][mA][mA][mU][fU][mU][fC][mU][mC][mU][mGs][mUs][mA] 3'), and a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3'); iii) an antisense strand of nucleic acid sequence according to SEQ ID NO: 457 (5' [MeEPmUs][fUs][fA][mG][fU][mA][fG][mA][mA][fU][mU][mU][mC][fU][mC][fU][mG][mU][mA][mGs][mGs][mC] 3'), and a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3'); or iv) an antisense strand of nucleic acid sequence according to SEQ ID NO: 459 (5' [MeEPmUs][fAs][fU][mG][fU][mA][fG][mU][mA][fG][mA][mA][mU][fU][mU][fC][mU][mC][mU][mGs][mUs][mA] 3'), and a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3').

The present disclosure also provides a vector encoding an isolated oligonucleotide disclosed herein.

The present disclosure also provides a delivery system comprising an isolated oligonucleotide or vector disclosed herein.

The present disclosure also provides a pharmaceutical composition comprising an isolated oligonucleotide, vector or delivery system disclosed herein, and a pharmaceutically acceptable carrier, diluent or excipient.

The present disclosure also provides a kit comprising an isolated oligonucleotide, vector, delivery system or a pharmaceutical composition disclosed herein.

The present disclosure also provides a method of inhibiting or downregulating the expression or level of C3 in a subject in need thereof, wherein the method comprises administering to the subject an effective amount of at least one isolated oligonucleotide, vector, delivery system or pharmaceutical composition disclosed herein.

The present disclosure also provides a method of treating or preventing a disease or disorder associated with aberrant or increased expression or activity of C3 or a disease or disorder where C3 plays a role in a subject in need thereof, wherein the method comprises administering to the subject an effective amount of at least one isolated oligonucleotide, vector, delivery system or pharmaceutical composition disclosed herein.

BRIEF DESCRIPTION OF THE DRAWINGS

Figure 5A:
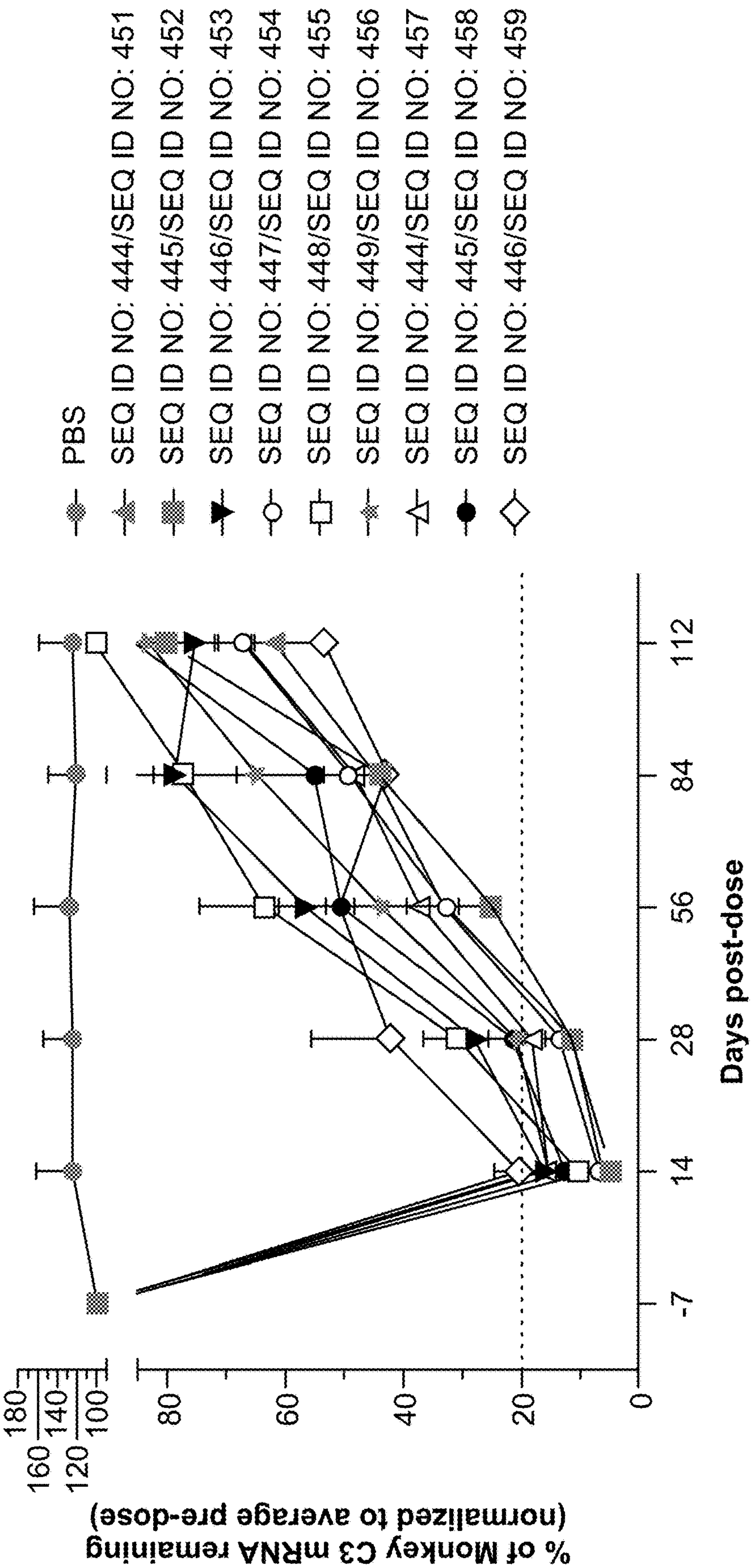
Figure 5B:
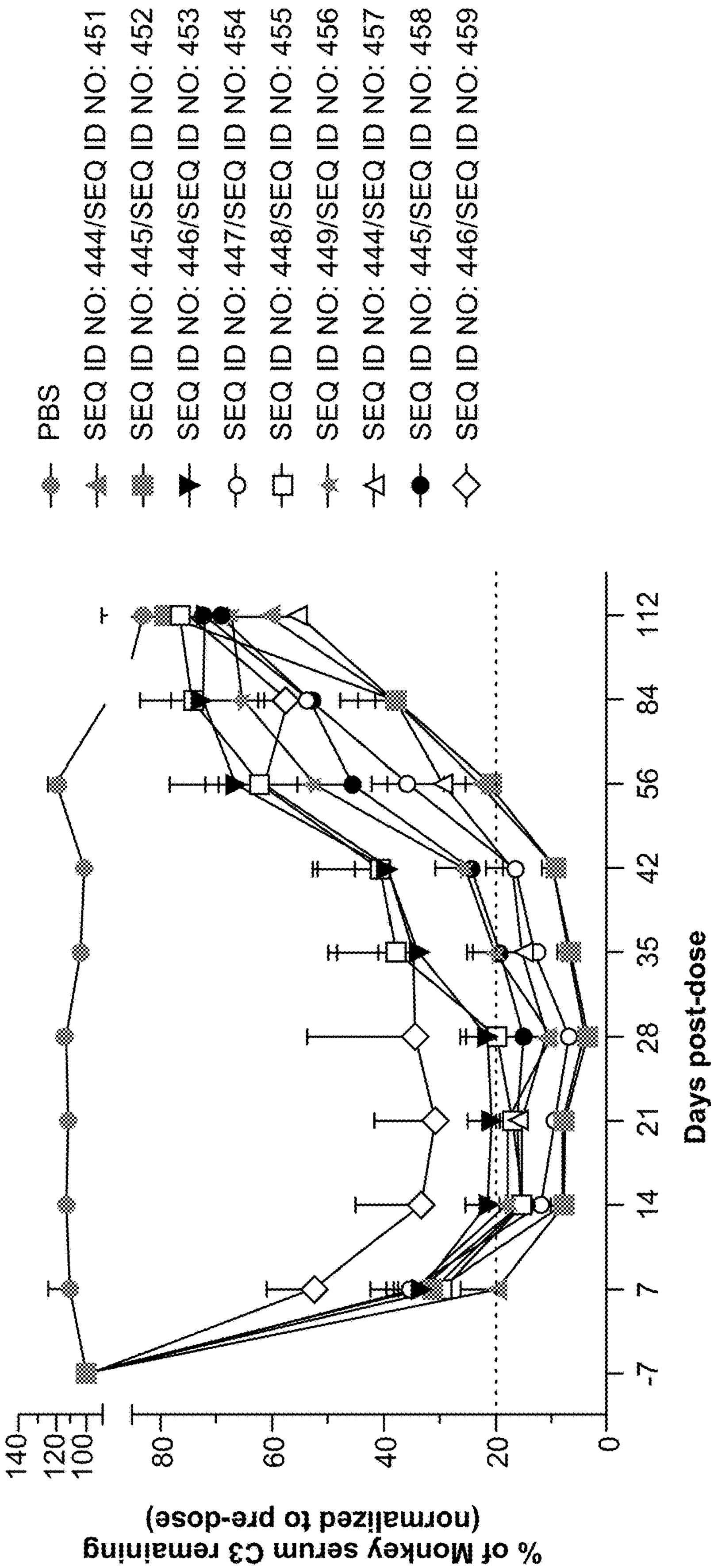

FIGS. 5A-5B are graphs showing in vivo potency evaluations of compounds listed in Table 3 in *Macaca fascicularis* after a 3 mg/kg single s.c. dosing. Cyno C3 mRNA remaining in liver (FIG. 5A) and serum C3 protein remaining (FIG. 5B) were measured over time. Data was normalized to pre-dose mRNA or protein levels of each animal.

Figure 6:
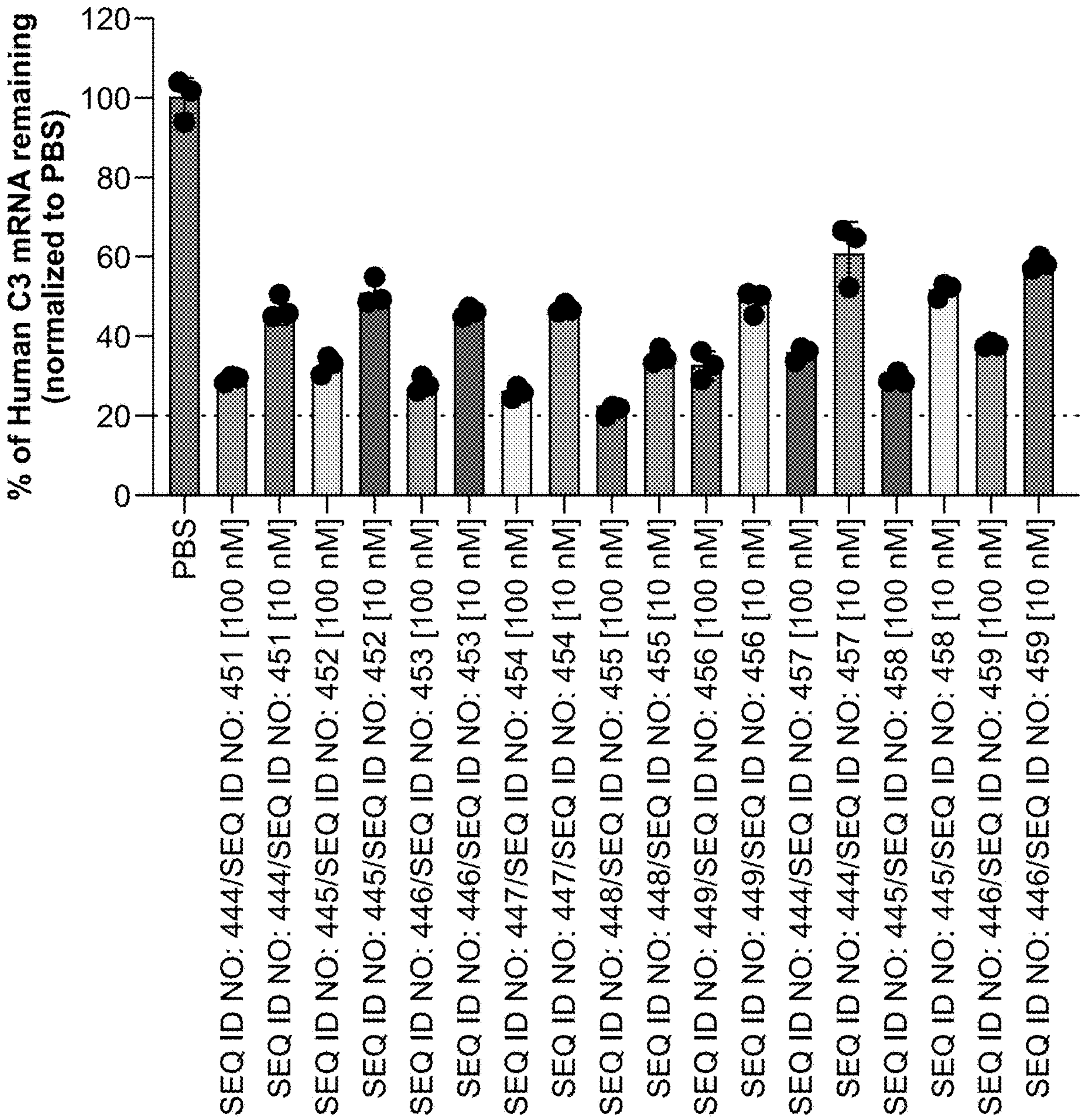

FIG. 6 is a graph showing human C3 mRNA remaining in human primary hepatocytes after being treated with compounds from Table 3.

DETAILED DESCRIPTION

The present disclosure provides isolated oligonucleotides (oligonucleotide(s)) that form a double stranded region, preferably small interfering RNAs (siRNAs), that can decrease complement C3 mRNA expression, in turn leading to a decrease in the degree of C3 protein expression in target cells. The oligonucleotides disclosed herein can have therapeutic application in regulating the expression of C3, for treatment of diseases involving a complement component-associated disease such as, but not limited to Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases.

In some aspects, the present invention provides compositions and methods of treating a subject having a disorder that would benefit from the reduction in complement C3 expression. In some aspects, the methods disclosed herein prevent at least one symptom in a subject having a disease or disorder that would benefit from reduction in complement C3 expression.

The present disclosure has identified specific regions within the C3 mRNA, that provide targets for binding double stranded oligonucleotides, e.g., siRNA, leading to reduction in level of expression of the C3 mRNA.

The C3 mRNA sequence described herein, is an mRNA sequence encoded by a complement C3 gene according to GenBank Accession No. NM_000064.4:

(SEQ ID NO: 1)

```
ACTCCTCCCCATCCTCTCCCTCTGTCCCTCTGTCCCTCTGACCCTGCAC

TGTCCCAGCACCATGGGACCCACCTCAGGTCCCAGCCTGCTGCTCCTGC

TACTAACCCACCTCCCCCTGGCTCTGGGGAGTCCCATGTACTCTATCAT

CACCCCCAACATCTTGCGGCTGGAGAGCGAGGAGACCATGGTGCTGGAG

GCCCACGACGCGCAAGGGGATGTTCCAGTCACTGTTACTGTCCACGACT

TCCCAGGCAAAAAACTAGTGCTGTCCAGTGAGAAGACTGTGCTGACCCC

TGCCACCAACCACATGGGCAACGTCACCTTCACGATCCCAGCCAACAGG

GAGTTCAAGTCAGAAAAGGGGCGCAACAAGTTCGTGACCGTGCAGGCCA

CCTTCGGGACCCAAGTGGTGGAGAAGGTGGTGCTGGTCAGCCTGCAGAG

CGGGTACCTCTTCATCCAGACAGACAAGACCATCTACACCCCTGGCTCC

ACAGTTCTCTATCGGATCTTCACCGTCAACCACAAGCTGCTACCCGTGG

GCCGGACGGTCATGGTCAACATTGAGAACCCGGAAGGCATCCCGGTCAA

GCAGGACTCCTTGTCTTCTCAGAACCAGCTTGGCGTCTTGCCCTTGTCT
```

-continued

```
TGGGACATTCCGGAACTCGTCAACATGGGCCAGTGGAAGATCCGAGCCT

ACTATGAAAACTCACCACAGCAGGTCTTCTCCACTGAGTTTGAGGTGAA

GGAGTACGTGCTGCCCAGTTTCGAGGTCATAGTGGAGCCTACAGAGAAA

TTCTACTACATCTATAACGAGAAGGGCCTGGAGGTCACCATCACCGCCA

GGTTCCTCTACGGGAAGAAAGTGGAGGGAACTGCCTTTGTCATCTTCGG

GATCCAGGATGGCGAACAGAGGATTTCCCTGCCTGAATCCCTCAAGCGC

ATTCCGATTGAGGATGGCTCGGGGGAGGTTGTGCTGAGCCGGAAGGTAC

TGCTGGACGGGGTGCAGAACCCCCGAGCAGAAGACCTGGTGGGGAAGTC

TTTGTACGTGTCTGCCACCGTCATCTTGCACTCAGGCAGTGACATGGTG

CAGGCAGAGCGCAGCGGGATCCCCATCGTGACCTCTCCCTACCAGATCC

ACTTCACCAAGACACCCAAGTACTTCAAACCAGGAATGCCCTTTGACCT

CATGGTGTTCGTGACGAACCCTGATGGCTCTCCAGCCTACCGAGTCCCC

GTGGCAGTCCAGGGCGAGGACACTGTGCAGTCTCTAACCCAGGGAGATG

GCGTGGCCAAACTCAGCATCAACACACACCCCAGCCAGAAGCCCTTGAG

CATCACGGTGCGCACGAAGAAGCAGGAGCTCTCGGAGGCAGAGCAGGCT

ACCAGGACCATGCAGGCTCTGCCCTACAGCACCGTGGGCAACTCCAACA

ATTACCTGCATCTCTCAGTGCTACGTACAGAGCTCAGACCCGGGGAGAC

CCTCAACGTCAACTTCCTCCTGCGAATGGACCGCGCCCACGAGGCCAAG

ATCCGCTACTACACCTACCTGATCATGAACAAGGGCAGGCTGTTGAAGG

CGGGACGCCAGGTGCGAGAGCCCGGCCAGGACCTGGTGGTGCTGCCCCT

GTCCATCACCACCGACTTCATCCCTTCCTTCCGCCTGGTGGCGTACTAC

ACGCTGATCGGTGCCAGCGGCCAGAGGGAGGTGGTGGCCGACTCCGTGT

GGGTGGACGTCAAGGACTCCTGCGTGGGCTCGCTGGTGGTAAAAAGCGG

CCAGTCAGAAGACCGGCAGCCTGTACCTGGGCAGCAGATGACCCTGAAG

ATAGAGGGTGACCACGGGGCCCGGGTGGTACTGGTGGCCGTGGACAAGG

GCGTGTTCGTGCTGAATAAGAAGAACAAACTGACGCAGAGTAAGATCTG

GGACGTGGTGGAGAAGGCAGACATCGGCTGCACCCCGGGCAGTGGGAAG

GATTACGCCGGTGTCTTCTCCGACGCAGGGCTGACCTTCACGAGCAGCA

GTGGCCAGCAGACCGCCCAGAGGGCAGAACTTCAGTGCCCGCAGCCAGC

CGCCCGCCGACGCCGTTCCGTGCAGCTCACGGAGAAGCGAATGGACAAA

GTCGGCAAGTACCCCAAGGAGCTGCGCAAGTGCTGCGAGGACGGCATGC

GGGAGAACCCCATGAGGTTCTCGTGCCAGCGCCGGACCCGTTTCATCTC

CCTGGGCGAGGCGTGCAAGAAGGTCTTCCTGGACTGCTGCAACTACATC

ACAGAGCTGCGGCGGCAGCACGCGCGGGCCAGCCACCTGGGCCTGGCCA

GGAGTAACCTGGATGAGGACATCATTGCAGAAGAGAACATCGTTTCCCG

AAGTGAGTTCCCAGAGAGCTGGCTGTGGAACGTTGAGGACTTGAAAGAG

CCACCGAAAAATGGAATCTCTACGAAGCTCATGAATATATTTTTGAAAG

ACTCCATCACCACGTGGGAGATTCTGGCTGTGAGCATGTCGGACAAGAA

AGGGATCTGTGTGGCAGACCCCTTCGAGGTCACAGTAATGCAGGACTTC

TTCATCGACCTGCGGCTACCCTACTCTGTTGTTCGAAACGAGCAGGTGG

AAATCCGAGCCGTTCTCTACAATTACCGGCAGAACCAAGAGCTCAAGGT
```

-continued

GAGGGTGGAACTACTCCACAATCCAGCCTTCTGCAGCCTGGCCACCACC

AAGAGGCGTCACCAGCAGACCGTAACCATCCCCCCCAAGTCCTCGTTGT

CCGTTCCATATGTCATCGTGCCGCTAAAGACCGGCCTGCAGGAAGTGGA

AGTCAAGGCTGCTGTCTACCATCATTTCATCAGTGACGGTGTCAGGAAG

TCCCTGAAGGTCGTGCCGGAAGGAATCAGAATGAACAAAACTGTGGCTG

TTCGCACCCTGGATCCAGAACGCCTGGGCCGTGAAGGAGTGCAGAAAGA

GGACATCCCACCTGCAGACCTCAGTGACCAAGTCCCGGACACCGAGTCT

GAGACCAGAATTCTCCTGCAAGGGACCCCAGTGGCCCAGATGACAGAGG

ATGCCGTCGACGCGGAACGGCTGAAGCACCTCATTGTGACCCCCTCGGG

CTGCGGGGAACAGAACATGATCGGCATGACGCCCACGGTCATCGCTGTG

CATTACCTGGATGAAACGGAGCAGTGGGAGAAGTTCGGCCTAGAGAAGC

GGCAGGGGGCCTTGGAGCTCATCAAGAAGGGGTACACCCAGCAGCTGGC

CTTCAGACAACCCAGCTCTGCCTTTGCGGCCTTCGTGAAACGGGCACCC

AGCACCTGGCTGACCGCCTACGTGGTCAAGGTCTTCTCTCTGGCTGTCA

ACCTCATCGCCATCGACTCCCAAGTCCTCTGCGGGGCTGTTAAATGGCT

GATCCTGGAGAAGCAGAAGCCCGACGGGGTCTTCCAGGAGGATGCGCCC

GTGATACACCAAGAAATGATTGGTGGATTACGGAACAACAACGAGAAAG

ACATGGCCCTCACGGCCTTTGTTCTCATCTCGCTGCAGGAGGCTAAAGA

TATTTGCGAGGAGCAGGTCAACAGCCTGCCAGGCAGCATCACTAAAGCA

GGAGACTTCCTTGAAGCCAACTACATGAACCTACAGAGATCCTACACTG

TGGCCATTGCTGGCTATGCTCTGGCCCAGATGGGCAGGCTGAAGGGGCC

TCTTCTTAACAAATTTCTGACCACAGCCAAAGATAAGAACCGCTGGGAG

GACCCTGGTAAGCAGCTCTACAACGTGGAGGCCACATCCTATGCCCTCT

TGGCCCTACTGCAGCTAAAAGACTTTGACTTTGTGCCTCCCGTCGTGCG

TTGGCTCAATGAACAGAGATACTACGGTGGTGGCTATGGCTCTACCCAG

GCCACCTTCATGGTGTTCCAAGCCTTGGCTCAATACCAAAAGGACGCCC

CTGACCACCAGGAACTGAACCTTGATGTGTCCCTCCAACTGCCCAGCCG

CAGCTCCAAGATCACCCACCGTATCCACTGGGAATCTGCCAGCCTCCTG

CGATCAGAAGAGACCAAGGAAAATGAGGGTTTCACAGTCACAGCTGAAG

GAAAAGGCCAAGGCACCTTGTCGGTGGTGACAATGTACCATGCTAAGGC

CAAAGATCAACTCACCTGTAATAAATTCGACCTCAAGGTCACCATAAAA

CCAGCACCGGAAACAGAAAAGAGGCCTCAGGATGCCAAGAACACTATGA

TCCTTGAGATCTGTACCAGGTACCGGGGAGACCAGGATGCCACTATGTC

TATATTGGACATATCCATGATGACTGGCTTTGCTCCAGACACAGATGAC

CTGAAGCAGCTGGCCAATGGTGTTGACAGATACATCTCCAAGTATGAGC

TGGACAAAGCCTTCTCCGATAGGAACACCCTCATCATCTACCTGGACAA

GGTCTCACACTCTGAGGATGACTGTCTAGCTTTCAAAGTTCACCAATAC

TTTAATGTAGAGCTTATCCAGCCTGGAGCAGTCAAGGTCTACGCCTATT

ACAACCTGGAGGAAAGCTGTACCCGGTTCTACCATCCGGAAAAGGAGGA

TGGAAAGCTGAACAAGCTCTGCCGTGATGAACTGTGCCGCTGTGCTGAG

-continued

GAGAATTGCTTCATACAAAAGTCGGATGACAAGGTCACCCTGGAAGAAC

GGCTGGACAAGGCCTGTGAGCCAGGAGTGGACTATGTGTACAAGACCCG

ACTGGTCAAGGTTCAGCTGTCCAATGACTTTGACGAGTACATCATGGCC

ATTGAGCAGACCATCAAGTCAGGCTCGGATGAGGTGCAGGTTGGACAGC

AGCGCACGTTCATCAGCCCCATCAAGTGCAGAGAAGCCCTGAAGCTGGA

GGAGAAGAAACACTACCTCATGTGGGGTCTCTCCTCCGATTTCTGGGGA

GAGAAGCCCAACCTCAGCTACATCATCGGGAAGGACACTTGGGTGGAGC

ACTGGCCCGAGGAGGACGAATGCCAAGACGAAGAGAACCAGAAACAATG

CCAGGACCTCGGCGCCTTCACCGAGAGCATGGTTGTCTTTGGGTGCCCC

AACTGACCACACCCCCATTCCCCCACTCCAGATAAAGCTTCAGTTATAT

CTCACGTGTCTGGAGTTCTTTGCCAAGAGGGAGAGGCTGAAATCCCCAG

CCGCCTCACCTGCAGCTCAGCTCCATCCTACTTGAAACCTCACCTGTTC

CCACCGCATTTTCTCCTGGCGTTCGCCTGCTAGTGTG

The present disclosure provides an isolated oligonucleotide comprising a sense strand and an antisense strand, wherein the sense strand comprises a nucleotide sequence that is substantially identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region.

In some embodiments of the isolated oligonucleotide of the present disclosure, the sense strand comprises a nucleotide sequence that is at least 70%, at least 80%, at least 90%, at least 95%, or at least 99% identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

In some embodiments of the isolated oligonucleotide of the present disclosure, the sense strand comprises a nucleotide sequence that is identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

In some embodiments of the isolated oligonucleotide of the present disclosure, the sense strand comprises a nucleotide sequence that is substantially identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, the sense strand comprises a nucleotide sequence that is at least 70%, at least 80%, at least 90%, at least 95%, or at least 99% identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, the sense strand comprises a nucleotide sequence that is identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, the sense strand comprises a nucleotide sequence that is substantially identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a sequence that is at least 70%, at least 80%, at least 90%, at least 95%, or at least 99% identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a sequence that is identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, the sense strand comprises a sequence that is substantially identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the sense strand comprises a sequence that is at least 70%, at least 80%, at least 90%, at least 95%, or at least 99% identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the sense strand comprises a sequence that is identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

The C3 mRNA sequence according to SEQ ID NO: 1, as described herein, is any heterologous mRNA sequence with sufficient identity to a C3 according to Accession No. NM 000064.4, as described herein, that allows binding to the antisense strand of the oligonucleotides of the present disclosure.

In some embodiments of the isolated oligonucleotide of the present disclosure, the isolated oligonucleotide is capable of inducing degradation of the C3 mRNA.

In some embodiments of the isolated oligonucleotide of the present disclosure, the sense strand is a single stranded RNA molecule. In some embodiments of the isolated oligonucleotide of the present disclosure, the antisense strand is a single stranded RNA molecule. In some embodiments of the isolated oligonucleotide of the present disclosure, both the sense strand and the antisense strand are single stranded RNA molecules.

In some embodiments, the isolated oligonucleotide of the present disclosure is a small interfering RNA (siRNA). Accordingly, the disclosure provides siRNAs, wherein the siRNA comprises a sense region and antisense region complementary to the sense region that together form an RNA duplex, and wherein the sense region comprises a sequence at least 70% to 100% identical to a C3 mRNA sequence.

Definitions

"RNAi" or "RNA interference" refers to the process of sequence-specific post-transcriptional gene silencing, mediated by double-stranded RNA (dsRNA). Duplex RNA siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof are all capable of mediating RNA interference. These dsRNA molecules may be commercially available or may be designed and prepared based on known sequence information, etc. The antisense strand of these molecules can include RNA, DNA, PNA, or a combination thereof. These DNA/RNA chimera polynucleotide includes, but is not limited to, a double-strand polynucleotide composed of DNA and RNA that inhibits the expression of a target gene. These dsRNA molecules can also include one or more modified nucleotides, as described herein, which can be incorporated on either strand.

In the RNAi gene silencing or knockdown process, dsRNA comprising a first (antisense) strand that is complementary to a portion of a target gene and a second (sense) strand that is fully or partially complementary to the first antisense strand is introduced into an organism. After introduction into the organism, the target gene-specific dsRNA is processed into relatively small fragments (siRNAs) and can subsequently become distributed throughout the organism, decrease messenger RNA of target gene, leading to a phenotype that may come to closely resemble the phenotype arising from a complete or partial deletion of the target gene.

Certain dsRNAs in cells can undergo the action of Dicer enzyme, a ribonuclease III enzyme. Dicer can process the dsRNA into shorter pieces of dsRNA, i.e. siRNAs. RNAi also involves an endonuclease complex known as the RNA induced silencing complex (RISC). Following cleavage by Dicer, siRNAs enter the RISC complex and direct cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex. siRNAs can thus down regulate or knock down gene expression by mediating RNA interference in a sequence-specific manner.

As used herein, "target gene" or "target sequence" refers to a gene or gene sequence whose corresponding RNA is targeted for degradation through the RNAi pathway using dsRNAs or siRNAs as described herein. To target a gene, for example using an siRNA, the siRNA comprises an antisense region complementary to, or substantially complementary to, at least a portion of the target gene or sequence, and sense strand complementary to the antisense strand. Once introduced into a cell, the siRNA directs the RISC complex to cleave an RNA comprising a target sequence, thereby degrading the RNA.

As used herein, "oligonucleotide", "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present disclosure further provides a nucleic acid that is the complement (which can be either a full complement or a partial complement) of a nucleic acid, nucleotide sequence, or polynucleotide of this disclosure. When dsRNA is produced synthetically, less common bases, such as inosine, 5-methylcytosine, 6-methyladenine, hypoxanthine and others can also be used for antisense, dsRNA, and ribozyme pairing. Other modifications, such as modification to the phosphodiester backbone, or the 2'-fluoro, the 2'-hydroxy or 2'O-methyl in the ribose sugar group of the RNA can also be made.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "region" or "fragment" is used interchangeably and as applied to an oligonucleotide.

The C3 mRNA sequence, as described herein, will be understood to mean a full length C3 mRNA nucleotide sequence, unless indicated otherwise. In some embodiments, the C3 mRNA sequence can be a nucleotide sequence of reduced length relative to a reference nucleic acid or nucleotide sequence of the C3 mRNA sequence comprising, consisting essentially of, and/or consisting of a nucleotide sequence of contiguous nucleotides identical or almost identical (e.g., 60%, 70%, 80%, 90%, 92%, 95%, 98% or 99% identical) to the reference nucleic acid or nucleotide sequence. Such a nucleic acid fragment according to the disclosure may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the disclosure.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the term "substantially complementary" is at least 90% (e.g., 91, 92, 93, 94, 95, 96, 97, 98 or 99%) complementary to the sense strand that is substantially identical to the nucleotide sequence within the defined regions in SEQ ID NO: 1. As used herein, the term "substantially complementary" means that two nucleic acid sequences are complementary at least at about 90%, 95% or 99% of their nucleotides.

In some embodiments, the two nucleic acid sequences can be complementary at least at 90%, 95%, 96%, 97%, 98%, 99% or more of their nucleotides. In some embodiments, the two nucleic acid sequences can be between 90% to 95% complementary, between 70% to 100% complementary, between 95% and 96% complementary, between 90% and 100% complementary, between 96% to 97% complementary, between 60% to 80% complementary, between 97% and 98% complementary, between 70% and 90% complementary, between 98% and 99% complementary, between 80% and 100% complementary, or between 99% and 100% complementary.

The term "substantially complementary" can also mean that two nucleic acid sequences, sense strand and antisense strand have sufficient complementarity that allows binding between the sense strand and antisense strand to form a double stranded region comprising of between 19-25 nucleotides in length. The term "substantially complementary" can also mean that two nucleic acid sequences can hybridize under high stringency conditions, and such conditions are well known in the art.

As used herein, the term "substantially identical" or "sufficient identity" used interchangeably herein, is at least 70%, at least 80%, at least 90%, at least 95%, or at least 99% (e.g., between 70% to 805, 8-% to 90% or 90% to 95% or 95% to 99% or 99% to 100%) identical to the nucleotide sequence within the defined regions in SEQ ID NO: 1.

As used herein, the term "identity" means that sequences are compared with one another as follows. In order to determine the percentage identity of two nucleic acid sequences, the sequences can first be aligned with respect to one another in order subsequently to make a comparison of these sequences possible. For this e.g., gaps can be inserted into the sequence of the first nucleic acid sequence and the nucleotides can be compared with the corresponding position of the second nucleic acid sequence. If a position in the first nucleic acid sequence is occupied by the same nucleotide as is the case at a position in the second sequence, the two sequences are identical at this position. The percentage identity between two sequences is a function of the number of identical positions divided by the number of all the positions compared in the sequences investigated.

A "percent identity" or "% identity" as used interchangeably herein, for aligned segments of a test sequence and a reference sequence is the percent of identical components which are shared by the two aligned sequences divided by the total number of components in reference sequence segment, i.e., the entire reference sequence or a smaller defined part of the reference sequence.

"Nucleotide sequence" and "nucleic acid sequence" are used interchangeably herein, unless indicated otherwise.

The percentage identity of two sequences can be determined with the aid of a mathematical algorithm. A preferred, but not limiting, example of a mathematical algorithm which can be used for comparison of two sequences is the algorithm of Karlin et al. (1993), PNAS USA, 90:5873-5877. Such an algorithm is integrated in the NBLAST program, with which sequences which have a desired identity to the sequences of the present disclosure can be identified. In order to obtain a gapped alignment, as described here, the "Gapped BLAST" program can be used, as is described in Altschul et al. (1997), Nucleic Acids Res, 25:3389-3402. If BLAST and Gapped BLAST programs are used, the preset parameters of the particular program (e.g. NBLAST) can be used. The sequences can be aligned further using version 9 of GAP (global alignment program) of the "Genetic Computing Group" using the preset (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of agreements as a percentage content of the nucleic acids in the sequence claimed. The methods described for determination of the percentage identity of two nucleic acid sequences can also be used correspondingly, if necessary, on the coded amino acid sequences.

Useful methods for determining sequence identity are also disclosed in Guide to Huge Computers (Martin J. Bishop, ed., Academic Press, San Diego (1994)), and Carillo, H., and Lipton, D., (Applied Math48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity. Percent identity can be 70% identity or greater, e.g., at least 70% identity, at least 75% identity, at least 80% identity, at least 85% identity, at least 90% identity, at least 95% identity, at least 98% identity, at least 99% identity or 100% identity.

As used herein, "heterologous" refers to a nucleic acid sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., a different copy number, and/or under the control of different regulatory sequences than that found in nature.

Double Stranded RNAs Targeting Human Complement C3

The disclosure provides isolated oligonucleotides comprising a double stranded RNAs (dsRNAs) duplex region which target a C3 mRNA sequence for degradation. The double stranded RNA molecule of the disclosure may be in the form of any type of RNA interference molecule known in the art. In some embodiments, the double stranded RNA molecule is a small interfering RNA (siRNA). In other embodiments, the double stranded RNA molecule is a short hairpin RNA (shRNA) molecule. In other embodiments, the double stranded RNA molecule is a Dicer substrate that is processed in a cell to produce an siRNA. In other embodiments the double stranded RNA molecule is part of a microRNA precursor molecule.

In some embodiments, the dsRNA is a small interfering RNA (siRNA) which targets a C3 mRNA sequence for degradation. In some embodiments, the siRNA targeting C3 is packaged in a delivery system described herein (e.g., nanoparticle).

The isolated oligonucleotides of the present disclosure targeting C3 for degradation can comprise a sense strand at least 70% identical to any fragment of a C3 mRNA, for example the C3 mRNA of SEQ ID NO: 1. In some embodiments, the sense strand comprises or consists essentially of a sequence at least 70%, at least 80%, at least 90%, at least 95% or is 100% identical to any fragment of SEQ ID NO: 1. The siRNAs targeting C3 for degradation can comprise an antisense strand at least 70% identical to a sequence complementary to any fragment of a C3 mRNA, for example the C3 mRNA of SEQ ID NO: 1. In some embodiments, the antisense strand comprises or consists essentially of a sequence at least 70%, at least 80%, at least 90%, at least 95% or is 100% identical to a sequence complementary to any fragment of SEQ ID NO: 1. In some embodiments, the sense region and antisense regions are complementary, and base pair to form an RNA duplex structure. The fragment of the C3 mRNA that has percent identity to the sense region of the siRNA, and which is complementary to the antisense region of the siRNA, can be protein coding sequence of the mRNA, an untranslated region (UTR) of the mRNA (5' UTR or 3' UTR), or both.

In some embodiments, the isolated oligonucleotides of the present disclosure comprises a sense region and antisense region complementary to the sense region that together form an RNA duplex, and the sense region comprises a sequence at least 70% identical to a C3 mRNA sequence. In some embodiments, the sense region is identical to a C3 mRNA sequence.

As used herein, the term "sense strand" or "sense region" refers to a nucleotide sequence of an siRNA molecule that is partially or fully complementary to at least a portion of a corresponding antisense strand or antisense region of the siRNA molecule. The sense strand of an isolated oligonucleotides of the present disclosure molecule can include a nucleic acid sequence having some percentage identity with a target nucleic acid sequence such as a C3 mRNA sequence. In some cases, the sense region may have 100% identity, i.e., complete identity or homology, to the target nucleic acid sequence. In other cases, there may be one or more mismatches between the sense region and the target nucleic acid sequence. For example, there may be 1, 2, 3, 4, 5, 6, or 7 mismatches between the sense region and the target nucleic acid sequence.

As used herein, the term "antisense strand" or "antisense region" refers to a nucleotide sequence of the isolated oligonucleotides of the present disclosure, that is partially or fully complementary to at least a portion of a target nucleic acid sequence. The antisense strand of an isolated oligonucleotides of the present disclosure molecule can include a nucleic acid sequence that is complementary to at least a portion of a corresponding sense strand of the isolated oligonucleotides.

In some embodiments, the sense region comprises a sequence that is at least 70% identical, at least 75% identical, at least 80% identical, at least 85% identical, at least 90% identical, at least 95% identical, at least 97% identical, at least 99% identical or 100% identical to a sequence of SEQ ID NO: 1 or a region of SEQ ID NO: 1, as disclosed herein. In some embodiments, the sense region consists essentially of a sequence that is at least 70% identical, at least 75% identical, at least 80% identical, at least 85% identical, at least 90% identical, at least 95% identical, at least 97% identical, at least 99% identical or 100% identical to a sequence of SEQ ID NO: 1 or a region of SEQ ID NO: 1, as disclosed herein. In some embodiments, the sense region comprises a sequence that is identical to a sequence of SEQ ID NO: 1 or a region of SEQ ID NO: 1, as disclosed herein. In some embodiments, the sense region consists essentially of a sequence that is identical to a sequence of SEQ ID NO: 1 or a region of SEQ ID NO: 1, as disclosed herein.

In some embodiments, the sense region of the isolated oligonucleotides of the present disclosure targeting C3 has one or more mismatches between the sequence of the isolated oligonucleotides and the C3 sequence. For example, the sequence of the sense region may have 1, 2, 3, 4 or 5 mismatches between the sequence of the sense region of the isolated oligonucleotides and the C3 sequence. In some embodiments, the C3 sequence is a C3 3' untranslated region sequence (3' UTR). Without wishing to be bound by theory, it is thought that siRNAs targeting the 3' UTR have elevated mismatch tolerance when compared to mismatches in the isolated oligonucleotides targeting coding regions of a gene. Further, the isolated oligonucleotides RNAs may be tolerant of mismatches outside the seed region. As used herein, the “seed region” of the isolated oligonucleotides refers to base pairs 2-8 of the antisense region of the isolated oligonucleotides, i.e., the strand of the isolated oligonucleotides that is complementary to and hybridizes to the target mRNA.

In some embodiments, the antisense region comprises a sequence that is at least 70% identical, at least 75% identical, at least 80% identical, at least 85% identical, at least 90% identical, at least 95% identical, at least 97% identical, at least 99% identical or 100% identical to a sequence complementary to a sequence of SEQ ID NO: 1 or a region of SEQ ID NO: 1, as disclosed herein. In some embodiments, the antisense region consists essentially of a sequence that is at least 70% identical, at least 75% identical, at least 80% identical, at least 85% identical, at least 90% identical, at least 95% identical, at least 97% identical, at least 99% or 100% identical to a sequence complementary to a sequence of SEQ ID NO: 1 or a region of SEQ ID NO: 1. In some embodiments, the antisense region comprises a sequence that is identical to a sequence complementary to a sequence of SEQ ID NO: 1 or a region of SEQ ID NO: 1. In some embodiments, the sense region consists essentially of a sequence that is complementary to a sequence of SEQ ID NO: 1 or a region of SEQ ID NO: 1.

The antisense region of the C3 targeting isolated oligonucleotide of the present disclosure is complementary to the sense region. In some embodiments, the sense region and the antisense region are fully complementary (no mismatches). In some embodiments the antisense region is partially complementary to the sense region, i.e., there are 1, 2, 3, 4 or 5 mismatches between the sense region and the antisense region.

In general, isolated oligonucleotide of the present disclosure comprise an RNA duplex that is about 16 to about 25 nucleotides in length. In some embodiments, the RNA duplex is between about 17 and about 24 nucleotides in length, between about 18 and about 23 nucleotides in length, or between about 19 and about 22 nucleotides in length. In some embodiments, the RNA duplex is 19 nucleotides in length. In some embodiments, the RNA duplex is 20 nucleotides in length.

In some embodiments of the isolated oligonucleotide of the present disclosure, the sense strand is a single stranded RNA molecule. In some embodiments of the isolated oligonucleotide of the present disclosure, the antisense strand is a single stranded RNA molecule. In some embodiments, both the sense strand and the antisense strand are single stranded RNA molecules. In some embodiments, the isolated oligonucleotide of the present disclosure is an siRNA targeting C3 that comprises two different single stranded RNAs, the first comprising the sense region and the second comprising the antisense region, which hybridize to form an RNA duplex.

In some embodiments, the isolated oligonucleotide of the present disclosure can have one or more overhangs from the duplex region. In some embodiments, the overhangs, which are non-base-paired, single strand regions, can be from one to eight nucleotides in length, or longer. In some embodiments, the overhang can be a 3' overhang, wherein the 3'-end of a strand has a single strand region of from one to eight nucleotides. In some embodiments, the overhang can be a 5' overhang, wherein the 5'-end of a strand has a single strand region of from one to eight nucleotides. In some embodiments, the overhangs of the isolated oligonucleotide are the same length. In some embodiments, the overhangs of the isolated oligonucleotide are different lengths.

In some embodiments of the isolated oligonucleotide of the present disclosure, the single stranded RNA molecule of the sense strand comprises a 3' overhang. In some embodiments, the 3' overhang of the single stranded RNA molecule of the sense strand comprises at least one nucleotide. In some embodiments, the 3' overhang of the single stranded RNA molecule of the sense strand comprises two nucleotides.

In some embodiments of the isolated oligonucleotide of the present disclosure, the single stranded RNA molecule of the antisense strand comprises a 3' overhang. In some embodiments, the 3' overhang of the single stranded RNA molecule of the antisense strand comprises at least one nucleotide. In some embodiments, the 3' overhang of the single stranded RNA molecule of the antisense strand comprises two nucleotides.

In some embodiments of the isolated oligonucleotide of the present disclosure, both ends of isolated oligonucleotide have an overhang, for example, a 3' dinucleotide overhang on each end. In some embodiments, the overhangs at the 5'- and 3'-ends are of different lengths. In some embodiments, the overhangs at the 5'- and 3'-ends are of the same length.

In some embodiments of the isolated oligonucleotide of the present disclosure, the overhang can contain one or more deoxyribonucleotides, one or more ribonucleotides, or a combination of deoxyribonucleotides and ribonucleotides. In some embodiments, one, or both, of the overhang nucleotides of an siRNA may be 2'-deoxyribonucleotides.

In some embodiments of the isolated oligonucleotide of the present disclosure, the first single stranded RNA molecule comprises a first 3' overhang. In some embodiments, the second single stranded RNA molecule comprises a second 3' overhang. In some embodiments, the first and second 3' overhangs comprise a dinucleotide.

In some embodiments of the isolated oligonucleotide of the present disclosure, the 3' overhang comprises any one of thymidine-thymidine (dTdT), Adenine-Adenine (AA), Cysteine-Cysteine (CC), Guanine-Guanine (GG) or Uracil-Uracil (UU). In some embodiments, the isolated oligonucleotide of the present disclosure, the 3' overhang comprises a thymidine-thymidine (dTdT) or a Uracil-Uracil (UU) overhang. In some embodiments, the 3' overhang comprises a Uracil-Uracil (UU) overhang. Without wishing to be bound by theory, it is thought that 3' overhangs, such as dinucleotide overhangs, enhance siRNA mediated mRNA degradation by enhancing siRNA-RISC complex formation, and/or rate of cleavage of the target mRNA by the siRNA-RISC complex.

In some embodiments, the isolated oligonucleotide of the present disclosure can have one or more blunt ends, in which the duplex region ends with no overhang, and the strands are base paired to the end of the duplex region. In some embodiments, the isolated oligonucleotide of the present disclosure can have one or more blunt ends, or can have one or more overhangs, or can have a combination of a blunt end and an overhang end. For example, the 5' end of the siRNA can be blunt and the 3' end of the same isolated oligonucleotide comprise an overhang, or vice versa.

In some embodiments, both ends of the isolated oligonucleotide of the present disclosure are blunt ends.

In some embodiments of the isolated oligonucleotide of the present disclosure, the double stranded region comprises an antisense strand and a sense strand, according to any one of the pairs of antisense strand and sense strand sequences in Table 1, as described below.

The Complement System

The complement system is a critical component of the innate immune system and comprises a group of proteins that are normally present in an inactive state. These proteins are organized in three activation pathways: the classical, the lectin, and the alternative pathways.

Molecules from microorganisms, antibodies or cellular components can activate these pathways resulting in the formation of protease complexes known as the C3-convertase and the C5-convertase. The first enzymatically-activated cascade, known as classical pathway, is a calcium/magnesium-dependent cascade, which is normally activated by the formation of antigen-antibody complexes. It can also be activated in an antibody-independent manner by the binding of C-reactive protein complexed to ligand and by many pathogens including Gram-negative bacteria.

As described in U.S. Pat. No. 8,703,136, the classical pathway comprises several components, C1, C4, C2, C3 and C5 (listed by order in the pathway). Initiation of the classical pathway of the complement system occurs following binding and activation of the first complement component (C1) by both immune and non-immune activators. C1 comprises a calcium-dependent complex of components C1q, C1r and C1s, and is activated through binding of the C1q component. C1q contains six identical subunits and each subunit comprises three chains (the A, B and C chains). Each chain has a globular head region that is connected to a collagen-like tail. Binding and activation of C1q by antigen-antibody complexes occurs through the C1q head group region. Numerous non-antibody C1q activators, including proteins, lipids and nucleic acids, bind and activate C1q through a distinct site on the collagen-like stalk region. The C1qrs complex then catalyzes the activation of complement components C4 and C2, forming the C4b2a complex which functions as a C3 convertase.

The second enzymatically activated cascade, known as the alternative pathway, is a rapid, antibody-independent route for complement system activation and amplification. The alternative pathway is a magnesium-dependent cascade which is activated by deposition and activation of C3 on certain susceptible surfaces (e.g., cell wall polysaccharides of yeast and bacteria, and certain biopolymer materials). The alternative pathway comprises several components, that include: C3, Factor B, and Factor D (listed by order in the pathway). Activation of the alternative pathway occurs when C3b, a proteolytically cleaved form of C3, is bound to an activating surface agent such as a bacterium. Factor B is then bound to C3b and cleaved by Factor D to yield the active enzyme, Ba. The enzyme Ba then cleaves more C3 to generate more C3b, producing extensive deposition of C3b-Ba complexes on the activating surface.

Thus, both the classical and alternate complement pathways produce C3 convertases that split factor C3 into C3a and C3b. At this point, both C3 convertases further assemble into C5 convertases (C4b2a3b and C3b3bBb). These complexes subsequently cleave complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The larger C5b fragment binds sequentially to later components of the complement cascade, C6, C7, C8 and C9 to form the C5b-9 membrane attack complex ("MAC"). The lipophylic C5b-9 MAC can directly lyse erythrocytes, and in greater quantities it is lytic for leukocytes and damaging to tissues such as muscle, epithelial and endothelial cells. In sublytic amounts, the C5b-9 MAC can stimulate upregulation of adhesion molecules, intracellular calcium increase and cytokine release. In addition, at sublytic concentrations the C5b-9 MAC can stimulate cells such as endothelial cells and platelets without causing cell lysis. The non-lytic effects of C5a and the C5b-9 MAC are comparable and interchangeable.

The lectin pathway is initiated when pattern-recognition molecules (MBL, CL-K1, and ficolins) bind to the so-called pathogen-associated molecular patterns (PAMPs) (D-mannose, N-acetyl-D-glucosamine, or acetyl groups), on the surface of pathogens or to apoptotic or necrotic cells (Beltrame et. al, 2015).

Although the complement system has an important role in the maintenance of health, it has the potential to cause or contribute to disease.

There are four diseases for which complement-targeted drugs are approved for routine clinical use by the US Food and Drug Administration (FDA) and the European Medicines Agency (Garred et. al., 2021). Eculizumab (Soliris), a mAb-blocking cleavage of C5, was shown to be very efficient in protecting from hemolysis in PNH in 2007 (Brodsky et al., 2008; Parker, 2009), and this was later followed by treatment of atypical hemolytic-uremic syndrome (aHUS) (Tschumi et al., 2011; Loirat et al., 2016). Recently it was also approved for the neurologic diseases generalized myasthenia gravis (Dhillon, 2018) and neuromyelitis optica spectrum disorders (Selmaj and Selmaj, 2019).

Eculizumab has been the only approved complement inhibitor for routine use until recently when ravulizumab (Ultomiris) and Zilucoplan were introduced. Ravulizumab is the second generation of eculizumab; in other words, some minor amino acid modifications were made in the eculizumab molecule, thereby increasing the half-life substantially so treatment intervals could be increased from every 2nd to every 8th week. It has the same binding site to C5 as eculizumab (i.e., blocking its cleavage and thereby preventing the release of C5a and formation of C5b-9) (Kulasekararaj et al., 2019; Lee et al., 2019; McKeage, 2019; Stern and Connell, 2019; Lee and Kulasekararaj, 2020).

Zilucoplan is an entirely different drug structurally from the antibody mentioned above but with the same principal function. It is a synthetic, macrocyclic peptide inhibitor for subcutaneous self-administration with principally the same function as eculizumab, blocking the cleavage of C5 (Beecher et al., 2019; Albazli et al., 2020; Howard et al., 2020). A phase 2 randomized, double blind, placebo-controlled, multicenter clinical trial demonstrated that Zilucoplan administration yielded rapid, meaningful, and sustained improvements over 12 weeks in a broad population of patients with moderate-to-severe acetylcholine-receptor-antibody-positive generalized myasthenia gravis (Howard et al., 2020). RA 101295, a close analog of Zilucoplan (RA101495), has been used in animal studies and has been shown to increase survival in baboon *Escherichia coli* sepsis (Keshari et al., 2017).

Accordingly, the isolated oligonucleotides disclosed in the present disclosure are useful in treating or preventing a disease or disorder associated with aberrant or increased expression or activity of C3 or a disease or disorder where C3 plays a role. Exemplary isolated oligonucleotides of the present disclosure are described in Table 1. In some embodiments of the isolated oligonucleotide of the present disclosure, the sense strand comprises a sequence selected from any one of the group of sense strand/passenger strand sequences listed in Table 1, Table 2 and Table 3. In some embodiments, the antisense strand comprises a sequence selected from any one of the group of antisense strand/guide strand sequences listed in Table 1, Table 2 and Table 3. In some embodiments, the sense and antisense regions comprise complementary sequences selected from the group listed in Table 1, Table 2 and Table 3.

In some embodiments of the isolated oligonucleotide of the present disclosure, the antisense strand comprises a nucleotide sequence according to any one of: SEQ ID NOs: 2-31.

In some embodiments of the isolated oligonucleotide of the present disclosure, the sense strand comprises a nucleotide sequence according to any one of: SEQ ID NOs: 32-61.

In some embodiments of the isolated oligonucleotide of the present disclosure, the antisense strand comprises a nucleotide sequence according to any one of: SEQ ID NOs: 2-31; and the sense strand comprises a nucleotide sequence according to any one of: SEQ ID NOs: 32-61, wherein the antisense strand and the sense strand sequences have sufficient complementarity to allow formation of a double stranded region between the antisense and the sense strand.

Sequences of the Present Disclosure

The present disclosure provides an isolated oligonucleotide comprising a sense and an antisense strand, wherein the sense strand comprises a nucleotide sequence that is substantially identical to a region between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region.

The present disclosure provides an isolated oligonucleotide comprising a sense and an antisense strand, wherein the sense strand comprises a nucleotide sequence that is at least 70%, at least 80%, at least 90%, at least 95%, or at least 99% identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is identical to a region comprising 19-25 nucleotides between any one of the nucleotide positions selected from: a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is substantially identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is at least 70%, at least 80%, at least 90%, at least 95%, or at least 99% identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is identical to a region comprising the sequence between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1.

In some embodiments of the isolated oligonucleotide of the present disclosure, wherein the sense strand comprises a nucleotide sequence that is identical to a region between any one of the nucleotide positions selected from: a) 1281 to 1301; b) 1797 to 1817; c) 2862 to 2882; d) 4402 to 4424; and e) 4520 to 4540, from the 5' end of a human complement C3 mRNA sequence according to SEQ ID NO: 1, the double stranded region comprises: i) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3'); ii) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3'); iii) an antisense strand of nucleic acid sequence according to SEQ ID NO: 15 (5' UUUUUGUUCAUUCUGAUUCCUU 3'), and a sense strand of nucleic acid sequence according to SEQ ID NO: 45

(5' GGAAUCAGAAUGAACAAAAA 3'); iv) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3'); v) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3'); or vi) an antisense strand of nucleic acid sequence according to SEQ ID NO: 27 (5' UGUAGAACCGGGUACAGCUUUC 3'), and a sense strand of nucleic acid sequence according to SEQ ID NO: 57 (5' AAGCUGUACCCGGUUCUACA 3').

The present disclosure provides an isolated oligonucleotide comprising a sense and an antisense strand, wherein the sense strand comprises a sequence that is substantially identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

The present disclosure provides an isolated oligonucleotide comprising a sense and an antisense strand, wherein the sense strand comprises a sequence that is at least 70%, at least 80%, at least 90%, at least 95%, or at least 99% identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1.

In some embodiments of the isolated oligonucleotide of the present disclosure, wherein the sense strand comprises a nucleotide sequence that is identical to a region comprising the sequence between any one of the nucleotide positions selected from: a) 772 to 801; b) 2424 to 2444; c) 3784 to 3805; d) 4123 to 4169; e) 4438 to 4509; and f) 4558 to 4621, from the 5' end of a human complement C3 mRNA sequence according to SEQ ID NO: 1, the double stranded region comprises: i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3'); ii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3'); iii) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3'); iv) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3'); v) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3'); vi) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3'); vii) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3'); viii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3'); ix) an antisense strand of nucleic acid sequence according to SEQ ID NO: 21 (5' UCUGGUUUUAUGGUGACCUUGA 3'), and a sense strand of nucleic acid sequence according to SEQ ID NO: 51 (5' AAGGUCACCAUAAAACCAGA 3'); x) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3'); xi) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3'); xii) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3'); or xiii) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3').

The present disclosure provides an isolated oligonucleotide comprising a sense and an antisense strand, wherein sense strand comprises a sequence that is substantially identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

The present disclosure provides an isolated oligonucleotide comprising a sense and an antisense strand, wherein sense strand comprises a sequence that is at least 70%, at least 80%, at least 90%, at least 95%, or at least 99% identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

The present disclosure provides an isolated oligonucleotide comprising a sense and an antisense strand, wherein the sense strand comprises a nucleotide sequence that is identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a human complement C3 mRNA sequence according to SEQ ID NO: 1.

In some embodiments of the isolated oligonucleotide of the present disclosure, the sense strand comprises a sequence that is identical to a region comprising the sequence between any one of the nucleotide positions selected from: a) 588 to 608; b) 773 to 800; c) 2533 to 2585; d) 3778 to 3836; e) 4492 to 4512; and f) 4600 to 4625, from the 5' end of a C3 mRNA sequence according to SEQ ID NO: 1, and the double stranded region comprises: i) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3'); ii) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3'); iii) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3'); iv) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3'); v) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3'); vi) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3'); vii) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3'); viii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3'); ix) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3'); x) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); or xi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

At Least 50% Knockdown of C3 at 0.1 nM

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, wherein the isolated oligonucleotide attenuates expression of the C3 mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.1 nM.

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.1 nM, wherein the double stranded region comprises: i) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3'); ii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3'); iii) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3'); iv) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3'); v) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3'); vi) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3'); vii) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3'); viii) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3'); ix) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3'); x) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3'); xi) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3'); xii) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3'); xiii) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3'); xiv) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3'); xv) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3'); xvi) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3'); xvii) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3'); xviii) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3'); xix) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); xx) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3'); xxi) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3'); xxii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3'); xxiii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3'); xxiv) an antisense strand of nucleic acid sequence according to SEQ ID NO: 15 (5' UUUUUGUUCAUUCUGAUUCCUU 3'), and a sense strand of nucleic acid sequence according to SEQ ID NO: 45 (5' GGAAUCAGAAUGAACAAAAA 3'); xxv) an antisense strand of nucleic acid sequence according to SEQ ID NO: 21 (5' UCUGGUUUUAUGGUGACCUUGA 3'), and a sense strand of nucleic acid sequence according to SEQ ID NO: 51 (5' AAGGUCACCAUAAAACCAGA 3'); xxvi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3'); xxvii) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3'); xxviii) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3'); xxix) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3'); or xxx) an antisense strand of nucleic acid sequence according to SEQ ID NO: 27 (5' UGUAGAACCGGGUACAGCUUUC 3'), and a sense strand of nucleic acid sequence according to SEQ ID NO: 57 (5' AAGCUGUACCCGGUUCUACA 3').

20-50% Knockdown of C3 at 0.1 nM

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, wherein the isolated oligonucleotide attenuates expression of the C3 mRNA by 20% to 50% (e.g., 20% to 25%, 25% to 30%, 30% to 35%, 35% to 40%, 40% to 45% or 45% to 50%), at a dose of 0.1 nM.

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%), at a dose of 0.1 nM, wherein the double stranded region comprises: i) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3'); ii) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3'); iii) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3'); iv) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3'); v) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3'); vi) an antisense strand of nucleic acid sequence according to SEQ ID NO: 15 (5' UUUUUGUUCAUUCUGAUUCCUU 3'), and a sense strand of nucleic acid sequence according to SEQ ID NO: 45 (5' GGAAUCAGAAUGAACAAAAA 3'); vii) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3'); or viii) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3').

At Least 50% Knockdown of C3 at 0.01 nM

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, wherein the isolated oligonucleotide attenuates expression of the C3 mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.01 nM.

In some embodiments of the isolated oligonucleotide of the present disclosure, the sense strand comprises a sequence that is identical to a region comprising the sequence between any one of the nucleotide positions selected from a) 588 to 608; b) 772 to 801; c) 1281 to 1301; d) 1797 to 1817; e) 2424 to 2444; f) 2533 to 2585; g) 2862 to 2882; h) 3778 to 3836; i) 4123 to 4169; and j) 4402 to 4625, from the 5' end of a human complement C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.01 nM, wherein the double stranded region comprises: i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3'); ii) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); iii) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3'); iv) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3'); v) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3'); vi) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3'); vii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3'); viii) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3'); ix) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3'); x) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3'); xi) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3'); xii) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3'); xiii) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3'); xiv) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3'); xv) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3'); xvi) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3'); xvii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3'); xviii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3'); xix) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3'); xx) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3'); xxi) an antisense strand of nucleic acid sequence according to SEQ ID NO: 27 (5' UGUAGAACCGGGUACAGCUUUC 3'), and a sense strand of nucleic acid sequence according to SEQ ID NO: 57 (5' AAGCUGUACCCGGUUCUACA 3'); or xxii) an antisense strand of nucleic acid sequence according to SEQ ID NO: 21 (5' UCUGGUUUUAUGGUGACCUUGA 3'), and a sense strand of nucleic acid sequence according to SEQ ID NO: 51 (5' AAGGUCACCAUAAAACCAGA 3').

The present disclosure provides an isolated oligonucleotide comprising a sense strand and an antisense strand, wherein the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%) at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%) at a dose of 0.1 nM, wherein the double stranded region comprises: i) an antisense strand of nucleic acid sequence according to SEQ ID NO: 71 (5' UGUAGAUGGUCUUGUCUGUCUG 3'), and a sense strand of nucleic acid sequence according to SEQ ID NO: 236 (5' GACAGACAAGACCAUCUACA 3'); ii) an antisense strand of nucleic acid sequence according to SEQ ID NO: 106 (5' UUGAUGCUCAAGGGCUUCUGGC 3'), and a sense strand of nucleic acid sequence according to SEQ ID NO: 271 (5' CAGAAGCCCUUGAGCAUCAA 3'); iii) an antisense strand of nucleic acid sequence according to SEQ ID NO: 97 (5' UAAGAUGACAAAGGCAGUUCCC 3'), and a sense strand of nucleic acid sequence according to SEQ ID NO: 262 (5' GAACUGCCUUUGUCAUCUUA 3'); iv) an antisense strand of nucleic acid sequence according to SEQ ID NO: 168 (5' UCAAAGUCAAAGUCUUUUAGCU 3'), and a sense strand of nucleic acid sequence according to SEQ ID NO: 333 (5' CUAAAAGACUUUGACUUUGA 3'); v) an antisense strand of nucleic acid sequence according to SEQ ID NO: 115 (5' UGAAGGAAGGGAUGAAGUCGGU 3'), and a sense strand of nucleic acid sequence according to SEQ ID NO: 280 (5' CGACUUCAUCCCUUCCUUCA 3'); vi) an antisense strand of nucleic acid sequence according to SEQ ID NO: 173 (5' UCUUUUGGUAUUGAGCCAAGGC 3'), and a sense strand of nucleic acid sequence according to SEQ ID NO: 338 (5' CUUGGCUCAAUACCAAAAGA 3'); vii) an antisense strand of nucleic acid sequence according to SEQ ID NO: 116 (5' UUUCUGACUGGCCGCUUUUUAC 3'), and a sense strand of nucleic acid sequence according to SEQ ID NO: 281 (5' AAAAAGCGGCCAGUCAGAAA 3'); viii) an antisense strand of nucleic acid sequence according to SEQ ID NO: 169 (5' UCACAAAGUCAAAGUCUUUUAG 3'), and a sense strand of nucleic acid sequence according to SEQ ID NO: 334 (5' AAAAGACUUUGACUUUGUGA 3'); ix) an antisense strand of nucleic acid sequence according to SEQ ID NO: 66 (5' UGUUUUUUGCCUGGGAAGUCGU 3'), and a sense strand of nucleic acid sequence according to SEQ ID NO: 231 (5' GACUUCCCAGGCAAAAAACA 3'); x) an antisense strand of nucleic acid sequence according to SEQ ID NO: 153 (5' UUGAAGGCCAGCUGCUGGGUGU 3'), and a sense strand of nucleic acid sequence according to SEQ ID NO: 318 (5' ACCCAGCAGCUGGCCUUCAA 3'); xi) an antisense strand of nucleic acid sequence according to SEQ ID NO: 189 (5' UCUGUUUCCGGUGCUGGUUUUA 3'), and a sense strand of nucleic acid sequence according to SEQ ID NO: 354 (5' AAACCAGCACCGGAAACAGA 3'); xii) an antisense strand of nucleic acid sequence according to SEQ ID NO: 103 (5' UUGUUGAUGCUGAGUUUGGCCA 3'), and a sense strand of nucleic acid sequence according to SEQ ID NO: 268 (5' GCCAAACUCAGCAUCAACAA 3'); xiii) an antisense strand of nucleic acid sequence according to SEQ ID NO: 225 (5' UGUCCAACCUGCACCUCAUCCG 3'), and a sense strand of nucleic acid sequence according to SEQ ID NO: 390 (5' GAUGAGGUGCAGGUUGGACA 3'); xiv) an antisense strand of nucleic acid sequence according to SEQ ID NO: 117 (5' UAUCUUCAGGGUCAUCUGCUGC 3'), and a sense strand of nucleic acid sequence according to SEQ ID NO: 282 (5' AGCAGAUGACCCUGAAGAUA 3'); xv) an antisense strand of nucleic acid sequence according to SEQ ID NO: 81 (5' UCAUAGUAGGCUCGGAUCUUCC 3'), and a sense strand of nucleic acid sequence according to SEQ ID NO: 246 (5' AAGAUCCGAGCCUACUAUGA 3'); xvi) an antisense strand of nucleic acid sequence according to SEQ ID NO: 133 (5' UGUUUCGAACAACAGAGUAGGG 3'), and a sense strand of nucleic acid sequence according to SEQ ID NO: 298 (5' CUACUCUGUUGUUCGAAACA 3'); xvii) an antisense strand of nucleic acid sequence according to SEQ ID NO: 107 (5' UCAGGUAAUUGUUGGAGUUGCC 3'), and a sense strand of nucleic acid sequence according to SEQ ID NO: 272 (5' CAACUCCAACAAUUACCUGA 3'); xviii) an antisense strand of nucleic acid sequence according to SEQ ID NO: 68 (5' UGUCUGUCUGGAUGAAGAGGUA 3'), and a sense strand of nucleic acid sequence according to SEQ ID NO: 233 (5' CCUCUUCAUCCAGACAGACA 3'); xix) an antisense strand of nucleic acid sequence according to SEQ ID NO: 222 (5' UGUACUCGUCAAAGUCAUUGGA 3'), and a sense strand of nucleic acid sequence according to SEQ ID NO: 387 (5' CAAUGACUUUGACGAGUACA 3'); xx) an antisense strand of nucleic acid sequence according to SEQ ID NO: 139 (5' UGGAUUGUGGAGUAGUUCCACC 3'), and a sense strand of nucleic acid sequence according to SEQ ID NO: 304 (5' UGGAACUACUCCACAAUCCA 3'); xxi) an antisense strand of nucleic acid sequence according to SEQ ID NO: 158 (5' UGGAAGUCUCCUGCUUUAGUGA 3'), and a sense strand of nucleic acid sequence according to SEQ ID NO: 323 (5' ACUAAAGCAGGAGACUUCCA 3'); xxii) an antisense strand of nucleic acid sequence according to SEQ ID NO: 83 (5' UUUUCAUAGUAGGCUCGGAUCU 3'), and a sense strand of nucleic acid sequence according to SEQ ID NO:

248 (5' AUCCGAGCCUACUAUGAAAA 3'); xxiii) an antisense strand of nucleic acid sequence according to SEQ ID NO: 156 (5' UCAGGAUCAGCCAUUUAACAGC 3'), and a sense strand of nucleic acid sequence according to SEQ ID NO: 321 (5' UGUUAAAUGGCUGAUCCUGA 3'); xxiv) an antisense strand of nucleic acid sequence according to SEQ ID NO: 208 (5' UCUUGUCCAGGUAGAUGAUGAG 3'), and a sense strand of nucleic acid sequence according to SEQ ID NO: 373 (5' CAUCAUCUACCUGGACAAGA 3'); XXV) an antisense strand of nucleic acid sequence according to SEQ ID NO: 62 (5' UGACAGUGCAGGGUCAGAGGGA 3'), and a sense strand of nucleic acid sequence according to SEQ ID NO: 227 (5' CCUCUGACCCUGCACUGUCA 3'); xxvi) an antisense strand of nucleic acid sequence according to SEQ ID NO: 202 (5' UCUAUCGGAGAAGGCUUUGUCC 3'), and a sense strand of nucleic acid sequence according to SEQ ID NO: 367 (5' ACAAAGCCUUCUCCGAUAGA 3'); xxvii) an antisense strand of nucleic acid sequence according to SEQ ID NO: 80 (5' UCUUCCACUGGCCCAUGUUGAC 3'), and a sense strand of nucleic acid sequence according to SEQ ID NO: 245 (5' CAACAUGGGCCAGUGGAAGA 3'); xxviii) an antisense strand of nucleic acid sequence according to SEQ ID NO: 174 (5' UGAUUCCCAGUGGAUACGGUGG 3'), and a sense strand of nucleic acid sequence according to SEQ ID NO: 339 (5' ACCGUAUCCACUGGGAAUCA 3'); xxix) an antisense strand of nucleic acid sequence according to SEQ ID NO: 65 (5' UUUUUUUGCCUGGGAAGUCGUG 3'), and a sense strand of nucleic acid sequence according to SEQ ID NO: 230 (5' CGACUUCCCAGGCAAAAAAA 3'); xxx) an antisense strand of nucleic acid sequence according to SEQ ID NO: 214 (5' UGGUUGUAAUAGGCGUAGACCU 3'), and a sense strand of nucleic acid sequence according to SEQ ID NO: 379 (5' GUCUACGCCUAUUACAACCA 3'); xxxi) an antisense strand of nucleic acid sequence according to SEQ ID NO: 141 (5' UCUGCAGAAGGCUGGAUUGUGG 3'), and a sense strand of nucleic acid sequence according to SEQ ID NO: 306 (5' ACAAUCCAGCCUUCUGCAGA 3'); xxxii) an antisense strand of nucleic acid sequence according to SEQ ID NO: 91 (5' UCUCUGUAGGCUCCACUAUGAC 3'), and a sense strand of nucleic acid sequence according to SEQ ID NO: 256 (5' CAUAGUGGAGCCUACAGAGA 3'); xxxiii) an antisense strand of nucleic acid sequence according to SEQ ID NO: 88 (5' UGAAACUGGGCAGCACGUACUC 3'), and a sense strand of nucleic acid sequence according to SEQ ID NO: 253 (5' GUACGUGCUGCCCAGUUUCA 3'); xxxiv) an antisense strand of nucleic acid sequence according to SEQ ID NO: 165 (5' UCUGCAGUAGGGCCAAGAGGGC 3'), and a sense strand of nucleic acid sequence according to SEQ ID NO: 330 (5' CCUCUUGGCCCUACUGCAGA 3'); xxxv) an antisense strand of nucleic acid sequence according to SEQ ID NO: 140 (5' UCUGGAUUGUGGAGUAGUUCCA 3'), and a sense strand of nucleic acid sequence according to SEQ ID NO: 305 (5' GAACUACUCCACAAUCCAGA 3'); xxxvi) an antisense strand of nucleic acid sequence according to SEQ ID NO: 183 (5' UCUUUUCCUUCAGCUGUGACUG 3'), and a sense strand of nucleic acid sequence according to SEQ ID NO: 348 (5' GUCACAGCUGAAGGAAAAGA 3'); xxxvii) an antisense strand of nucleic acid sequence according to SEQ ID NO: 179 (5' UCUGUGAAACCCUCAUUUUCCU 3'), and a sense strand of nucleic acid sequence according to SEQ ID NO: 344 (5' GAAAAUGAGGGUUUCACAGA 3'); xxxviii) an antisense strand of nucleic acid sequence according to SEQ ID NO: 127 (5' UCAUUACUGUGACCUCGAAGGG 3'), and a sense strand of nucleic acid sequence according to SEQ ID NO: 292 (5' CUUCGAGGUCACAGUAAUGA 3'); xxxix) an antisense strand of nucleic acid sequence according to SEQ ID NO: 185 (5' UGAGGUCGAAUUUAUUACAGGU 3'), and a sense strand of nucleic acid sequence according to SEQ ID NO: 350 (5' CUGUAAUAAAUUCGACCUCA 3'); xL) an antisense strand of nucleic acid sequence according to SEQ ID NO: 111 (5' UCAUUCGCAGGAGGAAGUUGAC 3'), and a sense strand of nucleic acid sequence according to SEQ ID NO: 276 (5' CAACUUCCUCCUGCGAAUGA 3'); xLi) an antisense strand of nucleic acid sequence according to SEQ ID NO: 157 (5' UGUAUCACGGGCGCAUCCUCCU 3'), and a sense strand of nucleic acid sequence according to SEQ ID NO: 322 (5' GAGGAUGCGCCCGUGAUACA 3'); xLii) an antisense strand of nucleic acid sequence according to SEQ ID NO: 164 (5' UCAGCAAUGGCCACAGUGUAGG 3'), and a sense strand of nucleic acid sequence according to SEQ ID NO: 329 (5' UACACUGUGGCCAUUGCUGA 3'); xLiii) an antisense strand of nucleic acid sequence according to SEQ ID NO: 90 (5' UCACUAUGACCUCGAAACUGGG 3'), and a sense strand of nucleic acid sequence according to SEQ ID NO: 255 (5' CAGUUUCGAGGUCAUAGUGA 3'); xLiv) an antisense strand of nucleic acid sequence according to SEQ ID NO: 87 (5' UGUACUCCUUCACCUCAAACUC 3'), and a sense strand of nucleic acid sequence according to SEQ ID NO: 252 (5' GUUUGAGGUGAAGGAGUACA 3'); xLx) an antisense strand of nucleic acid sequence according to SEQ ID NO: 199 (5' UCUCAUACUUGGAGAUGUAUCU 3'), and a sense strand of nucleic acid sequence according to SEQ ID NO: 364 (5' AUACAUCUCCAAGUAUGAGA 3'); xLvi) an antisense strand of nucleic acid sequence according to SEQ ID NO: 184 (5' UCUUAGCAUGGUACAUUGUCAC 3'), and a sense strand of nucleic acid sequence according to SEQ ID NO: 349 (5' GACAAUGUACCAUGCUAAGA 3'); xLvii) an antisense strand of nucleic acid sequence according to SEQ ID NO: 400 (5' UUGUAGUUGCAGCAGUCCAGGA 3'), and a sense strand of nucleic acid sequence according to SEQ ID NO: 426 (5' CUGGACUGCUGCAACUACAA 3'); xLiii) an antisense strand of nucleic acid sequence according to SEQ ID NO: 110 (5' UGAGGAAGUUGACGUUGAGGGU 3'), and a sense strand of nucleic acid sequence according to SEQ ID NO: 275 (5' CCUCAACGUCAACUUCCUCA 3'); xLix) an antisense strand of nucleic acid sequence according to SEQ ID NO: 147 (5' UGGCAUCCUCUGUCAUCUGGGC 3'), and a sense strand of nucleic acid sequence according to SEQ ID NO: 312 (5' CCAGAUGACAGAGGAUGCCA 3'); L) an antisense strand of nucleic acid sequence according to SEQ ID NO: 218 (5' UUUUUGUAUGAAGCAAUUCUCC 3'), and a sense strand of nucleic acid sequence according to SEQ ID NO: 383 (5' AGAAUUGCUUCAUACAAAAA 3'); Li) an antisense strand of nucleic acid sequence according to SEQ ID NO: 138 (5' UGAUUGUGGAGUAGUUCCACCC 3'), and a sense strand of nucleic acid sequence according to SEQ ID NO: 303 (5' GUGGAACUACUCCACAAUCA 3'); Lii) an antisense strand of nucleic acid sequence according to SEQ ID NO: 114 (5' UGAUGAAGUCGGUGGUGAUGGA 3'), and a sense strand of nucleic acid sequence according to SEQ ID NO: 279 (5' CAUCACCACCGACUUCAUCA 3'); Liii) an antisense strand of nucleic acid sequence according to SEQ ID NO: 85 (5' UCUCCUUCACCUCAAACUCAGU 3'), and a sense strand of nucleic acid sequence according to SEQ ID NO: 250 (5' UGAGUUUGAGGUGAAGGAGA 3'); Liv) an antisense strand of nucleic acid sequence according to SEQ ID NO: 152 (5' UCUUCUUGAUGAGCUCCAAGGC 3'), and a sense strand of nucleic acid sequence according to SEQ ID NO: 317 (5' CUUGGAGCUCAUCAAGAAGA 3'); LV) an antisense strand of nucleic acid sequence according to SEQ ID NO: 402 (5' UCUCAUCCAGGUUACUCCUGGC 3'), and a sense strand of nucleic acid sequence according to SEQ ID NO: 428 (5' CAGGAGUAACCUGGAUGAGA 3'); L.vi) an antisense strand of nucleic acid sequence according to SEQ ID NO: 136 (5' UCUUGGUUCUGCCG-GUAAUUGU 3'), and a sense strand of nucleic acid sequence according to SEQ ID NO: 301 (5' AAUUACCGGCAGAACCAAGA 3'); Lvii) an antisense strand of nucleic acid sequence according to SEQ ID NO: 209 (5' UGACCUUGUCCAGGUAGAUGAU 3'), and a sense strand of nucleic acid sequence according to SEQ ID NO: 374 (5' CAUCUACCUGGACAAGGUCA 3'); or Lviii) an antisense strand of nucleic acid sequence according to SEQ ID NO: 412 (5' UCUCUGGGAACUCACUUCGGGA 3'), and a sense strand of nucleic acid sequence according to SEQ ID NO: 438 (5' CCGAAGUGAGUUCCCAGAGA 3').

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.1 nM, wherein the double stranded region comprises: i) an antisense strand of nucleic acid sequence according to SEQ ID NO: 94 (5' UUAGAUGUAGUAGAAUUUCUCU 3'), and a sense strand of nucleic acid sequence according to SEQ ID NO: 259 (5' AGAAAUUCUACUACAUCUAA 3'); ii) an antisense strand of nucleic acid sequence according to SEQ ID NO: 74 (5' UGACAAGGAGUCCUGCUUGACC 3'), and a sense strand of nucleic acid sequence according to SEQ ID NO: 239 (5' UCAAGCAGGACUCCUUGUCA 3'); iii) an antisense strand of nucleic acid sequence according to SEQ ID NO: 70 (5' UUAGAUGGUCUUGUCUGUCUGG 3'), and a sense strand of nucleic acid sequence according to SEQ ID NO: 235 (5' AGACAGACAAGACCAUCUAA 3'); iv) an antisense strand of nucleic acid sequence according to SEQ ID NO: 64 (5' UUUUUUGCCUGGGAAGUCGUGG 3'), and a sense strand of nucleic acid sequence according to SEQ ID NO: 229 (5' ACGACUUCCCAGGCAAAAAA 3'); v) an antisense strand of nucleic acid sequence according to SEQ ID NO: 172 (5' UUAGUAUCUCUGUUCAUUGAGC 3'), and a sense strand of nucleic acid sequence according to SEQ ID NO: 337 (5' UCAAUGAACAGAGAUACUAA 3'); vi) an antisense strand of nucleic acid sequence according to SEQ ID NO: 226 (5' UGUCAGUUGGGGCACCCAAAGA 3'), and a sense strand of nucleic acid sequence according to SEQ ID NO: 391 (5' UUUGGGUGCCCCAACUGACA 3'); vii) an antisense strand of nucleic acid sequence according to SEQ ID NO: 217 (5' UUUGUAUGAAGCAAUUCUC-CUC 3'), and a sense strand of nucleic acid sequence according to SEQ ID NO: 382 (5' GGAGAAUUGCUU-CAUACAAA 3'); viii) an antisense strand of nucleic acid sequence according to SEQ ID NO: 131 (5' UGAACAACAGAGUAGGGUAGCC 3'), and a sense strand of nucleic acid sequence according to SEQ ID NO: 296 (5' CUACCCUACUCUGUUGUUCA 3'); ix) an antisense strand of nucleic acid sequence according to SEQ ID NO: 113 (5' UAUCAGGUAGGUGUAGUAGCGG 3'), and a sense strand of nucleic acid sequence according to SEQ ID NO: 278 (5' GCUACUACACCUACCUGAUA 3'); x) an antisense strand of nucleic acid sequence according to SEQ ID NO: 126 (5' UAUUACUGUGACCUCGAAGGGG 3'), and a sense strand of nucleic acid sequence according to SEQ ID NO: 291 (5' CCUUCGAGGUCACAGUAAUA 3'); xi) an antisense strand of nucleic acid sequence according to SEQ ID NO: 146 (5' UGAAUUCUGGUCUCAGACUCGG 3'), and a sense strand of nucleic acid sequence according to SEQ ID NO: 311 (5' GAGUCUGAGACCAGAAUUCA 3'); xii) an antisense strand of nucleic acid sequence according to SEQ ID NO: 170 (5' UGUAUCUCUGUU-CAUUGAGCCA 3'), and a sense strand of nucleic acid sequence according to SEQ ID NO: 335 (5' GCU-CAAUGAACAGAGAUACA 3'); xiii) an antisense strand of nucleic acid sequence according to SEQ ID NO: 123 (5' UUUUCAAAAAUAUAUUCAUGAG 3'), and a sense strand of nucleic acid sequence according to SEQ ID NO: 288 (5' CAUGAAUAUAUUUUUGAAAA 3'); xiv) an antisense strand of nucleic acid sequence according to SEQ ID NO: 93 (5' UAGUAGAAUUUCUCUGUAGGCU 3'), and a sense strand of nucleic acid sequence according to SEQ ID NO: 258 (5' CCUACAGAGAAAUUCUACUA 3'); xv) an antisense strand of nucleic acid sequence according to SEQ ID NO: 124 (5' UCUUUCAAAAAUAUAUUCAUGA 3'), and a sense strand of nucleic acid sequence according to SEQ ID NO: 289 (5' AUGAAUAUAUUUUUGAAAGA 3'); xvi) an antisense strand of nucleic acid sequence according to SEQ ID NO: 198 (5' UCAUACUUGGAGAU-GUAUCUGU 3'), and a sense strand of nucleic acid sequence according to SEQ ID NO: 363 (5' AGAUACAU-CUCCAAGUAUGA 3'); xvii) an antisense strand of nucleic acid sequence according to SEQ ID NO: 145 (5' UAAUUCUGGUCUCAGACUCGGU 3'), and a sense strand of nucleic acid sequence according to SEQ ID NO: 310 (5' CGAGUCUGAGACCAGAAUUA 3'); xviii) an antisense strand of nucleic acid sequence according to SEQ ID NO: 188 (5' UGUUUUAUGGUGACCUUGAGGU 3'), and a sense strand of nucleic acid sequence according to SEQ ID NO: 353 (5' CUCAAGGUCACCAUAAAACA 3');

xix) an antisense strand of nucleic acid sequence according to SEQ ID NO: 67 (5' UCUGUCUGGAUGAAGAGGUACC 3'), and a sense strand of nucleic acid sequence according to SEQ ID NO: 232 (5' UACCUCUUCAUCCAGACAGA 3'); xx) an antisense strand of nucleic acid sequence according to SEQ ID NO: 72 (5' UUGUAGAUGGUCUUGUCUGUCU 3'), and a sense strand of nucleic acid sequence according to SEQ ID NO: 237 (5' ACAGACAAGACCAUCUACAA 3'); xxi) an antisense strand of nucleic acid sequence according to SEQ ID NO: 159 (5' UAAGGAAGUCUCCUGCUUUAGU 3'), and a sense strand of nucleic acid sequence according to SEQ ID NO: 324 (5' UAAAGCAGGAGACUUCCUUA 3'); xxii) an antisense strand of nucleic acid sequence according to SEQ ID NO: 181 (5' UUUCCUUCAGCUGUGACUGUGA 3'), and a sense strand of nucleic acid sequence according to SEQ ID NO: 346 (5' ACAGUCACAGCUGAAGGAAA 3'); xxiii) an antisense strand of nucleic acid sequence according to SEQ ID NO: 108 (5' UGAGAUGCAGGUAAUUGUUGGA 3'), and a sense strand of nucleic acid sequence according to SEQ ID NO: 273 (5' CAACAAUUACCUGCAUCUCA 3'); xxiv) an antisense strand of nucleic acid sequence according to SEQ ID NO: 96 (5' UAGAUGACAAAGGCAGUUCCCU 3'), and a sense strand of nucleic acid sequence according to SEQ ID NO: 261 (5' GGAACUGCCUUUGUCAUCUA 3'); xxv) an antisense strand of nucleic acid sequence according to SEQ ID NO: 129 (5' UGAAGAAGUCCUGCAUUACUGU 3'), and a sense strand of nucleic acid sequence according to SEQ ID NO: 294 (5' AGUAAUGCAGGACUUCUUCA 3'); xxvi) an antisense strand of nucleic acid sequence according to SEQ ID NO: 196 (5' UUACUUGGAGAUGUAUCUGUCA 3'), and a sense strand of nucleic acid sequence according to SEQ ID NO: 361 (5' ACAGAUACAUCUCCAAGUAA 3'); xxvii) an antisense strand of nucleic acid sequence according to SEQ ID NO: 122 (5' UUUCAAAAAUAUAUUCAUGAGC 3'), and a sense strand of nucleic acid sequence according to SEQ ID NO: 287 (5' UCAUGAAUAUAUUUUUGAAA 3'); xxviii) an antisense strand of nucleic acid sequence according to SEQ ID NO: 160 (5' UUUCAUGUAGUUGGCUUCAAGG 3'), and a sense strand of nucleic acid sequence according to SEQ ID NO: 325 (5' UUGAAGCCAACUACAUGAAA 3'); xxix) an antisense strand of nucleic acid sequence according to SEQ ID NO: 162 (5' UAUCUCUGUAGGUUCAUGUAGU 3'), and a sense strand of nucleic acid sequence according to SEQ ID NO: 327 (5' UACAUGAACCUACAGAGAUA 3'); xxx) an antisense strand of nucleic acid sequence according to SEQ ID NO: 104 (5' UGUGUUGAUGCUGAGUUUGGCC 3'), and a sense strand of nucleic acid sequence according to SEQ ID NO: 269 (5' CCAAACUCAGCAUCAACACA 3'); xxxi) an antisense strand of nucleic acid sequence according to SEQ ID NO: 201 (5' UCUUUGUCCAGCUCAUACUUGG 3'), and a sense strand of nucleic acid sequence according to SEQ ID NO: 366 (5' AAGUAUGAGCUGGACAAAGA 3'); xxxii) an antisense strand of nucleic acid sequence according to SEQ ID NO: 63 (5' UUUUUGCCUGGGAAGUCGUGGA 3'), and a sense strand of nucleic acid sequence according to SEQ ID NO: 228 (5' CACGACUUCCCAGGCAAAAA 3'); xxxiii) an antisense strand of nucleic acid sequence according to SEQ ID NO: 178 (5' UCAUUUUCCUUGGUCUCUUCUG 3'), and a sense strand of nucleic acid sequence according to SEQ ID NO: 343 (5' GAAGAGACCAAGGAAAAUGA 3'); xxxiv) an antisense strand of nucleic acid sequence according to SEQ ID NO: 203 (5' UUUCCUAUCGGAGAAGGCUUUG 3'), and a sense strand of nucleic acid sequence according to SEQ ID NO: 368 (5' AAGCCUUCUCCGAUAGGAAA 3'); xxxV) an antisense strand of nucleic acid sequence according to SEQ ID NO: 216 (5' UGAAGCAAUUCUCCUCAGCACA 3'), and a sense strand of nucleic acid sequence according to SEQ ID NO: 381 (5' UGCUGAGGAGAAUUGCUUCA 3'); xxxvi) an antisense strand of nucleic acid sequence according to SEQ ID NO: 220 (5' UGUACACAUAGUCCACUCCUGG 3'), and a sense strand of nucleic acid sequence according to SEQ ID NO: 385 (5' AGGAGUGGACUAUGUGUACA 3'); xxxvii) an antisense strand of nucleic acid sequence according to SEQ ID NO: 118 (5' UUAUCUUCAGGGUCAUCUGCUG 3'), and a sense strand of nucleic acid sequence according to SEQ ID NO: 283 (5' GCAGAUGACCCUGAAGAUAA 3'); xxxviii) an antisense strand of nucleic acid sequence according to SEQ ID NO: 194 (5' UUAGACAUAGUGGCAUCCUGGU 3'), and a sense strand of nucleic acid sequence according to SEQ ID NO: 359 (5' CAGGAUGCCACUAUGUCUAA 3'); xxxix) an antisense strand of nucleic acid sequence according to SEQ ID NO: 219 (5' UUACACAUAGUCCACUCCUGGC 3'), and a sense strand of nucleic acid sequence according to SEQ ID NO: 384 (5' CAGGAGUGGACUAUGUGUAA 3'); xL) an antisense strand of nucleic acid sequence according to SEQ ID NO: 99 (5' UGUCUUGGUGAAGUGGAUCUGG 3'), and a sense strand of nucleic acid sequence according to SEQ ID NO: 264 (5' AGAUCCACUUCACCAAGACA 3'); xLi) an antisense strand of nucleic acid sequence according to SEQ ID NO: 154 (5' UAAGACCUUGACCACGUAGGCG 3'), and a sense strand of nucleic acid sequence according to SEQ ID NO: 319 (5' CCUACGUGGUCAAGGUCUUA 3'); xIii) an antisense strand of nucleic acid sequence according to SEQ ID NO: 171 (5' UAGUAUCUCUGUUCAUUGAGCC 3'), and a sense strand of nucleic acid sequence according to SEQ ID NO: 336 (5' CUCAAUGAACAGAGAUACUA 3'); xLiii) an antisense strand of nucleic acid sequence according to SEQ ID NO: 195 (5' UCAGUCAUCAUGGAUAUGUCCA 3'), and a sense strand of nucleic acid sequence according to SEQ ID NO: 360 (5' GACAUAUCCAUGAUGACUGA 3'); xLiv) an antisense strand of nucleic acid sequence according to SEQ ID NO: 73 (5' UGUGUAGAUGGUCUUGUCUGUC 3'), and a sense strand of nucleic acid sequence according to SEQ ID NO: 238 (5' CAGACAAGACCAUCUACACA 3'); xLv) an antisense strand of nucleic acid sequence according to SEQ ID NO: 180 (5' UUUCAGCUGUGACUGUGAAACC 3'), and a sense strand of nucleic acid sequence according to SEQ ID NO: 345 (5' UUUCACAGUCACAGCUGAAA 3'); xLvi) an antisense strand of nucleic acid sequence according to SEQ ID NO: 92 (5' UUUCUCUGUAGGCUCCACUAUG 3'), and a sense strand of nucleic acid sequence according to SEQ ID NO: 257 (5' UAGUGGAGCCUACAGAGAAA 3'); xLvii) an antisense strand of nucleic acid sequence according to SEQ ID NO: 75 (5' UAAGACAAGGAGUCCUGCUUGA 3'), and a sense strand of nucleic acid sequence according to SEQ ID NO: 240 (5' AAGCAGGACUCCUUGUCUUA 3'); xLviii) an antisense strand of nucleic acid sequence according to SEQ ID NO: 137 (5' UGUAGUUCCACCCUCACCUUGA 3'), and a sense strand of nucleic acid sequence according to SEQ ID NO: 302 (5' AAGGUGAGGGUGGAACUACA 3'); xLix) an antisense strand of nucleic acid sequence according to SEQ ID NO: 89 (5' UCUAUGACCUCGAAACUGGGCA 3'), and a sense strand of nucleic acid sequence according to SEQ ID NO: 254 (5' CCCAGUUUCGAGGUCAUAGA 3'); L) an antisense strand of nucleic acid sequence according to SEQ ID NO:

130 (5' UGAUGAAGAAGUCCUGCAUUAC 3'), and a sense strand of nucleic acid sequence according to SEQ ID NO: 295 (5' AAUGCAGGACUUCUUCAUCA 3'); Li) an antisense strand of nucleic acid sequence according to SEQ ID NO: 69 (5' UUUGUCUGUCUGGAUGAAGAGG 3'), and a sense strand of nucleic acid sequence according to SEQ ID NO: 234 (5' UCUUCAUCCAGACAGACAAA 3'); Lii) an antisense strand of nucleic acid sequence according to SEQ ID NO: 176 (5' UUUUUCCUUGGUCUCUUCUGAU 3'), and a sense strand of nucleic acid sequence according to SEQ ID NO: 341 (5' CAGAAGAGACCAAGGAAAAA 3'); Liii) an antisense strand of nucleic acid sequence according to SEQ ID NO: 100 (5' UGAGGUCAAAGGGCAUUCCUGG 3'), and a sense strand of nucleic acid sequence according to SEQ ID NO: 265 (5' AGGAAUGCCCUUUGACCUCA 3'); Liv) an antisense strand of nucleic acid sequence according to SEQ ID NO: 82 (5' UUUCAUAGUAGGCUCGGAUCUU 3'), and a sense strand of nucleic acid sequence according to SEQ ID NO: 247 (5' GAUCCGAGCCUACUAUGAAA 3'); Lv) an antisense strand of nucleic acid sequence according to SEQ ID NO: 212 (5' UGUAAUAGGCGUAGACCUUGAC 3'), and a sense strand of nucleic acid sequence according to SEQ ID NO: 377 (5' CAAGGUCUACGCCUAUUACA 3'); Lvi) an antisense strand of nucleic acid sequence according to SEQ ID NO: 191 (5' UAUCAUAGUGUUCUUGGCAUCC 3'), and a sense strand of nucleic acid sequence according to SEQ ID NO: 356 (5' AUGCCAAGAACACUAUGAUA 3'); Lvii) an antisense strand of nucleic acid sequence according to SEQ ID NO: 161 (5' UUGUAGGUUCAUGUAGUUGGCU 3'), and a sense strand of nucleic acid sequence according to SEQ ID NO: 326 (5' CCAACUACAUGAACCUACAA 3'); Lviii) an antisense strand of nucleic acid sequence according to SEQ ID NO: 112 (5' UGUGUAGUAGCGGAUCUUGGCC 3'), and a sense strand of nucleic acid sequence according to SEQ ID NO: 277 (5' CCAAGAUCCGCUACUACACA 3'); Lix) an antisense strand of nucleic acid sequence according to SEQ ID NO: 151 (5' UUUCUUGAUGAGCUCCAAGGCC 3'), and a sense strand of nucleic acid sequence according to SEQ ID NO: 316 (5' CCUUGGAGCUCAUCAAGAAA 3'); Lx) an antisense strand of nucleic acid sequence according to SEQ ID NO: 213 (5' UGUUGUAAUAGGCGUAGACCUU 3'), and a sense strand of nucleic acid sequence according to SEQ ID NO: 378 (5' GGUCUACGCCUAUUACAACA 3'); Lxi) an antisense strand of nucleic acid sequence according to SEQ ID NO: 206 (5' UGAUGAUGAGGGUGUUCCUAUC 3'), and a sense strand of nucleic acid sequence according to SEQ ID NO: 371 (5' UAGGAACACCCUCAUCAUCA 3'); Lxii) an antisense strand of nucleic acid sequence according to SEQ ID NO: 155 (5' UGAGAGAAGACCUUGACCACGU 3'), and a sense strand of nucleic acid sequence according to SEQ ID NO: 320 (5' GUGGUCAAGGUCUUCUCUCA 3'); Lxiii) an antisense strand of nucleic acid sequence according to SEQ ID NO: 143 (5' UUUGUUCAUUCUGAUUCCUUCC 3'), and a sense strand of nucleic acid sequence according to SEQ ID NO: 308 (5' AAGGAAUCAGAAUGAACAAA 3'); Lxiv) an antisense strand of nucleic acid sequence according to SEQ ID NO: 193 (5' UCAAGGAUCAUAGUGUUCUUGG 3'), and a sense strand of nucleic acid sequence according to SEQ ID NO: 358 (5' AAGAACACUAUGAUCCUUGA 3'); Lxv) an antisense strand of nucleic acid sequence according to SEQ ID NO: 163 (5' UCAGUGUAGGAUCUCUGUAGGU 3'), and a sense strand of nucleic acid sequence according to SEQ ID NO: 328 (5' CUACAGAGAUCCUACACUGA 3'); Lxvi) an antisense strand of nucleic acid sequence according to SEQ ID NO: 149 (5' UUUCAUCCAGGUAAUGCACAGC 3'), and a sense strand of nucleic acid sequence according to SEQ ID NO: 314 (5' UGUGCAUUACCUGGAUGAAA 3'); Lxvii) an antisense strand of nucleic acid sequence according to SEQ ID NO: 200 (5' UUUUGUCCAGCUCAUACUUGGA 3'), and a sense strand of nucleic acid sequence according to SEQ ID NO: 365 (5' CAAGUAUGAGCUGGACAAAA 3'); Lxviii) an antisense strand of nucleic acid sequence according to SEQ ID NO: 210 (5' UCUCAGAGUGUGAGACCUUGUC 3'), and a sense strand of nucleic acid sequence according to SEQ ID NO: 375 (5' CAAGGUCUCACACUCUGAGA 3'); Lxix) an antisense strand of nucleic acid sequence according to SEQ ID NO: 215 (5' UUGUUCAGCUUUCCAUCCUCCU 3'), and a sense strand of nucleic acid sequence according to SEQ ID NO: 380 (5' GAGGAUGGAAAGCUGAACAA 3'); Lxx) an antisense strand of nucleic acid sequence according to SEQ ID NO: 98 (5' UCUUGGUGAAGUGGAUCUGGUA 3'), and a sense strand of nucleic acid sequence according to SEQ ID NO: 263 (5' CCAGAUCCACUUCACCAAGA 3'); Lxxi) an antisense strand of nucleic acid sequence according to SEQ ID NO: 182 (5' UUUUUCCUUCAGCUGUGACUGU 3'), and a sense strand of nucleic acid sequence according to SEQ ID NO: 347 (5' AGUCACAGCUGAAGGAAAAA 3'); Lxxii) an antisense strand of nucleic acid sequence according to SEQ ID NO: 150 (5' UGUUUCAUCCAGGUAAUGCACA 3'), and a sense strand of nucleic acid sequence according to SEQ ID NO: 315 (5' UGCAUUACCUGGAUGAAACA 3'); Lxxiii) an antisense strand of nucleic acid sequence according to SEQ ID NO: 223 (5' UAUGAUGUACUCGUCAAAGUCA 3'), and a sense strand of nucleic acid sequence according to SEQ ID NO: 388 (5' ACUUUGACGAGUACAUCAUA 3'); Lxxiv) an antisense strand of nucleic acid sequence according to SEQ ID NO: 177 (5' UAUUUUCCUUGGUCUCUUCUGA 3'), and a sense strand of nucleic acid sequence according to SEQ ID NO: 342 (5' AGAAGAGACCAAGGAAAAUA 3'); LXXV) an antisense strand of nucleic acid sequence according to SEQ ID NO: 128 (5' UGAAGUCCUGCAUUACUGUGAC 3'), and a sense strand of nucleic acid sequence according to SEQ ID NO: 293 (5' CACAGUAAUGCAGGACUUCA 3'); Lxxvi) an antisense strand of nucleic acid sequence according to SEQ ID NO: 224 (5' UCUCAUCCGAGCCUGACUUGAU 3'), and a sense strand of nucleic acid sequence according to SEQ ID NO: 389 (5' CAAGUCAGGCUCGGAUGAGA 3'); Lxxvii) an antisense strand of nucleic acid sequence according to SEQ ID NO: 205 (5' UAUGAUGAGGGUGUUCCUAUCG 3'), and a sense strand of nucleic acid sequence according to SEQ ID NO: 370 (5' AUAGGAACACCCUCAUCAUA 3'); Lxxviii) an antisense strand of nucleic acid sequence according to SEQ ID NO: 186 (5' UUUUAUGGUGACCUUGAGGUCG 3'), and a sense strand of nucleic acid sequence according to SEQ ID NO: 351 (5' ACCUCAAGGUCACCAUAAAA 3'); Lxxix) an antisense strand of nucleic acid sequence according to SEQ ID NO: 77 (5' UGACGAGUUCCGGAAUGUCCCA 3'), and a sense strand of nucleic acid sequence according to SEQ ID NO: 242 (5' GGACAUUCCGGAACUCGUCA 3'); Lxxx) an antisense strand of nucleic acid sequence according to SEQ ID NO: 197 (5' UAUACUUGGAGAUGUAUCUGUC 3'), and a sense strand of nucleic acid sequence according to SEQ ID NO: 362 (5' CAGAUACAUCUCCAAGUAUA 3'); Lxxxi) an antisense strand of nucleic acid sequence according to SEQ ID NO: 95 (5' UGUUAUAGAUGUAGUAGAAUUU 3'), and a sense strand of nucleic acid sequence according to SEQ ID NO: 260 (5' AUUCUACUACAUC- UAUAACA 3'); lxxxii) an antisense strand of nucleic acid sequence according to SEQ ID NO: 78 (5' UUUGACGAGUUCCGGAAUGUCC 3'), and a sense strand of nucleic acid sequence according to SEQ ID NO: 243 (5' ACAUUCCGGAACUCGUCAAA 3'); lxxxiii) an antisense strand of nucleic acid sequence according to SEQ ID NO: 101 (5' UAACACCAUGAGGUCAAAGGGC 3'), and a sense strand of nucleic acid sequence according to SEQ ID NO: 266 (5' CCUUUGACCUCAUGGUGUUA 3'); lxxxiv) an antisense strand of nucleic acid sequence according to SEQ ID NO: 79 (5' UGUUGACGAGUUCCGGAAUGUC 3'), and a sense strand of nucleic acid sequence according to SEQ ID NO: 244 (5' CAUUCCGGAACUCGUCAACA 3'); lXXXV) an antisense strand of nucleic acid sequence according to SEQ ID NO: 221 (5' UGUCUUGUACACAUAGUCCACU 3'), and a sense strand of nucleic acid sequence according to SEQ ID NO: 386 (5' UGGACUAUGUGUACAAGACA 3'); lxxxvi) an antisense strand of nucleic acid sequence according to SEQ ID NO: 167 (5' UGUCUUUUAGCUGCAGUAGGGC 3'), and a sense strand of nucleic acid sequence according to SEQ ID NO: 332 (5' CCUACUGCAGCUAAAAGACA 3'); lxxxvii) an antisense strand of nucleic acid sequence according to SEQ ID NO: 84 (5' UCAAACUCAGUGGAGAAGACCU 3'), and a sense strand of nucleic acid sequence according to SEQ ID NO: 249 (5' GUCUUCUCCACUGAGUUUGA 3'); lxxxviii) an antisense strand of nucleic acid sequence according to SEQ ID NO: 144 (5' UGUUUUGUUCAUUCUGAUUCCU 3'), and a sense strand of nucleic acid sequence according to SEQ ID NO: 309 (5' GAAUCAGAAUGAACAAAACA 3'); lxxxix) an antisense strand of nucleic acid sequence according to SEQ ID NO: 166 (5' UUCUUUUAGCUGCAGUAGGGCC 3'), and a sense strand of nucleic acid sequence according to SEQ ID NO: 331 (5' CCCUACUGCAGCUAAAAGAA 3'); xc) an antisense strand of nucleic acid sequence according to SEQ ID NO: 76 (5' UUUCUGAGAAGACAAGGAGUCC 3'), and a sense strand of nucleic acid sequence according to SEQ ID NO: 241 (5' ACUCCUUGUCUUCUCAGAAA 3'); xci) an antisense strand of nucleic acid sequence according to SEQ ID NO: 204 (5' UGUGUUCCUAUCGGAGAAGGCU 3'), and a sense strand of nucleic acid sequence according to SEQ ID NO: 369 (5' CCUUCUCCGAUAGGAACACA 3'); xcii) an antisense strand of nucleic acid sequence according to SEQ ID NO: 211 (5' UCAUCCUCAGAGUGUGAGACCU 3'), and a sense strand of nucleic acid sequence according to SEQ ID NO: 376 (5' GUCUCACACUCUGAGGAUGA 3'); xciii) an antisense strand of nucleic acid sequence according to SEQ ID NO: 132 (5' UUUUCGAACAACAGAGUAGGGU 3'), and a sense strand of nucleic acid sequence according to SEQ ID NO: 297 (5' CCUACUCUGUUGUUCGAAAA 3'); xciv) an antisense strand of nucleic acid sequence according to SEQ ID NO: 142 (5' UGGAUGGUUACGGUCUGCUGGU 3'), and a sense strand of nucleic acid sequence according to SEQ ID NO: 307 (5' CAGCAGACCGUAACCAUCCA 3'); xcv) an antisense strand of nucleic acid sequence according to SEQ ID NO: 148 (5' UCAGGUAAUGCACAGCGAUGAC 3'), and a sense strand of nucleic acid sequence according to SEQ ID NO: 313 (5' CAUCGCUGUGCAUUACCUGA 3'); xcvi) an antisense strand of nucleic acid sequence according to SEQ ID NO: 207 (5' UGUAGAUGAUGAGGGUGUUCCU 3'), and a sense strand of nucleic acid sequence according to SEQ ID NO: 372 (5' GAACACCCUCAUCAUCUACA 3'); xcvii) an antisense strand of nucleic acid sequence according to SEQ ID NO: 86 (5' UUACUCCUUCACCUCAAACUCA 3'), and a sense strand of nucleic acid sequence according to SEQ ID NO: 251 (5' AGUUUGAGGUGAAGGAGUAA 3'); xcviii) an antisense strand of nucleic acid sequence according to SEQ ID NO: 192 (5' UAAGGAUCAUAGUGUUCUUGGC 3'), and a sense strand of nucleic acid sequence according to SEQ ID NO: 357 (5' CAAGAACACUAUGAUCCUUA 3'); xcix) an antisense strand of nucleic acid sequence according to SEQ ID NO: 175 (5' UCAGAUUCCCAGUGGAUACGGU 3'), and a sense strand of nucleic acid sequence according to SEQ ID NO: 340 (5' CGUAUCCACUGGGAAUCUGA 3'); c) an antisense strand of nucleic acid sequence according to SEQ ID NO: 187 (5' UUUUUAUGGUGACCUUGAGGUC 3'), and a sense strand of nucleic acid sequence according to SEQ ID NO: 352 (5' CCUCAAGGUCACCAUAAAAA 3'); ci) an antisense strand of nucleic acid sequence according to SEQ ID NO: 109 (5' UCUGAGAGAUGCAGGUAAUUGU 3'), and a sense strand of nucleic acid sequence according to SEQ ID NO: 274 (5' AAUUACCUGCAUCUCUCAGA 3'); cii) an antisense strand of nucleic acid sequence according to SEQ ID NO: 102 (5' UGACUCGGUAGGCUGGAGAGCC 3'), and a sense strand of nucleic acid sequence according to SEQ ID NO: 267 (5' CUCUCCAGCCUACCGAGUCA 3'); ciii) an antisense strand of nucleic acid sequence according to SEQ ID NO: 121 (5' UCAAAAAUAUAUUCAUGAGCUU 3'), and a sense strand of nucleic acid sequence according to SEQ ID NO: 286 (5' GCUCAUGAAUAUAUUUUUGA 3'); civ) an antisense strand of nucleic acid sequence according to SEQ ID NO: 134 (5' UGAUUUCCACCUGCUCGUUUCG 3'), and a sense strand of nucleic acid sequence according to SEQ ID NO: 299 (5' AAACGAGCAGGUGGAAAUCA 3'); cv) an antisense strand of nucleic acid sequence according to SEQ ID NO: 135 (5' UUUGGUUCUGCCGGUAAUUGUA 3'), and a sense strand of nucleic acid sequence according to SEQ ID NO: 300 (5' CAAUUACCGGCAGAACCAAA 3'); cvi) an antisense strand of nucleic acid sequence according to SEQ ID NO: 105 (5' UGAUGCUCAAGGGCUUCUGGCU 3'), and a sense strand of nucleic acid sequence according to SEQ ID NO: 270 (5' CCAGAAGCCCUUGAGCAUCA 3'); cvii) an antisense strand of nucleic acid sequence according to SEQ ID NO: 125 (5' UGUCUUUCAAAAAUAUAUUCAU 3'), and a sense strand of nucleic acid sequence according to SEQ ID NO: 290 (5' GAAUAUAUUUUUGAAAGACA 3'); cviii) an antisense strand of nucleic acid sequence according to SEQ ID NO: 190 (5' UGUGUUCUUGGCAUCCUGAGGC 3'), and a sense strand of nucleic acid sequence according to SEQ ID NO: 355 (5' CUCAGGAUGCCAAGAACACA 3'); cix) an antisense strand of nucleic acid sequence according to SEQ ID NO: 119 (5' UAUGUAGUUGCAGCAGUCCAGG 3'), and a sense strand of nucleic acid sequence according to SEQ ID NO: 284 (5' UGGACUGCUGCAACUACAUA 3'); cx) an antisense strand of nucleic acid sequence according to SEQ ID NO: 120 (5' UGUGAUGUAGUUGCAGCAGUCC 3'), and a sense strand of nucleic acid sequence according to SEQ ID NO: 285 (5' ACUGCUGCAACUACAUCACA 3'); or cxi) an antisense strand of nucleic acid sequence according to SEQ ID NO: 394 (5' UAAAUAUAUUCAUGAGCUUCGU 3'), and a sense strand of nucleic acid sequence according to SEQ ID NO: 420 (5' GAAGCUCAUGAAUAUAUUUA 3').

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% (e.g., 20% to 25%, 25% to 30%, 30% to 35%, 35% to 40%, 40% to 45% or 45% to 50%) at a dose of 0.01 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by 20% to 50% at a dose (e.g., 20% to 25%, 25% to 30%, 30% to 35%, 35% to 40%, 40% to 45% or 45% to 50%) of 0.01 nM, wherein the double stranded region comprises: i) an antisense strand of nucleic acid sequence according to SEQ ID NO: 96 (5' UAGAUGACAAAGGCAGUUCCCU 3'), and a sense strand of nucleic acid sequence according to SEQ ID NO: 261 (5' GGAACUGCCUUUGUCAUCUA 3'); ii) an antisense strand of nucleic acid sequence according to SEQ ID NO: 217 (5' UUUGUAUGAAGCAAUUCUCCUC 3'), and a sense strand of nucleic acid sequence according to SEQ ID NO: 382 (5' GGAGAAUUGCUUCAUACAAA 3'); iii) an antisense strand of nucleic acid sequence according to SEQ ID NO: 70 (5' UUAGAUGGUCUUGUCUGUCUGG 3'), and a sense strand of nucleic acid sequence according to SEQ ID NO: 235 (5' AGACAGACAAGACCAUCUAA 3'); iv) an antisense strand of nucleic acid sequence according to SEQ ID NO: 198 (5' UCAUACUUGGAGAUGUAUCUGU 3'), and a sense strand of nucleic acid sequence according to SEQ ID NO: 363 (5' AGAUACAUCUCCAAGUAUGA 3'); v) an antisense strand of nucleic acid sequence according to SEQ ID NO: 113 (5' UAUCAGGUAGGUGUAGUAGCGG 3'), and a sense strand of nucleic acid sequence according to SEQ ID NO: 278 (5' GCUACUACACCUACCUGAUA 3'); vi) an antisense strand of nucleic acid sequence according to SEQ ID NO: 126 (5' UAUUACUGUGACCUCGAAGGGG 3'), and a sense strand of nucleic acid sequence according to SEQ ID NO: 291 (5' CCUUCGAGGUCACAGUAAUA 3'); vii) an antisense strand of nucleic acid sequence according to SEQ ID NO: 170 (5' UGUAUCUCUGUUCAUUGAGCCA 3'), and a sense strand of nucleic acid sequence according to SEQ ID NO: 335 (5' GCUCAAUGAACAGAGAUACA 3'); viii) an antisense strand of nucleic acid sequence according to SEQ ID NO: 123 (5' UUUUCAAAAAUAUAUUCAUGAG 3'), and a sense strand of nucleic acid sequence according to SEQ ID NO: 288 (5' CAUGAAUAUAUUUUUGAAAA 3'); ix) an antisense strand of nucleic acid sequence according to SEQ ID NO: 226 (5' UGUCAGUUGGGGCACCCAAAGA 3'), and a sense strand of nucleic acid sequence according to SEQ ID NO: 391 (5' UUUGGGUGCCCCAACUGACA 3'); x) an antisense strand of nucleic acid sequence according to SEQ ID NO: 67 (5' UCUGUCUGGAUGAAGAGGUACC 3'), and a sense strand of nucleic acid sequence according to SEQ ID NO: 232 (5' UACCUCUUCAUCCAGACAGA 3'); xi) an antisense strand of nucleic acid sequence according to SEQ ID NO: 172 (5' UUAGUAUCUCUGUUCAUUGAGC 3'), and a sense strand of nucleic acid sequence according to SEQ ID NO: 337 (5' UCAAUGAACAGAGAUACUAA 3'); xii) an antisense strand of nucleic acid sequence according to SEQ ID NO: 74 (5' UGACAAGGAGUCCUGCUUGACC 3'), and a sense strand of nucleic acid sequence according to SEQ ID NO: 239 (5' UCAAGCAGGACUCCUUGUCA 3'); xiii) an antisense strand of nucleic acid sequence according to SEQ ID NO: 64 (5' UUUUUUGCCUGGGAAGUCGUGG 3'), and a sense strand of nucleic acid sequence according to SEQ ID NO: 229 (5' ACGACUUCCCAGGCAAAAAA 3'); xiv) an antisense strand of nucleic acid sequence according to SEQ ID NO: 181 (5' UUUCCUUCAGCUGUGACUGUGA 3'), and a sense strand of nucleic acid sequence according to SEQ ID NO: 346 (5' ACAGUCACAGCUGAAGGAAA 3'); xv) an antisense strand of nucleic acid sequence according to SEQ ID NO: 131 (5' UGAACAACAGAGUAGGGUAGCC 3'), and a sense strand of nucleic acid sequence according to SEQ ID NO: 296 (5' CUACCCUACUCUGUUGUUCA 3'); xvi) an antisense strand of nucleic acid sequence according to SEQ ID NO: 196 (5' UUACUUGGAGAUGUAUCUGUCA 3'), and a sense strand of nucleic acid sequence according to SEQ ID NO: 361 (5' ACAGAUACAUCUCCAAGUAA 3'); xvii) an antisense strand of nucleic acid sequence according to SEQ ID NO: 129 (5' UGAAGAAGUCCUGCAUUACUGU 3'), and a sense strand of nucleic acid sequence according to SEQ ID NO: 294 (5' AGUAAUGCAGGACUUCUUCA 3'); xviii) an antisense strand of nucleic acid sequence according to SEQ ID NO: 212 (5' UGUAAUAGGCGUAGACCUUGAC 3'), and a sense strand of nucleic acid sequence according to SEQ ID NO: 377 (5' CAAGGUCUACGCCUAUUACA 3'); xix) an antisense strand of nucleic acid sequence according to SEQ ID NO: 93 (5' UAGUAGAAUUUCUCUGUAGGCU 3'), and a sense strand of nucleic acid sequence according to SEQ ID NO: 258 (5' CCUACAGAGAAAUUCUACUA 3'); xx) an antisense strand of nucleic acid sequence according to SEQ ID NO: 194 (5' UUAGACAUAGUGGCAUCCUGGU 3'), and a sense strand of nucleic acid sequence according to SEQ ID NO: 359 (5' CAGGAUGCCACUAUGUCUAA 3'); xxi) an antisense strand of nucleic acid sequence according to SEQ ID NO: 154 (5' UAAGACCUUGACCACGUAGGCG 3'), and a sense strand of nucleic acid sequence according to SEQ ID NO: 319 (5' CCUACGUGGUCAAGGUCUUA 3'); xxii) an antisense strand of nucleic acid sequence according to SEQ ID NO: 108 (5' UGAGAUGCAGGUAAUUGUUGGA 3'), and a sense strand of nucleic acid sequence according to SEQ ID NO: 273 (5' CAACAAUUACCUGCAUCUCA 3'); xxiii) an antisense strand of nucleic acid sequence according to SEQ ID NO: 72 (5' UUGUAGAUGGUCUUGUCUGUCU 3'), and a sense strand of nucleic acid sequence according to SEQ ID NO: 237 (5' ACAGACAAGACCAUCUACAA 3'); xxiv) an antisense strand of nucleic acid sequence according to SEQ ID NO: 78 (5' UUUGACGAGUUCCGGAAUGUCC 3'), and a sense strand of nucleic acid sequence according to SEQ ID NO: 243 (5' ACAUUCCGGAACUCGUCAAA 3'); XXV) an antisense strand of nucleic acid sequence according to SEQ ID NO: 211 (5' UCAUCCUCAGAGUGUGA- GACCU 3'), and a sense strand of nucleic acid sequence according to SEQ ID NO: 376 (5' GUCUCACACU-CUGAGGAUGA 3'); xxvi) an antisense strand of nucleic acid sequence according to SEQ ID NO: 188 (5' UGUUUUAUGGUGACCUUGAGGU 3'), and a sense strand of nucleic acid sequence according to SEQ ID NO: 353 (5' CUCAAGGUCACCAUAAAACA 3'); xxvii) an antisense strand of nucleic acid sequence according to SEQ ID NO: 124 (5' UCUUUCAAAAAUAUAUUCAUGA 3'), and a sense strand of nucleic acid sequence according to SEQ ID NO: 289 (5' AUGAAUAUAUUUUUGAAAGA 3'); xxviii) an antisense strand of nucleic acid sequence according to SEQ ID NO: 159 (5' UAAGGAAGUCUCCUGC-UUUAGU 3'), and a sense strand of nucleic acid sequence according to SEQ ID NO: 324 (5' UAAAGCAGGAGAC-UUCCUUA 3'); xxix) an antisense strand of nucleic acid sequence according to SEQ ID NO: 208 (5' UCUUGU-CCAGGUAGAUGAUGAG 3'), and a sense strand of nucleic acid sequence according to SEQ ID NO: 373 (5' CAUCAUCUACCUGGACAAGA 3'); xxx) an antisense strand of nucleic acid sequence according to SEQ ID NO: 137 (5' UGUAGUUCCACCCUCACCUUGA 3'), and a sense strand of nucleic acid sequence according to SEQ ID NO: 302 (5' AAGGUGAGGGUGGAACUACA 3'); xxxi) an antisense strand of nucleic acid sequence according to SEQ ID NO: 122 (5' UUUCAAAAAUAUAUUCAUGAGC 3'), and a sense strand of nucleic acid sequence according to SEQ ID NO: 287 (5' UCAUGAAUAUAUUUUUGAAA 3'); xxxii) an antisense strand of nucleic acid sequence according to SEQ ID NO: 63 (5' UUUUUGCCUGGGAAGU-CGUGGA 3'), and a sense strand of nucleic acid sequence according to SEQ ID NO: 228 (5' CACGAC-UUCCCAGGCAAAAA 3'); xxxiii) an antisense strand of nucleic acid sequence according to SEQ ID NO: 219 (5' UUACACAUAGUCCACUCCUGGC 3'), and a sense strand of nucleic acid sequence according to SEQ ID NO: 384 (5' CAGGAGUGGACUAUGUGUAA 3'); xxxiv) an antisense strand of nucleic acid sequence according to SEQ ID NO: 195 (5' UCAGUCAUCAUGGAUAUGUCCA 3'), and a sense strand of nucleic acid sequence according to SEQ ID NO: 360 (5' GACAUAUCCAUGAUGACUGA 3'); xxxV) an antisense strand of nucleic acid sequence according to SEQ ID NO: 95 (5' UGUUAUAGAUGUAGUA-GAAUUU 3'), and a sense strand of nucleic acid sequence according to SEQ ID NO: 260 (5' AUUCUACUACAUC-UAUAACA 3'); xxxvi) an antisense strand of nucleic acid sequence according to SEQ ID NO: 146 (5' UGAAUUCUG-GUCUCAGACUCGG 3'), and a sense strand of nucleic acid sequence according to SEQ ID NO: 311 (5' GAGUCUGA-GACCAGAAUUCA 3'); xxxvii) an antisense strand of nucleic acid sequence according to SEQ ID NO: 220 (5' UGUACACAUAGUCCACUCCUGG 3'), and a sense strand of nucleic acid sequence according to SEQ ID NO: 385 (5' AGGAGUGGACUAUGUGUACA 3'); xxxviii) an antisense strand of nucleic acid sequence according to SEQ ID NO: 151 (5' UUUCUUGAUGAGCUCCAAGGCC 3'), and a sense strand of nucleic acid sequence according to SEQ ID NO: 316 (5' CCUUGGAGCUCAUCAAGAAA 3'); xxxix) an antisense strand of nucleic acid sequence according to SEQ ID NO: 118 (5' UUAUCUUCAGGGU-CAUCUGCUG 3'), and a sense strand of nucleic acid sequence according to SEQ ID NO: 283 (5' GCAGAUGACCCUGAAGAUAA 3'); xL) an antisense strand of nucleic acid sequence according to SEQ ID NO: 180 (5' UUUCAGCUGUGACUGUGAAACC 3'), and a sense strand of nucleic acid sequence according to SEQ ID NO: 345 (5' UUUCACAGUCACAGCUGAAA 3'); xLi) an antisense strand of nucleic acid sequence according to SEQ ID NO: 210 (5' UCUCAGAGUGUGAGACCUUGUC 3'), and a sense strand of nucleic acid sequence according to SEQ ID NO: 375 (5' CAAGGUCUCACACUCUGAGA 3'); xLii) an antisense strand of nucleic acid sequence according to SEQ ID NO: 187 (5' UUUUUAUGGUGACCUUGAG-GUC 3'), and a sense strand of nucleic acid sequence according to SEQ ID NO: 352 (5' CCUCAAGGUCAC-CAUAAAAA 3'); xLiii) an antisense strand of nucleic acid sequence according to SEQ ID NO: 162 (5' UAUCUCU-GUAGGUUCAUGUAGU 3'), and a sense strand of nucleic acid sequence according to SEQ ID NO: 327 (5' UACAUGAACCUACAGAGAUA 3'); xLiv) an antisense strand of nucleic acid sequence according to SEQ ID NO: 145 (5' UAAUUCUGGUCUCAGACUCGGU 3'), and a sense strand of nucleic acid sequence according to SEQ ID NO: 310 (5' CGAGUCUGAGACCAGAAUUA 3'); xLv) an antisense strand of nucleic acid sequence according to SEQ ID NO: 201 (5' UCUUUGUCCAGCUCAUACUUGG 3'), and a sense strand of nucleic acid sequence according to SEQ ID NO: 366 (5' AAGUAUGAGCUGGACAAAGA 3'); xLvi) an antisense strand of nucleic acid sequence according to SEQ ID NO: 81 (5' UCAUAGUAGGCUCGGAUC-UUCC 3'), and a sense strand of nucleic acid sequence according to SEQ ID NO: 246 (5' AAGAUCCGAGCCUA-CUAUGA 3'); xLvii) an antisense strand of nucleic acid sequence according to SEQ ID NO: 206 (5' UGAUGAUGAGGGUGUUCCUAUC 3'), and a sense strand of nucleic acid sequence according to SEQ ID NO: 371 (5' UAGGAACACCCUCAUCAUCA 3'); xLviii) an antisense strand of nucleic acid sequence according to SEQ ID NO: 215 (5' UUGUUCAGCUUUCCAUCCUCCU 3'), and a sense strand of nucleic acid sequence according to SEQ ID NO: 380 (5' GAGGAUGGAAAGCUGAACAA 3'); xLix) an antisense strand of nucleic acid sequence according to SEQ ID NO: 213 (5' UGUUGUAAUAGGCGUAGAC-CUU 3'), and a sense strand of nucleic acid sequence according to SEQ ID NO: 378 (5' GGUCUACGCC-UAUUACAACA 3'); L) an antisense strand of nucleic acid sequence according to SEQ ID NO: 189 (5' UCU-GUUUCCGGUGCUGGUUUUA 3'), and a sense strand of nucleic acid sequence according to SEQ ID NO: 354 (5' AAACCAGCACCGGAAACAGA 3'); Li) an antisense strand of nucleic acid sequence according to SEQ ID NO: 207 (5' UGUAGAUGAUGAGGGUGUUCCU 3'), and a sense strand of nucleic acid sequence according to SEQ ID NO: 372 (5' GAACACCCUCAUCAUCUACA 3'); Lii) an antisense strand of nucleic acid sequence according to SEQ ID NO: 139 (5' UGGAUUUGUGGAGUAGUUCCACC 3'), and a sense strand of nucleic acid sequence according to SEQ ID NO: 304 (5' UGGAACUACUCCACAAUCCA 3'); Liii) an antisense strand of nucleic acid sequence according to SEQ ID NO: 143 (5' UUUGUUCAUUCUGAUUCC-UUCC 3'), and a sense strand of nucleic acid sequence according to SEQ ID NO: 308 (5' AAGGAAUCAGAAUGAACAAA 3'); Liv) an antisense strand of nucleic acid sequence according to SEQ ID NO: 178 (5' UCAUUUUCCUUGGUCUCUUCUG 3'), and a sense strand of nucleic acid sequence according to SEQ ID NO: 343 (5' GAAGAGACCAAGGAAAAUGA 3'); Lv) an antisense strand of nucleic acid sequence according to SEQ ID NO: 128 (5' UGAAGUCCUGCAUUACUGUGAC 3'), and a sense strand of nucleic acid sequence according to SEQ ID NO: 293 (5' CACAGUAAUGCAGGACUUCA 3'); Lvi) an antisense strand of nucleic acid sequence according to SEQ ID NO: 160 (5' UUUCAUGUAGUUGGCUU-CAAGG 3'), and a sense strand of nucleic acid sequence according to SEQ ID NO: 325 (5' UUGAAGCCAACUACAUGAAA 3'); Lvii) an antisense strand of nucleic acid sequence according to SEQ ID NO: 176 (5' UUUUUCCUUGGUCUCUUCUGAU 3'), and a sense strand of nucleic acid sequence according to SEQ ID NO: 341 (5' CAGAAGAGACCAAGGAAAAA 3'); Lviii) an antisense strand of nucleic acid sequence according to SEQ ID NO: 80 (5' UCUUCCACUGGCCCAUGUUGAC 3'), and a sense strand of nucleic acid sequence according to SEQ ID NO: 245 (5' CAACAUGGGCCAGUGGAAGA 3'); Lix) an antisense strand of nucleic acid sequence according to SEQ ID NO: 203 (5' UUUCCUAUCGGAGAAGGCUUUG 3'), and a sense strand of nucleic acid sequence according to SEQ ID NO: 368 (5' AAGCCUUCUCCGAUAGGAAA 3'); Lx) an antisense strand of nucleic acid sequence according to SEQ ID NO: 87 (5' UGUACUCCUUCACCUCAAACUC 3'), and a sense strand of nucleic acid sequence according to SEQ ID NO: 252 (5' GUUUGAGGUGAAGGAGUACA 3'); Lxi) an antisense strand of nucleic acid sequence according to SEQ ID NO: 104 (5' UGUGUUGAUGCUGAGUUUGGCC 3'), and a sense strand of nucleic acid sequence according to SEQ ID NO: 269 (5' CCAAACUCAGCAUCAACACA 3'); Lxii) an antisense strand of nucleic acid sequence according to SEQ ID NO: 69 (5' UUUGUCUGUCUGGAUGAAGAGG 3'), and a sense strand of nucleic acid sequence according to SEQ ID NO: 234 (5' UCUUCAUCCAGACAGACAAA 3'); Lxiii) an antisense strand of nucleic acid sequence according to SEQ ID NO: 197 (5' UAUACUUGGAGAUGUAUCUGUC 3'), and a sense strand of nucleic acid sequence according to SEQ ID NO: 362 (5' CAGAUACAUCUCCAAGUAUA 3'); Lxiv) an antisense strand of nucleic acid sequence according to SEQ ID NO: 223 (5' UAUGAUGUACUCGUCAAAGUCA 3'), and a sense strand of nucleic acid sequence according to SEQ ID NO: 388 (5' ACUUUGACGAGUACAUCAUA 3'); Lxv) an antisense strand of nucleic acid sequence according to SEQ ID NO: 142 (5' UGGAUGGUUACGGUCUGCUGGU 3'), and a sense strand of nucleic acid sequence according to SEQ ID NO: 307 (5' CAGCAGACCGUAACCAUCCA 3'); Lxvi) an antisense strand of nucleic acid sequence according to SEQ ID NO: 138 (5' UGAUUGUGGAGUAGUUCCACCC 3'), and a sense strand of nucleic acid sequence according to SEQ ID NO: 303 (5' GUGGAACUACUCCACAAUCA 3'); Lxvii) an antisense strand of nucleic acid sequence according to SEQ ID NO: 75 (5' UAAGACAAGGAGUCCUGCUUGA 3'), and a sense strand of nucleic acid sequence according to SEQ ID NO: 240 (5' AAGCAGGACUCCUUGUCUUA 3'); Lxviii) an antisense strand of nucleic acid sequence according to SEQ ID NO: 163 (5' UCAGUGUAGGAUCUCUGUAGGU 3'), and a sense strand of nucleic acid sequence according to SEQ ID NO: 328 (5' CUACAGAGAUCCUACACUGA 3'); Lxix) an antisense strand of nucleic acid sequence according to SEQ ID NO: 116 (5' UUUCUGACUGGCCGCUUUUUAC 3'), and a sense strand of nucleic acid sequence according to SEQ ID NO: 281 (5' AAAAAGCGGCCAGUCAGAAA 3'); Lxx) an antisense strand of nucleic acid sequence according to SEQ ID NO: 112 (5' UGUGUAGUAGCGGAUCUUGGCC 3'), and a sense strand of nucleic acid sequence according to SEQ ID NO: 277 (5' CCAAGAUCCGCUACUACACA 3'); Lxxi) an antisense strand of nucleic acid sequence according to SEQ ID NO: 204 (5' UGUGUUCCUAUCGGAGAAGGCU 3'), and a sense strand of nucleic acid sequence according to SEQ ID NO: 369 (5' CCUUCUCCGAUAGGAACACA 3'); Lxxii) an antisense strand of nucleic acid sequence according to SEQ ID NO: 169 (5' UCACAAAGUCAAAGUCUUUUAG 3'), and a sense strand of nucleic acid sequence according to SEQ ID NO: 334 (5' AAAAGACUUUGACUUUGUGA 3'); Lxxiii) an antisense strand of nucleic acid sequence according to SEQ ID NO: 99 (5' UGUCUUGGUGAAGUGGAUCUGG 3'), and a sense strand of nucleic acid sequence according to SEQ ID NO: 264 (5' AGAUCCACUUCACCAAGACA 3'); Lxxiv) an antisense strand of nucleic acid sequence according to SEQ ID NO: 140 (5' UCUGGAUUGUGGAGUAGUUCCA 3'), and a sense strand of nucleic acid sequence according to SEQ ID NO: 305 (5' GAACUACUCCACAAUCCAGA 3'); Lxxv) an antisense strand of nucleic acid sequence according to SEQ ID NO: 130 (5' UGAUGAAGAAGUCCUGCAUUAC 3'), and a sense strand of nucleic acid sequence according to SEQ ID NO: 295 (5' AAUGCAGGACUUCUUCAUCA 3'); Lxxvi) an antisense strand of nucleic acid sequence according to SEQ ID NO: 68 (5' UGUCUGUCUGGAUGAAGAGGUA 3'), and a sense strand of nucleic acid sequence according to SEQ ID NO: 233 (5' CCUCUUCAUCCAGACAGACA 3'); Lxxvii) an antisense strand of nucleic acid sequence according to SEQ ID NO: 73 (5' UGUGUAGAUGGUCUUGUCUGUC 3'), and a sense strand of nucleic acid sequence according to SEQ ID NO: 238 (5' CAGACAAGACCAUCUACACA 3'); Lxxviii) an antisense strand of nucleic acid sequence according to SEQ ID NO: 100 (5' UGAGGUCAAAGGGCAUUCCUGG 3'), and a sense strand of nucleic acid sequence according to SEQ ID NO: 265 (5' AGGAAUGCCCUUUGACCUCA 3'); Lxxix) an antisense strand of nucleic acid sequence according to SEQ ID NO: 205 (5' UAUGAUGAGGGUGUUCCUAUCG 3'), and a sense strand of nucleic acid sequence according to SEQ ID NO: 370 (5' AUAGGAACACCCUCAUCAUA 3'); Lxxx) an antisense strand of nucleic acid sequence according to SEQ ID NO: 119 (5' UAUGUAGUUGCAGCAGUCCAGG 3'), and a sense strand of nucleic acid sequence according to SEQ ID NO: 284 (5' UGGACUGCUGCAACUACAUA 3'); Lxxxi) an antisense strand of nucleic acid sequence according to SEQ ID NO: 82 (5' UUUCAUAGUAGGCUCGGAUCUU 3'), and a sense strand of nucleic acid sequence according to SEQ ID NO: 247 (5' GAUCCGAGCCUACUAUGAAA 3'); Lxxxii) an antisense strand of nucleic acid sequence according to SEQ ID NO: 79 (5' UGUUGACGAGUUCCGGAAUGUC 3'), and a sense strand of nucleic acid sequence according to SEQ ID NO: 244 (5' CAUUCCGGAACUCGUCAACA 3'); Lxxxiii) an antisense strand of nucleic acid sequence according to SEQ ID NO: 171 (5' UAGUAUCUCUGUUCAUUGAGCC 3'), and a sense strand of nucleic acid sequence according to SEQ ID NO: 336 (5' CUCAAUGAACAGAGAUACUA 3'); Lxxxiv) an antisense strand of nucleic acid sequence according to SEQ ID NO: 182 (5' UUUUUCCUUCAGCUGUGACUGU 3'), and a sense strand of nucleic acid sequence according to SEQ ID NO: 347 (5' AGUCACAGCUGAAGGAAAAA 3'); Lxxxv) an antisense strand of nucleic acid sequence according to SEQ ID NO: 153 (5' UUGAAGGCCAGCUGCUGGGUGU 3'), and a sense strand of nucleic acid sequence according to SEQ ID NO: 318 (5' ACCCAGCAGCUGGCCUUCAA 3'); Lxxxvi) an antisense strand of nucleic acid sequence according to SEQ ID NO: 186 (5' UUUUAUGGUGACCUUGAGGUCG 3'), and a sense strand of nucleic acid sequence according to SEQ ID NO: 351 (5' ACCUCAAGGUCACCAUAAAA 3'); Lxxxvii) an antisense strand of nucleic acid sequence according to SEQ ID NO: 191 (5' UAUCAUAGUGUUCUUGGCAUCC 3'), and a sense strand of nucleic acid sequence according to SEQ ID NO: 356 (5' AUGCCAAGAACACUAUGAUA 3'); Lxxxviii) an antisense strand of nucleic acid sequence according to SEQ ID NO: 141 (5' UCUGCAGAAGGCUGGAUUGUGG 3'), and a sense strand of nucleic acid sequence according to SEQ ID NO: 306 (5' ACAAUCCAGCCUUCUGCAGA 3'); Lxxxix) an antisense strand of nucleic acid sequence according to SEQ ID NO: 144 (5' UGUUUUGUUCAUUCUGAUUCCU 3'), and a sense strand of nucleic acid sequence according to SEQ ID NO: 309 (5' GAAUCAGAAUGAACAAAACA 3'); XC) an antisense strand of nucleic acid sequence according to SEQ ID NO: 200 (5' UUUUGUCCAGCUCAUACUUGGA 3'), and a sense strand of nucleic acid sequence according to SEQ ID NO: 365 (5' CAAGUAUGAGCUGGACAAAA 3'); XCi) an antisense strand of nucleic acid sequence according to SEQ ID NO: 89 (5' UCUAUGACCUCGAAACUGGGCA 3'), and a sense strand of nucleic acid sequence according to SEQ ID NO: 254 (5' CCCAGUUUCGAGGUCAUAGA 3'); XCii) an antisense strand of nucleic acid sequence according to SEQ ID NO: 120 (5' UGUGAUGUAGUUGCAGCAGUCC 3'), and a sense strand of nucleic acid sequence according to SEQ ID NO: 285 (5' ACUGCUGCAACUACAUCACA 3'); XCiii) an antisense strand of nucleic acid sequence according to SEQ ID NO: 86 (5' UUACUCCUUCACCUCAAACUCA 3'), and a sense strand of nucleic acid sequence according to SEQ ID NO: 251 (5' AGUUUGAGGUGAAGGAGUAA 3'); XCiv) an antisense strand of nucleic acid sequence according to SEQ ID NO: 166 (5' UUCUUUUAGCUGCAGUAGGGCC 3'), and a sense strand of nucleic acid sequence according to SEQ ID NO: 331 (5' CCCUACUGCAGCUAAAAGAA 3'); XCv) an antisense strand of nucleic acid sequence according to SEQ ID NO: 101 (5' UAACACCAUGAGGUCAAAGGGC 3'), and a sense strand of nucleic acid sequence according to SEQ ID NO: 266 (5' CCUUUGACCUCAUGGUGUUA 3'); XCvi) an antisense strand of nucleic acid sequence according to SEQ ID NO: 161 (5' UUGUAGGUUCAUGUAGUUGGCU 3'), and a sense strand of nucleic acid sequence according to SEQ ID NO: 326 (5' CCAACUACAUGAACCUACAA 3'); XCvii) an antisense strand of nucleic acid sequence according to SEQ ID NO: 175 (5' UCAGAUUCCCAGUGGAUACGGU 3'), and a sense strand of nucleic acid sequence according to SEQ ID NO: 340 (5' CGUAUCCACUGGGAAUCUGA 3'); XCviii) an antisense strand of nucleic acid sequence according to SEQ ID NO: 149 (5' UUUCAUCCAGGUAAUGCACAGC 3'), and a sense strand of nucleic acid sequence according to SEQ ID NO: 314 (5' UGUGCAUUACCUGGAUGAAA 3'); XCix) an antisense strand of nucleic acid sequence according to SEQ ID NO: 214 (5' UGGUUGUAAUAGGCGUAGACCU 3'), and a sense strand of nucleic acid sequence according to SEQ ID NO: 379 (5' GUCUACGCCUAUUACAACCA 3'); or C) an antisense strand of nucleic acid sequence according to SEQ ID NO: 62 (5' UGACAGUGCAGGGUCAGAGGGA 3'), and a sense strand of nucleic acid sequence according to SEQ ID NO: 227 (5' CCUCUGACCCUGCACUGUCA 3').

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.01 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 33 to 53; b) 237 to 260; c) 444 to 480; d) 583 to 879; e) 1118 to 1328; f) 1409 to 1542; g) 1619 to 1648; h) 1754 to 1816; i) 2232 to 2256; j) 2300 to 2368; k) 2423 to 2452; l) 2518 to 2726; m) 2860 to 2883; n) 2981 to 3043; o) 3125 to 3239; p) 3298 to 3437; q) 3567 to 3638; r) 3767 to 3913; s) 3985 to 4430; and t) 4490 to 5054, from the 5' end of a C3 mRNA sequence according to SEQ ID NO: 1, and the antisense strand is substantially complementary to the sense strand such that the sense strand and the antisense strand together form a double stranded region, and the isolated oligonucleotide attenuates expression of the C3 mRNA by at least 50% (e.g., 50% to 55%, 55% to 60%, 60% to 65%, 65% to 70%. 70% to 75%, 75% to 80%, 80% to 85%, 85% to 90%, 90% to 95% or 95% to 100%) at a dose of 0.01 nM, wherein the double stranded region comprises: i) an antisense strand of nucleic acid sequence according to SEQ ID NO: 94 (5' UUAGAUGUAGUAGAAUUUCUCU 3'), and a sense strand of nucleic acid sequence according to SEQ ID NO: 259 (5' AGAAAUUCUACUACAUCUAA 3'); or ii) an antisense strand of nucleic acid sequence according to SEQ ID NO: 216 (5' UGAAGCAAUUCUCCUCAGCACA 3'), and a sense strand of nucleic acid sequence according to SEQ ID NO: 381 (5' UGCUGAGGAGAAUUGCUUCA 3').

In some embodiments of the isolated oligonucleotide of the present disclosure, the antisense strand comprises a nucleotide sequence according to any one of: SEQ ID NOs: 3, 4, 5, 7, 29, or 31.

In some embodiments of the isolated oligonucleotide of the present disclosure, the sense strand comprises a nucleotide sequence according to any one of: SEQ ID NOs: 33, 34, 35, 37, 59, or 61.

In some embodiments of the isolated oligonucleotide of the present disclosure, the antisense strand comprises a nucleotide sequence according to any one of: SEQ ID NOs: 3, 4, 5, 7, 29, or 31; and the sense strand comprises a nucleotide sequence according to any one of: SEQ ID NOs: 33, 34, 35, 37, 59, or 61, wherein the antisense strand and the sense strand sequences have sufficient complementarity to allow formation of a double stranded region between the antisense and the sense strand.

In some embodiments of the isolated oligonucleotide of the present disclosure, the isolated oligonucleotide comprises: (a) a sense strand comprising X1 nucleotides, wherein at least one nucleotide is modified with a first modification, each of the remaining nucleotides is independently modified with a second modification, and X1 is an integer selected from 13-36, wherein the first modification and the second modification are different; and (b) an antisense strand comprising X2 nucleotides, wherein at least one nucleotide is modified with a third modification, each of the remaining nucleotides is independently modified with a fourth modification, and X2 is an integer selected from 18-31, wherein the third modification and the fourth modification are different.

In some embodiments, the X1 nucleotides of the sense strand of the isolated oligonucleotide of the present disclosure is 18-21 and the X2 nucleotides of the antisense strand of the isolated oligonucleotide of the present disclosure is 20-23. In some embodiments, the X1 nucleotides of the sense strand of the isolated oligonucleotide of the present disclosure is 20 or 21 and the X2 nucleotides of the antisense strand of the isolated oligonucleotide of the present disclosure is 22 or 23. In some embodiments, the X2 nucleotides of the antisense strand of the isolated oligonucleotide of the present disclosure equals the X1 nucleotides of the sense strand of the isolated oligonucleotide of the present disclosure plus 2. In some embodiments, the X1 nucleotides of the sense strand of the isolated oligonucleotide of the present disclosure is 21 and the X2 nucleotides of the antisense strand of the isolated oligonucleotide of the present disclosure is 23. In some embodiments, the X1 nucleotides of the sense strand of the isolated oligonucleotide of the present disclosure is 20 and the X2 nucleotides of the antisense strand of the isolated oligonucleotide of the present disclosure is 22.

In some embodiments of the isolated oligonucleotide of the present disclosure, the isolated oligonucleotide comprises: (a) a sense strand comprising 20 nucleotides, wherein at least one nucleotide is modified with a first modification, each of the remaining nucleotides is independently modified with a second modification, wherein the first modification and the second modification are the same or different; and (b) an antisense strand comprising 22 nucleotides, wherein at least one nucleotide is modified with a third modification, each of the remaining nucleotides is independently modified with a fourth modification, wherein the third modification and the fourth modification are the same or different.

In some embodiments, the sense strand of the isolated oligonucleotide of the present disclosure comprises at least one nucleotide having a modified phosphate backbone. In some embodiments, the antisense strand of the isolated oligonucleotide of the present disclosure comprises at least one nucleotide having a modified phosphate backbone. In some embodiments, in the sense strand or the antisense strand or both sense and antisense strands of the isolated oligonucleotide of the present disclosure, the modified phosphate backbone comprises a modified phosphodiester bond. In some embodiments, the modified phosphodiester bond is modified by replacing one or more oxygen atoms with a moiety, wherein the moiety is bonded to the phosphorus atom in the phosphodiester bond with a carbon, nitrogen, or sulfur atom in the moiety, or by forming a 2'-5' linkage. In some embodiments, the modified phosphodiester bond comprises phosphorothioate, phosphorodithioate, methylphosphonate, phosphoramidate diester, mesyl phosphoramidate, or phosphonoacetate.

In some embodiments, the isolated oligonucleotide of the present disclosure comprises one or more non-natural base-containing nucleotide, a locked nucleotide, or an abasic nucleotide. In some embodiments, the isolated oligonucleotide of the present disclosure, the terminal nucleotide at the 5' end comprises a phosphate mimic. In some embodiments, the 5'-phosphate mimic is ethylphosphonate, vinylphosphonate or an analog thereof.

In some embodiments, the antisense strand of the isolated oligonucleotide of the present disclosure comprises at least two single-stranded nucleotides at the 3'-terminus. In some embodiments, the antisense strand of the isolated oligonucleotide of the present disclosure comprises two single-stranded nucleotides at the 3'-terminus.

In some embodiments of the isolated oligonucleotide of the present disclosure, wherein the sense strand comprises a nucleotide sequence that is identical to a region between the nucleotide positions 774 to 792, from the 5' end of a C3 mRNA sequence according to SEQ ID NO: 1, the double stranded region comprises an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3').

In some embodiments of the isolated oligonucleotide of the present disclosure, wherein the sense strand comprises a nucleotide sequence that is identical to a region between the nucleotide positions 775 to 793, from the 5' end of a C3 mRNA sequence according to SEQ ID NO: 1, the double stranded region comprises an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3').

In some embodiments of the isolated oligonucleotide of the present disclosure, wherein the sense strand comprises a nucleotide sequence that is identical to a region between the nucleotide positions 777 to 795, from the 5' end of a C3 mRNA sequence according to SEQ ID NO: 1, the double stranded region comprises an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3').

In some embodiments of the isolated oligonucleotide of the present disclosure, wherein the sense strand comprises a nucleotide sequence that is identical to a region between the nucleotide positions 781 to 799, from the 5' end of a C3 mRNA sequence according to SEQ ID NO: 1, the double stranded region comprises an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3').

In some embodiments of the isolated oligonucleotide of the present disclosure, wherein the sense strand comprises a nucleotide sequence that is identical to a region between the nucleotide positions 4602 to 4620, from the 5' end of a C3 mRNA sequence according to SEQ ID NO: 1, the double stranded region comprises an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3').

In some embodiments of the isolated oligonucleotide of the present disclosure, wherein the sense strand comprises a nucleotide sequence that is identical to a region between the nucleotide positions 4607 to 4625, from the 5' end of a C3 mRNA sequence according to SEQ ID NO: 1, the double stranded region comprises an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, the isolated oligonucleotide attenuates expression of the C3 mRNA by 20% to 50% (e.g., between 20% to 25%, 25% to 30%, 30% to 35%, 35% to 40%, 40% to 45% or 45% to 50%), at a dose of 0.01 nM.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region and that attenuates expression of the C3 mRNA by 20% to 50%, at a dose of 0.01 nM, the double stranded region comprises: i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3'); ii) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3'); iii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3'); iv) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3'); v) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); or vi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, the isolated oligonucleotide attenuates expression of the C3 mRNA by at least 50% (e.g., between 50% to 55%, 55% to 60%, 60% to 65%, 65% to 70%, 70% to 75%, 75% to 80%, 80% to 85%, 85% to 90%, 90% to 95% or 95% to 100%), at a dose of 0.1 nM.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, that attenuate expression of the C3 mRNA by at least 50%, at a dose of 0.1 nM, the double stranded region comprises: i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3'); ii) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3'); iii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3'); iv) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3'); v) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); or vi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

In some embodiments, the isolated oligonucleotide of the present disclosure can comprise a linker, sometimes referred to as a loop. siRNAs comprising a linker or loop are sometimes referred to as short hairpin RNAs (shRNAs). In some embodiments, both the sense and the antisense regions of the siRNA are encoded by one single-stranded RNA. In these embodiments, and the antisense region and the sense region hybridize to form a duplex region. The sense and antisense regions are joined by a linker sequence, forming a "hairpin" or "stem-loop" structure. The siRNA can have complementary sense and antisense regions at opposing ends of a single stranded molecule, so that the molecule can form a duplex region with the complementary sequence portions, and the strands are linked at one end of the duplex region by a linker. The linker can be either a nucleotide or non-nucleotide linker or a combination thereof. The linker can interact with the first, and optionally, second strands through covalent bonds or non-covalent interactions.

Any suitable nucleotide linker sequence is envisaged as within the scope of the disclosure. An siRNA of this disclosure may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 3, 4, 5, 6, 7, 8, 9, 10, 11, 12, 13, 14, 15 or 16 nucleotides in length.

Examples of a non-nucleotide linker include an abasic nucleotide, polyether, polyamine, polyamide, peptide, carbohydrate, lipid, polyhydrocarbon, or other polymeric agents, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc, 1991, Vol. 113, pp. 6324-6326; Jaeschke et al., Tetrahedron Lett., 1993, Vol. 34, pp. 301; Arnold et al., WO 1989/002439; Usman et al., WO 1995/006731; Dudycz et al., WO 1995/011910, and Ferentz et al., J. Am. Chem. Soc, 1991, Vol. 113, pp. 4000-4002.

Examples of nucleotide linker sequences include, but are not limited to, AUG, CCC, UUCG, CCACC, AAGCAA, CCACACC and UUCAAGAGA.

In some embodiments, the isolated oligonucleotide of the present disclosure is an siRNA that can be a dsRNA of a length suitable as a Dicer substrate, which can be processed to produce a RISC active siRNA molecule. See, e.g., Rossi et al., US2005/0244858.

A Dicer substrate double stranded RNA (dsRNA) can be of a length sufficient that it is processed by Dicer to produce an active siRNA, and may further include one or more of the following properties: (i) the Dicer substrate dsRNA can be asymmetric, for example, having a 3' overhang on the antisense strand, (ii) the Dicer substrate dsRNA can have a modified 3' end on the sense strand to direct orientation of Dicer binding and processing of the dsRNA to an active siRNA, for example the incorporation of one or more DNA nucleotides, and (iii) the first and second strands of the Dicer substrate ds RNA can from 19-30 bp in length.

In some embodiments, the isolated oligonucleotide of the present disclosure comprises at least one modified nucleotide. In some embodiments of the isolated oligonucleotide of the present disclosure, the sense strand or the antisense strand or both comprise one or more modified nucleotide(s). In some embodiments, only the sense strand comprises one or more modified nucleotide(s). In some embodiments, only the antisense strand comprises one or more modified nucleotide(s). In some embodiments, both the sense strand and antisense strand comprise one or more modified nucleotide (s). In some embodiments, the isolated oligonucleotide is partially chemically modified. In some embodiments, the isolated oligonucleotide is fully chemically modified.

In some embodiments, the isolated oligonucleotide comprises at least two modified nucleotides. In some embodiments, the isolated oligonucleotide comprises at least three modified nucleotides. In some embodiments, the isolated oligonucleotide comprises at least four modified nucleotides. In some embodiments, the isolated oligonucleotide comprises at least five modified nucleotides. In some embodiments, the isolated oligonucleotide comprises at least six modified nucleotides. In some embodiments, the isolated oligonucleotide comprises at least seven modified nucleotides. In some embodiments, the isolated oligonucleotide comprises at least eight modified nucleotides. In some embodiments, the isolated oligonucleotide comprises at least nine modified nucleotides. In some embodiments, the isolated oligonucleotide comprises at least ten modified nucleotides. In some embodiments, the isolated oligonucleotide comprises at least eleven modified nucleotides. In some embodiments, the isolated oligonucleotide comprises at least twelve modified nucleotides. In some embodiments, the isolated oligonucleotide comprises at least thirteen modified nucleotides. In some embodiments, the isolated oligonucleotide comprises at least fourteen modified nucleotides. In some embodiments, the isolated oligonucleotide comprises at least fifteen modified nucleotides. In some embodiments, the isolated oligonucleotide comprises at least sixteen modified nucleotides. In some embodiments, the isolated oligonucleotide comprises at least seventeen modified nucleotides. In some embodiments, the isolated oligonucleotide comprises at least eighteen modified nucleotides. In some embodiments, the isolated oligonucleotide comprises at least nineteen modified nucleotides. In some embodiments, the isolated oligonucleotide comprises at least twenty modified nucleotides. In some embodiments, the isolated oligonucleotide comprises more than twenty modified nucleotides. In some embodiments, the isolated oligonucleotide comprises between twenty and thirty modified nucleotides. In some embodiments, the isolated oligonucleotide comprises between thirty and forty modified nucleotides. In some embodiments, the isolated oligonucleotide comprises between forty and fifty modified nucleotides.

In some embodiments, the sense strand and/or the antisense strand of the isolated oligonucleotide each comprise at least one modified nucleotides. In some embodiments, the sense strand and/or the antisense strand of the isolated oligonucleotide each comprise at least two modified nucleotides. In some embodiments, the sense strand and/or the antisense strand of the isolated oligonucleotide each comprise at least three modified nucleotides. In some embodiments, the sense strand and/or the antisense strand of the isolated oligonucleotide each comprise at least four modified nucleotides. In some embodiments, the sense strand and/or the antisense strand of the isolated oligonucleotide each comprise at least five modified nucleotides. In some embodiments, the sense strand and/or the antisense strand of the isolated oligonucleotide each comprise at least six modified nucleotides. In some embodiments, the sense strand and/or the antisense strand of the isolated oligonucleotide each comprise at least seven modified nucleotides. In some embodiments, the sense strand and/or the antisense strand of the isolated oligonucleotide each comprise at least eight modified nucleotides. In some embodiments, the sense strand and/or the antisense strand of the isolated oligonucleotide each comprise at least nine modified nucleotides. In some embodiments, the sense strand and/or the antisense strand of the isolated oligonucleotide each comprise at least ten modified nucleotides. In some embodiments, the sense strand and/or the antisense strand of the isolated oligonucleotide each comprise at least eleven modified nucleotides. In some embodiments, the sense strand and/or the antisense strand of the isolated oligonucleotide each comprise at least twelve modified nucleotides. In some embodiments, the sense strand and/or the antisense strand of the isolated oligonucleotide each comprise at least thirteen modified nucleotides. In some embodiments, the sense strand and/or the antisense strand of the isolated oligonucleotide each comprise at least fourteen modified nucleotides. In some embodiments, the sense strand and/or the antisense strand of the isolated oligonucleotide each comprise at least fifteen modified nucleotides. In some embodiments, the sense strand and/or the antisense strand of the isolated oligonucleotide each comprise at least sixteen modified nucleotides. In some embodiments, the sense strand and/or the antisense strand of the isolated oligonucleotide each comprise at least seventeen modified nucleotides. In some embodiments, the sense strand and/or the antisense strand of the isolated oligonucleotide each comprise at least eighteen modified nucleotides. In some embodiments, the sense strand and/or the antisense strand of the isolated oligonucleotide each comprise at least nineteen modified nucleotides. In some embodiments, the sense strand and/or the antisense strand of the isolated oligonucleotide each comprise at least twenty modified nucleotides.

In some embodiments, wherein the isolated oligonucleotide comprises more than one modified nucleotide, at least a first nucleotide comprises a first modification and at least a second nucleotide comprises a second modification. In some embodiments, the first modification and second modification are different. In some embodiments, the at least first nucleotide and the at least second nucleotide are located on different strands of the isolated oligonucleotide. In some embodiments, the at least first nucleotide and the at least second nucleotide are located on the same strand of the isolated oligonucleotide.

In some embodiments of the isolated oligonucleotide, wherein the isolated oligonucleotide comprises more than one modified nucleotide, at least a first modified nucleotide comprises a first modification, and at least a second modified nucleotide comprises a second modification, and at least a third nucleotide comprises a third modification. In some embodiments, the isolated oligonucleotide comprises a first, a second, a third and a fourth modifications. In some embodiments, the isolated oligonucleotide comprises more than four modifications. In some embodiments, all modifications are on the sense strand. In some embodiments, all modifications are on the antisense strand. Any combination of locations of the modifications between the sense strand and antisense strand is envisaged within the isolated oligonucleotides of the present disclosure.

In some embodiments, the modified nucleotides are consecutively located on the sense strand or the antisense strand or both. In some embodiments, some but not all of the modified nucleotides are consecutively located on the sense strand or the antisense strand or both. In some embodiments, the modified nucleotides on the sense strand or the antisense strand or both are not consecutively located.

Envisaged within the present disclosure is an isolated oligonucleotide, wherein any nucleotide on the sense strand or antisense strand can be modified. In some embodiments, any nucleotide on the antisense strand can be modified. In some embodiments, any nucleotide on the antisense strand can be modified.

In some embodiments of the isolated oligonucleotides of the present disclosure, the sense strand or the antisense strand or both comprise one or more modified nucleotide(s). In some embodiments, only the sense strand comprises one modified nucleotide. In some embodiments, only the sense strand comprises one or more modified nucleotide(s). In some embodiments, only the antisense strand comprises one modified nucleotide. In some embodiments, only the antisense strand comprises one or more modified nucleotide(s).

In some embodiments, the isolated oligonucleotides of the present disclosure comprises at least one modified nucleotide(s). In some embodiments, the one or more modified nucleotide(s) increases the stability or potency or both of the isolated oligonucleotide. In some embodiments, the one or more modified nucleotide(s) increases the stability of the RNA duplex, and siRNA.

Modifications that increase RNA stability include, but are not limited to, locked nucleic acids. As used herein, the term “locked nucleic acid” or “LNA” includes, but is not limited to, a modified RNA nucleotide in which the ribose moiety comprises a methylene bridge connecting the 2' oxygen and the 4' carbon. This methylene bridge locks the ribose in the 3'-endo confirmation, also known as the north confirmation, that is found in A-form RNA duplexes. The term inaccessible RNA can be used interchangeably with LNA. LNAs having a 2'-4' cyclic linkage, as described in the International Patent Application WO 99/14226, WO 00/56746, WO 00/56748, and WO 00/66604, the contents of which are incorporated herein by reference.

In some embodiments of the isolated oligonucleotide of the present disclosure, the sense strand or the antisense strand or both comprise at least one nucleotide having a modified phosphate backbone. In some embodiments, the sense strand of the isolated oligonucleotide comprises at least one nucleotide having a modified phosphate backbone. In some embodiments, the antisense strand of the isolated oligonucleotide comprises at least one nucleotide having a modified phosphate backbone. In some embodiments, wherein the isolated oligonucleotide of the present disclosure comprises a modified phosphate backbone, the modified phosphate backbone comprises a modified phosphodiester bond. In some embodiments, the modified phosphodiester bond is modified by replacing one or more oxygen atoms with a moiety, wherein the moiety is bonded to the phosphorus atom in the phosphodiester bond with a carbon, nitrogen, or sulfur atom in the moiety, or by forming a 2'-5' linkage. In some embodiments, the modified phosphodiester bond comprises phosphorothioate, phosphorodithioate, methylphosphonate, phosphoramidate diester, mesyl phosphoramidate, or phosphonoacetate.

In some embodiments, the isolated oligonucleotide of the present disclosure comprises one or more non-natural base-containing nucleotide, a locked nucleotide, or an abasic nucleotide. In some embodiments, the one or more modified nucleotide comprises a phosphorothioate derivative or an acridinine substituted nucleotide. In some embodiments, the isolated oligonucleotides of the present disclosure comprise a phosphate mimic at the 5'-terminus of antisense strand, including but not limited to vinylphosphonate or other phosphate analogues. In some embodiments, the 5'-phosphate mimic is ethylphosphonate, vinylphosphonate or an analog thereof.

In some embodiments, the modified nucleotide comprises 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-N-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, or 2, 6-diaminopurine.

In some embodiments of the isolated oligonucleotide of the present disclosure, the sense strand or the antisense strand or both comprise a terminal or internal nucleotide linked to one or more targeting ligands. In some embodiments, the terminal or internal nucleotide is linked to the one or more targeting ligands directly. In some embodiments, the terminal or internal nucleotide is linked to the one or more targeting ligands indirectly by a linker. In some embodiments, the one or more targeting ligands linked directly or indirectly to the terminal or internal nucleotide can further comprise a PK modulator. In some embodiments, the PK modulator is a competitive modulator, a positive allosteric modulator, a negative allosteric modulator or a neutral allosteric modulator. In some embodiments, the targeting ligand is selected from one or more of a carbohydrate, a peptide, a lipid, an antibody or a fragment thereof, an aptamer, an albumin, a fibrinogen, and a folate.

Modification of the Nucleotides

Provided herein is an isolated oligonucleotide, comprising: (a) a sense strand comprising X1 nucleotides, wherein at least one nucleotide is modified with a first modification, each of the remaining nucleotides is independently modified with a second modification, and X1 is an integer selected from 13-36, wherein the first modification and the second modification are different; and (b) an antisense strand comprising X2 nucleotides, wherein at least one nucleotide is modified with a third modification, each of the remaining nucleotides is independently modified with a fourth modification, and X2 is an integer selected from 18-31, wherein the third modification and the fourth modification are different.

In some embodiments, the X1 nucleotides of the sense strand of the isolated oligonucleotide of the present disclosure, is 18-21 and the X2 nucleotides of the antisense strand of the isolated oligonucleotide of the present disclosure is 20-23. In some embodiments, the X1 nucleotides of the sense strand of the isolated oligonucleotide of the present disclosure, is 20 or 21 and the X2 nucleotides of the antisense strand of the isolated oligonucleotide of the present disclosure is 22 or 23. In some embodiments, the X2 nucleotides of the antisense strand of the isolated oligonucleotide of the present disclosure equals the X1 nucleotides of the sense strand of the isolated oligonucleotide of the present disclosure plus 2. In some embodiments, the X1 nucleotides of the sense strand of the isolated oligonucleotide of the present disclosure is 21 and the X2 nucleotides of the antisense strand of the isolated oligonucleotide of the present disclosure is 23. In some embodiments, the X1 nucleotides of the sense strand of the isolated oligonucleotide of the present disclosure is 20 and the X2 nucleotides of the antisense strand of the isolated oligonucleotide of the present disclosure is 22.

In some embodiments of the isolated oligonucleotide of the present disclosure, the isolated oligonucleotide comprises: (a) a sense strand comprising 20 nucleotides, wherein at least one nucleotide is modified with a first modification, each of the remaining nucleotides is independently modified with a second modification, wherein the first modification and the second modification are the same or different; and (b) an antisense strand comprising 22 nucleotides, wherein at least one nucleotide is modified with a third modification, each of the remaining nucleotides is independently modified with a fourth modification, wherein the third modification and the fourth modification are the same or different.

In some embodiments, the first modification is modification of the sugar moiety of the at least one nucleotide at the 2'-position selected from 2'-F modification, 2'-CN modification, 2'-N3 modification, 2'-deoxy modification, and an equivalent thereof, and a combination thereof. In some embodiments, the first modification is 2'-F modification, 2'-CN modification, 2'-N3 modification, or 2'-deoxy modification, or a stereoisomer thereof. In some embodiments, the first modification is 2'-F modification, 2'-CN modification, or 2'-N3 modification, or a stereoisomer thereof. In some embodiments, the first modification is 2'-F modification or a stereoisomer thereof.

In some embodiments, the second modification is modification of the sugar moiety of one or more of the remaining nucleotides at the 2'-position selected from 2'-C1-C6 alkyl, 2'-OR modification wherein R is C1-C6 alkyl optionally substituted with C1-C6 alkoxy, acetamide, phenyl, or heteroaryl comprising a 5- or 6-membered ring and 1 or 2 heteroatoms selected from N, O, and S, 2'-amino, and morpholino replacement, and an equivalent thereof, and a combination thereof. In some embodiments, the second modification is 2'-OR modification, or morpholino replacement, or a combination thereof. In some embodiments, the second modification is 2'-OR modification. In some embodiments, the second modification is 2'-O-methyl modification or 2'-methoxyethoxy modification. In some embodiments, the second modification is 2'-O-methyl modification. In some embodiments, the second modification is morpholino replacement.

In some embodiments, the first modification is 2'-F modification or a stereoisomer thereof, and the second modification is 2'-O-methyl modification or 2'-methoxyethoxy modification. In some embodiments, the first modification is 2'-F modification or a stereoisomer thereof, and the second modification is 2'-O-methyl modification.

In some embodiments, the third modification is modification of the sugar moiety of the at least one nucleotide at the 2'-position selected from 2'-F modification, 2'-CN modification, 2'-N3 modification, 2'-deoxy modification, and an equivalent thereof, and a combination thereof. In some embodiments, the third modification is 2'-F modification, 2'-CN modification, 2'-N3 modification, or 2'-deoxy modification, or a stereoisomer thereof. In some embodiments, the third modification is 2'-F modification, 2'-CN modification, or 2'-N3 modification, or a stereoisomer thereof. In some embodiments, the third modification is 2'-F modification or a stereoisomer thereof.

In some embodiments, the fourth modification is modification of the sugar moiety of one or more of the remaining nucleotides at the 2'-position selected from 2'-C1-C6 alkyl, 2'-OR modification wherein R is C1-C6 alkyl optionally substituted with C1-C6 alkoxy, acetamide, phenyl, or heteroaryl comprising a 5- or 6-membered ring and 1 or 2 heteroatoms selected from N, O, and S, 2'-amino, and morpholino replacement, and an equivalent thereof, and a combination thereof. In some embodiments, the fourth modification is 2'-OR modification, or morpholino replacement, or a combination thereof. In some embodiments, the fourth modification is 2'-OR modification. In some embodiments, the fourth modification is 2'-O-methyl modification or 2'-methoxyethoxy modification. In some embodiments, the fourth modification is 2'-O-methyl modification. In some embodiments, the fourth modification is morpholino replacement.

In some embodiments, the third modification is 2'-F modification or a stereoisomer thereof, and the fourth modification is 2'-O-methyl modification or 2'-methoxyethoxy modification. In some embodiments, the third modification is 2'-F modification or a stereoisomer thereof, and the fourth modification is 2'-O-methyl modification.

Sense Strand

In some embodiments of the isolated oligonucleotide of the present disclosure comprising a sense and an antisense strand, in the sense strand of the isolated oligonucleotide of the present disclosure, at least three nucleotides are modified with the first modification. In some embodiments, in the sense strand of the isolated oligonucleotide of the present disclosure, at least two of the at least three nucleotides modified with the first modification are consecutively located. In some embodiments, in the sense strand of the isolated oligonucleotide of the present disclosure, at least three of the at least three nucleotides modified with the first modification are consecutively located.

In some embodiments, in the sense strand of the isolated oligonucleotide of the present disclosure, in the sense strand at least four nucleotides are modified with the first modification. In some embodiments, in the sense strand of the isolated oligonucleotide of the present disclosure, at least three of the at least four nucleotides modified with the first modification are consecutively located. In some embodiments, in the sense strand of the isolated oligonucleotide of the present disclosure, at least four of the at least four nucleotides modified with the first modification are consecutively located.

In some embodiments, in the sense strand of the isolated oligonucleotide of the present disclosure, in the sense strand at least five nucleotides are modified with the first modification. In some embodiments, in the sense strand of the isolated oligonucleotide of the present disclosure, at least three of the at least five nucleotides modified with the first modification are consecutively located. In some embodiments, in the sense strand of the isolated oligonucleotide of the present disclosure, at least four of the at least five nucleotides modified with the first modification are consecutively located.

In some embodiments, in the sense strand of the isolated oligonucleotide of the present disclosure, the at least three nucleotides, the at least four nucleotides, or the at least five nucleotides modified with the first modification are located from position 10 to position 15 from the nucleotide complementary to the first nucleotide at the 5'-terminus of the antisense strand.

In some embodiments, in the sense strand of the isolated oligonucleotide of the present disclosure, two of the at least three nucleotides modified with the first modification are located at positions selected from position 10, 11, 12, and 13 from the nucleotide complementary to the first nucleotide at the 5'-terminus of the antisense strand. In some embodiments, in the sense strand of the isolated oligonucleotide of the present disclosure, three of the at least three nucleotides modified with the first modification are located at positions selected from position 10, 11, 12, and 13 from the nucleotide complementary to the first nucleotide at the 5'-terminus of the antisense strand. In some embodiments, in the sense strand of the isolated oligonucleotide of the present disclosure, one of the at least three nucleotides modified with the first modification is located at position 11 from the nucleotide complementary to the first nucleotide at the 5'-terminus of the antisense strand.

In some embodiments, in the sense strand of the isolated oligonucleotide of the present disclosure, three of the at least three nucleotides modified with the first modification are located at positions 11, 12 and 13 from the nucleotide complementary to the first nucleotide at the 5'-terminus of the antisense strand. In some embodiments, in the sense strand of the isolated oligonucleotide of the present disclosure, three of the at least three nucleotides modified with the first modification are located at positions 12, 13 and 14 from the nucleotide complementary to the first nucleotide at the 5'-terminus of the antisense. In some embodiments, in the sense strand of the isolated oligonucleotide of the present disclosure, three of the at least three nucleotides modified with the first modification are located at positions 10, 11 and 12 from the nucleotide complementary to the first nucleotide at the 5'-terminus of the antisense strand.

In some embodiments, in the sense strand of the isolated oligonucleotide of the present disclosure, one of the at least four nucleotides modified with the first modification is located at position 10 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 11 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 12 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 13 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 14 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 15 from the nucleotide complementary to the first nucleotide at the 5'-terminus of the antisense strand.

In some embodiments, in the sense strand of the isolated oligonucleotide of the present disclosure, the at least four nucleotides modified with the first modification are located at positions 10, 11, 12 and 13 from the nucleotide complementary to the first nucleotide at the 5'-terminus of the antisense strand.

In some embodiments, in the sense strand of the isolated oligonucleotide of the present disclosure, the at least five nucleotides modified with the first modification are located at positions 10, 11, 12, 13 and 15 from the nucleotide complementary to the first nucleotide at the 5'-terminus of the antisense strand.

In some embodiments of the isolated oligonucleotide of the present disclosure, the sense strand comprises five nucleotides modified with the first modification, wherein the five nucleotides modified with the first modification are located at positions 10, 11, 12, 13 and 15 from the nucleotide complementary to the first nucleotide at the 5'-terminus of the antisense strand.

In some embodiments, in the sense strand of the isolated oligonucleotide of the present disclosure, not all of the at least three nucleotides, the at least four nucleotides, or the at least five nucleotides modified with the first modification are consecutively located. In some embodiments, in the sense strand of the isolated oligonucleotide of the present disclosure, the at least three nucleotides, the at least four nucleotides, or the at least five nucleotides are modified with 2'-F modification.

In some embodiments, the sense strand of the isolated oligonucleotide of the present disclosure comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3'.

In some embodiments of the isolated oligonucleotide of the present disclosure, the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3'.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', the sense strand comprises a nucleotide sequence according to any one of: SEQ ID NOs: 33, 34, 35, 36, 37, 59, or 61.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', the sense strand comprises a nucleotide sequence according to SEQ ID NO: 33.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_b(F)_c(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', and the sense strand comprises a nucleotide sequence according to SEQ ID NO: 33, the antisense strand comprises a nucleotide sequence according to SEQ ID NO: 3.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_f(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_1(F)_1(M)_1(F)_4(M)_9$ 3', the sense strand comprises a nucleotide sequence according to SEQ ID NO: 34.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', and the sense strand comprises a nucleotide sequence according to SEQ ID NO: 34, the antisense strand comprises a nucleotide sequence according to SEQ ID NO: 4.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', the sense strand comprises a nucleotide sequence according to SEQ ID NO: 35.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', and the sense strand comprises a nucleotide sequence according to SEQ ID NO: 35, the antisense strand comprises a nucleotide sequence according to SEQ ID NO: 5.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', the sense strand comprises a nucleotide sequence according to SEQ ID NO: 37.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)+(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', and the sense strand comprises a nucleotide sequence according to SEQ ID NO: 37, the antisense strand comprises a nucleotide sequence according to SEQ ID NO: 7.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_f(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', the sense strand comprises a nucleotide sequence according to SEQ ID NO: 59.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)_4(M)_9$ 3', and the sense strand comprises a nucleotide sequence according to SEQ ID NO: 59, the antisense strand comprises a nucleotide sequence according to SEQ ID NO: 29.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_1(F)_1(M)_1(F)+(M)_9$ 3', the sense strand comprises a nucleotide sequence according to SEQ ID NO: 61.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_a(M)_c(F)_b(M)_a$ 3', wherein M is 2'-O-methyl modified nucleotide, F is 2'-F modified nucleotide, and a, b, c, d, e, f and g is any one of 0-16, and wherein the sense strand is 5'$(M)_0(F)_0(M)_5(F)_1(M)_1(F)+(M)_9$ 3', and the sense strand comprises a nucleotide sequence according to SEQ ID NO: 61, the antisense strand comprises a nucleotide sequence according to SEQ ID NO: 31.

In some embodiments of the isolated oligonucleotide of the present disclosure, wherein the sense strand comprises a nucleotide sequence that is identical to a region between the nucleotide positions 774 to 792, from the 5' end of a C3 mRNA sequence according to SEQ ID NO: 1, the double stranded region comprises an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3').

In some embodiments of the isolated oligonucleotide of the present disclosure, wherein the sense strand comprises a nucleotide sequence that is identical to a region between the nucleotide positions 775 to 793, from the 5' end of a C3 mRNA sequence according to SEQ ID NO: 1, the double stranded region comprises an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3').

In some embodiments of the isolated oligonucleotide of the present disclosure, wherein the sense strand comprises a nucleotide sequence that is identical to a region between the nucleotide positions 777 to 795, from the 5' end of a C3 mRNA sequence according to SEQ ID NO: 1, the double stranded region comprises an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3').

In some embodiments of the isolated oligonucleotide of the present disclosure, wherein the sense strand comprises a nucleotide sequence that is identical to a region between the nucleotide positions 781 to 799, from the 5' end of a C3 mRNA sequence according to SEQ ID NO: 1, the double stranded region comprises an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3').

In some embodiments of the isolated oligonucleotide of the present disclosure, wherein the sense strand comprises a nucleotide sequence that is identical to a region between the nucleotide positions 4602 to 4620, from the 5' end of a C3 mRNA sequence according to SEQ ID NO: 1, the double stranded region comprises an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3').

In some embodiments of the isolated oligonucleotide of the present disclosure, wherein the sense strand comprises a nucleotide sequence that is identical to a region between the nucleotide positions 4607 to 4625, from the 5' end of a C3 mRNA sequence according to SEQ ID NO: 1, the double stranded region comprises an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

Antisense Strand

In some embodiments, in the antisense strand of the isolated oligonucleotide of the present disclosure, at most seven nucleotides are modified with the third modification.

In some embodiments, in the antisense strand of the isolated oligonucleotide of the present disclosure, at most four of the at most seven nucleotides modified with the third modification are located from position 2 to position 8 from the first nucleotide at the 5'-terminus of the antisense strand. In some embodiments, in the antisense strand of the isolated oligonucleotide of the present disclosure, at least one of the at most seven nucleotides are modified with the third modification is located at position 2 from the first nucleotide at the 5'-terminus of the antisense strand.

In some embodiments, in the antisense strand of the isolated oligonucleotide of the present disclosure, at most two of the at most seven nucleotides modified with the third modification are consecutively located. In some embodiments, in the antisense strand of the isolated oligonucleotide of the present disclosure, the at most two consecutively located of the at most seven nucleotides modified with the third modification are located at positions 2 and 3 from the first nucleotide at the 5'-terminus of the antisense strand.

In some embodiments, in the antisense strand of the isolated oligonucleotide of the present disclosure, at least one of the at most seven nucleotides modified with the third modification is located at position 14 from the first nucleotide at the 5'-terminus of the antisense strand. In some embodiments, in the antisense strand of the isolated oligonucleotide of the present disclosure, two or three of the at most seven nucleotides modified with the third modification are located at positions selected from position 2, 3, 5, and 6 from the first nucleotide at the 5'-terminus of the antisense strand. In some embodiments, in the antisense strand of the isolated oligonucleotide of the present disclosure, three of the at most seven nucleotides modified with the third modification are located at positions selected from position 2, 3, 5, and 6 from the first nucleotide at the 5'-terminus of the antisense strand. In some embodiments, in the antisense strand of the isolated oligonucleotide of the present disclosure, two of the at most seven nucleotides modified with the third modification are located at positions 2 and 5 from the first nucleotide at the 5'-terminus of the antisense strand. In some embodiments, in the antisense strand of the isolated oligonucleotide of the present disclosure, two of the at most seven nucleotides modified with the third modification are located at positions 2 and 3 from the first nucleotide at the 5'-terminus of the antisense strand.

In some embodiments, in the antisense strand of the isolated oligonucleotide of the present disclosure, three of the at most seven nucleotides modified with the third modification are located at positions 2, 3 and 5 from the first nucleotide at the 5'-terminus of the antisense strand.

In some embodiments, in the antisense strand of the isolated oligonucleotide of the present disclosure, one or two of the at most seven nucleotides modified with the third modification are located at positions selected from position 14 and 16 from the first nucleotide at the 5'-terminus of the antisense strand. In some embodiments, in the antisense strand of the isolated oligonucleotide of the present disclosure, two of the at most seven nucleotides modified with the third modification are located at positions 14 and 16 from the first nucleotide at the 5'-terminus of the antisense strand. In some embodiments, in the antisense strand of the isolated oligonucleotide of the present disclosure, the at most seven nucleotides are modified with 2'-F modification. In some embodiments, in the antisense strand of the isolated oligonucleotide of the present disclosure, one of the at most seven nucleotides modified with the third modification is located at position 14 from the first nucleotide at the 5'-terminus of the antisense strand. In some embodiments, in the antisense strand of the isolated oligonucleotide of the present disclosure, two of the at most seven nucleotides modified with the third modification is located at positions 14 and 16 from the first nucleotide at the 5'-terminus of the antisense strand.

In some embodiments of the isolated oligonucleotides of the present disclosure, wherein the antisense strand comprises at most seven nucleotides modified with the third modification, the at most seven nucleotides are modified with 2'-F modification. In some embodiments, in the antisense strand of the isolated oligonucleotide of the present disclosure, one of the at most seven nucleotides modified with the third modification is located at position 2 from the first nucleotide at the 5'-terminus of the antisense strand. In some embodiments, in the antisense strand of the isolated oligonucleotide of the present disclosure, one of the at most seven nucleotides modified with the third modification is located at position 3 from the first nucleotide at the 5'-terminus of the antisense strand. In some embodiments, in the antisense strand of the isolated oligonucleotide of the present disclosure, one of the at most seven nucleotides modified with the third modification is located at position 5 from the first nucleotide at the 5'-terminus of the antisense strand. In some embodiments, in the antisense strand of the isolated oligonucleotide of the present disclosure, one of the at most seven nucleotides modified with the third modification is located at position 7 from the first nucleotide at the 5'-terminus of the antisense strand. In some embodiments, in the antisense strand of the isolated oligonucleotide of the present disclosure, one of the at most seven nucleotides modified with the third modification is located at position 10 from the first nucleotide at the 5'-terminus of the antisense strand. In some embodiments, in the antisense strand of the isolated oligonucleotide of the present disclosure, one of the at most seven nucleotides modified with the third modification is located at position 14 from the first nucleotide at the 5'-terminus of the antisense strand. In some embodiments, in the antisense strand of the isolated oligonucleotide of the present disclosure, one of the at most seven nucleotides modified with the third modification is located at position 16 from the first nucleotide at the 5'-terminus of the antisense strand. In some embodiments, in the antisense strand of the isolated oligonucleotide of the present disclosure, the at most seven nucleotides modified with the third modification are located at positions 2, 3, 5, 7, 10, 14 and 16 from the first nucleotide at the 5'-terminus of the antisense strand.

In some embodiments, in the antisense strand of the isolated oligonucleotide of the present disclosure, the antisense strand comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, l, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)(M)_n$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$, the antisense strand comprises a nucleotide sequence according to any one of SEQ ID NOs: 3, 4, 5, 7, 29, or 31.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_i(F)_1(M)_1(F)_2(M)_1$ $5'$, and the antisense strand comprises a nucleotide sequence according to SEQ ID NO: 3.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_f(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$, and the antisense strand comprises a nucleotide sequence according to SEQ ID NO: 3, and the sense strand comprises a nucleotide sequence according to SEQ ID NO: 33.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$, and the antisense strand comprises a nucleotide sequence according to SEQ ID NO: 4.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$, and the antisense strand comprises a nucleotide sequence according to SEQ ID NO: 4, and the sense strand comprises a nucleotide sequence according to SEQ ID NO: 34.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: $3'$ $(M)_a(F)_b(M)_c(F)_d(M)_e(F)_f(M)_g(F)_h(M)_i(F)_j(M)_k(F)_l(M)_m(F)_n(M)_o$ $5'$, wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: $3'(M)_0(F)_0(M)_6(F)_1(M)_1(F)_1(M)_3(F)_1(M)_2(F)_1(M)_1(F)_1(M)_1(F)_2(M)_1$ $5'$, and the antisense strand comprises a nucleotide sequence according to SEQ ID NO: 5.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_1(F)_f(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 5, and the sense strand comprises a nucleotide sequence according to SEQ ID NO: 35.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 7.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 7, and the sense strand comprises a nucleotide sequence according to SEQ ID NO: 37.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, l, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 29.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 29, and the sense strand comprises a nucleotide sequence according to SEQ ID NO: 59.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 31.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_d(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, 1, m, n and o is any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 31, and the sense strand comprises a nucleotide sequence according to SEQ ID NO: 61.

Targeting Ligand

In some embodiments, in the sense strand or the antisense strand or both of the isolated oligonucleotide of the present disclosure, a terminal or internal nucleotide is linked to a targeting ligand. In some embodiments, the targeting ligand is attached to one or more nucleotides at the 5' end of the sense strand of the isolated oligonucleotide of the present disclosure. In some embodiments, the targeting ligand is attached to one or more nucleotides at the 3' end of the sense strand of the isolated oligonucleotide of the present disclosure. In some embodiments, the targeting ligand is attached to one or more nucleotides at the 5' end of the antisense strand of the isolated oligonucleotide of the present disclosure. In some embodiments, the targeting ligand is attached to one or more nucleotides at the 3' end of the antisense strand of the isolated oligonucleotide of the present disclosure. In some embodiments, the targeting ligand is attached to one or more nucleotides of the at least two single-stranded nucleotides at the 3'-terminus of the antisense strand of the isolated oligonucleotide of the present disclosure.

In some embodiments, the targeting ligand is selected from one or more of a carbohydrate, a peptide, a lipid, an antibody or a fragment thereof, an aptamer, an albumin, a fibrinogen, and a folate. In some embodiments, the targeting ligand binds to a surface protein on a cell expressing a target mRNA of the isolated oligonucleotide of the present disclosure. In some embodiments, the targeting ligand mediates entry of the isolated oligonucleotide of the present disclosure, into a cell expressing a target mRNA of the isolated oligonucleotide of the present disclosure.

In some embodiments, the targeting ligand is a therapeutic ligand. In some embodiments, the targeting ligand is a therapeutic antibody.

In some embodiments, the targeting ligand is attached to the isolated oligonucleotide of the present disclosure by a linker. In some embodiments, the linker is any one or a protein, a DNA, an RNA or a chemical compound. In some embodiments, the isolated oligonucleotide, the linker and the targeting ligand, of the present disclosure form a scaffold. As used herein, the term "scaffold" refers to a compound or complex that comprises a linker of the present disclosure, wherein the linker is covalently attached to either a ligand or an isolated oligonucleotide or both.

In some embodiments, the isolated oligonucleotide, the linker and the targeting ligand, of the present disclosure form a conjugate. As used herein, the term "conjugate" refers to a compound or complex that comprises an isolated oligonucleotide being covalently attached to a ligand via a linker of the present disclosure.

As used herein, the term "targeting ligand" or "ligand" refers to a moiety that, when being covalently attached to GalNAc an oligonucleotide), is capable of mediating its entry into, or facilitating or allowing its delivery to, a target site (e.g., a target cell or tissue). In some embodiments, the targeting ligand comprises a sugar ligand moiety (e.g., N-acetylgalactosamine (GalNAc)) which may direct uptake of an oligonucleotide into the liver.

In some embodiments, the targeting ligand binds to the asialoglycoprotein receptor (ASGPR). In some embodiments, the targeting ligand binds to (e.g., through ASGPR) the liver, such as the parenchymal cells of the liver.

Suitable targeting ligands include, but are not limited to, the ligands disclosed in Winkler (Ther. Deliv., 2013, 4(7): 791-809), PCT Patent Appl'n Pub. Nos. WO/2016/100401, WO/2012/089352, and WO/2009/082607, and U.S. Patent Appl'n Pub. Nos. 2009/0239814, 2012/0136042, 2013/0158824, and 2009/0247608, each of which is incorporated by reference.

In some embodiments, the targeting ligand comprises a carbohydrate moiety.

As used herein, "carbohydrate moiety" refers to a moiety which comprises one or more monosaccharide units each having at least six carbon atoms (which may be linear, branched or cyclic), with an oxygen, nitrogen or sulfur atom bonded to each carbon atom. In some embodiments, the carbohydrate moiety comprises a monosaccharide, a disaccharide, a trisaccharide, or a tetrasaccharide. In some embodiments, the carbohydrate moiety comprises an oligosaccharide containing from about 4-9 monosaccharide units. In some embodiments, the carbohydrate moiety comprises a polysaccharide (e.g., a starch, a glycogen, a cellulose, or a polysaccharide gum).

In some embodiments, the carbohydrate moiety comprises a monosaccharide, a disaccharide, a trisaccharide, or a tetrasaccharide. In some embodiments, the carbohydrate moiety comprises an oligosaccharide (e.g., containing from about four to about nine monosaccharide units). In some embodiments, the carbohydrate moiety comprises a polysaccharide (e.g., a starch, a glycogen, a cellulose, or a polysaccharide gum).

In some embodiments, the ligand is capable of binding to a human asialoglycoprotein receptor (ASGPR), e.g., human asialoglycoprotein receptor 2 (ASGPR2).

In some embodiments, the carbohydrate moiety comprises a sugar (e.g., one, two, or three sugar). In some embodiments, the carbohydrate moiety comprises galactose or a derivative thereof (e.g., one, two, or three galactose or the derivative thereof). In some embodiments, the carbohydrate moiety comprises N-acetylgalactosamine or a derivative thereof (e.g., one, two, or three N-acetylgalactosamine or the derivative thereof). In some embodiments, the carbohydrate moiety comprises N-acetyl-D-galactosylamine or a derivative thereof (e.g., one, two, or three N-acetyl-D-galactosylamine or the derivative thereof).

In some embodiments, the carbohydrate moiety comprises N-acetylgalactosamine (e.g., one, two, or three N-acetylgalactosamine). In some embodiments, the carbohydrate moiety comprises N-acetyl-D-galactosylamine (e.g., one, two, or three N-acetyl-D-galactosylamine).

In some embodiments, the carbohydrate moiety comprises mannose or a derivative thereof (e.g., mannose-6-phosphate). In some embodiments, the carbohydrate moiety further comprises a linking moiety that connects the one or more sugar (e.g., N-acetyl-D-galactosylamine) with a linker.

In some embodiments the linker comprises thioether (e.g., thiosuccinimide, or the hydrolysis analogue thereof), disulfide, triazole, phosphorothioate, phosphodiester, ester, amide, or any combination thereof. In some embodiments, the linker is a triantennary linking moiety. Suitable targeting ligands include, but are not limited to, the ligands disclosed in PCT Appl'n Pub. Nos. WO/2015/006740, WO/2016/100401, WO/2017/214112, WO/2018/039364, and WO/2018/045317, each of which is incorporated herein by reference.

In some embodiments, the targeting ligand comprises a lipid or a lipid moiety (e.g., one, two, or three lipid moiety). In some embodiments the lipid moiety comprises (e.g., one, two, of three of) C8-C24 fatty acid, cholesterol, vitamin, sterol, phospholipid, or any combination thereof.

In some embodiments, the targeting ligand comprises a peptide or a peptide moiety (e.g., one, two, or three peptide moiety). In some embodiments, the peptide moiety comprises (e.g., one, two, or three of) integrin, insulin, glucagon-like peptide, or any combination thereof. In some embodiments, the targeting ligand comprises an antibody or an antibody moiety (e.g., transferrin). In some embodiments, the targeting ligand comprises one, two, or three antibody moieties (e.g., transferrin).

In some embodiments, the targeting ligand comprises an oligonucleotide (e.g., aptamer or CpG). In some embodiments, the targeting ligand comprises one, two, or three oligonucleotides (e.g., aptamer or CpG).

In some embodiments, the ligand comprises: one, two, or three sugar (e.g., N-acetyl-D-galactosylamine); one, two, or three lipid moieties; one, two, or three peptide moieties; one, two, or three antibody moieties; one, two, or three oligonucleotides; or any combination thereof.

In some embodiments, the linker is attached to the isolated oligonucleotide of the present disclosure, via a phosphate group, or an analog of a phosphate group, in the isolated oligonucleotide.

In some embodiments, the ligand comprises a sugar ligand moiety (e.g., N-acetylgalactosamine (GalNAc)) which may direct uptake of an oligonucleotide into the liver In some embodiments, the ligand comprises GalNAc, or a derivative thereof. In some embodiments, the ligand comprises a GalNAc G1b structure shown below

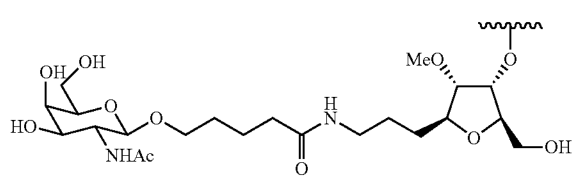

GalNAc G1b

In some embodiments, the ligand comprises three GalNAc moieties, or three derivatives thereof. In some embodiments, the ligand comprises three GalNAc G1b moieties. In some embodiments, wherein the ligand comprises three GalNAc G1b moieties, the GalNAc G1b moieties are consecutively located. In some embodiments, the consecutively located GalNAc G1b moieties are located on the 3' end of the sense strand. In some embodiments, wherein the ligand comprises three GalNAc G1b ("G1b") moieties that are consecutively located, the first G1b moiety is linked to the second G1b moiety and the second G1b is linked to the third G1b moiety. In some embodiments, the first GalNAc G1b moiety is linked to the sense strand of the isolated oligonucleotide of the present disclosure.

In some embodiments of the isolated oligonucleotide of the present disclosure, wherein the ligand comprises three GalNAc G1b ("G1b") moieties, wherein the first GalNAc G1b moiety is linked to the sense strand of the isolated oligonucleotide, the first GalNAc G1b moiety is also linked to the second GalNAc G1b moiety, and the second G1b is linked to the third G1b moiety. In some embodiments, wherein the ligand comprises three GalNAc G1b moieties, the three GalNAc G1b moieties are consecutively located on the 3' end of the sense strand.

In some embodiments of the isolated oligonucleotide of the present disclosure, the isolated oligonucleotide is linked to the ligand (e.g., GalNAc G1b, or three GalNAc G1b moieties). In some embodiments, the isolated oligonucleotide is linked to the ligand via an internal or terminal nucleotide of the isolated oligonucleotide. In some embodiments, the isolated oligonucleotide is linked to the ligand via a ligand linker. In some embodiments, the In some embodiments of the isolated oligonucleotide of the present disclosure, wherein the isolated oligonucleotide comprises a sense and an antisense strand, and wherein the ligand comprises three GalNAc G1b moieties, and the three GalNAc G1b moieties are consecutively located on the 3' end of the sense strand, the ligand is linked to a terminal nucleotide on the sense strand of the isolated oligonucleotide. In some embodiments, the ligand is linked to a terminal nucleotide on the sense strand via a ligand linker. In some embodiments, the ligand linker is a monovalent linker. In some embodiments, the ligand linker is a bivalent linker. In some embodiments, the ligand linker is a trivalent linker.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, a targeting ligand is attached to the 3' end of the sense strand. In some embodiments, the targeting ligand comprising three GalNAc G1b moieties.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, wherein the targeting ligand comprises three GalNAc G1b moieties attached to the 3' end of the sense strand, the sense strand comprises a nucleic acid sequence according to SEQ ID NO: 33 (5' CUACAGAGAAAUUCUACUAA 3'); SEQ ID NO: 34 (5' UACAGAGAAAUUCUACUACA 3'); SEQ ID NO: 35 (5' CAGAGAAAUUCUACUACAUA 3'); SEQ ID NO: 37 (5' GAAAUUCUACUACAUCUAUA 3'); SEQ ID NO: 59 (5' CUGAGGAGAAUUGCUUCAUA 3'); or SEQ ID NO: 61 (5' GAGAAUUGCUUCAUACAAAA 3').

The linkage at the 3' end of the isolated oligonucleotide of the present disclosure may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 3' terminal nucleotide. In some embodiments, the ligand described herein can be attached to the isolated oligonucleotide of the present disclosure with various ligand linkers that can be cleavable or non-cleavable.

Modification of the Phosphate Groups

Modified Terminal Phosphate Groups

The present disclosure further provides oligonucleotides and conjugates containing modified phosphate groups (also referred to as phosphate mimics or phosphate derivatives) for nucleic acid delivery. The present disclosure also relates to uses of oligonucleotides and conjugates containing modified phosphate groups, e.g., in delivering nucleic acid and/or treating or preventing diseases.

In some embodiments, the present disclosure provides phosphate mimics of 5'-terminal nucleotides. Without wishing to be bound by theory, it is understood that, when being incorporated into oligonucleotides (e.g., at the 5'-terminus of the antisense strand), the phosphate mimics could improve the Ago2 binding/loading and enhance the metabolic stability of the oligonucleotides, thus enhancing the potency and duration of the isolated oligonucleotides (e.g., dsRNA or siRNA).

In some embodiments of the isolated oligonucleotides of the present disclosure, the oligonucleotides comprise 5'-terminal nucleotide modifications. In some embodiments, the 5'-terminal modifications provide the functional effect of a phosphate group, but are more stable in the environmental conditions that the oligonucleotide will be exposed to when administered to a subject. In some embodiments, the isolated oligonucleotide comprises phosphate mimics that are more resistant to phosphatases and other enzymes while minimizing negative impact on the oligonucleotide's function (e.g., minimizing any reduction in gene target knockdown when used as an RNAi inhibitor molecule).

In some embodiments, the 5'-terminal modification is a chemical modification. In some embodiments, the chemical modification enhances stability against nucleases or other enzymes that degrade or interfere with the structure or activity of the isolated oligonucleotide.

In some embodiments, the sense or antisense strand of the isolated oligonucleotides of the present disclosure comprise a 5'-terminal phosphate group. In some embodiments, the 5'-terminal phosphate group comprises an unmodified phosphate having the formula: $—O—P(=O)(OH)OH$. In some embodiments, the 5'-terminal phosphate group comprises a modified phosphate. In some embodiments, the 5'-terminal phosphate group comprises a modified phosphate having the formula $—CH_2—P(=X)(OR^1)OR^2$, wherein X is O or S, $R^1$ is H or $C_1$-$C_6$ alkyl, and $R^2$ is H or $C_1$-$C_6$ alkyl. In some embodiments, the modified phosphate is referred to as a "phosphate mimic".

The term, "halo" or "halogen", as used herein, refers to fluoro, chloro, bromo and iodo.

The term, "aryl", as used herein, includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

The term, "alkyl" or "$C_1$-$C_6$ alkyl", as used herein, is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms. In some embodiments, the straight chain alkyl has one carbon atom. In some embodiments, the straight chain alkyl has two carbon atoms.

In some embodiments, the phosphate mimic is linked to the 5'-terminus of the isolated oligonucleotides (e.g., siRNAs) as shown in the following formula:

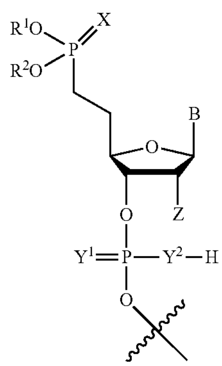

wherein:

B is H or a nucleobase moiety;

X is O or S;

$R^1$ is H or $C_1$-$C_6$ alkyl;

$R^2$ is H or $C_1$-$C_6$ alkyl;

$Y^1$ is O or S;

$Y^2$ is O or S;

Z is H, halogen, or —$OR^2$;

$R^Z$ is H, $C_1$-$C_6$ alkyl, or —($C_1$-$C_6$ alkyl)—($C_6$-$C_{10}$ aryl), wherein the $C_1$-$C_6$ alkyl or —($C_1$-$C_6$ alkyl)—($C_6$-$C_{10}$ aryl) is optionally substituted with one or more $R^{Za}$, each $R^{Za}$ independently is halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen; and

indicates an attachment to a nucleotide of the isolated oligonucleotide (e.g., siRNA).

In some embodiments, the phosphate mimic is linked to the 5'-terminus of the isolated oligonucleotides (e.g., siRNAs) as shown in the following formula:

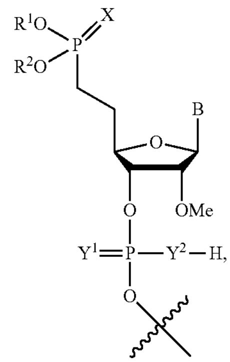

wherein:

B is H or a nucleobase moiety;

X is O or S;

$R^1$ is H or $C_1$-$C_6$ alkyl;

$R^2$ is H or $C_1$-$C_6$ alkyl;

$Y^1$ is O or S;

$Y^2$ is O or S; and

indicates an attachment to a nucleotide of the isolated oligonucleotide (e.g., siRNA).

In some embodiments, the phosphate mimic is linked to the 5'-terminus of the isolated oligonucleotides (e.g., siRNAs) as shown in the following formula:

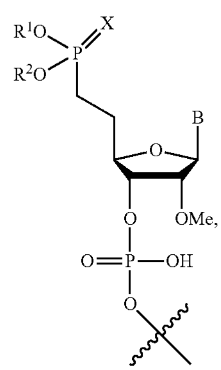

wherein:

B is H or a nucleobase moiety;

X is O or S;

$R^1$ is H or $C_1$-$C_6$ alkyl;

$R^2$ is H or $C_1$-$C_6$ alkyl; and

indicates an attachment to a nucleotide of the isolated oligonucleotide (e.g., siRNA).

In some embodiments, X is O.

In some embodiments, X is S.

In some embodiments, $R^1$ is H.

In some embodiments, $R^1$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^1$ is methyl.

In some embodiments, $R^2$ is H.

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^2$ is methyl.

In some embodiments, $Y^1$ is O.

In some embodiments, $Y^1$ is S.

In some embodiments, $Y^2$ is O.

In some embodiments, $Y^2$ is S.

In some embodiments, Z is H.

In some embodiments, Z is not H.

In some embodiments, Z is halogen (e.g., F, Cl, Br, or I).

In some embodiments, Z is F or $C_1$.

In some embodiments, Z is F

In some embodiments, Z is —$OR^Z$.

In some embodiments, Z is —OH.

In some embodiments, Z is not —OH.

In some embodiments, Z is —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, Z is —$OCH_3$.

In some embodiments, Z is —O—($C_1$-$C_6$ alkyl)-O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, Z is —$OCH_2CH_2OCH_3$.

In some embodiments, Z is —O—($C_1$-$C_6$ alkyl)-($C_6$-$C_{10}$ aryl) optionally substituted with one or more $R^{Za}$.

In some embodiments, Z is —O—($C_1$-$C_6$ alkyl)-($C_6$-$C_{10}$ aryl).

In some embodiments, Z is

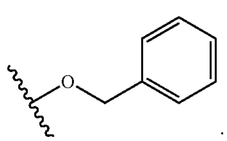 [SMILES: *OCc1ccccc1]

.

In some embodiments, Z is

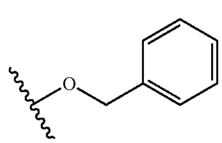 [SMILES: *OCc1ccccc1]

optionally substituted with one or more $R^{Za}$.

In some embodiments, Z is

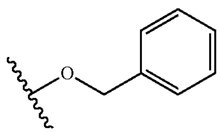 [SMILES: *OCc1ccccc1]

optionally substituted with one or more halogen.

In some embodiments, Z is

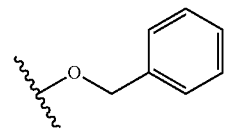 [SMILES: *OCc1ccccc1]

optionally substituted with one or more $C_1$-$C_6$ alkyl or —O—($C_1$-$C_6$ alkyl), wherein the $C_1$-$C_6$ alkyl or —O—($C_1$-$C_6$ alkyl) is optionally substituted with one or more halogen.

In some embodiments, $R^Z$ is H.

In some embodiments, $R^Z$ is not H.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more $R^{Za}$.

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl) optionally substituted with one or more halogen.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^2$ is methyl, ethyl, or propyl.

In some embodiments, $R^Z$ is methyl.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) substituted with one or more —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the —O—($C_1$-$C_6$ alkyl) is optionally substituted with one or more halogen.

In some embodiments, $R^Z$ is —($C_1$-$C_6$ alkyl)-($C_6$-$C_{10}$ aryl) optionally substituted with one or more $R^{Za}$.

In some embodiments, $R^Z$ is —($C_1$-$C_6$ alkyl)-($C_6$-$C_{10}$ aryl) optionally substituted with one or more halogen (e.g., F, Cl, Br, or I), $C_1$-$C_6$ alkyl (e.g., methyl, ethyl, n-propyl, i-propyl, n-butyl, i-butyl, s-butyl, t-butyl, pentyl, or hexyl), or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the $C_1$-$C_6$ alkyl or —O—($C_1$-$C_6$ alkyl) is optionally substituted with one or more halogen.

In some embodiments, $R^Z$ is —($C_1$-$C_6$ alkyl)-($C_6$-$C_{10}$ aryl).

In some embodiments, at least one $R^{Za}$ is halogen (e.g., F, Cl, Br, or I).

In some embodiments, at least one $R^{Za}$ is F or Cl.

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl).

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, at least one $R^{Za}$ is —O—($C_1$-$C_6$ alkyl) optionally substituted with one or more halogen (e.g., F, Cl, Br, or I).

In some embodiments, at least one $R^{Za}$ is —O—($C_1$-$C_6$ alkyl).

In some embodiments, at least one $R^{Za}$ is —O—($C_1$-$C_6$ alkyl) substituted with one or more halogen (e.g., F, Cl, Br, or I).

In some embodiments, B is H.

In some embodiments, B is a nucleobase moiety.

The term "nucleobase moiety", as used herein, refers to a nucleobase that is attached to the rest of the isolated oligonucleotides (e.g., dsRNA or siRNA) of the present disclosure, e.g., via an atom of the nucleobase or a functional group thereof.

In some embodiments, the nucleobase moiety is adenine (A), cytosine (C), guanine (G), thymine (T), or uracil (U).

In some embodiments, the nucleobase moiety is uracil (U).

In some embodiments, the phosphate mimic is linked to the 5'-terminus of the isolated oligonucleotides as shown in the following formula:

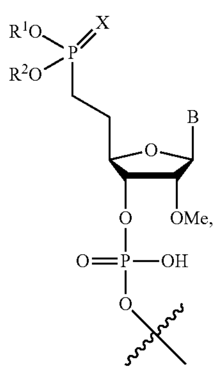

wherein:

B is a nucleobase moiety, wherein the nucleobase moiety is uracil (U), wherein the uracil is at position 1 from the 5'-terminus of the sense strand or at position 1 from the 5'-terminus of the antisense strand;

X is O;

$R^1$ is $C_1$ alkyl;

$R^2$ is H; and

indicates an attachment to a nucleotide of the isolated oligonucleotide (e.g., siRNA).

In some embodiments of the isolated oligonucleotides of the present disclosure, the phosphate mimic is attached to the 5'-terminus of the antisense strand of the isolated oligonucleotide.

In some embodiments, the phosphate mimic is attached to a 5'-terminal uridine of the antisense strand of the isolated oligonucleotide, having the following structure (5'-MeEPmU).

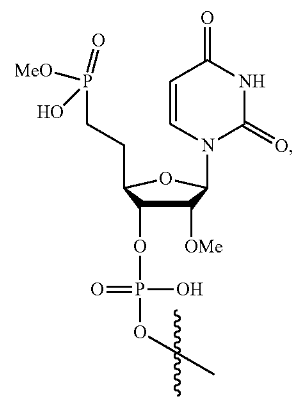

5'-MeEPmU wherein "mU" is a 2'-O-methyl modified uridine nucleotide and "MeEP" is a mono methyl protected phosphate mimic.

In some embodiments, the phosphate mimic is attached to a 5'-terminal uridine of the antisense strand of the isolated oligonucleotide, having the following structure (5'-MeEP-mUs).

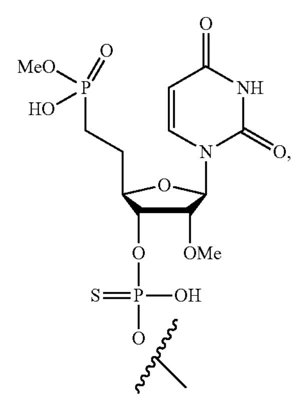

5'-MeEPmUs wherein "mU" is a 2'-O-methyl modified uridine nucleotide, "MeEP" is a mono methyl protected phosphate mimic, and "s" is a phosphorothioate internucleotide linkage.

In some embodiments, the phosphate mimic is attached to a 5'-terminal uridine of the antisense strand of the isolated oligonucleotide, having the following structure (5'-EPmUs).

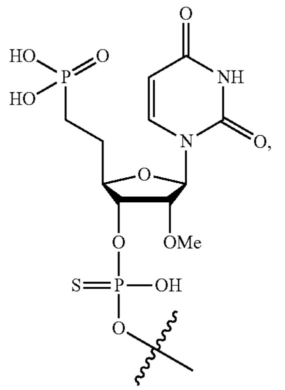

5'-EPmUs wherein "mU" is a 2'-O-methyl modified uridine nucleotide, "EP" is a phosphate mimic, and "s" is a phosphorothioate internucleotide linkage.

The terms "5'-MeEP", "5'-MeEP", and "5' MeEP" are used interchangeably herein.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, the antisense strand comprises a mono methyl protected phosphate mimic (MeEP). In some embodiments, the MeEP is linked to the 5' end of the antisense strand (5'-MeEP).

In some embodiments, wherein the MeEP is linked to the 5' end of the antisense strand, the phosphate mimic is attached to a 5'-terminal uridine of the antisense strand.

In some embodiments, the 5'-terminal uridine is a 2'-O-methyl modified nucleotide.

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a C3 mRNA sequence according to SEQ ID NO: 1, and the antisense strand is substantially complementary to the sense strand such that the sense strand and the antisense strand together form a double stranded region, wherein the antisense strand comprises a 5'-MeEP linked to the 5' end of the antisense strand, the antisense strand comprises a nucleic acid sequence according to SEQ ID NO: 3 (5' UUAGUAGAAUUUCUCUGUAGGC 3'); SEQ ID NO: 4 (5' UGUAGUAGAAUUUCUCUGUAGG 3'); SEQ ID NO: 5 (5' UAUGUAGUAGAAUUUCUCUGUA 3'); SEQ ID NO: 7 (5' UAUAGAUGUAGUAGAAUUUCUC 3'); SEQ ID NO: 29 (5' UAUGAAGCAAUUCUCCUCAGCA 3'); or SEQ ID NO: 31 (5' UUUUGUAUGAAGCAAUUCUCCU 3').

In some embodiments of the isolated oligonucleotide of the present disclosure wherein the sense strand comprises a nucleotide sequence that is identical to a region between any one of the nucleotide positions selected from: a) 774 to 799; and b) 4602 to 4625, from the 5' end of a $C_3$ mRNA sequence according to SEQ ID NO: 1, and the antisense strand is substantially complementary to the sense strand such that the sense strand and the antisense strand together form a double stranded region, wherein the antisense strand comprises a 5'-MeEP linked to the 5' end of the antisense strand, the sense strand comprises a targeting ligand comprising three GalNAc G1b moieties attached to the 3' end of the sense strand.

Modified Backbone Phosphate/Phosphodiester Bond

In some embodiments of the isolated oligonucleotide of the present disclosure, the sense strand or the antisense strand or both comprise at least one nucleotide having a modified phosphate backbone. In some embodiments, the sense strand of the isolated oligonucleotide comprises at least one nucleotide having a modified phosphate backbone. In some embodiments, the antisense strand of the isolated oligonucleotide comprises at least one nucleotide having a modified phosphate backbone. In some embodiments, wherein the isolated oligonucleotide of the present disclosure comprises a modified phosphate backbone, the modified phosphate backbone comprises a modified phosphodiester bond. A phosphodiester bond comprises a linkage having the formula:

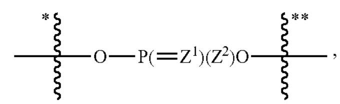

wherein

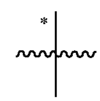

denotes attachment to a 3' carbon of a first nucleotide in the isolated oligonucleotide of the present disclosure; and

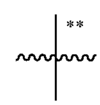

denotes attachment to a 5' carbon of a second nucleotide in the isolated oligonucleotide of the present disclosure. In some embodiments, the phosphodiester bond is unmodified, wherein $Z^1$ is O and $Z^2$ is OH or $O^-$. In some embodiments, the phosphodiester bond is modified, wherein $Z^1$ is O, S, NH, or N($C_1$-$C_6$ alkyl) and $Z^2$ is OH, SH, $NH_2$, NH($C_1$-$C_6$ alkyl), $O^-$, $S^-$, $HN^-$, or ($C_1$-$C_6$ alkyl)$N^-$, and wherein when $Z^1$ is O, $Z^2$ is not OH or $O^-$.

In some embodiments, $Z_1$ is O.

In some embodiments, $Z_1$ is S.

In some embodiments, $Z_1$ is NH.

In some embodiments, $Z_1$ is N($C_1$-$C_6$ alkyl).

In some embodiments, $Z_2$ is OH.

In some embodiments, $Z_2$ is SH.

In some embodiments, $Z_2$ is $NH_2$.

In some embodiments, $Z_2$ is NH($C_1$-$C_6$ alkyl).

In some embodiments, $Z_2$ is SH, $NH_2$, or NH($C_1$-$C_6$ alkyl).

In some embodiments, $Z_2$ is $O^-$.

In some embodiments, $Z_2$ is $S^-$.

In some embodiments, $Z_2$ is $HN^-$.

In some embodiments, $Z_2$ is ($C_1$-$C_6$ alkyl)$N^-$.

In some embodiments, $Z_2$ is $S^-$, $HN^-$, or ($C_1$-$C_6$ alkyl)$N^-$.

In some embodiments, $Z_1$ is O and $Z_2$ is SH.

In some embodiments, $Z_1$ is O and $Z_2$ is $NH_2$.

In some embodiments, $Z_1$ is O and $Z_2$ is $NH(C_1\text{-}C_6$ alkyl).

In some embodiments, $Z_1$ is S and $Z_2$ is OH.

In some embodiments, $Z_1$ is S and $Z_2$ is SH.

In some embodiments, $Z_1$ is S and $Z_2$ is $NH_2$.

In some embodiments, $Z_1$ is S and $Z_2$ is $NH(C_1\text{-}C_6$ alkyl).

In some embodiments, $Z_1$ is NH and $Z_2$ is OH.

In some embodiments, $Z_1$ is NH and $Z_2$ is SH.

In some embodiments, $Z_1$ is NH and $Z_2$ is $NH_2$.

In some embodiments, $Z_1$ is NH and $Z_2$ is $NH(C_1\text{-}C_6$ alkyl).

In some embodiments, $Z_1$ is $N(C_1\text{-}C_6$ alkyl) and $Z_2$ is OH.

In some embodiments, $Z_1$ is $N(C_1\text{-}C_6$ alkyl) and $Z_2$ is SH.

In some embodiments, $Z_1$ is $N(C_1\text{-}C_6$ alkyl) and $Z_2$ is $NH_2$.

In some embodiments, $Z_1$ is $N(C_1\text{-}C_6$ alkyl) and $Z_2$ is $NH(C_1\text{-}C_6$ alkyl).

In some embodiments, $Z_1$ is O and $Z_2$ is $S^-$.

In some embodiments, $Z_1$ is O and $Z_2$ is $HN^-$.

In some embodiments, $Z_1$ is O and $Z_2$ is $(C_1\text{-}C_6$ alkyl)$N^-$.

In some embodiments, $Z_1$ is S and $Z_2$ is $O^-$.

In some embodiments, $Z_1$ is S and $Z_2$ is $S^-$.

In some embodiments, $Z_1$ is S and $Z_2$ is $HN^-$.

In some embodiments, $Z_1$ is S and $Z_2$ is $(C_1\text{-}C_6$ alkyl)$N^-$.

In some embodiments, $Z_1$ is NH and $Z_2$ is $O^-$.

In some embodiments, $Z_1$ is NH and $Z_2$ is $S^-$.

In some embodiments, $Z_1$ is NH and $Z_2$ is $HN^-$.

In some embodiments, $Z_1$ is NH and $Z_2$ is $(C_1\text{-}C_6$ alkyl)$N^-$.

In some embodiments, $Z_1$ is $N(C_1\text{-}C_6$ alkyl) and $Z_2$ is $O^-$.

In some embodiments, $Z_1$ is $N(C_1\text{-}C_6$ alkyl) and $Z_2$ is $S^-$.

In some embodiments, $Z_1$ is $N(C_1\text{-}C_6$ alkyl) and $Z_2$ is $HN^-$.

In some embodiments, $Z_1$ is $N(C_1\text{-}C_6$ alkyl) and $Z_2$ is $(C_1\text{-}C_6$ alkyl)$N^-$.

In some embodiments, the modified phosphodiester bond comprises a phosphorothioate internucleotide linkage.

In some embodiments, the modified phosphodiester bond comprises

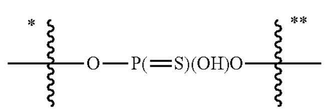

or

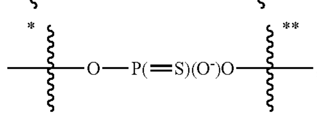

, wherein

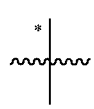

denotes attachment to a 3' carbon of a first nucleotide in the isolated oligonucleotide of the present disclosure; and

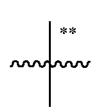

denotes attachment to a 5' carbon of a second nucleotide in the isolated oligonucleotide of the present disclosure.

In some embodiments, the modified phosphodiester bond comprises

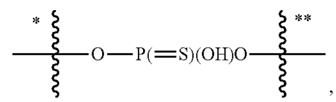

, wherein

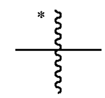

denotes attachment to a 3' carbon of a first nucleotide in the isolated oligonucleotide of the present disclosure; and

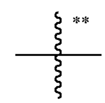

denotes attachment to a 5' carbon of a second nucleotide in the isolated oligonucleotide of the present disclosure.

In some embodiments, the modified phosphodiester bond comprises

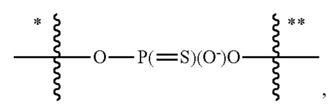

, wherein

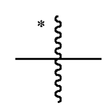

denotes attachment to a 3' carbon of a first nucleotide in the isolated oligonucleotide of the present disclosure; and

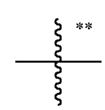

denotes attachment to a 5' carbon of a second nucleotide in the isolated oligonucleotide of the present disclosure.

In some embodiments, the isolated oligonucleotide of the present disclosure comprises at least one modified phosphodiester bond(s). In some embodiments of the isolated oligonucleotide of the present disclosure, the sense strand or the antisense strand or both comprise one or more modified phosphodiester bonds. In some embodiments, only the sense strand comprises one or more modified phosphodiester bonds. In some embodiments, only the antisense strand comprises one or more modified phosphodiester bonds. In some embodiments, both the sense strand and antisense strand comprise one or more modified phosphodiester bonds.

In some embodiments, the isolated oligonucleotide comprises at least two modified phosphodiester bonds. In some embodiments, the isolated oligonucleotide comprises at least three modified phosphodiester bonds. In some embodiments, the isolated oligonucleotide comprises at least four modified phosphodiester bonds. In some embodiments, the isolated oligonucleotide comprises at least five modified phosphodiester bonds. In some embodiments, the isolated oligonucleotide comprises at least six modified phosphodiester bonds. In some embodiments, the isolated oligonucleotide comprises at least seven modified phosphodiester bonds. In some embodiments, the isolated oligonucleotide comprises at least eight modified phosphodiester bonds. In some embodiments, the isolated oligonucleotide comprises at least nine modified phosphodiester bonds. In some embodiments, the isolated oligonucleotide comprises at least ten modified phosphodiester bonds. In some embodiments, the isolated oligonucleotide comprises at least eleven modified phosphodiester bonds. In some embodiments, the isolated oligonucleotide comprises at least twelve modified phosphodiester bonds. In some embodiments, the isolated oligonucleotide comprises at least thirteen modified phosphodiester bonds. In some embodiments, the isolated oligonucleotide comprises at least fourteen modified phosphodiester bonds. In some embodiments, the isolated oligonucleotide comprises at least fifteen modified phosphodiester bonds, some embodiments, the isolated oligonucleotide comprises at least sixteen modified phosphodiester bonds. In some embodiments, the isolated oligonucleotide comprises at least seventeen modified phosphodiester bonds. In some embodiments, the isolated oligonucleotide comprises at least eighteen modified phosphodiester bonds. In some embodiments, the isolated oligonucleotide comprises at least nineteen modified phosphodiester bonds. In some embodiments, the isolated oligonucleotide comprises at least twenty modified phosphodiester bonds. In some embodiments, the isolated oligonucleotide comprises more than twenty modified phosphodiester bonds. In some embodiments, the isolated oligonucleotide comprises between twenty and thirty modified phosphodiester bonds. In some embodiments, the isolated oligonucleotide comprises between thirty and forty modified phosphodiester bonds. In some embodiments, the isolated oligonucleotide comprises between forty and fifty modified phosphodiester bonds.

In some embodiments, the isolated oligonucleotide comprises at least two phosphorothioate internucleotide linkages. In some embodiments, the isolated oligonucleotide comprises at least three phosphorothioate internucleotide linkages. In some embodiments, the isolated oligonucleotide comprises at least four phosphorothioate internucleotide linkages. In some embodiments, the isolated oligonucleotide comprises at least five phosphorothioate internucleotide linkages. In some embodiments, the isolated oligonucleotide comprises at least six phosphorothioate internucleotide linkages. In some embodiments, the isolated oligonucleotide comprises at least seven phosphorothioate internucleotide linkages. In some embodiments, the isolated oligonucleotide comprises at least eight phosphorothioate internucleotide linkages. In some embodiments, the isolated oligonucleotide comprises at least nine phosphorothioate internucleotide linkages. In some embodiments, the isolated oligonucleotide comprises at least ten phosphorothioate internucleotide linkages. In some embodiments, the isolated oligonucleotide comprises at least eleven phosphorothioate internucleotide linkages. In some embodiments, the isolated oligonucleotide comprises at least twelve phosphorothioate internucleotide linkages. In some embodiments, the isolated oligonucleotide comprises at least thirteen phosphorothioate internucleotide linkages. In some embodiments, the isolated oligonucleotide comprises at least fourteen phosphorothioate internucleotide linkages. In some embodiments, the isolated oligonucleotide comprises at least fifteen phosphorothioate internucleotide linkages. In some embodiments, the isolated oligonucleotide comprises at least sixteen phosphorothioate internucleotide linkages. In some embodiments, the isolated oligonucleotide comprises at least seventeen phosphorothioate internucleotide linkages. In some embodiments, the isolated oligonucleotide comprises at least eighteen phosphorothioate internucleotide linkages. In some embodiments, the isolated oligonucleotide comprises at least nineteen phosphorothioate internucleotide linkages. In some embodiments, the isolated oligonucleotide comprises at least twenty phosphorothioate internucleotide linkages. In some embodiments, the isolated oligonucleotide comprises more than twenty phosphorothioate internucleotide linkages. In some embodiments, the isolated oligonucleotide comprises between twenty and thirty phosphorothioate internucleotide linkages. In some embodiments, the isolated oligonucleotide comprises between thirty and forty phosphorothioate internucleotide linkages. In some embodiments, the isolated oligonucleotide comprises between forty and fifty phosphorothioate internucleotide linkages.

In some embodiments, the sense strand and/or the antisense strand of the isolated oligonucleotide each comprise at least one modified phosphodiester bond(s). In some embodiments, the sense strand and/or the antisense strand of the isolated oligonucleotide each comprise at least two modified phosphodiester bonds. In some embodiments, the sense strand and/or the antisense strand of the isolated oligonucleotide each comprise at least three modified phosphodiester bonds. In some embodiments, the sense strand and/or the antisense strand of the isolated oligonucleotide each comprise at least four modified phosphodiester bonds. In some embodiments, the sense strand and/or the antisense strand of the isolated oligonucleotide each comprise at least five modified phosphodiester bonds. In some embodiments, the sense strand and/or the antisense strand of the isolated oligonucleotide each comprise at least six modified phosphodiester bonds. In some embodiments, the sense strand and/or the antisense strand of the isolated oligonucleotide each comprise at least seven modified phosphodiester bonds. In some embodiments, the sense strand and/or the antisense strand of the isolated oligonucleotide each comprise at least eight modified phosphodiester bonds. In some embodiments, the sense strand and/or the antisense strand of the isolated oligonucleotide each comprise at least nine modified phosphodiester bonds. In some embodiments, the sense strand and/or the antisense strand of the isolated oligonucleotide each comprise at least ten modified phosphodiester bonds. In some embodiments, the sense strand and/or the antisense strand of the isolated oligonucleotide each comprise at least eleven modified phosphodiester bonds. In some embodiments, the sense strand and/or the antisense strand of the isolated oligonucleotide each comprise at least twelve modified phosphodiester bonds. In some embodiments, the sense strand and/or the antisense strand of the isolated oligonucleotide each comprise at least thirteen modified phosphodiester bonds. In some embodiments, the sense strand and/or the antisense strand of the isolated oligonucleotide each comprise at least fourteen modified phosphodiester bonds. In some embodiments, the sense strand and/or the antisense strand of the isolated oligonucleotide each comprise at least fifteen modified phosphodiester bonds. In some embodiments, the sense strand and/or the antisense strand of the isolated oligonucleotide each comprise at least sixteen modified phosphodiester bonds. In some embodiments, the sense strand and/or the antisense strand of the isolated oligonucleotide each comprise at least seventeen modified phosphodiester bonds. In some embodiments, the sense strand and/or the antisense strand of the isolated oligonucleotide each comprise at least eighteen modified phosphodiester bonds. In some embodiments, the sense strand and/or the antisense strand of the isolated oligonucleotide each comprise at least nineteen modified phosphodiester bonds. In some embodiments, the sense strand and/or the antisense strand of the isolated oligonucleotide each comprise at least twenty modified phosphodiester bonds.

In some embodiments, the sense strand and/or the antisense strand of the isolated oligonucleotide each comprise at least one phosphorothioate internucleotide linkage(s). In some embodiments, the sense strand and/or the antisense strand of the isolated oligonucleotide each comprise at least two phosphorothioate internucleotide linkages. In some embodiments, the sense strand and/or the antisense strand of the isolated oligonucleotide each comprise at least three phosphorothioate internucleotide linkages. In some embodiments, the sense strand and/or the antisense strand of the isolated oligonucleotide each comprise at least four phosphorothioate internucleotide linkages. In some embodiments, the sense strand and/or the antisense strand of the isolated oligonucleotide each comprise at least five phosphorothioate internucleotide linkages. In some embodiments, the sense strand and/or the antisense strand of the isolated oligonucleotide each comprise at least six phosphorothioate internucleotide linkages, some embodiments, the sense strand and/or the antisense strand of the isolated oligonucleotide each comprise at least seven phosphorothioate internucleotide linkages. In some embodiments, the sense strand and/or the antisense strand of the isolated oligonucleotide each comprise at least eight phosphorothioate internucleotide linkages. In some embodiments, the sense strand and/or the antisense strand of the isolated oligonucleotide each comprise at least nine phosphorothioate internucleotide linkages. In some embodiments, the sense strand and/or the antisense strand of the isolated oligonucleotide each comprise at least ten phosphorothioate internucleotide linkages. In some embodiments, the sense strand and/or the antisense strand of the isolated oligonucleotide each comprise at least eleven phosphorothioate internucleotide linkages. In some embodiments, the sense strand and/or the antisense strand of the isolated oligonucleotide each comprise at least twelve phosphorothioate internucleotide linkages. In some embodiments, the sense strand and/or the antisense strand of the isolated oligonucleotide each comprise at least thirteen phosphorothioate internucleotide linkages. In some embodiments, the sense strand and/or the antisense strand of the isolated oligonucleotide each comprise at least fourteen phosphorothioate internucleotide linkages. In some embodiments, the sense strand and/or the antisense strand of the isolated oligonucleotide each comprise at least fifteen phosphorothioate internucleotide linkages. In some embodiments, the sense strand and/or the antisense strand of the isolated oligonucleotide each comprise at least sixteen phosphorothioate internucleotide linkages. In some embodiments, the sense strand and/or the antisense strand of the isolated oligonucleotide each comprise at least seventeen phosphorothioate internucleotide linkages. In some embodiments, the sense strand and/or the antisense strand of the isolated oligonucleotide each comprise at least eighteen phosphorothioate internucleotide linkages. In some embodiments, the sense strand and/or the antisense strand of the isolated oligonucleotide each comprise at least nineteen phosphorothioate internucleotide linkages. In some embodiments, the sense strand and/or the antisense strand of the isolated oligonucleotide each comprise at least twenty phosphorothioate internucleotide linkages.

In some embodiments, the modified phosphodiester bonds are consecutively located on the sense strand or the antisense strand or both. In some embodiments, some but not all of the modified phosphodiester bonds are consecutively located on the sense strand or the antisense strand or both. In some embodiments, the modified phosphodiester bonds on the sense strand or the antisense strand or both are not consecutively located.

Envisaged within the present disclosure is an isolated oligonucleotide, wherein any phosphodiester bond on the sense strand or antisense strand can be modified. In some embodiments, any phosphodiester bond on the antisense strand can be modified. In some embodiments, any phosphodiester bond on the antisense strand can be modified.

In some embodiments of the isolated oligonucleotide of the present disclosure, the antisense strand comprises between one and twenty, between one and fifteen, between one and ten, between one and five, or less than five modified phosphodiester bonds. In some embodiments, the between one and twenty, between one and fifteen, between one and ten, between one and five, or less than five modified phosphodiester bonds comprise phosphorothioate internucleotide linkages. In some embodiments, the antisense strand comprises less than five modified phosphodiester bonds. In some embodiments, the antisense strand comprises one, two, three, or four modified phosphodiester bonds. In some embodiments, wherein the antisense strand comprises one, two, three, or four modified phosphodiester bonds, the one, two, three, or four modified phosphodiester bonds comprise phosphorothioate internucleotide linkages. In some embodiments, the antisense strand comprises four modified phosphodiester bonds. In some embodiments, wherein the antisense strand comprises four modified phosphodiester bonds, the modified phosphodiester bonds comprise phosphorothioate.

In some embodiments, wherein the antisense strand comprises at least one, at least two, at least three, or at least four phosphorothioate internucleotide linkages, the phosphorothioate internucleotide linkages connect the nucleotides at position 1 and position 2 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 2 and position 3 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 20 and position 21 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 21 and position 22 from the first nucleotide at the 5'-terminus of the antisense strand. In some embodiments, wherein the antisense strand comprises at least one, at least two, at least three, or at least four modified phosphodiester bonds, wherein the modified phosphodiester bonds comprise phosphorothioate internucleotide linkages, the phosphorothioate internucleotide linkages are located between nucleotides at position 1 and 2, position 2 and 3, position 20 and 21, and position 21 and 22 from the first nucleotide at the 5'-terminus of the antisense strand.

In some embodiments of the isolated oligonucleotide of the present disclosure, wherein the antisense strand comprises at least one, at least two, at least three, or at least four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, wherein the antisense strand comprises at least four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, the antisense strand comprises four phosphorothioate internucleotide linkages. In some embodiments, wherein the antisense strand comprises four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, the sense strand comprises between one and twenty, between one and fifteen, between one and ten, between one and five, or less than five modified phosphodiester bonds. In some embodiments, the between one and twenty, between one and fifteen, between one and ten, between one and five, or less than five modified phosphodiester bonds comprise phosphorothioate internucleotide linkages. In some embodiments, the sense strand comprises less than five modified phosphodiester bonds. In some embodiments, wherein the sense strand comprises less than five modified phosphodiester bonds, the sense strand comprises one, two, three, or four modified phosphodiester bonds. In some embodiments, wherein the sense strand comprises one, two, three, or four modified phosphodiester bonds, the one, two, three, or four modified phosphodiester bonds comprise phosphorothioate internucleotide linkages. In some embodiments, the sense strand comprises four modified phosphodiester bonds. In some embodiments, wherein the sense strand comprises four modified phosphodiester bonds, the modified phosphodiester bonds comprise phosphorothioate internucleotide linkages.

In some embodiments, wherein the sense strand comprises at least one, at least two, at least three, or at least four modified phosphodiester bonds, the phosphodiester bonds comprise phosphorothioate internucleotide linkages. In some embodiments, wherein the sense strand comprises at least one, at least two, at least three, or at least four phosphorothioate internucleotide linkages, the phosphorothioate internucleotide linkages connect the nucleotides at position 1 and position 2 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 2 and position 3 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 18 and position 19 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 19 and position 20 from the first nucleotide at the 5'-terminus of the sense strand. In some embodiments, wherein the sense strand comprises at least one, at least two, at least three, or at least four modified phosphodiester bonds, wherein the modified phosphodiester bonds comprise phosphorothioate internucleotide linkages, the phosphorothioate internucleotide linkages are located between nucleotides at position 1 and 2, position 2 and 3, position 18 and 19, and position 19 and 20 from the first nucleotide at the 5'-terminus of the sense strand.

In some embodiments of the isolated oligonucleotide of the present disclosure, wherein the sense strand comprises at least one, at least two, at least three, or at least four phosphorothioate internucleotide linkages, the phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, wherein the sense strand comprises at least four phosphorothioate internucleotide linkages, the at least four phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, the sense strand comprises four phosphorothioate internucleotide linkages. In some embodiments, wherein the sense strand comprises four phosphorothioate internucleotide linkages, the phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, wherein the antisense strand and the sense strand comprise four phosphorothioate internucleotide linkages, the antisense strand comprises phosphorothioate internucleotide linkages located between nucleotides at position 1 to 3 and nucleotides at position 20 to 22 from the first nucleotide at the 5'-terminus of the antisense strand, and the sense strand comprises phosphorothioate internucleotide linkages located between nucleotides at position 1 to 3 and nucleotides at position 18 to 20 from the first nucleotide at the 5'-terminus of the sense strand.

In some embodiments of the isolated oligonucleotide of the present disclosure, the antisense strand comprises any one of: i) an antisense strand of nucleic acid sequence according to SEQ ID NO: 451 (5' [mUs][fUs][fA][mG][fU][mA][fG][mA][mA][fU][mU][mU][mC][fU][mC][fU][mG][mU][mA][mGs][mGs][mC] 3');

ii) an antisense strand of nucleic acid sequence according to SEQ ID NO: 452 (5' [mUs][fGs][fU][mA][fG][mU][fA][mG][mA][fA][mU][mU][mU][fC][mU][fC][mU][mG][mU][mAs][mGs][mG] 3');

iii) an antisense strand of nucleic acid sequence according to SEQ ID NO: 453 (5' [mUs][fAs][fU][mG][fU][mA][fG][mU][mA][fG][mA][mA][mU][fU][mU][fC][mU][mC][mU][mGs][mUs][mA] 3'), iv) an antisense strand of nucleic acid sequence according to SEQ ID NO: 454 (5' [mUs][fAs][fU][mA][fG][mA][fU][mG][mU][fA][G][mU][mA][fG][mA][fA][mU][mU][mU][mCs][mUs][mC] 3');

v) an antisense strand of nucleic acid sequence according to SEQ ID NO: 455 (5' [mUs][fAs][fU][mG][fA][mA][fG][mC][mA][fA][mU][mU][mC][fU][mC][fC][mU][mC][mA][mGs][mCs][mA] 3');

vi) an antisense strand of nucleic acid sequence according to SEQ ID NO: 456 (5' [mUs][fUs][fU][mU][fG][mU][fA][mU][mG][fA][mA][mG][mC][fA][mA][fU][mU][mC][mU][mCs][mCs][mU] 3'), vii) an antisense strand of nucleic acid sequence according to SEQ ID NO: 457 (5' [MeEPmUs][fUs][fA][mG][fU][mA][fG][mA][mA][fU][mU][mU][mC][fU][mC][fU][mG][mU][mA][mGs][mGs][mC] 3');

viii) an antisense strand of nucleic acid sequence according to SEQ ID NO: 458 (5' [MeEPmUs][fGs][fU][mA][fG][mU][fA][mG][mA][fA][mU][mU][mU][fC][mU][fC][mU][mG][mU][mAs][mGs][mG] 3'); or ix) an antisense strand of nucleic acid sequence according to SEQ ID NO: 459 (5' [MeEPmUs][fAs][fU][mG][fU][mA][fG][mU][mA][fG][mA][mA][mU][fU][mU][fC][mU][mC][mU][mGs][mUs][mA] 3'), wherein "m" is a 2'-O-methyl modified nucleotide, "f" is a 2'-F modified nucleotide, "s" is a phosphorothioate internucleotide linkage, "MeEP" is a mono methyl protected phosphate mimic.

In some embodiments of the isolated oligonucleotide of the present disclosure, wherein the sense strand comprises any one of:

i) a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3');

ii) a sense strand of nucleic acid sequence according to SEQ ID NO: 445 (5' [mUs][mAs][mC][mA][mG][fA][mG][fA][fA][fA][fU][mU][mC][mU][mA][mC][mU][mAs][mCs][mA][G1b][G1b][G1b] 3');

iii) a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3').

iv) a sense strand of nucleic acid sequence according to SEQ ID NO: 447 (5' [mGs][mAs][mA][mA][mU][fU][mC][fU][fA][fC][fU][mA][mC][mA][mU][mC][mU][mAs][mUs][mA][G1b][G1b][G1b] 3');

v) a sense strand of nucleic acid sequence according to SEQ ID NO: 448 (5' [mCs][mUs][mG][mA][mG][fG][mA][fG][fA][fA][fU][mU][mG][mC][mU][mU][mC][mAs][mUs][mA][G1b][G1b][G1b] 3'); or vi) a sense strand of nucleic acid sequence according to SEQ ID NO: 449 (5' [mGs][mAs][mG][mA][mA][fU][mU][fG][fC][fU][fU][mC][mA][mU][mA][mC][mA][mAs][mAs][mA][G1b][G1b][G1b] 3'), wherein "m" is a 2'-O-methyl modified nucleotide, "f" is a 2'-F modified nucleotide, "s" is a phosphorothioate internucleotide linkage, and "G1b" is a GalNac G1b moiety.

In some embodiments of the isolated oligonucleotide of the present disclosure is selected from:

i) an antisense strand of SEQ ID NO: 451 (5' [mUs][fUs][fA][mG][fU][mA][fG][mA][mA][fU][mU][mU][mC][fU][mC][fU][mG][mU][mA][mGs][mGs][mC] 3'), and a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3');

ii) an antisense strand of SEQ ID NO: 452 (5' [mUs][fGs][fU][mA][fG][mU][fA][mG][mA][fA][mU][mU][mU][fC][mU][fC][mU][mG][mU][mAs][mGs][mG] 3'), and a sense strand of nucleic acid sequence according to SEQ ID NO: 445 (5' [mUs][mAs][mC][mA][mG][fA][mG][fA][fA][fA][fU][mU][mC][mU][mA][mC][mU][mAs][mCs][mA][G1b][G1b][G1b] 3');

iii) an antisense strand of SEQ ID NO: 453 (5' [mUs][fAs][fU][mG][fU][mA][fG][mU][mA][fG][mA][mA][mU][fU][mU][fC][mU][mC][mU][mGs][mUs][mA] 3'), and a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3');

iv) an antisense strand of SEQ ID NO: 454 (5' [mUs][fAs][fU][mA][fG][mA][fU][mG][mU][fA][mG][mU][mA][fG][mA][fA][mU][mU][mU][mCs][mUs][mC] 3'), and a sense strand of nucleic acid sequence according to SEQ ID NO: 447 (5' [mGs][mAs][mA][mA][mU][fU][mC][fU][fA][fC][fU][mA][mC][mA][mU][mC][mU][mAs][mUs][mA][G1b][G1b][G1b] 3');

v) an antisense strand of SEQ ID NO: 455 (5' [mUs][fAs][fU][mG][fA][mA][fG][mC][mA][fA][mU][mU][mC][fU][mC][fC][mU][mC][mA][mGs][mCs][mA] 3'), and a sense strand of nucleic acid sequence according to SEQ ID NO: 448 (5' [mCs][mUs][mG][mA][mG][fG][mA][fG][fA][fA][fU][mU][mG][mC][mU][mU][mC][mAs][mUs][mA][G1b][G1b][G1b] 3');

vi) an antisense strand of SEQ ID NO: 456 (5' [mUs][fUs][fU][mU][fG][mU][fA][mU][mG][fA][mA][mG][mC][fA][mA][fU][mU][mC][mU][mCs][mCs][mU] 3'), and a sense strand of nucleic acid sequence according to SEQ ID NO: 449 (5' [mGs][mAs][mG][mA][mA][fU][mU][fG][fC][fU][fU][mC][mA][mU][mA][mC][mA][mAs][mAs][mA][G1b][G1b][G1b] 3');

vii) an antisense strand of SEQ ID NO: 457 (5' [MeEP-mUs][fUs][fA][mG][fU][mA][fG][mA][mA][fU][mU][mU][mC][fU][mC][fU][mG][mU][mA][mGs][mGs][mC] 3'), and a sense strand of nucleic acid sequence according to SEQ ID NO: 444 (5' [mCs][mUs][mA][mC][mA][fG][mA][fG][fA][fA][fA][mU][mU][mC][mU][mA][mC][mUs][mAs][mA][G1b][G1b][G1b] 3');

viii) an antisense strand of SEQ ID NO: 458 (5' [MeEP-mUs][fGs][fU][mA][fG][mU][fA][mG][mA][fA][mU][mU][mU][fC][mU][fC][mU][mG][mU][mAs][mGs][mG] 3'), and a sense strand of nucleic acid sequence according to SEQ ID NO: 445 (5' [mUs][mAs][mC][mA][mG][fA][mG][fA][fA][fA][fU][mU][mC][mU][mA][mC][mU][mAs][mCs][mA][G1b][G1b][G1b] 3'); and ix) an antisense strand of SEQ ID NO: 459 (5' [MeEP-mUs][fAs][fU][mG][fU][mA][fG][mU][mA][fG][mA][mA][mU][fU][mU][fC][mU][mC][mU][mGs][mUs][mA] 3'), and a sense strand of nucleic acid sequence according to SEQ ID NO: 446 (5' [mCs][mAs][mG][mA][mG][fA][mA][fA][fU][fU][fC][mU][mA][mC][mU][mA][mC][mAs][mUs][mA][G1b][G1b][G1b] 3'), wherein "m" is a 2'-O-methyl modified nucleotide, "f" is a 2'-F modified nucleotide, "s" is a phosphorothioate internucleotide linkage, "MeEP" is a mono methyl protected phosphate mimic, and "G1b" is a GalNAc G1b moiety.

Nucleic Acids and Vectors

The present disclosure also provides a vector encoding at least one isolated oligonucleotide disclosed herein. In some embodiments, the vector is any one of a plasmid, a cosmid or a viral vector. In some embodiments, the vector is an adenoviral vector. In some embodiments, the vector is a lentiviral vector. In some embodiments, the plasmid is an expression plasmid. In some embodiments, the vector encodes one isolated oligonucleotide disclosed herein. In some embodiments, the vector encodes more than one isolated oligonucleotide disclosed herein. In some embodiments, the vector encodes, two, three, four, or five isolated oligonucleotides disclosed herein. In some embodiments, the vector encodes more than five isolated oligonucleotides disclosed herein.

The disclosure provides nucleic acids comprising the sequences encoding the isolated oligonucleotides (e.g., dsRNAs or siRNAs) targeting C3 described herein.

In some embodiments, the nucleic acids are ribonucleic acids (RNAs). In some embodiments, the nucleic acids are deoxyribonucleic acids (DNAs). The DNAs may be a vector or a plasmid, e.g., an expression vector.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

By the term "express" or "expression" of a polynucleotide coding sequence, it is meant that the sequence is transcribed, and optionally, translated. Typically, according to the present disclosure, expression of a coding sequence of the disclosure will result in production of the polypeptide of the disclosure. The entire expressed polypeptide or fragment can also function in intact cells without purification.

In some embodiments, the vector is an expression vector for manufacturing siRNAs of the disclosure. Exemplary expression vectors may comprise a sequence encoding the sense and/or antisense strand of the isolated oligonucleotide of the present disclosure, under the control of a suitable promoter for transcription. Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

The isolated oligonucleotide of the present disclosure (e.g., dsRNAs and siRNAs) can be expressed endogenously from plasmid or viral expression vectors, or from minimal expression cassettes, for example, PCR generated fragments comprising one or more promoters and an appropriate template or templates for transcribing the siRNA. Examples of commercially available plasmid-based expression vectors for shRNA include members of the pSilencer series (Ambion) and pCpG-siRNA (InvivoGen). Examples of kits for production of PCR-generated shRNA expression cassettes include Silencer Express (Ambion) and siXpress (Mirus)

Viral vectors for the in vivo expression of the isolated oligonucleotides (e.g., siRNAs and dsRNAs) in eukaryotic cells are also contemplated as within the scope of the instant disclosure. Viral vectors may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion) and pLenti6/BLOCK-iT™-DEST (Invitrogen). Selection of viral vectors, methods for expressing the siRNA from the vector and methods of delivering the viral vector, for example incorporated within a nanoparticle, are within the ordinary skill of one in the art.

It will be apparent to those skilled in the art that any suitable vector, optionally incorporated into a nanoparticle, can be used to deliver the isolated oligonucleotides of the present disclosure (e.g., dsRNAs or siRNAs) described herein to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Delivery Systems

The present disclosure also provides a delivery system comprising at least one isolated oligonucleotide disclosed herein or vector of the present disclosure encoding at least one isolated oligonucleotide disclosed herein. In some embodiments, the delivery system is any one of a liposome, a nanoparticle, a polymer based delivery system or a ligand-conjugate delivery system. In some embodiments, the ligand-conjugate delivery system comprises one or more of an antibody, a peptide, a sugar moiety or a combination thereof.

In some embodiments, the delivery system of the present disclosure comprises nanoparticles comprising the isolated oligonucleotides of the present disclosure (e.g., siRNA or dsRNAs) targeting a C3 mRNA for degradation. In some embodiments, the nanoparticle comprises a polymer-based nanoparticle, a lipid-polymer based nanoparticle, a metal based nanoparticle, a carbon nanotube based nanoparticle, a nanocrystal or a polymeric micelle. In some embodiments, the polymer-based nanoparticle comprises a multiblock copolymer, a diblock copolymer, a polymeric micelle or a hyperbranched macromolecule. In some embodiments, the polymer-based nanoparticle comprises a multiblock copolymer a diblock copolymer. In some embodiments, the polymer-based nanoparticle is pH responsive. In some embodiments, the polymer-based nanoparticle further comprises a buffering component.

In some embodiments, the delivery system comprises a liposome. Liposomes are spherical vesicles having at least one lipid bilayer, and in some embodiments, an aqueous core. In some embodiments, the lipid bilayer of the liposome may comprise phospholipids. An exemplary but non-limiting example of a phospholipid is phosphatidylcholine, but the lipid bilayer may comprise additional lipids, such as phosphatidylethanolamine. Liposomes may be multilamellar, i.e. consisting of several lamellar phase lipid bilayers, or unilamellar liposomes with a single lipid bilayer. Liposomes can be made in a particular size range that makes them viable targets for phagocytosis. Liposomes can range in size from 20 nm to 100 nm, 100 nm to 400 nm, 1 μM and larger, or 200 nm to 3 μM. Examples of lipidoids and lipid-based formulations are provided in U.S. Published application Ser. No. 20090023673. In other embodiments, the one or more lipids are one or more cationic lipids. One skilled in the art will recognize which liposomes are appropriate for siRNA encapsulation.

In some embodiments, the liposome or the nanoparticle of the present disclosure comprises a micelle. A micelle is an aggregate of surfactant molecules. An exemplary micelle comprises an aggregate of amphiphilic macromolecules, polymers or copolymers in aqueous solution, wherein the hydrophilic head portions contact the surrounding solvent, while the hydrophobic tail regions are sequestered in the center of the micelle.

In some embodiments, the nanoparticle comprises a nanocrystal. Exemplary nanocrystals are crystalline particles with at least one dimension of less than 1000 nanometers, preferably of less than 100 nanometers.

In some embodiments, the nanoparticle comprises a polymer-based nanoparticle. In some embodiments, the polymer comprises a multiblock copolymer, a diblock copolymer, a polymeric micelle or a hyperbranched macromolecule. In some embodiments, the particle comprises one or more cationic polymers. In some embodiments, the cationic polymer is chitosan, protamine, polylysine, polyhistidine, polyarginine or poly(ethylene)imine. In other embodiments, the one or more polymers contain the buffering component, degradable component, hydrophilic component, cleavable bond component or some combination thereof.

In some embodiments, the nanoparticles or some portion thereof are degradable. In other embodiments, the lipids and/or polymers of the nanoparticles are degradable.

In some embodiments, any of these delivery systems of the present disclosure can comprise a buffering component. In other embodiments, any of the of the present disclosure can comprise a buffering component and a degradable component. In still other embodiments, any of the of the present disclosure can comprise a buffering component and a hydrophilic component. In yet other embodiments, any of the of the present disclosure can comprise a buffering component and a cleavable bond component. In yet other embodiments, any of the of the present disclosure can comprise a buffering component, a degradable component and a hydrophilic component. In still other embodiments, any of the of the present disclosure can comprise a buffering component, a degradable component and a cleavable bond component. In further embodiments, any of the of the present disclosure can comprise a buffering component, a hydrophilic component and a cleavable bond component. In yet another embodiment, any of the of the present disclosure can comprise a buffering component, a degradable component, a hydrophilic component and a cleavable bond component. In some embodiments, the particle is composed of one or more polymers that contain any of the aforementioned combinations of components.

In some embodiments of the isolated oligonucleotides of the present disclosure, the delivery system comprises a ligand-conjugate delivery system. In some embodiments, the ligand-conjugate delivery system comprises one or more of an antibody, a peptide, a sugar moiety, lipid or a combination thereof In further embodiments, the isolated oligonucleotide of the present disclosure targeting a C3 mRNA (e.g., siRNA or dsRNA) is conjugated to, complexed to, or encapsulated by the one or more lipids or polymers of the delivery system. In further embodiments, the isolated oligonucleotide of the present disclosure targeting a C3 mRNA (e.g., siRNA or dsRNA) can be encapsulated in the hollow core of a nanoparticle. Alternatively, or in addition, the isolated oligonucleotide of the present disclosure targeting a C3 mRNA (e.g., siRNA or dsRNA) can be incorporated into the lipid or polymer-based shell of the delivery system, for example via intercalation. Alternatively, or in addition, the isolated oligonucleotide of the present disclosure targeting a C3 mRNA (e.g., siRNA or dsRNA) can be attached to the surface of the delivery system. In some embodiments, the isolated oligonucleotide of the present disclosure targeting a C3 mRNA (e.g., siRNA or dsRNA) is conjugated to one or more lipids or polymers of the delivery system, e.g. via covalent attachment.

In some embodiments, the ligand conjugate delivery system further comprises a targeting agent. In some embodiments, the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment.

In some embodiments, the isolated oligonucleotide disclosed herein may further comprise a ligand that facilitates delivery or uptake of the isolated oligonucleotide to a particular tissue or cell, such as a liver cell. In certain embodiments, the ligand targets delivery of the RNAi construct to hepatocytes. In these and other embodiments, the ligand may comprise galactose, galactosamine or N-acetyl-galactosamine (GalNAc). In certain embodiments, the ligand comprises a multivalent galactose or multivalent GalNAc moiety, such as a trivalent or tetravalent galactose or GalNAc moiety. The ligand can be covalently attached to the 5' or 3' end of the sense strand of the RNAi construct, optionally via a linker.

In some embodiments, the targeting agent comprises a binding partner for a cell surface protein that is upregulated or overexpressed or normally expressed in a target cell encoding C3 mRNA and expressing C3 protein. In some embodiments, the binding partner can be a transmembrane peptidoglycan expressed on the surface of many types of such cells. Targeting of cell surface protein by the delivery system of the present disclosure thus provides superior delivery and specificity of the compositions of the disclosure to target cells. In some embodiments, the target cell can be any one of an intestinal cell, an arterial cell, a cell of the cardiovascular system, a hepatocyte, a pancreatic cell or a combination thereof.

In some embodiments, the delivery system of the present disclosure comprises a polymer based delivery system. In some embodiments, polymer based delivery system comprises a blending polymer. In some embodiments, the blending polymer is a copolymer comprising a degradable component and hydrophilic component. In some embodiments, the degradable component of the blending polymer is a polyester, poly(ortho ester), poly(ethylene imine), poly(caprolactone), polyanhydride, poly(acrylic acid), polyglycolide or poly(urethane). In some embodiments, the degradable component of the blending polymer is poly(lactic acid) (PLA) or poly(lactic-co-glycolic acid) (PLGA). In some embodiments, the hydrophilic component of the blending polymer is a polyalkylene glycol or a polyalkylene oxide. In some embodiments, the polyalkylene glycol is polyethylene glycol (PEG). In other embodiments, the polyalkylene oxide is polyethylene oxide (PEO).

In some embodiments, the delivery system of the present disclosure is a polymer-based nanoparticle. Polymer based nanoparticles comprise one or more polymers. In some embodiments, the one or more polymers comprise a polyester, poly(ortho ester), poly(ethylene imine), poly(caprolactone), polyanhydride, poly(acrylic acid), polyglycolide or poly(urethane). In still other embodiments, the one or more polymers comprise poly(lactic acid) (PLA) or poly(lactic-co-glycolic acid) (PLGA). In some embodiments, the one or more polymers comprise poly(lactic-co-glycolic acid) (PLGA). In some embodiments, the one or more polymers comprise poly(lactic acid) (PLA). In some embodiments, the one or more polymers comprise polyalkylene glycol or a polyalkylene oxide. In some embodiments, the polyalkylene glycol is polyethylene glycol (PEG) or the polyalkylene oxide is polyethylene oxide (PEO).

In some embodiments, the polymer-based nanoparticle comprises poly(lactic-co-glycolic acid) PLGA polymers. In some embodiments, the PLGA nanoparticle further comprises a targeting agent, as described herein.

In some embodiments, the delivery system of the present disclosure is a nanoparticle of average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In other embodiments, the nanoparticle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In further embodiments, the nanoparticle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

Therapeutic Agents

In some embodiments, the delivery system of the present disclosure is administered with one or more additional therapeutic agents. In some embodiments, the additional therapeutic agents can be a steroid, an anti-inflammatory agent, an antibody, a fusion protein, a small molecule, or combination thereof. In some embodiments, the additional therapeutic agent is incorporated into a delivery system of the present disclosure comprising at least one isolated oligonucleotide targeting C3 disclosed herein. In some embodiments, the additional therapeutic agent is conjugated to, complexed to, or encapsulated by the one or more lipids or polymers of the delivery system. Additional therapeutic agents can be encapsulated in the hollow core of delivery system. Alternatively, additionally, additional therapeutic agents can be incorporated into the lipid or polymer-based shell of the delivery system, for example via intercalation. Alternatively, additionally, additional therapeutic agents can be attached to the surface of the delivery system. In some embodiments, the additional therapeutic agents are conjugated to one or more lipids or polymers of the delivery system, e.g. via covalent attachment.

In some embodiments, the additional therapeutic agent and the delivery system comprising at least one isolated oligonucleotide targeting C3 disclosed herein are formulated in the same composition. For example, the delivery system comprising at least one isolated oligonucleotide of the present disclosure targeting C3 and the additional therapeutic agent can be formulated in the same pharmaceutical composition.

In some embodiments, the additional therapeutic agent and the delivery system comprising at least one isolated oligonucleotide targeting C3 disclosed herein are formulated as separate compositions, e.g., for separate administration to a subject.

Pharmaceutical Compositions

The present disclosure also provides a pharmaceutical composition comprising at least one oligonucleotide disclosed herein, a vector of the present disclosure encoding at least one isolated oligonucleotide disclosed herein, or a delivery system of the present disclosure, and a pharmaceutically acceptable carrier, diluent, or excipient.

The pharmaceutical compositions of the disclosure can optionally comprise therapeutic agents, pharmaceutical agents, carriers, adjuvants, dispersing agents, diluents, and the like. In some embodiments, the pharmaceutical composition comprises a therapeutic agent, such as a chemotherapeutic agent. In some embodiments, the therapeutic agent is formulated in the delivery system comprising the one or more isolated oligonucleotides (e.g., dsRNA or siRNA) targeting C3 of the present disclosure.

In some embodiments, an additional therapeutic agent is not formulated in the delivery system comprising the one or more isolated oligonucleotides (e.g., dsRNA or siRNA) targeting C3 of the present disclosure, but both the delivery system and the therapeutic agent are formulated in the same pharmaceutical composition. In some embodiments, an additional therapeutic agent is not formulated in the delivery system comprising the one or more isolated oligonucleotides (e.g., dsRNA or siRNA) targeting C3 of the present disclosure, and the delivery system and the therapeutic agent are formulated in separate pharmaceutical compositions.

Pharmaceutical compositions of the present disclosure can contain any of the reagents discussed above, and one or more of a pharmaceutically acceptable carrier, a diluent or an excipient.

A pharmaceutical composition of the present disclosure is in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed agent) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of this disclosure include powders, sprays, ointments, pastes, creams, lotions, gels, solutions, patches and inhalants. In one embodiment, the active agent is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), intraperitoneal (into the body cavity) and transmucosal administration. Solutions or suspensions used for parenteral, intradermal, intraperitoneal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. These preparations can contain antioxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

The pharmaceutical compositions containing the nanoparticles described herein may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active agents into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required nanoparticle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Oral compositions generally include an inert diluent or an edible pharmaceutically acceptable carrier. They can be enclosed in gelatin capsules or compressed into tablets. For the purpose of oral therapeutic administration, the active age can be incorporated with excipients and used in the form of tablets, troches, or capsules. Oral compositions can also be prepared using a fluid carrier for use as a mouthwash, wherein the agents in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the agents are delivered in the form of an aerosol spray from pressured container or dispenser, which contains a suitable propellant, e.g., a gas such as carbon dioxide, or a nebulizer.

The pharmaceutical compositions of the present disclosure can be prepared with pharmaceutically acceptable carriers that will protect the one or more isolated oligonucleotides (e.g., dsRNAs or siRNAs) targeting C3 mRNA of the present disclosure against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art, and the materials can be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms of the disclosure are dictated by and directly dependent on the unique characteristics of the active agent and the particular therapeutic effect to be achieved.

The pharmaceutical compositions can be included in a container, pack, or dispenser together with instructions for administration.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

Techniques for formulation and administration of the disclosed compositions of the disclosure can be found in Remington: the Science and Practice of Pharmacy, 19th edition, Mack Publishing Co., Easton, PA (1995).

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Methods of Making Isolated Oligonucleotides

Provided herein are methods of making the one or more oligonucleotides of (e.g., dsRNAs or siRNAs) targeting C3 of the present disclosure and delivery systems comprising same.

The one or more oligonucleotides of (e.g., dsRNAs or siRNAs) targeting C3 of the present disclosure, may be generated exogenously by chemical synthesis, by in vitro transcription, or by cleavage of longer double-stranded RNA with Dicer or another appropriate nuclease with similar activity. Chemically synthesized siRNAs, produced from protected ribonucleoside phosphoramidites using a conventional DNA/RNA synthesizer, may be obtained from commercial suppliers. The siRNAs can be purified by extraction with a solvent or resin, precipitation, electrophoresis, chromatography, or a combination thereof, for example. Alternatively, siRNAs may be used with little if any purification to avoid losses due to sample processing.

In some embodiments, the one or more oligonucleotides of (e.g., dsRNAs or siRNAs) targeting C3 of the present disclosure can be produced using an expression vector into which a nucleic acid encoding the double stranded RNA has been cloned, for example under control of a suitable promoter.

In some embodiments, the one or more oligonucleotides of (e.g., dsRNAs or siRNAs) targeting C3 of the present disclosure can be incorporated in a delivery system of the present disclosure (e.g., a nanoparticle).

Delivery systems comprising dsRNAs or siRNAs of the disclosure can be prepared by any suitable means known in the art. For example, polymeric nanoparticles can be prepared using various methods including, but not limited to, solvent evaporation, spontaneous emulsification, solvent diffusion, desolation, dialysis, ionic gelation, nanoprecipitation, salting out, spray drying and supercritical fluid methods. The dispersion of preformed polymers and the polymerization of monomers are two additional strategies for preparation of polymeric nanoparticles. However, the choice of an appropriate method depends upon various factors, which will be known to the person of ordinary skill in the art.

Sterile injectable solutions comprising a delivery system of the disclosure can be prepared by incorporating the one or more isolated oligonucleotides (e.g. dsRNA and siRNA) targeting C3 disclosed herein, in the delivery systems (e.g. nanoparticle) in the required amount in an appropriate solvent with one or a combination of ingredients enumerated herein, as required, followed by filtered sterilization. Alternatively, or in addition, sterilization can be achieved through other means such as radiation or gas. Generally, dispersions are prepared by incorporating the delivery particles into a sterile vehicle that contains a basic dispersion medium and the required other ingredients from those enumerated above. In the case of sterile powders for the preparation of sterile injectable solutions, methods of preparation are vacuum drying and freeze drying that yields a powder of delivery system comprising the one or more isolated oligonucleotides (e.g. dsRNA and siRNA) targeting C3 disclosed herein, plus any additional desired ingredient from a previously sterile filtered solution thereof.

Methods of Use

The present disclosure also provides a method of inhibiting or downregulating the expression or level of complement C3 in a subject in need thereof, wherein the method comprises administering to the subject an effective amount at least one isolated oligonucleotide disclosed herein, at least one vector disclosed herein, at least one delivery system disclosed herein, or at least one pharmaceutical composition disclosed herein.

The present disclosure also provides a method of treating or preventing a disease or disorder associated with aberrant or increased expression or activity of complement C3 or a disease or disorder where complement C3 plays a role in a subject in need thereof, wherein the method comprises administering to the subject an effective amount of at least one isolated oligonucleotide disclosed herein, at least one vector disclosed herein, at least one delivery system disclosed herein, or at least one pharmaceutical composition disclosed herein.

The present disclosure also provides at least one isolated oligonucleotide disclosed herein, a vector of the of the present disclosure encoding at least one isolated oligonucleotide disclosed herein, a delivery system of the present disclosure, or a pharmaceutical composition of the present disclosure, for use in treatment or prevention of a disease or disorder associated with aberrant or increased expression or activity of C3 or a disease or disorder where C3 plays a role, in a subject in need thereof.

The present disclosure also provides use of at least one isolated oligonucleotide disclosed herein, a vector of the of the present disclosure encoding at least one isolated oligonucleotide disclosed herein, a delivery system of the present disclosure, or a pharmaceutical composition of the present disclosure, in the manufacture of a medicament for treatment or prevention of a disease or disorder associated with aberrant or increased expression or activity of C3 or a disease or disorder where C3 plays a role in a subject in need thereof.

Provided herein are methods of inhibiting or downregulating C3 expression or activity in a cell, comprising contacting the cell with the one or more oligonucleotides (e.g., dsRNA or siRNA) targeting C3 as described herein. The one or more oligonucleotides (e.g., dsRNA or siRNA) targeting C3 as described herein can reduce or inhibit C3 activity through the RNAi pathway. The cell can be in vitro, in vivo or ex vivo. For example, the cell can be from a cell line, or in vivo in a subject in need thereof.

In some embodiments, the one or more oligonucleotides (e.g., dsRNA or siRNA) targeting C3 as described herein are capable of inducing RNAi-mediated degradation of an C3 mRNA in a cell of a subject.

As used herein, the terms "contacting," "introducing" and "administering" are used interchangeably and refer to a process by which dsRNA or siRNA of the present disclosure or a nucleic acid molecule encoding a dsRNA or siRNA of this disclosure is delivered to a cell in order to inhibit or alter or modify expression of a target gene. The dsRNA may be administered in a number of ways including, but not limited to, direct introduction into a cell (i.e., intracellularly) and/or extracellular introduction into a cavity, interstitial space, or into the circulation of the organism.

"Introducing" in the context of a cell or organism means presenting the nucleic acid molecule to the organism and/or cell in such a manner that the nucleic acid molecule gains access to the interior of a cell. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event or in separate transformation events. Thus, the term "transformation" as used herein refers to the introduction of a heterologous nucleic acid into a cell. Transformation of a cell may be stable or transient.

The term "inhibit" or "reduce" or grammatical variations thereof, as used herein, refer to a decrease or diminishment in the specified level or activity of at least about 5%, about 10%, about 15%, about 25%, about 35%, about 40%, about 50%, about 60%, about 75%, about 80%, about 90%, about 95% or more. In some embodiments, the inhibition or reduction results in little or essentially no detectible activity (at most, an insignificant amount, e.g., less than about 10% or even 5%).

In contrast, the term "increase" or grammatical variations thereof as used herein refers to an increase or elevation in the specified level or activity of at least about 5%, about 10%, about 15%, about 25%, about 35%, about 40%, about 50%, about 60%, about 75%, about 80%, about 90%, about 95% or more. Increases in activity can be described in terms of fold change. For example, activity can be increased 1.2×, 1.5×, 2×, 3×, 5×, 6×, 7×, 8×, 9×, 10× or more compared to a baseline level of activity.

As used herein, the term "$IC_{50}$" or "$IC_{50}$ value" refers to the concentration of an agent where cell viability is reduced by half. The $IC_{50}$ is thus a measure of the effectiveness of an agent in inhibiting a biological process. In an exemplary model, cell lines are cultured using standard techniques, treated with any of the one or more oligonucleotides (e.g., dsRNA or siRNA) targeting C3 as described herein, and the $IC_{50}$ value of the oligonucleotides (e.g., dsRNA or siRNA) targeting C3 is calculated after 24, 48 and/or 72 hours to determine its effectiveness in downregulating or inhibiting the level of C3 mRNA or protein to 50%, as compared to the level of C3 mRNA or protein in an untreated cell or in the same cell before initiation of treatment with the isolated oligonucleotide.

Methods of monitoring of C3 mRNA and/or protein expression can be used to characterize gene silencing, and to determine the effectiveness of the compositions described herein. Expression of C3 may be evaluated by any technique known in the art. Examples thereof include immunoprecipitations methods, utilizing C3 antibodies in assays such as ELISAs, western blotting, or immunohistochemistry to visualize C3 protein expression in cells, or flow cytometry. Additional methods include various hybridization methods utilizing a nucleic acid that specifically hybridizes with a nucleic acid encoding C3 or a unique fragment thereof, or a transcription product (e.g., mRNA) or splicing product of said nucleic acid, northern blotting methods, Southern blotting methods, and various PCR-based methods such as RT-PCR, qPCR or digital droplet PCR. C3 mRNA expression may additionally be assessed using high throughput sequencing techniques.

Methods of assaying the effect of individual isolated oligonucleotides (e.g., dsRNA or siRNA) targeting C3 include transfecting representative cell lines with isolated oligonucleotides and measuring viability. For example, cells from representative cell lines can be transfected using methods known in the art, such as the RNAiMAX Lipofectamine kit (Invitrogen) and cultured using any suitable technique known in the art. Optionally additional therapeutic agents as described herein can be added at variable concentrations to cell culture media following transfection. Following a suitable incubation period, such as 24-96 hours, cell viability can be measured using methods such as Cell Titer Glo 2.0 (Promega) to determine cell viability, and/or C3 mRNA and protein levels can be assessed using the methods described herein.

In some embodiments of the methods of inhibiting or downregulating C3 expression or activity in a cell of the present disclosure, the at least one isolated oligonucleotide, the vector, the delivery system, or the pharmaceutical composition is administered parenterally. In some embodiments, the parenteral administration is intravenous, subcutaneous, intraperitoneal, or intramuscular.

In some embodiments of the methods of inhibiting or downregulating C3 expression or activity in a cell of the present disclosure, the subject is a human. In some embodiments of the methods of inhibiting or downregulating C3 expression or activity in a cell of the present disclosure, the subject experiences symptoms of or suffers from Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases.

In some embodiments of the methods of inhibiting or downregulating C3 expression or activity in a cell of the present disclosure, the method comprises administering the at least one isolated oligonucleotide, the vector, the delivery system, or the pharmaceutical composition, in combination with at least a second therapeutic agent. In some embodiments, the second therapeutic agent is an antibody, a small molecule drug, a peptide, a nucleotide molecule, or a combination thereof. In some embodiments, the second therapeutic agent is an isolated oligonucleotide of the present disclosure.

The present disclosure also provides a method of inhibiting or downregulating the expression or level of C3 in a subject in need thereof, wherein the method comprises administering to the subject an effective amount of a first and at least a second oligonucleotides disclosed herein, wherein the first and at least second oligonucleotides comprise different sequences. In some embodiments, the first and at least second oligonucleotides are administered simultaneously. In some embodiments, the first and at least second oligonucleotides are administered sequentially.

In some embodiments of the methods of inhibiting or downregulating C3 expression or activity in a cell of the present disclosure, the subject is a human. In some embodiments of the methods of inhibiting or downregulating C3 expression or activity in a cell of the present disclosure, the subject experiences symptoms of or suffers from Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases, or a related disorder or symptom associated with an overreactive inflammatory response. In some embodiments of the method of treating or preventing a disease or disorder associated with aberrant or increased expression or activity of C3 or a disease or disorder where C3 plays a role of the present disclosure, the subject is a human. In some embodiments of the method of treating or preventing a disease or disorder associated with aberrant or increased expression or activity of C3 or a disease or disorder where C3 plays a role of the present disclosure, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, a neurodegenerative diseases, or a related disorder or symptom associated with an overreactive inflammatory response. In some embodiments of the use for treating or preventing a disease or disorder associated with aberrant or increased expression or activity of C3 or a disease or disorder where C3 plays a role of the present disclosure, the subject is a human. In some embodiments of the use for treating or preventing a disease or disorder associated with aberrant or increased expression or activity of C3 or a disease or disorder where C3 plays a role of the present disclosure, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, neurodegenerative diseases, or a related disorder or symptom associated with an overreactive inflammatory response.

In some embodiments of the use in the manufacture of a medicament for treatment or prevention of a disease or disorder associated with aberrant or increased expression or activity of C3 of the present disclosure, the subject is a human. In some embodiments, the subject is not a human. In some embodiments, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis (C3G), atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, neurodegenerative diseases, or a related disorder or symptom associated with an overreactive inflammatory response.

Routes of Administration

Nanoparticles comprising the one or more isolated oligonucleotides (e.g., dsRNA or siRNA) targeting C3 mRNA of the present disclosure can be administered to a subject by many of the well-known methods currently used for therapeutic treatment. For example, for treatment of mammalian diseases associated with expression or activity of C3, a compositions comprising the one or more isolated oligonucleotides (e.g., dsRNA or siRNA) targeting C3 of the present disclosure may be injected directly into cells, injected into the blood stream or body cavities, taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

The compositions comprising the one or more isolated oligonucleotides (e.g., dsRNA or siRNA) targeting C3 mRNA of the present disclosure can be administered orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the parenteral administration comprises intramuscular, intraperitoneal, subcutaneous or intravenous administration. One skilled in the art will recognize the advantages of certain routes of administration.

Compositions of the disclosure may be administered parenterally. Systemic administration of compositions comprising nanoparticles of the disclosure can also be by intravenous, transmucosal, subcutaneous, intraperitoneal, intramuscular or transdermal means. For intravenous parenteral administration, compositions comprising nanoparticles may be administered by injection or by infusion. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

Dosages

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing or treatment of the condition or symptom associated with expression or activity of C3. Dosages may vary depending on the age and size of the subject and the type and severity of the disease or disorder associated with C3 expression.

The term “effective amount” or “therapeutically effective amount”, as used interchangeably herein, refers to an amount of a pharmaceutical agent to treat, ameliorate, inhibit, downregulate or control the expression of C3 or symptoms associated with aberrant or abnormal expression of C3 in a subject, or to exhibit a detectable therapeutic or inhibitory effect in a subject. The effect can be detected by any assay method known in the art. The precise effective amount for a subject will depend upon the subject’s body weight, size, and health; the nature and extent of the condition; and the therapeutic or combination of therapeutics selected for administration. Therapeutically effective amounts for a given situation can be determined by routine experimentation that is within the skill and judgment of the clinician.

For any of the one or more isolated oligonucleotides (e.g., dsRNA or siRNA) targeting C3 mRNA of the present disclosure, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. In some embodiments, a standard xenograft or patient derived xenograft mouse model can be used to determine the effectiveness of the one or more isolated oligonucleotides (e.g., dsRNA or siRNA) targeting C3 mRNA of the present disclosure. Such information can then be used to determine useful doses and routes for administration in humans. Therapeutic/prophylactic efficacy and toxicity may be determined by standard pharmaceutical procedures in cell cultures or experimental animals, e.g., the maximum tolerated dose and no observable adverse effect dose. Pharmaceutical compositions that exhibit large therapeutic windows are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The dosage of nanoparticles comprising the one or more isolated oligonucleotides (e.g., dsRNA or siRNA) targeting C3 mRNA of the present disclosure, required depends on the choice of the route of administration; the nature of the formulation; the nature of the patient’s illness; the subject’s size, weight, surface area, age, and sex; other drugs being administered; and the judgment of the attending physician. Wide variations in the needed dosage are to be expected in view of the differing efficiencies of various routes of administration. For example, oral administration would be expected to require higher dosages than administration by intravenous injection (e.g., 2-, 3-, 4-, 6-, 8-, 10-; 20-, 50-, 100-, 150-, or more fold). Variations in these dosage levels can be adjusted using standard empirical routines for optimization as is well understood in the art. Administrations can be single or multiple. Encapsulation of the inhibitor in a suitable delivery vehicle (e.g., capsules or implantable devices) may increase the efficiency of delivery, particularly for oral delivery.

A therapeutically effective dose of the one or more isolated oligonucleotides (e.g., dsRNA or siRNA) targeting C3 mRNA of the present disclosure, can optionally be combined with approved amounts of therapeutic agents, and described herein.

Kits and Articles of Manufacture

The present disclosure also provides kits comprising at least one isolated oligonucleotide disclosed herein, a vector of the present disclosure encoding an isolated oligonucleotide disclosed herein, a delivery system of the present disclosure, or a pharmaceutical composition of the present disclosure. In some embodiments, the vector encodes one isolated oligonucleotide disclosed herein. In some embodiments, the vector encodes more than one isolated oligonucleotide disclosed herein.

The kits are for use in the treatment of diseases related to abnormal or aberrant expression of human complement C3. The kits are for use in downregulating or inhibiting expression of complement C3 partially or completely. In some embodiments, the kit is for use in the treatment of disease or downregulating or inhibiting expression of C3 in a mammal. In some embodiments, the mammal is a human, a mouse, a rat, a rabbit, a pig, a bovine, a canine, a feline, an ungulate, an ape, a monkey or an equine species. In some embodiments, the mammal is a human In some embodiments of the kits of the disclosure, the kit comprises nanoparticles. Nanoparticles comprising the one or more isolated oligonucleotides (e.g., dsRNA or siRNA) targeting complement C3 mRNA of the present disclosure, can be lyophilized before being packaged in the kit, or can be provided in solution with a pharmaceutically acceptable carrier, diluent of excipient.

In some embodiments of the kits of the disclosure, the kit comprises a therapeutically effective amount of a composition comprising the delivery system of the present disclosure comprising one or more of the isolated oligonucleotides of the present disclosure targeting complement C3 (dsRNA or siRNA), and instructions for use of the same. In some embodiments, the kit further comprises at least one additional therapeutic agents, as described herein.

Articles of manufacture of the present disclosure include, but are not limited to, instructions for use of the kit in treating diseases related to abnormal or aberrant expression of complement C3 or diseases related to expression of complement C3.

In some embodiments, the kits further comprise instructions for administering the isolated oligonucleotides, the vector, the delivery systems and the pharmaceutical compositions of the disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed invention. Based on the present disclosure the skilled artisan can identify and employ other components and methodology useful for practicing the present disclosure.

Sequences of the Disclosure

TABLE 1

Exemplary Pairs of Antisense and Sense Strand Sequences of the Disclosure

| SEQ ID NO: | Antisense strand (guide) sequence | start pos. | end pos. | SEQ ID NO: | Sense strand (passenger) sequence | start pos. | end pos. |
|---|---|---|---|---|---|---|---|
| 2 | UGAGAAGACAAGGAGUCCUGCU | 588 | 608 | 32 | CAGGACUCCUUGUCUUCUCA | 590 | 608 |
| 3 | UUAGUAGAAUUUCUCUGUAGGC | 772 | 792 | 33 | CUACAGAGAAAUUCUACUAA | 774 | 792 |
| 4 | UGUAGUAGAAUUUCUCUGUAGG | 773 | 793 | 34 | UACAGAGAAAUUCUACUACA | 775 | 793 |
| 5 | UAUGUAGUAGAAUUUCUCUGUA | 775 | 795 | 35 | CAGAGAAAUUCUACUACAUA | 777 | 795 |
| 6 | UGAUGUAGUAGAAUUUCUCUGU | 776 | 796 | 36 | AGAGAAAUUCUACUACAUCA | 778 | 796 |
| 7 | UAUAGAUGUAGUAGAAUUUCUC | 779 | 799 | 37 | GAAAUUCUACUACAUCUAUA | 781 | 799 |
| 8 | UUAUAGAUGUAGUAGAAUUUCU | 780 | 800 | 38 | AAAUUCUACUACAUCUAUAA | 782 | 800 |
| 9 | UUUAUAGAUGUAGUAGAAUUUC | 781 | 801 | 39 | AAUUCUACUACAUCUAUAAA | 783 | 801 |
| 10 | UGUGUGUUGAUGCUGAGUUUGG | 1281 | 1301 | 40 | AAACUCAGCAUCAACACACA | 1283 | 1301 |
| 11 | UCUAUCUUCAGGGUCAUCUGCU | 1797 | 1817 | 41 | CAGAUGACCCUGAAGAUAGA | 1799 | 1817 |
| 12 | UAAAAUAUAUUCAUGAGCUUCG | 2424 | 2444 | 42 | AAGCUCAUGAAUAUAUUUUA | 2426 | 2444 |
| 13 | UAUGAAGAAGUCCUGCAUUACU | 2533 | 2553 | 43 | UAAUGCAGGACUUCUUCAUA | 2535 | 2553 |
| 14 | UUUCGAACAACAGAGUAGGGUA | 2565 | 2585 | 44 | CCCUACUCUGUUGUUCGAAA | 2567 | 2585 |
| 15 | UUUUUGUUCAUUCUGAUUCCUU | 2862 | 2882 | 45 | GGAAUCAGAAUGAACAAAAA | 2864 | 2882 |
| 16 | UAAGUCUUUUAGCUGCAGUAGG | 3778 | 3798 | 46 | UACUGCAGCUAAAAGACUUA | 3780 | 3798 |
| 17 | UAAGUCAAAGUCUUUUAGCUGC | 3784 | 3804 | 47 | AGCUAAAAGACUUUGACUUA | 3786 | 3804 |
| 18 | UAAAGUCAAAGUCUUUUAGCUG | 3785 | 3805 | 48 | GCUAAAAGACUUUGACUUUA | 3787 | 3805 |
| 19 | UGUUCAUUGAGCCAACGCACGA | 3816 | 3836 | 49 | GUGCGUUGGCUCAAUGAACA | 3818 | 3836 |
| 20 | UAAUUUAUUACAGGUGAGUUGA | 4123 | 4143 | 50 | AACUCACCUGUAAUAAAUUA | 4125 | 4143 |
| 21 | UCUGGUUUUAUGGUGACCUUGA | 4149 | 4169 | 51 | AAGGUCACCAUAAAACCAGA | 4151 | 4169 |
| 22 | UGAGUGUGAGACCUUGUCCAGG | 4402 | 4422 | 52 | UGGACAAGGUCUCACACUCA | 4404 | 4422 |
| 23 | UCAGAGUGUGAGACCUUGUCCA | 4404 | 4424 | 53 | GACAAGGUCUCACACUCUGA | 4406 | 4424 |
| 24 | UUAUUGGUGAACUUUGAAAGCU | 4438 | 4458 | 54 | CUUUCAAAGUUCACCAAUAA | 4440 | 4458 |
| 25 | UUAAUAGGCGUAGACCUUGACU | 4489 | 4509 | 55 | UCAAGGUCUACGCCUAUUAA | 4491 | 4509 |
| 26 | UUUGUAAUAGGCGUAGACCUUG | 4492 | 4512 | 56 | AGGUCUACGCCUAUUACAAA | 4494 | 4512 |
| 27 | UGUAGAACCGGGUACAGCUUUC | 4520 | 4540 | 57 | AAGCUGUACCCGGUUCUACA | 4522 | 4540 |
| 28 | UCAGAGCUUGUUCAGCUUUCCA | 4558 | 4578 | 58 | GAAAGCUGAACAAGCUCUGA | 4560 | 4578 |
| 29 | UAUGAAGCAAUUCUCCUCAGCA | 4600 | 4620 | 59 | CUGAGGAGAAUUGCUUCAUA | 4602 | 4620 |
| 30 | UUAUGAAGCAAUUCUCCUCAGC | 4601 | 4621 | 60 | UGAGGAGAAUUGCUUCAUAA | 4603 | 4621 |
| 31 | UUUUGUAUGAAGCAAUUCUCCU | 4605 | 4625 | 61 | GAGAAUUGCUUCAUACAAAA | 4607 | 4625 |

TABLE 1

Exemplary Sequences of the Disclosure and Their Potency

| Guide Strand position 3' | Start | End | Guide strand sequence (5'-3') | SEQ ID | Passenger strand sequence (5'-3') | SEQ ID | | % of gene remaining at 0.1 nM Mean | % of gene remaining at 0.1 nM SEM | % of gene remaining at 0.1 nM Mean | % of gene remaining at 0.1 nM SEM |
|---|---|---|---|---|---|---|---|---|---|---|---|
| 609 | 588 | 608 | **UGAGAAGACAAGGAGUCCUGCU** | 2 | **CAGGACUCCUUGUCUUCUCA** | 32 | * | 18.03 | 2.43 | 49.10 | 2.87 |
| 793 | 772 | 792 | **UUAGUAGAAUUUCUCUGUAGGC** | 3 | **CUACAGAGAAAUUCUACUAA** | 33 | *^ | 11.07 | 0.78 | 28.67 | 0.61 |
| 794 | 773 | 793 | **UGUAGUAGAAUUUCUCUGUAGG** | 4 | **UACAGAGAAAUUCUACUACA** | 34 | *^ | 12.43 | 0.60 | 42.83 | 3.50 |
| 796 | 775 | 795 | **UAUGUAGUAGAAUUUCUCUGUA** | 5 | **CAGAGAAAUUCUACUACAUA** | 35 | *^ | 10.80 | 1.18 | 39.13 | 1.37 |
| 797 | 776 | 796 | **UGAUGUAGUAGAAUUUCUCUGU** | 6 | **AGAGAAAUUCUACUACAUCA** | 36 | *^ | 16.23 | 3.50 | 44.67 | 1.87 |
| 800 | 779 | 799 | **UAUAGAUGUAGUAGAAUUUCUC** | 7 | **GAAAUUCUACUACAUCUAUA** | 37 | *^ | 16.03 | 2.20 | 40.87 | 0.96 |
| 801 | 780 | 800 | **UUAUAGAUGUAGUAGAAUUUCU** | 8 | **AAAUUCUACUACAUCUAUAA** | 38 | *^ | 16.03 | 2.20 | 33.13 | 1.25 |
| 802 | 781 | 801 | **UUUAUAGAUGUAGUAGAAUUUC** | 9 | **AAUUCUACUACAUCUAUAAA** | 39 | *^ | 10.77 | 1.08 | 33.13 | 1.25 |
| 1302 | 1281 | 1301 | **UGUGUGUUGAUGCUGAGUUUGG** | 10 | **AAACUCAGCAUCAACACACA** | 40 | | 17.97 | 0.18 | 58.50 | 2.52 |
| 1818 | 1797 | 1817 | **UCUAUCUUCAGGGUCAUCUGCU** | 11 | **CAGAUGACCCUGAAGAUAGA** | 41 | *^ | 21.13 | 2.38 | 52.07 | 1.28 |
| 2445 | 2424 | 2444 | **UAAAAUAUAUUCAUGAGCUUCG** | 12 | **AAGCUCAUGAAUAUAUUUUA** | 42 | *^ | 18.13 | 1.09 | 54.33 | 0.79 |
| 2554 | 2533 | 2553 | **UAUGAAGAAGUCCUGCAUUACU** | 13 | **UAAUGCAGGACUUCUUCAUA** | 43 | * | 18.77 | 1.17 | 57.57 | 0.95 |
| 2586 | 2565 | 2585 | **UUUCGAACAACAGAGUAGGGUA** | 14 | **CCCUACUCUGUUGUUCGAAA** | 44 | * | 18.90 | 1.72 | 44.00 | 1.76 |
| 2883 | 2862 | 2882 | **UUUUUGUUCAUUCUGAUUCCUU** | 15 | **GGAAUCAGAAUGAACAAAAA** | 45 | *^ | 19.53 | 0.41 | 54.33 | 0.86 |
| 3799 | 3778 | 3798 | **UAAGUCUUUUAGCUGCAGUAGG** | 16 | **UACUGCAGCUAAAAGACUUA** | 46 | | 21.17 | 0.50 | 53.40 | 2.22 |
| 3805 | 3784 | 3804 | **UAAGUCAAAGUCUUUUAGCUGC** | 17 | **AGCUAAAAGACUUUGACUUA** | 47 | * | 17.03 | 0.35 | 40.60 | 0.98 |
| 3806 | 3785 | 3805 | **UAAAGUCAAAGUCUUUUAGCUG** | 18 | **GCUAAAAGACUUUGACUUUA** | 48 | * | 12.40 | 0.40 | 41.13 | 2.34 |
| 3837 | 3816 | 3836 | **UGUUCAUUGAGCCAACGCACGA** | 19 | **GUGCGUUGGCUCAAUGAACA** | 49 | * | 19.17 | 1.66 | 46.57 | 0.48 |
| 4144 | 4123 | 4143 | **UAAUUUAUUACAGGUGAGUUGA** | 20 | **AACUCACCUGUAAUAAAUUA** | 50 | * | 19.17 | 0.49 | 46.57 | 1.39 |
| 4170 | 4149 | 4169 | **UCUGGUUUUAUGGUGACCUUGA** | 21 | **AAGGUCACCAUAAAACCAGA** | 51 | *^ | 19.77 | 0.43 | 49.57 | 2.45 |
| 4423 | 4402 | 4422 | **UGAGUGUGAGACCUUGUCCAGG** | 22 | **UGGACAAGGUCUCACACUCA** | 52 | *^ | 15.80 | 0.60 | 43.80 | 3.58 |
| 4425 | 4404 | 4424 | **UCAGAGUGUGAGACCUUGUCCA** | 23 | **GACAAGGUCUCACACUCUGA** | 53 | *^ | 16.20 | 1.76 | 44.47 | 1.54 |
| 4459 | 4438 | 4458 | **UUAUUGGUGAACUUUGAAAGCU** | 24 | **CUUUCAAAGUUCACCAAUAA** | 54 | | 21.43 | 2.86 | 53.27 | 1.63 |
| 4510 | 4489 | 4509 | **UUAAUAGGCGUAGACCUUGACU** | 25 | **UCAAGGUCUACGCCUAUUAA** | 55 | * | 14.93 | 0.88 | 32.43 | 2.38 |
| 4513 | 4492 | 4512 | **UUUGUAAUAGGCGUAGACCUUG** | 26 | **AGGUCUACGCCUAUUACAAA** | 56 | * | 14.20 | 1.17 | 33.20 | 0.75 |
| 4541 | 4520 | 4540 | **UGUAGAACCGGGUACAGCUUUC** | 27 | **AAGCUGUACCCGGUUCUACA** | 57 | *^ | 21.57 | 1.33 | 49.47 | 1.27 |
| 4579 | 4558 | 4578 | **UCAGAGCUUGUUCAGCUUUCCA** | 28 | **GAAAGCUGAACAAGCUCUGA** | 58 | *^ | 17.23 | 1.50 | 43.1 | 2.99 |
| 4621 | 4600 | 4620 | **UAUGAAGCAAUUCUCCUCAGCA** | 29 | **CUGAGGAGAAUUGCUUCAUA** | 59 | *^ | 18.70 | 1.57 | 31.47 | 0.79 |
| 4622 | 4601 | 4621 | **UUAUGAAGCAAUUCUCCUCAGC** | 30 | **UGAGGAGAAUUGCUUCAUAA** | 60 | *^ | 18.20 | 1.10 | 47.07 | 1.04 |
| 4626 | 4605 | 4625 | **UUUUGUAUGAAGCAAUUCUCCU** | 31 | **GAGAAUUGCUUCAUACAAAA** | 61 | *^ | 20.80 | 1.62 | 53.40 | 0.90 |
| 54 | 33 | 53 | **UGACAGUGCAGGGUCAGAGGGA** | 62 | **CCUCUGACCCUGCACUGUCA** | 227 | | 60.70 | 4.54 | 80.07 | 5.59 |
| 258 | 237 | 257 | **UUUUUGCCUGGGAAGUCGUGGA** | 63 | **CACGACUUCCCAGGCAAAAA** | 228 | | 28.93 | 1.35 | 66.77 | 4.79 |
| 259 | 238 | 258 | **UUUUUUGCCUGGGAAGUCGUGG** | 64 | **ACGACUUCCCAGGCAAAAAA** | 229 | | 21.33 | 1.03 | 60.47 | 0.87 |
| 260 | 239 | 259 | UUUUUUUGCCUGGGAAGUCGUG | 65 | CGACUUCCCAGGCAAAAAAA | 230 | | 61.70 | 1.20 | 93.33 | 2.16 |
| 261 | 240 | 260 | UGUUUUUUGCCUGGGAAGUCGU | 66 | GACUUCCCAGGCAAAAAACA | 231 | | 53.50 | 2.31 | 89.43 | 1.76 |
| 465 | 444 | 464 | **UCUGUCUGGAUGAAGAGGUACC** | 67 | **UACCUCUUCAUCCAGACAGA** | 232 | | 24.93 | 2.11 | 58.93 | 0.75 |

TABLE 1-continued

Exemplary Sequences of the Disclosure and Their Potency

| Guide Strand position 3' | Start | End | Guide strand sequence (5′-3′) | SEQ ID | Passenger strand sequence (5′-3′) | SEQ ID | % of gene remaining at 0.1 nM Mean | % of gene remaining at 0.1 nM SEM | % of gene remaining at 0.1 nM Mean | % of gene remaining at 0.1 nM SEM |
|---|---|---|---|---|---|---|---|---|---|---|
| 467 | 446 | 466 | **UGUCUGUCUGGAUGAAGAGGUA** | 68 | **CCUCUUCAUCCAGACAGACA** | 233 | 57.40 | 1.93 | 75.77 | 5.29 |
| 469 | 448 | 468 | **UUUGUCUGUCUGGAUGAAGAGG** | 69 | **UCUUCAUCCAGACAGACAAA** | 234 | 33.93 | 0.84 | 74.07 | 2.03 |
| 478 | 457 | 477 | **UUAGAUGGUCUUGUCUGUCUGG** | 70 | **AGACAGACAAGACCAUCUAA** | 235 | 20.33 | 0.44 | 55.07 | 1.09 |
| 479 | 458 | 478 | UGUAGAUGGUCUUGUCUGUCUG | 71 | GACAGACAAGACCAUCUACA | 236 | 50.13 | 1.11 | 80.97 | 0.19 |
| 480 | 459 | 479 | **UUGUAGAUGGUCUUGUCUGUCU** | 72 | **ACAGACAAGACCAUCUACAA** | 237 | 25.03 | 1.59 | 63.63 | 1.28 |
| 481 | 460 | 480 | **UGUGUAGAUGGUCUUGUCUGUC** | 73 | **CAGACAAGACCAUCUACACA** | 238 | 31.67 | 1.39 | 76.07 | 1.48 |
| 604 | 583 | 603 | **UGACAAGGAGUCCUGCUUGACC** | 74 | **UCAAGCAGGACUCCUUGUCA** | 239 | 19.57 | 1.55 | 59.43 | 5.40 |
| 606 | 585 | 605 | **UAAGACAAGGAGUCCUGCUUGA** | 75 | **AAGCAGGACUCCUUGUCUUA** | 240 | 32.67 | 1.16 | 74.83 | 3.11 |
| 613 | 592 | 612 | UUUCUGAGAAGACAAGGAGUCC | 76 | ACUCCUUGUCUUCUCAGAAA | 241 | 45.10 | 1.63 | 82.80 | 4.68 |
| 659 | 638 | 658 | UGACGAGUUCCGGAAUGUCCCA | 77 | GGACAUUCCGGAACUCGUCA | 242 | 40.87 | 1.52 | 81.37 | 2.02 |
| 661 | 640 | 660 | **UUUGACGAGUUCCGGAAUGUCC** | 78 | **ACAUUCCGGAACUCGUCAAA** | 243 | 43.37 | 0.92 | 63.73 | 0.35 |
| 662 | 641 | 661 | **UGUUGACGAGUUCCGGAAUGUC** | 79 | **CAUUCCGGAACUCGUCAACA** | 244 | 43.80 | 0.35 | 76.80 | 4.23 |
| 677 | 656 | 676 | **UCUUCCACUGGCCCAUGUUGAC** | 80 | **CAACAUGGGCCAGUGGAAGA** | 245 | 60.83 | 0.73 | 73.00 | 6.12 |
| 693 | 672 | 692 | **UCAUAGUAGGCUCGGAUCUUCC** | 81 | **AAGAUCCGAGCCUACUAUGA** | 246 | 55.63 | 1.91 | 70.10 | 2.20 |
| 695 | 674 | 694 | **UUUCAUAGUAGGCUCGGAUCUU** | 82 | **GAUCCGAGCCUACUAUGAAA** | 247 | 34.43 | 9.03 | 76.47 | 3.59 |
| 696 | 675 | 695 | UUUUCAUAGUAGGCUCGGAUCU | 83 | AUCCGAGCCUACUAUGAAAA | 248 | 60.00 | 12.5 | 87.57 | 0.19 |
| 729 | 708 | 728 | UCAAACUCAGUGGAGAAGACCU | 84 | GUCUUCUCCACUGAGUUUGA | 249 | 44.73 | 4.92 | 86.23 | 4.00 |
| 740 | 719 | 739 | UCUCCUUCACCUCAAACUCAGU | 85 | UGAGUUUGAGGUGAAGGAGA | 250 | 78.67 | 0.19 | 95.70 | 5.95 |
| 742 | 721 | 741 | **UUACUCCUUCACCUCAAACUCA** | 86 | **AGUUUGAGGUGAAGGAGUAA** | 251 | 46.80 | 2.69 | 79.23 | 12.04 |
| 743 | 722 | 742 | **UGUACUCCUUCACCUCAAACUC** | 87 | **GUUUGAGGUGAAGGAGUACA** | 252 | 73.13 | 3.65 | 73.73 | 4.90 |
| 758 | 737 | 757 | UGAAACUGGGCAGCACGUACUC | 88 | GUACGUGCUGCCCAGUUUCA | 253 | 65.47 | 2.12 | 93.17 | 8.50 |
| 768 | 747 | 767 | **UCUAUGACCUCGAAACUGGGCA** | 89 | **CCCAGUUUCGAGGUCAUAGA** | 254 | 33.83 | 1.45 | 79.17 | 1.56 |
| 770 | 749 | 769 | UCACUAUGACCUCGAAACUGGG | 90 | CAGUUUCGAGGUCAUAGUGA | 255 | 72.53 | 1.53 | 83.63 | 0.41 |
| 782 | 761 | 781 | UCUCUGUAGGCUCCACUAUGAC | 91 | CAUAGUGGAGCCUACAGAGA | 256 | 65.20 | 0.15 | 85.97 | 0.41 |
| 784 | 763 | 783 | UUUCUCUGUAGGCUCCACUAUG | 92 | UAGUGGAGCCUACAGAGAAA | 257 | 32.20 | 1.31 | 84.97 | 7.53 |
| 792 | 771 | 791 | **UAGUAGAAUUUCUCUGUAGGCU** | 93 | **CCUACAGAGAAAUUCUACUA** | 258 | 23.47 | 4.90 | 62.77 | 5.64 |
| 799 | 778 | 798 | **UUAGAUGUAGUAGAAUUUCUCU** | 94 | **AGAAAUUCUACUACAUCUAA** | 259 *^ | 10.67 | 0.20 | 20.67 | 0.09 |
| 803 | 782 | 802 | **UGUUUAUAGAUGUAGUAGAAUUU** | 95 | **AUUCUACUACAUCUAUAACA** | 260 | 42.07 | 1.73 | 67.73 | 5.26 |
| 879 | 858 | 878 | **UAGAUGACAAAGGCAGUUCCCU** | 96 | **GGAACUGCCUUUGUCAUCUA** | 261 | 25.97 | 1.40 | 54.53 | 0.87 |
| 880 | 859 | 879 | UAAGAUGACAAAGGCAGUUCCC | 97 | GAACUGCCUUUGUCAUCUUA | 262 | 50.93 | 3.01 | 90.07 | 8.75 |
| 1139 | 1118 | 1138 | UCUUGGUGAAGUGGAUCUGGUA | 98 | CCAGAUCCACUUCACCAAGA | 263 | 38.67 | 0.46 | 83.87 | 7.16 |
| 1141 | 1120 | 1140 | **UGUCUUGGUGAAGUGGAUCUGG** | 99 | **AGAUCCACUUCACCAAGACA** | 264 | 31.00 | 2.18 | 75.60 | 2.84 |
| 1178 | 1157 | 1177 | **UGAGGUCAAAGGGCAUUCCUGG** | 100 | **AGGAAUGCCCUUUGACCUCA** | 265 | 34.27 | 0.55 | 76.10 | 2.38 |
| 1186 | 1165 | 1185 | **UAACACCAUGAGGUCAAAGGGC** | 101 | **CCUUUGACCUCAUGGUGUUA** | 266 | 43.77 | 1.52 | 79.43 | 2.22 |
| 1223 | 1202 | 1222 | UGACUCGGUAGGCUGGAGAGCC | 102 | CUCUCCAGCCUACCGAGUCA | 267 | 48.10 | 2.60 | 82.23 | 2.12 |

TABLE 1-continued

Exemplary Sequences of the Disclosure and Their Potency

| Guide Strand posi-tion 3' | Start | End | Guide strand sequence (5'-3') | SEQ ID | Passenger strand sequence (5'-3') | SEQ ID | % of gene remaining at 0.1 nM Mean | SEM | % of gene remaining at 0.1 nM Mean | SEM |
|---|---|---|---|---|---|---|---|---|---|---|
| 1299 | 1278 | 1298 | UUGUUGAUGCUGAGUUUGGCCA | 103 | GCCAAACUCAGCAUCAACAA | 268 | 54.93 | 1.96 | 84.50 | 2.00 |
| 1300 | 1279 | 1299 | **UGUGUUGAUGCUGAGUUUGGCC** | 104 | **CCAAACUCAGCAUCAACACA** | 269 | 28.27 | 1.57 | 73.87 | 3.93 |
| 1328 | 1307 | 1327 | UGAUGCUCAAGGGCUUCUGGCU | 105 | CCAGAAGCCCUUGAGCAUCA | 270 | 49.30 | 1.36 | 88.07 | 2.09 |
| 1329 | 1308 | 1328 | UUGAUGCUCAAGGGCUUCUGGC | 106 | CAGAAGCCCUUGAGCAUCAA | 271 | 50.77 | 4.27 | 88.57 | 5.06 |
| 1430 | 1409 | 1429 | UCAGGUAAUUGUUGGAGUUGCC | 107 | CAACUCCAACAAUUACCUGA | 272 | 57.00 | 1.66 | 85.40 | 3.78 |
| 1436 | 1415 | 1435 | **UGAGAUGCAGGUAAUUGUUGGA** | 108 | **CAACAAUUACCUGCAUCUCA** | 273 | 25.43 | 1.73 | 63.43 | 1.27 |
| 1440 | 1419 | 1439 | UCUGAGAGAUGCAGGUAAUUGU | 109 | AAUUACCUGCAUCUCUCAGA | 274 | 47.80 | 0.40 | 80.77 | 2.36 |
| 1490 | 1469 | 1489 | UGAGGAAGUUGACGUUGAGGGU | 110 | CCUCAACGUCAACUUCCUCA | 275 | 76.57 | 3.68 | 87.10 | 1.45 |
| 1499 | 1478 | 1498 | UCAUUCGCAGGAGGAAGUUGAC | 111 | CAACUUCCUCCUGCGAAUGA | 276 | 69.33 | 1.38 | 90.17 | 5.93 |
| 1534 | 1513 | 1533 | **UGUGUAGUAGCGGAUCUUGGCC** | 112 | **CCAAGAUCCGCUACUACACA** | 277 | 34.77 | 2.55 | 75.57 | 4.62 |
| 1543 | 1522 | 1542 | **UAUCAGGUAGGUGUAGUAGCGG** | 113 | **GCUACUACACCUACCUGAUA** | 278 | 22.23 | 0.88 | 57.13 | 0.64 |
| 1640 | 1619 | 1639 | UGAUGAAGUCGGUGGUGAUGGA | 114 | CAUCACCACCGACUUCAUCA | 279 | 78.63 | 1.16 | 97.33 | 8.05 |
| 1649 | 1628 | 1648 | UGAAGGAAGGGAUGAAGUCGGU | 115 | CGACUUCAUCCCUUCCUUCA | 280 | 51.17 | 1.37 | 85.50 | 2.08 |
| 1775 | 1754 | 1774 | **UUUCUGACUGGCCGCUUUUUAC** | 116 | **AAAAAGCGGCCAGUCAGAAA** | 281 | 52.60 | 2.25 | 75.37 | 5.02 |
| 1816 | 1795 | 1815 | UAUCUUCAGGGUCAUCUGCUGC | 117 | AGCAGAUGACCCUGAAGAUA | 282 | 55.50 | 0.96 | 89.70 | 3.60 |
| 1817 | 1796 | 1816 | **UUAUCUUCAGGGUCAUCUGCUG** | 118 | **GCAGAUGACCCUGAAGAUAA** | 283 | 29.63 | 2.19 | 68.10 | 3.55 |
| 2254 | 2233 | 2253 | **UAUGUAGUUGCAGCAGUCCAGG** | 119 | **UGGACUGCUGCAACUACAUA** | 284 | 76.23 | 1.19 | 76.23 | 1.19 |
| 2257 | 2236 | 2256 | **UGUGAUGUAGUUGCAGCAGUCC** | 120 | **ACUGCUGCAACUACAUCACA** | 285 | 79.20 | 2.52 | 79.20 | 2.52 |
| 2447 | 2426 | 2446 | UCAAAAAUAUAUUCAUGAGCUU | 121 | GCUCAUGAAUAUAUUUUUGA | 286 | 48.17 | 1.45 | 82.53 | 3.23 |
| 2449 | 2428 | 2448 | **UUUCAAAAAUAUAUUCAUGAGC** | 122 | **UCAUGAAUAUAUUUUUGAAA** | 287 | 27.63 | 0.94 | 66.60 | 0.60 |
| 2450 | 2429 | 2449 | **UUUUCAAAAAUAUAUUCAUGAG** | 123 | **CAUGAAUAUAUUUUUGAAAA** | 288 | 23.37 | 0.12 | 58.27 | 2.64 |
| 2451 | 2430 | 2450 | **UCUUUCAAAAAUAUAUUCAUGA** | 124 | **AUGAAUAUAUUUUUGAAAGA** | 289 | 23.90 | 1.63 | 64.47 | 2.15 |
| 2453 | 2432 | 2452 | UGUCUUUCAAAAAUAUAUUCAU | 125 | GAAUAUAUUUUUGAAAGACA | 290 | 49.70 | 0.96 | 82.77 | 5.16 |
| 2539 | 2518 | 2538 | **UAUUACUGUGACCUCGAAGGGG** | 126 | **CCUUCGAGGUCACAGUAAUA** | 291 | 22.37 | 3.02 | 57.73 | 1.87 |
| 2540 | 2519 | 2539 | UCAUUACUGUGACCUCGAAGGG | 127 | CUUCGAGGUCACAGUAAUGA | 292 | 68.83 | 2.46 | 86.87 | 3.07 |
| 2549 | 2528 | 2548 | **UGAAGUCCUGCAUUACUGUGAC** | 128 | **CACAGUAAUGCAGGACUUCA** | 293 | 39.63 | 0.98 | 72.67 | 3.68 |
| 2552 | 2531 | 2551 | **UGAAGAAGUCCUGCAUUACUGU** | 129 | **AGUAAUGCAGGACUUCUUCA** | 294 | 27.07 | 1.36 | 61.47 | 0.47 |
| 2555 | 2534 | 2554 | **UGAUGAAGAAGUCCUGCAUUAC** | 130 | **AAUGCAGGACUUCUUCAUCA** | 295 | 33.90 | 1.08 | 75.70 | 6.81 |
| 2583 | 2562 | 2582 | **UGAACAACAGAGUAGGGUAGCC** | 131 | **CUACCCUACUCUGUUGUUCA** | 296 | 22.07 | 0.85 | 60.87 | 4.75 |
| 2587 | 2566 | 2586 | UUUUCGAACAACAGAGUAGGGU | 132 | CCUACUCUGUUGUUCGAAAA | 297 | 45.73 | 1.89 | 85.53 | 4.76 |
| 2588 | 2567 | 2587 | UGUUUCGAACAACAGAGUAGGG | 133 | CUACUCUGUUGUUCGAAACA | 298 | 56.10 | 1.53 | 91.07 | 5.39 |
| 2603 | 2582 | 2602 | UGAUUUCCACCUGCUCGUUUCG | 134 | AAACGAGCAGGUGGAAAUCA | 299 | 48.57 | 0.29 | 95.67 | 6.68 |
| 2636 | 2615 | 2635 | UUUGGUUCUGCCGGUAAUUGUA | 135 | CAAUUACCGGCAGAACCAAA | 300 | 49.00 | 0.93 | 87.23 | 4.72 |
| 2637 | 2616 | 2636 | UCUUGGUUCUGCCGGUAAUUGU | 136 | AAUUACCGGCAGAACCAAGA | 301 | 79.33 | 2.83 | 101.77 | 4.54 |
| 2661 | 2640 | 2660 | **UGUAGUUCCACCCUCACCUUGA** | 137 | **AAGGUGAGGGUGGAACUACA** | 302 | 33.73 | 3.21 | 66.43 | 5.30 |
| 2670 | 2649 | 2669 | **UGAUUGUGGAGUAGUUCCACCC** | 138 | **GUGGAACUACUCCACAAUCA** | 303 | 77.50 | 8.48 | 74.63 | 7.67 |

TABLE 1-continued

Exemplary Sequences of the Disclosure and Their Potency

| Guide Strand position 3' | Start | End | Guide strand sequence (5'-3') | SEQ ID | Passenger strand sequence (5'-3') | SEQ ID | % of gene remaining at 0.1 nM Mean | SEM | % of gene remaining at 0.1 nM Mean | SEM |
|---|---|---|---|---|---|---|---|---|---|---|
| 2671 | 2650 | 2670 | **UGGAUUGUGGAGUAGUUCCACC** | 139 | **UGGAACUACUCCACAAUCCA** | 304 | 58.23 | 2.94 | 72.47 | 0.91 |
| 2673 | 2652 | 2672 | **UCUGGAUUGUGGAGUAGUUCCA** | 140 | **GAACUACUCCACAAUCCAGA** | 305 | 67.77 | 3.12 | 75.60 | 3.19 |
| 2683 | 2662 | 2682 | **UCUGCAGAAGGCUGGAUUGUGG** | 141 | **ACAAUCCAGCCUUCUGCAGA** | 306 | 62.63 | 2.90 | 78.33 | 1.25 |
| 2727 | 2706 | 2726 | **UGGAUGGUUACGGUCUGCUGGU** | 142 | **CAGCAGACCGUAACCAUCCA** | 307 | 46.07 | 1.11 | 74.50 | 3.07 |
| 2881 | 2860 | 2880 | **UUUGUUCAUUCUGAUUCCUUCC** | 143 | **AAGGAAUCAGAAUGAACAAA** | 308 | 36.90 | 0.46 | 72.60 | 0.84 |
| 2884 | 2863 | 2883 | **UGUUUUGUUCAUUCUGAUUCCU** | 144 | **GAAUCAGAAUGAACAAAACA** | 309 | 44.90 | 1.76 | 78.50 | 2.17 |
| 3002 | 2981 | 3001 | **UAAUUCUGGUCUCAGACUCGGU** | 145 | **CGAGUCUGAGACCAGAAUUA** | 310 | 24.47 | 1.76 | 69.10 | 1.27 |
| 3003 | 2982 | 3002 | **UGAAUUCUGGUCUCAGACUCGG** | 146 | **GAGUCUGAGACCAGAAUUCA** | 311 | 22.43 | 0.35 | 67.80 | 4.07 |
| 3044 | 3023 | 3043 | UGGCAUCCUCUGUCAUCUGGGC | 147 | CCAGAUGACAGAGGAUGCCA | 312 | 76.70 | 5.95 | 86.33 | 3.64 |
| 3146 | 3125 | 3145 | UCAGGUAAUGCACAGCGAUGAC | 148 | CAUCGCUGUGCAUUACCUGA | 313 | 46.07 | 0.90 | 81.80 | 2.23 |
| 3152 | 3131 | 3151 | **UUUCAUCCAGGUAAUGCACAGC** | 149 | **UGUGCAUUACCUGGAUGAAA** | 314 | 37.57 | 0.38 | 79.80 | 1.33 |
| 3154 | 3133 | 3153 | UGUUUCAUCCAGGUAAUGCACA | 150 | UGCAUUACCUGGAUGAAACA | 315 | 39.03 | 1.04 | 80.97 | 1.24 |
| 3214 | 3193 | 3213 | **UUUCUUGAUGAGCUCCAAGGCC** | 151 | **CCUUGGAGCUCAUCAAGAAA** | 316 | 35.00 | 0.55 | 68.07 | 3.05 |
| 3215 | 3194 | 3214 | UCUUCUUGAUGAGCUCCAAGGC | 152 | CUUGGAGCUCAUCAAGAAGA | 317 | 79.17 | 1.63 | 94.93 | 1.13 |
| 3240 | 3219 | 3239 | **UUGAAGGCCAGCUGCUGGGUGU** | 153 | **ACCCAGCAGCUGGCCUUCAA** | 318 | 53.73 | 1.28 | 77.07 | 3.08 |
| 3319 | 3298 | 3318 | **UAAGACCUUGACCACGUAGGCG** | 154 | **CCUACGUGGUCAAGGUCUUA** | 319 | 31.27 | 1.68 | 63.40 | 1.65 |
| 3324 | 3303 | 3323 | UGAGAGAAGACCUUGACCACGU | 155 | GUGGUCAAGGUCUUCUCUCA | 320 | 36.47 | 1.17 | 86.73 | 1.77 |
| 3389 | 3368 | 3388 | UCAGGAUCAGCCAUUUAACAGC | 156 | UGUUAAAUGGCUGAUCCUGA | 321 | 60.13 | 1.47 | 103.33 | 1.38 |
| 3438 | 3417 | 3437 | UGUAUCACGGGCGCAUCCUCCU | 157 | GAGGAUGCGCCCGUGAUACA | 322 | 70.27 | 3.35 | 81.20 | 5.36 |
| 3588 | 3567 | 3587 | UGGAAGUCUCCUGCUUUAGUGA | 158 | ACUAAAGCAGGAGACUUCCA | 323 | 59.70 | 0.93 | 93.90 | 3.46 |
| 3590 | 3569 | 3589 | **UAAGGAAGUCUCCUGCUUUAGU** | 159 | **UAAAGCAGGAGACUUCCUUA** | 324 | 25.27 | 0.09 | 64.53 | 1.56 |
| 3607 | 3586 | 3606 | **UUUCAUGUAGUUGGCUUCAAGG** | 160 | **UUGAAGCCAACUACAUGAAA** | 325 | 27.83 | 0.84 | 72.70 | 2.05 |
| 3613 | 3592 | 3612 | **UUGUAGGUUCAUGUAGUUGGCU** | 161 | **CCAACUACAUGAACCUACAA** | 326 | 34.60 | 0.49 | 79.63 | 1.01 |
| 3618 | 3597 | 3617 | **UAUCUCUGUAGGUUCAUGUAGU** | 162 | **UACAUGAACCUACAGAGAUA** | 327 | 28.07 | 0.15 | 68.67 | 2.48 |
| 3627 | 3606 | 3626 | **UCAGUGUAGGAUCUCUGUAGGU** | 163 | **CUACAGAGAUCCUACACUGA** | 328 | 37.20 | 0.25 | 75.37 | 4.17 |
| 3639 | 3618 | 3638 | UCAGCAAUGGCCACAGUGUAGG | 164 | UACACUGUGGCCAUUGCUGA | 329 | 71.73 | 2.77 | 87.63 | 2.43 |
| 3788 | 3767 | 3787 | UCUGCAGUAGGGCCAAGAGGGC | 165 | CCUCUUGGCCCUACUGCAGA | 330 | 66.70 | 1.70 | 97.83 | 6.33 |
| 3796 | 3775 | 3795 | **UUCUUUUAGCUGCAGUAGGGCC** | 166 | **CCCUACUGCAGCUAAAAGAA** | 331 | 45.07 | 3.75 | 79.37 | 4.81 |
| 3797 | 3776 | 3796 | UGUCUUUUAGCUGCAGUAGGGC | 167 | CCUACUGCAGCUAAAAGACA | 332 | 44.30 | 0.70 | 88.13 | 2.57 |
| 3807 | 3786 | 3806 | UCAAAGUCAAAGUCUUUUAGCU | 168 | CUAAAAGACUUUGACUUUGA | 333 | 50.93 | 0.96 | 87.23 | 2.49 |
| 3809 | 3788 | 3808 | **UCACAAAGUCAAAGUCUUUUAG** | 169 | **AAAAGACUUUGACUUUGUGA** | 334 | 52.87 | 1.56 | 75.57 | 4.48 |
| 3845 | 3824 | 3844 | **UGUAUCUCUGUUCAUUGAGCCA** | 170 | **GCUCAAUGAACAGAGAUACA** | 335 | 23.20 | 1.17 | 58.00 | 1.92 |
| 3846 | 3825 | 3845 | **UAGUAUCUCUGUUCAUUGAGCC** | 171 | **CUCAAUGAACAGAGAUACUA** | 336 | 31.27 | 0.62 | 76.87 | 1.04 |
| 3847 | 3826 | 3846 | **UUAGUAUCUCUGUUCAUUGAGC** | 172 | **UCAAUGAACAGAGAUACUAA** | 337 | 21.60 | 0.21 | 58.97 | 1.68 |
| 3914 | 3893 | 3913 | UCUUUUGGUAUUGAGCCAAGGC | 173 | CUUGGCUCAAUACCAAAAGA | 338 | 51.83 | 4.34 | 96.83 | 3.31 |

TABLE 1-continued

| Exemplary Sequences of the Disclosure and Their Potency | | | | | | | | | | |
|---|---|---|---|---|---|---|---|---|---|---|
| Guide Strand posi- tion | | | Guide strand sequence | SEQ | Passenger strand | SEQ | % of gene remaining at 0.1 nM | | % of gene remaining at 0.1 nM | |
| 3' | Start | End | (5'-3') | ID | sequence (5'-3') | ID | Mean | SEM | Mean | SEM |
| 4006 | 3985 | 4005 | UGAUUCCCAGUGGAUACGGUGG | 174 | ACCGUAUCCACUGGGAAUCA | 339 | 61.53 | 2.94 | 84.27 | 9.32 |
| 4008 | 3987 | 4007 | **UCAGAUUCCCAGUGGAUACGGU** | 175 | **CGUAUCCACUGGGAAUCUGA** | 340 | 47.57 | 2.76 | 79.67 | 0.47 |
| 4042 | 4021 | 4041 | **UUUUUCCUUGGUCUCUUCUGAU** | 176 | **CAGAAGAGACCAAGGAAAAA** | 341 | 34.13 | 2.64 | 72.77 | 1.93 |
| 4043 | 4022 | 4042 | UAUUUUCCUUGGUCUCUUCUGA | 177 | AGAAGAGACCAAGGAAAAUA | 342 | 39.27 | 1.15 | 80.73 | 2.28 |
| 4044 | 4023 | 4043 | **UCAUUUUCCUUGGUCUCUUCUG** | 178 | **GAAGAGACCAAGGAAAAUGA** | 343 | 28.97 | 0.69 | 72.63 | 3.17 |
| 4056 | 4035 | 4055 | UCUGUGAAACCCUCAUUUUCCU | 179 | GAAAAUGAGGGUUUCACAGA | 344 | 68.37 | 2.01 | 96.50 | 3.84 |
| 4067 | 4046 | 4066 | **UUUCAGCUGUGACUGUGAAACC** | 180 | **UUUCACAGUCACAGCUGAAA** | 345 | 31.70 | 0.21 | 68.23 | 1.46 |
| 4071 | 4050 | 4070 | **UUUCCUUCAGCUGUGACUGUGA** | 181 | **ACAGUCACAGCUGAAGGAAA** | 346 | 25.40 | 0.38 | 60.80 | 2.58 |
| 4073 | 4052 | 4072 | **UUUUUCCUUCAGCUGUGACUGU** | 182 | **AGUCACAGCUGAAGGAAAAA** | 347 | 38.97 | 1.87 | 76.93 | 1.57 |
| 4074 | 4053 | 4073 | UCUUUUCCUUCAGCUGUGACUG | 183 | GUCACAGCUGAAGGAAAAGA | 348 | 67.97 | 1.62 | 91.77 | 7.07 |
| 4115 | 4094 | 4114 | UCUUAGCAUGGUACAUUGUCAC | 184 | GACAAUGUACCAUGCUAAGA | 349 | 73.70 | 6.41 | 80.60 | 3.92 |
| 4151 | 4130 | 4150 | UGAGGUCGAAUUUAUUACAGGU | 185 | CUGUAAUAAAUUCGACCUCA | 350 | 68.90 | 0.90 | 84.87 | 1.78 |
| 4165 | 4144 | 4164 | **UUUUAUGGUGACCUUGAGGUCG** | 186 | **ACCUCAAGGUCACCAUAAAA** | 351 | 40.67 | 1.18 | 77.13 | 1.73 |
| 4166 | 4145 | 4165 | **UUUUUAUGGUGACCUUGAGGUC** | 187 | **CCUCAAGGUCACCAUAAAAA** | 352 | 47.63 | 1.19 | 68.30 | 2.77 |
| 4167 | 4146 | 4166 | **UGUUUUAUGGUGACCUUGAGGU** | 188 | **CUCAAGGUCACCAUAAAACA** | 353 | 24.53 | 1.08 | 64.43 | 1.15 |
| 4182 | 4161 | 4181 | **UCUGUUUCCGGUGCUGGUUUUA** | 189 | **AAACCAGCACCGGAAACAGA** | 354 | 54.43 | 2.88 | 71.10 | 2.08 |
| 4210 | 4189 | 4209 | UGUGUUCUUGGCAUCCUGAGGC | 190 | CUCAGGAUGCCAAGAACACA | 355 | 49.77 | 4.49 | 91.77 | 3.83 |
| 4216 | 4195 | 4215 | **UAUCAUAGUGUUCUUGGCAUCC** | 191 | **AUGCCAAGAACACUAUGAUA** | 356 | 34.57 | 1.40 | 77.60 | 1.12 |
| 4220 | 4199 | 4219 | UAAGGAUCAUAGUGUUCUUGGC | 192 | CAAGAACACUAUGAUCCUUA | 357 | 47.37 | 1.37 | 98.47 | 7.55 |
| 4221 | 4200 | 4220 | UCAAGGAUCAUAGUGUUCUUGG | 193 | AAGAACACUAUGAUCCUUGA | 358 | 36.97 | 1.01 | 82.13 | 1.21 |
| 4266 | 4245 | 4265 | **UUAGACAUAGUGGCAUCCUGGU** | 194 | **CAGGAUGCCACUAUGUCUAA** | 359 | 29.73 | 0.71 | 62.90 | 5.76 |
| 4290 | 4269 | 4289 | **UCAGUCAUCAUGGAUAUGUCCA** | 195 | **GACAUAUCCAUGAUGACUGA** | 360 | 31.27 | 1.09 | 67.47 | 0.64 |
| 4357 | 4336 | 4356 | **UUACUUGGAGAUGUAUCUGUCA** | 196 | **ACAGAUACAUCUCCAAGUAA** | 361 | 27.50 | 1.04 | 61.20 | 1.10 |
| 4358 | 4337 | 4357 | **UAUACUUGGAGAUGUAUCUGUC** | 197 | **CAGAUACAUCUCCAAGUAUA** | 362 | 40.87 | 1.73 | 74.10 | 1.40 |
| 4359 | 4338 | 4358 | **UCAUACUUGGAGAUGUAUCUGU** | 198 | **AGAUACAUCUCCAAGUAUGA** | 363 | 24.00 | 0.26 | 55.27 | 2.44 |
| 4361 | 4340 | 4360 | UCUCAUACUUGGAGAUGUAUCU | 199 | AUACAUCUCCAAGUAUGAGA | 364 | 73.27 | 1.22 | 90.03 | 1.69 |
| 4370 | 4349 | 4369 | **UUUUGUCCAGCUCAUACUUGGA** | 200 | **CAAGUAUGAGCUGGACAAAA** | 365 | 38.40 | 1.79 | 78.87 | 3.49 |
| 4371 | 4350 | 4370 | **UCUUUGUCCAGCUCAUACUUGG** | 201 | **AAGUAUGAGCUGGACAAAGA** | 366 | 28.67 | 1.30 | 69.70 | 1.01 |
| 4384 | 4363 | 4383 | UCUAUCGGAGAAGGCUUUGUCC | 202 | ACAAAGCCUUCUCCGAUAGA | 367 | 60.77 | 4.24 | 82.67 | 5.01 |
| 4387 | 4366 | 4386 | **UUUCCUAUCGGAGAAGGCUUUG** | 203 | **AAGCCUUCUCCGAUAGGAAA** | 368 | 29.10 | 1.22 | 73.10 | 4.76 |
| 4390 | 4369 | 4389 | **UGUGUUCCUAUCGGAGAAGGCU** | 204 | **CCUUCUCCGAUAGGAACACA** | 369 | 45.10 | 4.04 | 75.57 | 4.62 |
| 4399 | 4378 | 4398 | **UAUGAUGAGGGUGUUCCUAUCG** | 205 | **AUAGGAACACCCUCAUCAUA** | 370 | 40.10 | 0.95 | 76.13 | 2.44 |
| 4400 | 4379 | 4399 | **UGAUGAUGAGGGUGUUCCUAUC** | 206 | **UAGGAACACCCUCAUCAUCA** | 371 | 36.17 | 1.52 | 70.33 | 0.66 |
| 4403 | 4382 | 4402 | **UGUAGAUGAUGAGGGUGUUCCU** | 207 | **GAACACCCUCAUCAUCUACA** | 372 | 46.47 | 2.94 | 71.73 | 1.66 |
| 4412 | 4391 | 4411 | **UCUUGUCCAGGUAGAUGAUGAG** | 208 | **CAUCAUCUACCUGGACAAGA** | 373 | 60.60 | 3.65 | 66.10 | 2.74 |
| 4415 | 4394 | 4414 | UGACCUUGUCCAGGUAGAUGAU | 209 | CAUCUACCUGGACAAGGUCA | 374 | 79.67 | 2.09 | 86.63 | 0.18 |

TABLE 1-continued

Exemplary Sequences of the Disclosure and Their Potency

| Guide Strand position 3' | Start | End | Guide strand sequence (5'-3') | SEQ ID | Passenger strand sequence (5'-3') | SEQ ID | % of gene remaining at 0.1 nM Mean | % of gene remaining at 0.1 nM SEM | % of gene remaining at 0.1 nM Mean | % of gene remaining at 0.1 nM SEM |
|---|---|---|---|---|---|---|---|---|---|---|
| 4427 | 4406 | 4426 | **UCUCAGAGUGUGAGACCUUGUC** | 210 | **CAAGGUCUCACACUCUGAGA** | 375 | 38.53 | 1.21 | 68.27 | 1.68 |
| 4431 | 4410 | 4430 | **UCAUCCUCAGAGUGUGAGACCU** | 211 | **GUCUCACACUCUGAGGAUGA** | 376 | 45.30 | 0.82 | 64.40 | 1.97 |
| 4511 | 4490 | 4510 | **UGUAAUAGGCGUAGACCUUGAC** | 212 | **CAAGGUCUACGCCUAUUACA** | 377 | 34.43 | 2.47 | 62.30 | 3.15 |
| 4514 | 4493 | 4513 | **UGUUGUAAUAGGCGUAGACCUU** | 213 | **GGUCUACGCCUAUUACAACA** | 378 | 35.07 | 0.69 | 70.70 | 4.64 |
| 4515 | 4494 | 4514 | **UGGUUGUAAUAGGCGUAGACCU** | 214 | **GUCUACGCCUAUUACAACCA** | 379 | 61.70 | 2.81 | 79.80 | 5.88 |
| 4572 | 4551 | 4571 | **UUGUUCAGCUUUCCAUCCUCCU** | 215 | **GAGGAUGGAAAGCUGAACAA** | 380 | 38.57 | 1.92 | 70.50 | 5.45 |
| 4619 | 4598 | 4618 | **UGAAGCAAUUCUCCUCAGCACA** | 216 | **UGCUGAGGAGAAUUGCUUCA** | 381 | 29.10 | 1.88 | 48.40 | 0.93 |
| 4625 | 4604 | 4624 | **UUUGUAUGAAGCAAUUCUCCUC** | 217 | **GGAGAAUUGCUUCAUACAAA** | 382 | 21.97 | 0.90 | 54.67 | 0.95 |
| 4627 | 4606 | 4626 | UUUUUGUAUGAAGCAAUUCUCC | 218 | AGAAUUGCUUCAUACAAAAA | 383 | 77.47 | 6.74 | 103.60 | 3.09 |
| 4696 | 4675 | 4695 | **UUACACAUAGUCCACUCCUGGC** | 219 | **CAGGAGUGGACUAUGUGUAA** | 384 | 30.20 | 3.96 | 67.07 | 2.78 |
| 4697 | 4676 | 4696 | **UGUACACAUAGUCCACUCCUGG** | 220 | **AGGAGUGGACUAUGUGUACA** | 385 | 29.53 | 2.57 | 67.93 | 5.89 |
| 4702 | 4681 | 4701 | UGUCUUGUACACAUAGUCCACU | 221 | UGGACUAUGUGUACAAGACA | 386 | 44.27 | 3.33 | 89.13 | 3.18 |
| 4745 | 4724 | 4744 | UGUACUCGUCAAAGUCAUUGGA | 222 | CAAUGACUUUGACGAGUACA | 387 | 57.53 | 3.74 | 86.30 | 0.83 |
| 4750 | 4729 | 4749 | **UAUGAUGUACUCGUCAAAGUCA** | 223 | **ACUUUGACGAGUACAUCAUA** | 388 | 39.13 | 1.26 | 74.20 | 1.68 |
| 4787 | 4766 | 4786 | UCUCAUCCGAGCCUGACUUGAU | 224 | CAAGUCAGGCUCGGAUGAGA | 389 | 40.07 | 0.27 | 83.10 | 7.76 |
| 4800 | 4779 | 4799 | UGUCCAACCUGCACCUCAUCCG | 225 | GAUGAGGUGCAGGUUGGACA | 390 | 55.47 | 5.00 | 89.00 | 1.80 |
| 5055 | 5034 | 5054 | **UGUCAGUUGGGGCACCCAAAGA** | 226 | **UUUGGGUGCCCCAACUGACA** | 391 | 21.67 | 0.94 | 58.47 | 2.84 |
| 773 | 752 | 772 | UCUCCACUAUGACCUCGAAACU | 392 | UUUCGAGGUCAUAGUGGAGA | 418 | 80.67 | 0.95 | 86.23 | 2.68 |
| 649 | 628 | 648 | UGGAAUGUCCCAAGACAAGGGC | 393 | CCUUGUCUUGGGACAUUCCA | 419 | 82.03 | 2.36 | 86.43 | 5.04 |
| 2444 | 2423 | 2443 | UAAAUAUAUUCAUGAGCUUCGU | 394 | GAAGCUCAUGAAUAUAUUUA | 420 | 83.27 | 1.83 | 83.27 | 1.83 |
| 4226 | 4205 | 4225 | UGAUCUCAAGGAUCAUAGUGUU | 395 | CACUAUGAUCCUUGAGAUCA | 421 | 84.33 | 1.78 | 119.93 | 3.13 |
| 4628 | 4607 | 4627 | UCUUUUGUAUGAAGCAAUUCUC | 396 | GAAUUGCUUCAUACAAAAGA | 422 | 85.80 | 3.79 | 86.10 | 7.59 |
| 3400 | 3379 | 3399 | UUUCUGCUUCUCCAGGAUCAGC | 397 | UGAUCCUGGAGAAGCAGAAA | 423 | 86.57 | 1.29 | 113.47 | 1.69 |
| 3398 | 3377 | 3397 | UCUGCUUCUCCAGGAUCAGCCA | 398 | GCUGAUCCUGGAGAAGCAGA | 424 | 88.33 | 1.09 | 109.80 | 5.66 |
| 4760 | 4739 | 4759 | UCUCAAUGGCCAUGAUGUACUC | 399 | GUACAUCAUGGCCAUUGAGA | 425 | 88.40 | 3.38 | 92.13 | 1.48 |
| 2253 | 2232 | 2252 | UUGUAGUUGCAGCAGUCCAGGA | 400 | CUGGACUGCUGCAACUACAA | 426 | 89.23 | 0.91 | 89.23 | 0.91 |
| 3894 | 3873 | 3893 | UCUUGGAACACCAUGAAGGUGG | 401 | ACCUUCAUGGUGUUCCAAGA | 427 | 90.57 | 8.72 | 108.50 | 2.15 |
| 2321 | 2300 | 2320 | UCUCAUCCAGGUUACUCCUGGC | 402 | CAGGAGUAACCUGGAUGAGA | 428 | 91.20 | 2.83 | 91.20 | 2.83 |
| 2324 | 2303 | 2323 | UGUCCUCAUCCAGGUUACUCCU | 403 | GAGUAACCUGGAUGAGGACA | 429 | 91.27 | 2.30 | 91.27 | 2.30 |
| 4897 | 4876 | 4896 | UCAGAAAUCGGAGGAGAGACCC | 404 | GUCUCUCCUCCGAUUUCUGA | 430 | 92.13 | 3.24 | 94.30 | 4.85 |
| 4715 | 4694 | 4714 | UCUUGACCAGUCGGGUCUUGUA | 405 | CAAGACCCGACUGGUCAAGA | 431 | 93.87 | 4.64 | 92.80 | 0.90 |
| 3614 | 3593 | 3613 | UCUGUAGGUUCAUGUAGUUGGC | 406 | CAACUACAUGAACCUACAGA | 432 | 94.37 | 2.01 | 104.60 | 2.98 |
| 3320 | 3299 | 3319 | UGAAGACCUUGACCACGUAGGC | 407 | CUACGUGGUCAAGGUCUUCA | 433 | 94.47 | 2.91 | 105.63 | 3.94 |
| 2177 | 2156 | 2176 | UGAACCUCAUGGGGUUCUCCCG | 408 | GGAGAACCCCAUGAGGUUCA | 434 | 94.67 | 2.29 | 94.67 | 2.29 |
| 1820 | 1799 | 1819 | UCUCUAUCUUCAGGGUCAUCUG | 409 | GAUGACCCUGAAGAUAGAGA | 435 | 95.23 | 1.07 | 95.23 | 1.07 |

TABLE 1-continued

Exemplary Sequences of the Disclosure and Their Potency

| Guide Strand position 3' | Start | End | Guide strand sequence (5'-3') | SEQ ID | Passenger strand sequence (5'-3') | SEQ ID | % of gene remaining at 0.1 nM Mean | % of gene remaining at 0.1 nM SEM | % of gene remaining at 0.1 nM Mean | % of gene remaining at 0.1 nM SEM |
|---|---|---|---|---|---|---|---|---|---|---|
| 2178 | 2157 | 2177 | UAGAACCUCAUGGGGUUCUCCC | 410 | GAGAACCCCAUGAGGUUCUA | 436 | 95.53 | 0.92 | 95.53 | 0.92 |
| 524 | 503 | 523 | UGUGGUUGACGGUGAAGAUCCG | 411 | GAUCUUCACCGUCAACCACA | 437 | 96.80 | 18.43 | 94.30 | 5.82 |
| 2369 | 2348 | 2368 | UCUCUGGGAACUCACUUCGGGA | 412 | CCGAAGUGAGUUCCCAGAGA | 438 | 98.23 | 1.72 | 98.23 | 1.72 |
| 527 | 506 | 526 | UCUUGUGGUUGACGGUGAAGAU | 413 | CUUCACCGUCAACCACAAGA | 439 | 98.60 | 9.60 | 88.80 | 6.01 |
| 4223 | 4202 | 4222 | UCUCAAGGAUCAUAGUGUUCUU | 414 | GAACACUAUGAUCCUUGAGA | 440 | 98.63 | 2.02 | 103.90 | 0.95 |
| 3893 | 3872 | 3892 | UUUGGAACACCAUGAAGGUGGC | 415 | CACCUUCAUGGUGUUCCAAA | 441 | 102.90 | 3.52 | 107.90 | 3.26 |
| 3401 | 3380 | 3400 | UCUUCUGCUUCUCCAGGAUCAG | 416 | GAUCCUGGAGAAGCAGAAGA | 442 | 107.50 | 3.90 | 112.07 | 2.86 |
| 731 | 710 | 730 | UCUCAAACUCAGUGGAGAAGAC | 417 | CUUCUCCACUGAGUUUGAGA | 443 | 111.27 | 8.88 | 97.53 | 3.24 |

Figure 3:
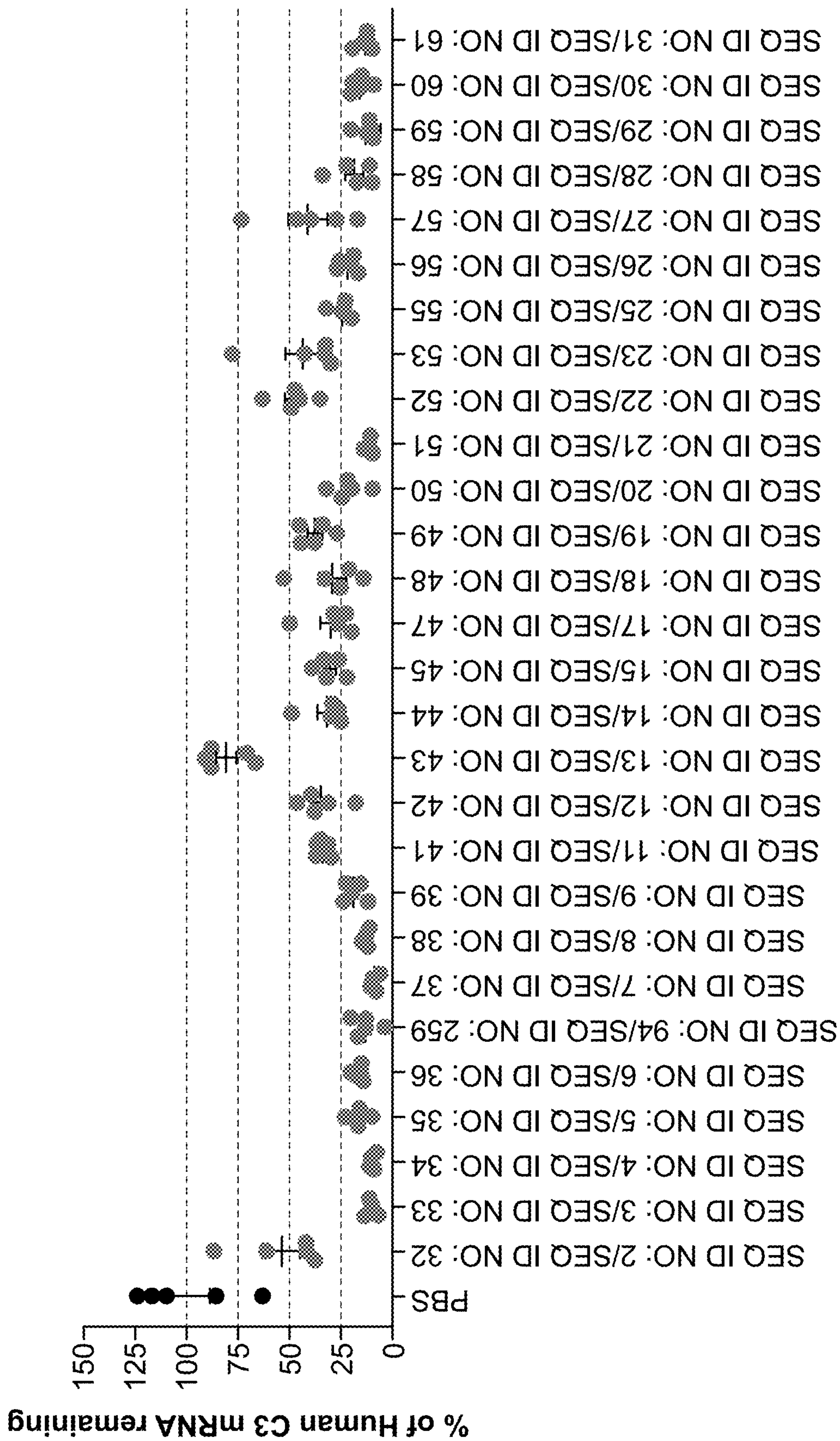
FIG. 3 is a graph showing the in vivo potency of a subset of compounds listed in Table 2 in mouse HDI liver at 1 mg/kg at day 4 post-dosing. Data is presented as % of human C3 mRNA remaining relative to PBS when normalized to NeoR mRNA levels (Mean, +/−SEM).

*Exemplary results of in vivo C3 dose response in HDI mouse liver are shown in FIG. 3

Figure 4:
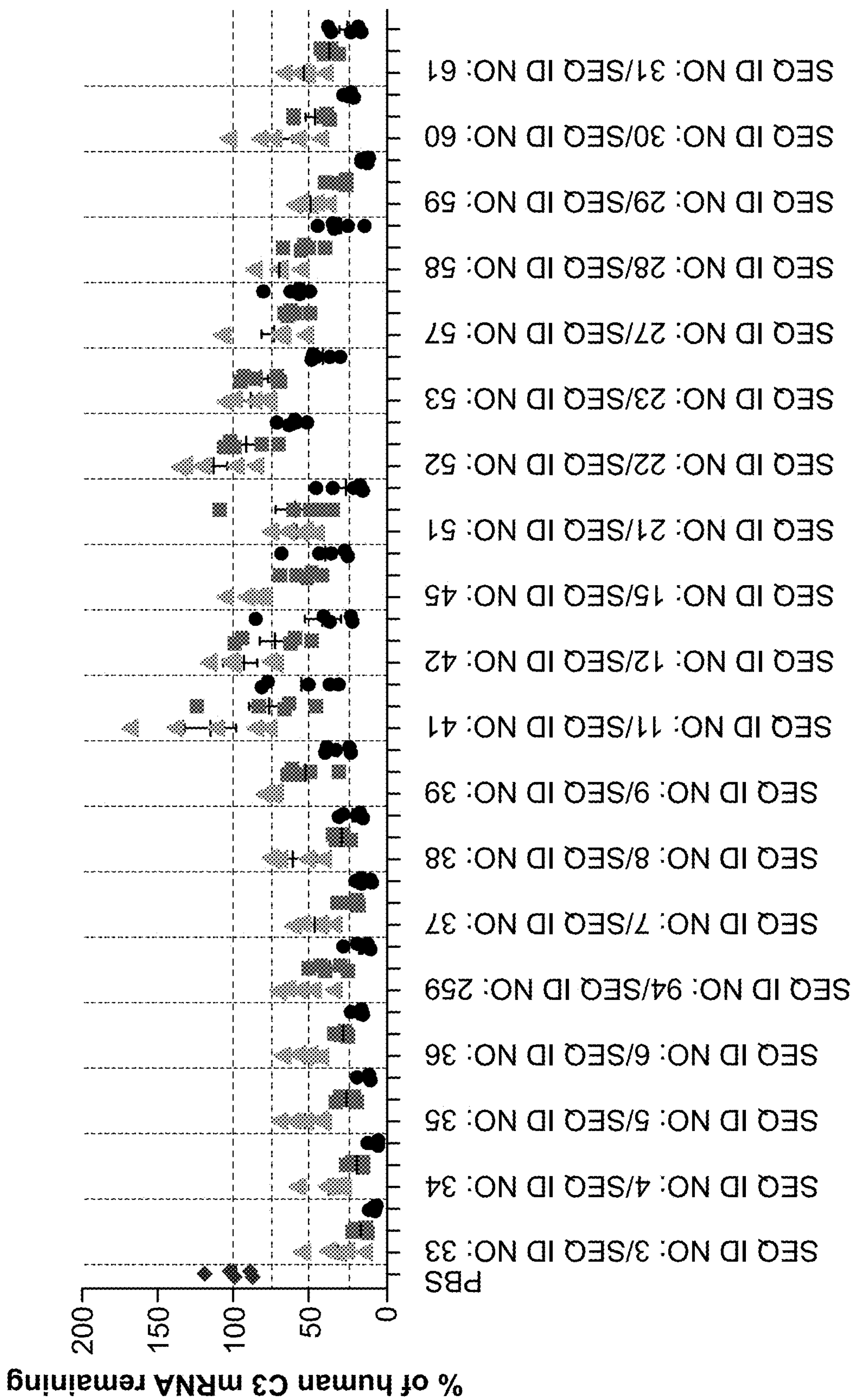
FIG. 4 is a graph showing the in vivo dose response of a subset of compounds listed in Table 2 in mouse HDI liver at 0.25, 0.5, or 1 mg/kg at day 4 post-dosing. Data is presented as % of human C3 mRNA remaining relative to PBS when normalized to NeoR mRNA levels (Mean, +/−SEM).

^Exemplary results of in vivo C3 dose response in HDI mouse liver are shown in FIG. 4

TABLE 3

Exemplary Modified Sequences of the Disclosure

| | | |
|---|---|---|
| G (5'-3') | [mUs][fUs][fA][mG][fU][mA][fG][mA][mA][fU][mU][mU][mC][fU][mC][fU][mG][mU][mA][mGs][mGs][mC] | SEQ ID NO: 451 |
| P (5'-3') | [mCs][mUs][mA][mC][mA][fG][mA][fG][fA][fA][fA][mU][mU][mC][mU][mA][mC][mUs][mAs][mA][G1b][G1b][G1b] | SEQ ID NO: 444 |
| G (5'-3') | [mUs][fGs][fU][mA][fG][mU][fA][mG][mA][fA][mU][mU][mU][fC][mU][fC][mU][mG][mU][[mAs][mGs][mG] | SEQ ID NO: 452 |
| P (5'-3') | [mUs][mAs][mC][mA][mG][fA][mG][fA][fA][fA][fU][mU][mC][mU][mA][mC][mU][mAs][mCs][mA][G1b][G1b][G1b] | SEQ ID NO: 445 |
| G (5'-3') | [mUs][fAs][fU][mG][fU][mA][fG][mU][mA][fG][mA][mA][mU][fU][mU][fC][mU][mC][mU][mGs][mUs][mA] | SEQ ID NO: 453 |
| P (5'-3') | [mCs][mAs][mG][mA][mG][fA][mA][fA][fU][fU][fC][mU][mA][mC][mU][mA][mC][mAs][mUs][mA][G1b][G1b][G1b] | SEQ ID NO: 446 |
| G (5'-3') | [mUs][fAs][fU][mA][fG][mA][fU][mG][mU][fA][mG][mU][mA][fG][mA][fA][mU][mU][mU][mCs][mUs][mC] | SEQ ID NO: 454 |
| P (5'-3') | [mGs][mAs][mA][mA][mU][fU][mC][fU][fA][fC][fU][mA][mC][mA][mU][mC][mU][mAs][mUs][mA][G1b][G1b][G1b] | SEQ ID NO: 447 |
| G (5'-3') | [mUs][fAs][fU][mG][fA][mA][fG][mC][mA][fA][mU][mU][mC][fU][mC][fC][mU][mC][mA][mGs][mCs][mA] | SEQ ID NO: 455 |
| P (5'-3') | [mCs][mUs][mG][mA][mG][fG][mA][fG][fA][fA][fU][mU][mG][mC][mU][mU][mC][mAs][mUs][mA][G1b][G1b][G1b] | SEQ ID NO: 448 |
| G (5'-3') | [mUs][fUs][fU][mU][fG][mU][fA][mU][mG][fA][mA][mG][mC][fA][mA][fU][mU][mC][mU][mCs][mCs][mU] | SEQ ID NO: 456 |
| P (5'-3') | [mGs][mAs][mG][mA][mA][fU][mU][fG][fC][fU][fU][mC][mA][mU][mA][mC][mA][mAs][mAs][mA][G1b][G1b][G1b] | SEQ ID NO: 449 |
| G (5'-3') | [MeEPmUs][fUs][fA][mG][fU][mA][fG][mA][mA][fU][mU][mU][mC][fU][mC][fU][mG][mU][mA][mGs][mGs][mC] | SEQ ID NO: 457 |
| P (5'-3') | [mCs][mUs][mA][mC][mA][fG][mA][fG][fA][fA][fA][mU][mU][mC][mU][mA][mC][mUs][mAs][mA][G1b][G1b][G1b] | SEQ ID NO: 444 |
| G (5'-3') | [MeEPmUs][fGs][fU][mA][fG][mU][fA][mG][mA][fA][mU][mU][mU][fC][mU][fC][mU][mG][mU][mAs][mGs][mG] | SEQ ID NO: 458 |
| P (5'-3') | [mUs][mAs][mC][mA][mG][fA][mG][fA][fA][fA][fU][mU][mC][mU][mA][mC][mU][mAs][mCs][mA][G1b][G1b][G1b] | SEQ ID NO: 445 |

TABLE 3-continued

| Exemplary Modified Sequences of the Disclosure | | |
|---|---|---|
| G (5'-3') | [MeEPmUs][fAs][fU][mG][fU][mA][fG][mU][mA][fG][mA][mA][mU][fU][mU][fC][mU][mC][mU][mGs][mUs][mA] | SEQ ID NO: 459 |
| P (5'-3') | [mCs][mAs][mG][mA][mG][fA][mA][fA][fU][fU][fC][mU][mA][mC][mU][mA][mC][mAs][mUs][mA][G1b][G1b][G1b] | SEQ ID NO: 446 |

G: guide strand, P: passenger strand

"m" indicates 2'-O-methyl modification, "f" indicates a 2'-F modification, "EPmU" is a phosphate mimic linked to a 5'-terminal uracil (shown below); "MeEPmU" is a mono methyl protected phosphate mimic linked to a 5'-terminal uracil (shown below), "s" is a phosphorothioate internucleotide linkage, and "G1b" is a GalNAc G1b moiety (shown below).

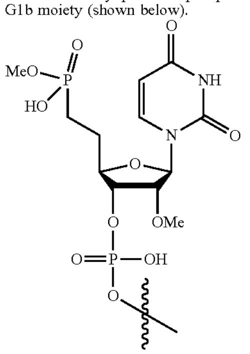

(5′-MeEPmU)

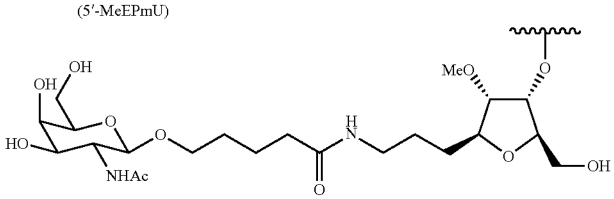

(GalNAc G1b)

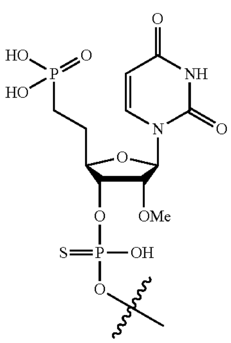

(5′-EPmUs)

EXAMPLES

Example 1: Design and Testing of siRNA Compounds Against Human Complement C3 mRNA Compound Design A set of 221 siRNAs compounds against human complement C3 transcript (Accession No: NM_000064.4) were designed (see Table 2).

Oligonucleotide Synthesis

Oligonucleotides were prepared by solid-phase synthesis according to standard protocols. Briefly, oligonucleotide synthesis was conducted on a solid support to incorporate each nucleoside phosphoramidites from 3'-end to 5'-end to prepare oligo single strands. ETT or BTT was used as an activator for the coupling reaction. Iodine in water/pyridine/THF was used to oxidize phosphite-triester (P(III)) to afford phosphate backbones and DDTT was used for the preparation of phosphorothioate linkages. Aqueous ammonium was used to cleave oligos from solid support and to remove protecting groups globally. The oligonucleotide crude was then concentrated by Genevac and purified by AEX-HPLC. The pure fractions were combined and concentrated, and their purity was analyzed by LC-MS. The oligonucleotides were then dialyzed against water using Midi Trap G-25 column, concentrated, and their OD amounts were measured.

To prepare siRNA duplexes, the sense and antisense strands were annealed at 95° C. for 10 min, based on equal molar amounts, and cooled down to room temperature. The duplex purity was determined by AEX-HPLC, and the solutions were lyophilized to afford the desired siRNA duplex powder.

In Vitro Screening

The compounds were diluted into the desired concentration with PBS. The diluted compounds were then transfected into the cultured Huh-7 cells with Lipofectamine RNAiMAX (Invitrogen-13778-150) reagents on Day 0. Each compound was tested at four concentrations of 0.01 nM and 0.1 nM. At 24 hours post transfection on Day 1, mRNA was extracted from the transfected cells using RNeasy 96 kit (Qiagen-74182).

Figure 1:
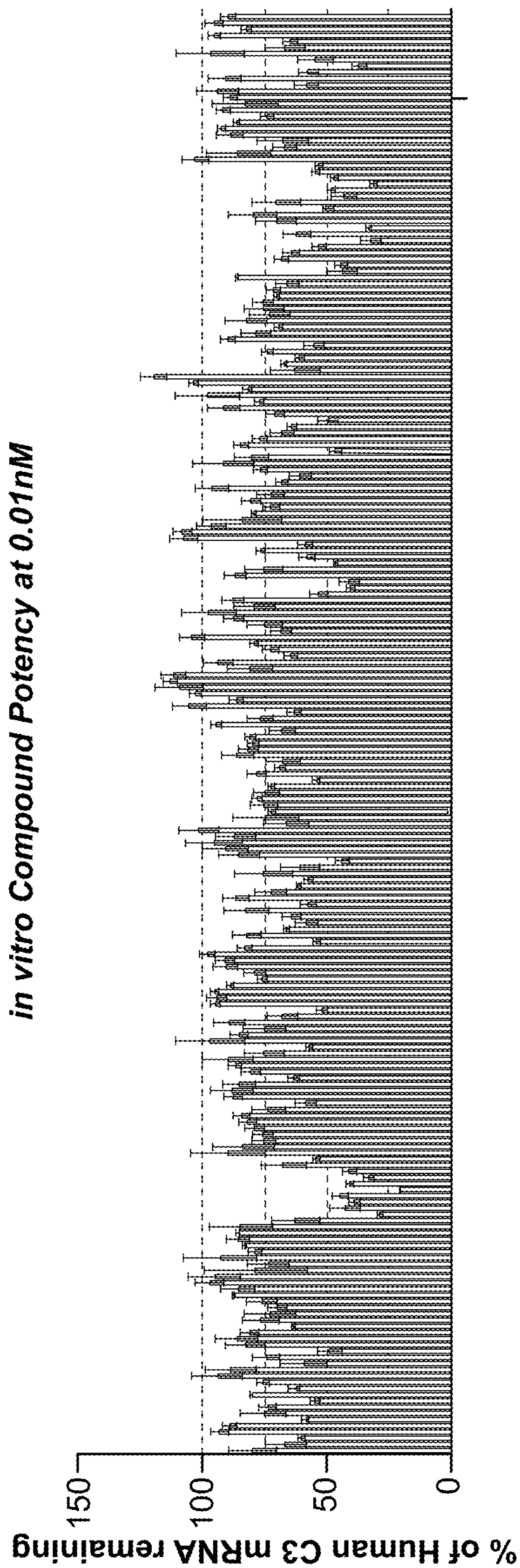
FIG. 1 is a graph showing the efficacy of siRNA compounds listed in Table 2, in silencing human complement C3 in cultured Huh-7 cells. The compounds were transfected into cells at 0.01 nM concentration. Data is presented as % of human C3 mRNA remaining relative to mock transfection when normalized to Gapdh mRNA levels (Mean, +/−SEM). Each bar represents a single compound tested.
Figure 2:
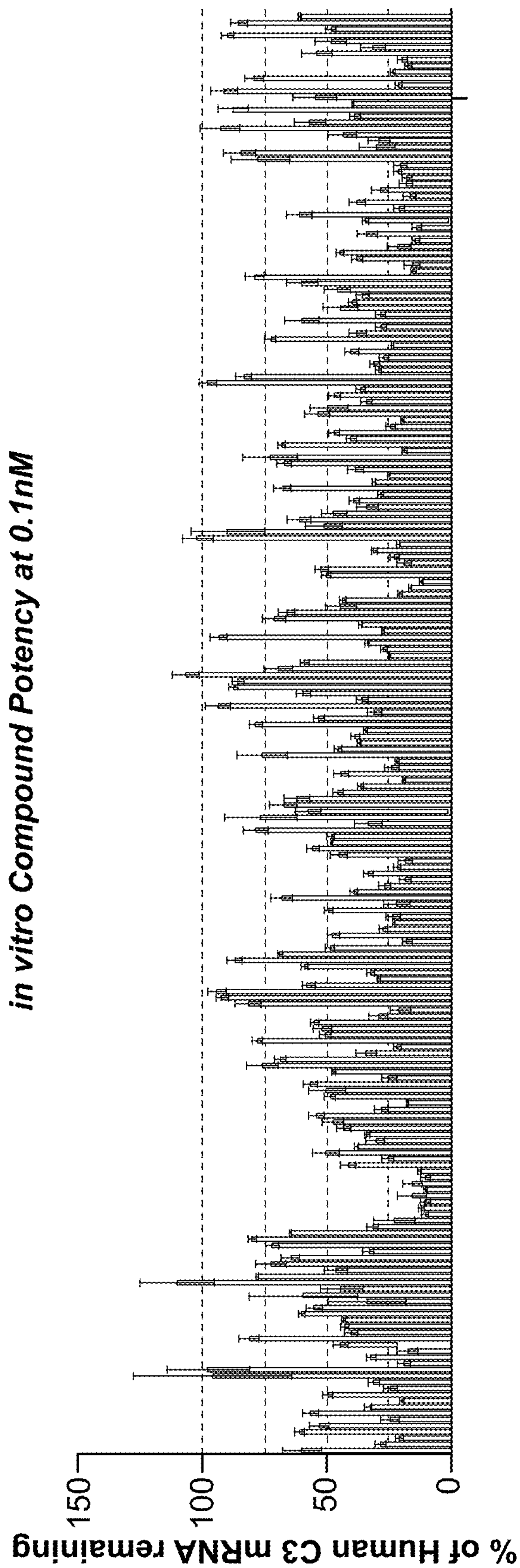
FIG. 2 is a graph showing the efficacy of siRNA compounds listed in Table 2, in silencing human complement C3 in cultured Huh-7 cells. The compounds were transfected into cells at 0.1 nM concentration. Data is presented as % of human C3 mRNA remaining relative to mock transfection when normalized to Gapdh mRNA levels (Mean, +/−SEM). Each bar represents a single compound tested.

The percentage of human C3 mRNA remaining in cells relative to mock transfection when normalized to Gapdh mRNA levels, was determined for each compound at a concentration of either 0.01 nM and 0.1 nM. The results identified several compounds that were able to reduce the level of human C3 mRNA in transfected cells by 20% to 50% or more than 50% at the defined concentrations as described in Table 2 and FIG. 1 and FIG. 2). Also, several compounds from shown in bold in Table 2 were able to reduce the level of human C3 mRNA in transfected cells by between 20% to 50% or at least 50% at 0.01 nM and 0.1 nM (see Table 2, and FIG. 1 and FIG. 2).

In Vivo HDI Screening

A subset of compounds with GalNAc conjugations from Table 2 were formulated in 1×PBS dosed on day 1 through subcutaneous dosing to BALB/c female animals (6~8 weeks old). Animals then received 10 μg of pcDNA3.1-hsC3 plasmids on day 4. Liver biopsies were taken on day 5 for mRNA remaining analysis through RT-qPCR.

For dose response study, 6-8 weeks old female BALB/c mice were dosed subcutaneously at 0.25 mg/kg (grey triangles), 0.5 mg/kg (grey squares) or 1 mg/kg (black circles) (FIG. 4). The control animals were dosed with PBS. Animals were sacrificed 4 days post-dose and liver samples were collected for RNA extraction and human C3 mRNA expression analysis by RT-qPCR. The results of the experiments are shown in FIG. 3 and FIG. 4. The tested compounds were able to reduce the level of human C3 mRNA.

In Vivo Potency and Duration Evaluation in *Macaca fascicularis*

To determine C3 knockdown in non-human primates, a nonterminal study was conducted in cynomolgus macaques. A liver biopsy was taken from cyno monkeys in the study to determine the baseline mRNA expression level one week before dosing (Day −7). Animals were dosed with a single dose of 3 mg/kg subcutaneously a week after a biopsy (Day 0). A biopsy of the liver was taken at 14, 28, 56, 84 and 112 days post dosing. Serum samples were collected 7, 14, 21, 28, 35, 42, 56, 84 and 112 days post dosing. Liver samples were used for mRNA remaining analysis by RT-qPCR and blood samples were used for serum C3 protein analysis by ELISA.

RT-qPCR

Liver mRNA samples were prepared with RNeasy Plus mini kit (Qiagen, 74104). mRNAs were reverse transcribed into cDNAs using High-Capacity cDNA Reverse transcription kits with RNase Inhibitors (Thermo, 4374967). TaqMan multiplex qPCR assays (Thermo, 4444557) were performed to determine the relative C3 mRNA levels over time.

ELISA

C3 Human ELISA kit (Hycult HK366) was validated for cross reactivity to Cynomolgus monkey. Serum samples were diluted 1:40,000 and ELISA were performed. C3 protein level (μg/ml) was calculated based on standard curve and normalized to pre-dose. The results of the experiment are shown in FIGS. 5A and 5B. As shown in FIG. 5A by Day 14, all compounds had reduced liver C3 mRNA by at least 80% relative to pre-dosing levels (Day-7). The maximum reduction in C3 mRNA for all compounds was seen at Day 14 post-dosing, as shown in FIG. 5A. As shown in FIG. 5B by Days, 14, 21 or 28, all compounds had reduced serum C3 protein by at least 60% relative to pre-dosing levels (Day-7). The maximum reduction in serum C3 protein for all compounds was seen at Day 14, 21 or 28 post-dosing, as shown in FIG. 5B.

Ex Vivo Potency Evaluation in Primary Human Hepatocytes (PHH)

A subset of the compounds with GalNAc conjugations (Table 3) were tested through free-uptake in PHH. Results are shown in FIG. 6. The compounds were directly added to the cultured primary hepatocytes at 2 doses (10 nM and 100 nM). 48 hrs later, the cells were harvested for mRNA analysis through RT-qPCR. Data shown as Mean+/−SD. All compounds reduced the % of human C3 mRNA by at least 40% and at least 60% at 10 nM and 100 nM doses, respectively.

Additional embodiments of the disclosure include the following:

Embodiment 1. An isolated oligonucleotide comprising a sense strand and an antisense strand, wherein:
the sense strand comprises a nucleotide sequence that is substantially identical to a region comprising 19-25 nucleotides between any one of the nucleotide positions selected from:
a) 588 to 608;
b) 772 to 801;
c) 1281 to 1301;
d) 1797 to 1817;
e) 2424 to 2444;
f) 2533 to 2585;
g) 2862 to 2882;
h) 3778 to 3836;
i) 4123 to 4169; and
j) 4402 to 4625,
from the 5' end of a human complement C3 mRNA sequence according to SEQ ID NO: 1,
and the antisense strand is substantially complementary to the sense strand such that the sense strand and the antisense strand together form a double stranded region.

Embodiment 2. The isolated oligonucleotide of embodiment 1, wherein the sense strand comprises a nucleotide sequence that is at least 70%, at least 80%, at least 90%, at least 95%, or at least 99% identical to a region comprising 19-25 nucleotides between any one of the nucleotide positions selected from:
a) 588 to 608;
b) 772 to 801;
c) 1281 to 1301;
d) 1797 to 1817;
e) 2424 to 2444;
f) 2533 to 2585;
g) 2862 to 2882;
h) 3778 to 3836;
i) 4123 to 4169; and
j) 4402 to 4625,
from the 5' end of a human complement C3 mRNA sequence according to SEQ ID NO: 1.

Embodiment 3. The isolated oligonucleotide of embodiment 1, wherein the sense strand comprises a nucleotide sequence that is identical to a region comprising 19-25 nucleotides between any one of the nucleotide positions selected from:
a) 588 to 608;
b) 772 to 801;
c) 1281 to 1301;
d) 1797 to 1817;
e) 2424 to 2444;

f) 2533 to 2585;
g) 2862 to 2882;
h) 3778 to 3836;
i) 4123 to 4169; and
j) 4402 to 4625, from the 5' end of a human complement C3 mRNA sequence according to SEQ ID NO: 1.

Embodiment 4. The isolated oligonucleotide of any one of embodiments 1-3, wherein the sense strand comprises a nucleotide sequence that is substantially identical to a region between any one of the nucleotide positions selected from:
a) 1281 to 1301;
b) 1797 to 1817;
c) 2862 to 2882;
d) 4402 to 4424; and
e) 4520 to 4540, from the 5' end of a human complement C3 mRNA sequence according to SEQ ID NO: 1.

Embodiment 5. The isolated oligonucleotide of embodiment 4, wherein the sense strand comprises a nucleotide sequence that is at least 70%, at least 80%, at least 90%, at least 95%, or at least 99% identical to a region between any one of the nucleotide positions selected from:
a) 1281 to 1301;
b) 1797 to 1817;
c) 2862 to 2882;
d) 4402 to 4424; and
e) 4520 to 4540, from the 5' end of a human complement C3 mRNA sequence according to SEQ ID NO: 1.

Embodiment 6. The isolated oligonucleotide of embodiment 4, wherein the sense strand comprises a nucleotide sequence that is identical to a region between any one of the nucleotide positions selected from:
a) 1281 to 1301;
b) 1797 to 1817;
c) 2862 to 2882;
d) 4402 to 4424; and
e) 4520 to 4540, from the 5' end of a human complement C3 mRNA sequence according to SEQ ID NO: 1.

Embodiment 7. The isolated oligonucleotide of any one of embodiments 1-3, wherein the sense strand comprises a nucleotide sequence that is substantially identical to a region comprising the sequence between any one of the nucleotide positions selected from:
a) 772 to 801;
b) 2424 to 2444;
c) 3784 to 3805;
d) 4123 to 4169;
e) 4438 to 4509; and
f) 4558 to 4621, from the 5' end of a human complement C3 mRNA sequence according to SEQ ID NO: 1.

Embodiment 8. The isolated oligonucleotide of embodiment 7, wherein the sense strand comprises a nucleotide sequence that is at least 70%, at least 80%, at least 90%, at least 95%, or at least 99% identical to a region comprising the sequence between any one of the nucleotide positions selected from:
a) 772 to 801;
b) 2424 to 2444;
c) 3784 to 3805;
d) 4123 to 4169;
e) 4438 to 4509; and
f) 4558 to 4621, from the 5' end of a human complement C3 mRNA sequence according to SEQ ID NO: 1.

Embodiment 9. The isolated oligonucleotide of embodiment 7, wherein the sense strand comprises a nucleotide sequence that is identical to a region comprising the sequence between any one of the nucleotide positions selected from:
a) 772 to 801;
b) 2424 to 2444;
c) 3784 to 3805;
d) 4123 to 4169;
e) 4438 to 4509; and
f) 4558 to 4621, from the 5' end of a human complement C3 mRNA sequence according to SEQ ID NO: 1.

Embodiment 10. The isolated oligonucleotide of any one of embodiments 1-3, wherein the sense strand comprises a sequence that is substantially identical to a region comprising the sequence between any one of the nucleotide positions selected from:
a) 588 to 608;
b) 773 to 800;
c) 2533 to 2585;
d) 3778 to 3836;
e) 4492 to 4512; and
f) 4600 to 4625, from the 5' end of a human complement C3 mRNA sequence according to SEQ ID NO: 1.

Embodiment 11. The isolated oligonucleotide of embodiment 7, wherein the sense strand comprises a sequence that is at least 70%, at least 80%, at least 90%, at least 95%, or at least 99% identical to a region comprising the sequence between any one of the nucleotide positions selected from:
a) 588 to 608;
b) 773 to 800;
c) 2533 to 2585;
d) 3778 to 3836;
e) 4492 to 4512; and
f) 4600 to 4625, from the 5' end of a human complement C3 mRNA sequence according to SEQ ID NO: 1.

Embodiment 12. The isolated oligonucleotide of embodiment 7, wherein the sense strand comprises a sequence that is identical to a region comprising the sequence between any one of the nucleotide positions selected from:
a) 588 to 608;
b) 773 to 800;
c) 2533 to 2585;
d) 3778 to 3836;
e) 4492 to 4512; and
f) 4600 to 4625, from the 5' end of a human complement C3 mRNA sequence according to SEQ ID NO: 1.

Embodiment 13. The isolated oligonucleotide of any one of embodiments 1-12, wherein the isolated oligonucleotide is capable of inducing degradation of the C3 mRNA.

Embodiment 14. The isolated oligonucleotide of any one of embodiments 1-13, wherein the sense strand is a single stranded RNA molecule.

Embodiment 15. The isolated oligonucleotide of any one of embodiments 1-13, wherein the antisense strand is a single stranded RNA molecule.

Embodiment 16. The isolated oligonucleotide of any one of embodiments 1-13, wherein both the sense strand and the antisense strand are single stranded RNA molecules.

Embodiment 17. The isolated oligonucleotide of embodiment 15 or 16, wherein the antisense strand comprises a 3' overhang.

Embodiment 18. The isolated oligonucleotide of embodiment 17, wherein the 3' overhang comprise at least one nucleotide.

Embodiment 19. The isolated oligonucleotide of embodiment 18, wherein the 3' overhang comprise two nucleotides.

Embodiment 20. The isolated oligonucleotide of embodiment 19, wherein the 3' overhang comprises any one of thymidine-thymidine (dTdT), Adenine-Adenine (AA), Cysteine-Cysteine (CC), Guanine-Guanine (GG) or Uracil-Uracil (UU).

Embodiment 21. The isolated oligonucleotide of any one of embodiments 1-20, wherein the sense strand comprises an RNA sequence of at least 20 nucleotides in length.

Embodiment 22. The isolated oligonucleotide of embodiment 21, wherein the sense strand comprises an RNA sequence of 20 nucleotides in length.

Embodiment 23. The isolated oligonucleotide of any one of embodiments 1-22, wherein the antisense strand comprises an RNA sequence of at least 22 nucleotides in length.

Embodiment 24. The isolated oligonucleotide of embodiment 23, wherein the antisense strand comprises an RNA sequence of 22 nucleotides in length.

Embodiment 25. The isolated oligonucleotide of any one of embodiments 1-24, wherein the double stranded region is between 19 and 21 nucleotides in length.

Embodiment 26. The isolated oligonucleotide of embodiment 25, wherein the double stranded region is 20 nucleotides in length.

Embodiment 27. The isolated oligonucleotide of any one of embodiments 1-26, wherein the antisense strand comprises a nucleotide sequence according to any one of: SEQ ID NOs: 2-31

Embodiment 28. The isolated oligonucleotide of any one of embodiments 1-24, wherein the sense strand comprises a nucleotide sequence according to any one of: SEQ ID NOs: 32-61.

Embodiment 29. The isolated oligonucleotide of embodiment 6, wherein the double stranded region comprises:

i) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3');

ii) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3');

iii) an antisense strand of nucleic acid sequence according to SEQ ID NO: 15 (5' UUUUUGUUCAUUCUGAUUCCUU 3'), and a sense strand of nucleic acid sequence according to SEQ ID NO: 45 (5' GGAAUCAGAAUGAACAAAAA 3');

iv) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3');

v) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3'); or vi) an antisense strand of nucleic acid sequence according to SEQ ID NO: 27 (5' UGUAGAACCGGGUACAGCUUUC 3'), and a sense strand of nucleic acid sequence according to SEQ ID NO: 57 (5' AAGCUGUACCCGGUUCUACA 3').

Embodiment 30. The isolated oligonucleotide of embodiment 9, wherein the double stranded region comprises:

i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3');

ii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3');

iii) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3');

iv) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3');

v) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3');

vi) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3');

vii) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3');

viii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3');

ix) an antisense strand of nucleic acid sequence according to SEQ ID NO: 21 (5' UCUGGUUUUAUGGUGACCUUGA 3'), and a sense strand of nucleic acid sequence according to SEQ ID NO: 51 (5' AAGGUCACCAUAAAACCAGA 3');

x) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3');

xi) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3');

xii) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3'); or xiii) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3').

Embodiment 31. The isolated oligonucleotide of embodiment 12, wherein the double stranded region comprises:

i) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3');

ii) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3');

iii) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3');

iv) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3');

v) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3');

vi) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3');

vii) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3');

viii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3');

ix) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3');

x) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3'); or xi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3').

Embodiment 32. The isolated oligonucleotide of any one of embodiments 1-31, wherein the isolated oligonucleotide attenuates expression of the C3 mRNA by at least 50% at a dose of 0.1 nM.

Embodiment 33. The isolated oligonucleotide of embodiment 32, wherein the double stranded region comprises:

i) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3') (87.0);

ii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3') (89.2);

iii) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3') (88.9);

iv) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3') (87.6);

v) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3') (87.6);

vi) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3') (85.8);

vii) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3') (85.1);

viii) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3') (84.2);

ix) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3') (84.0);

x) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3') (89.2);

xi) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3') (83.8);

xii) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3') (83.8);

xiii) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3') (83.0);

xiv) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3') (82.8);

xv) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3') (82.0);

xvi) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3') (82.0);

xvii) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3') (81.9);

xviii) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3') (81.8);

xix) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3') (81.3);

xx) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3') (81.2);

xxi) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3') (81.1);

xxii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3') (80.8);

xxiii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3') (80.8);

xxiv) an antisense strand of nucleic acid sequence according to SEQ ID NO: 15 (5' UUUUUGUUCAUUCUGAUUCCUU 3'), and a sense strand of nucleic acid sequence according to SEQ ID NO: 45 (5' GGAAUCAGAAUGAACAAAAA 3') (80.5);

xxv) an antisense strand of nucleic acid sequence according to SEQ ID NO: 21 (5' UCUGGUUUUAUGGUGACCUUGA 3'), and a sense strand of nucleic acid sequence according to SEQ ID NO: 51 (5' AAGGUCACCAUAAAACCAGA 3') (80.2);

xxvi) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3') (79.2);

xxvii) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3') (78.9);

xxviii) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3') (78.8);

xxix) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3') (78.6); or xxx) an antisense strand of nucleic acid sequence according to SEQ ID NO: 27 (5' UGUAGAACCGGGUACAGCUUUC 3'), and a sense strand of nucleic acid sequence according to SEQ ID NO: 57 (5' AAGCUGUACCCGGUUCUACA 3') (78.4).

Embodiment 34. The isolated oligonucleotide of any one of embodiments 1-31, wherein the isolated oligonucleotide attenuates expression of the C3 mRNA by 20% to 50% at a dose of 0.01 nM.

Embodiment 35. The isolated oligonucleotide of embodiment 34, wherein the double stranded region comprises:

i) an antisense strand of nucleic acid sequence according to SEQ ID NO: 11 (5' UCUAUCUUCAGGGUCAUCUGCU 3'), and a sense strand of nucleic acid sequence according to SEQ ID NO: 41 (5' CAGAUGACCCUGAAGAUAGA 3') (47.9);

ii) an antisense strand of nucleic acid sequence according to SEQ ID NO: 24 (5' UUAUUGGUGAACUUUGAAAGCU 3'), and a sense strand of nucleic acid sequence according to SEQ ID NO: 54 (5' CUUUCAAAGUUCACCAAUAA 3') (46.7);

iii) an antisense strand of nucleic acid sequence according to SEQ ID NO: 31 (5' UUUUGUAUGAAGCAAUUCUCCU 3'), and a sense strand of nucleic acid sequence according to SEQ ID NO: 61 (5' GAGAAUUGCUUCAUACAAAA 3') (46.6);

iv) an antisense strand of nucleic acid sequence according to SEQ ID NO: 16 (5' UAAGUCUUUUAGCUGCAGUAGG 3'), and a sense strand of nucleic acid sequence according to SEQ ID NO: 46 (5' UACUGCAGCUAAAAGACUUA 3') (46.6);

v) an antisense strand of nucleic acid sequence according to SEQ ID NO: 12 (5' UAAAAUAUAUUCAUGAGCUUCG 3'), and a sense strand of nucleic acid sequence according to SEQ ID NO: 42 (5' AAGCUCAUGAAUAUAUUUUA 3') (45.7);

vi) an antisense strand of nucleic acid sequence according to SEQ ID NO: 15 (5' UUUUUGUUCAUUCUGAUUCCUU 3'), and a sense strand of nucleic acid sequence according to SEQ ID NO: 45 (5' GGAAUCAGAAUGAACAAAAA 3') (45.7);

vii) an antisense strand of nucleic acid sequence according to SEQ ID NO: 13 (5' UAUGAAGAAGUCCUGCAUUACU 3'), and a sense strand of nucleic acid sequence according to SEQ ID NO: 43 (5' UAAUGCAGGACUUCUUCAUA 3') (42.4); or viii) an antisense strand of nucleic acid sequence according to SEQ ID NO: 10 (5' UGUGUGUUGAUGCUGAGUUUGG 3'), and a sense strand of nucleic acid sequence according to SEQ ID NO: 40 (5' AAACUCAGCAUCAACACACA 3') (41.5).

Embodiment 36. The isolated oligonucleotide of any one of embodiments 1-31, wherein the isolated oligonucleotide attenuates expression of the C3 mRNA by at least 50% at a dose of 0.01 nM.

Embodiment 37. The isolated oligonucleotide of embodiment 36, wherein the double stranded region comprises:

i) an antisense strand of nucleic acid sequence according to SEQ ID NO: 3 (5' UUAGUAGAAUUUCUCUGUAGGC 3'), and a sense strand of nucleic acid sequence according to SEQ ID NO: 33 (5' CUACAGAGAAAUUCUACUAA 3') (71.3);

ii) an antisense strand of nucleic acid sequence according to SEQ ID NO: 29 (5' UAUGAAGCAAUUCUCCUCAGCA 3'), and a sense strand of nucleic acid sequence according to SEQ ID NO: 59 (5' CUGAGGAGAAUUGCUUCAUA 3') (68.5);

iii) an antisense strand of nucleic acid sequence according to SEQ ID NO: 25 (5' UUAAUAGGCGUAGACCUUGACU 3'), and a sense strand of nucleic acid sequence according to SEQ ID NO: 55 (5' UCAAGGUCUACGCCUAUUAA 3') (67.6);

iv) an antisense strand of nucleic acid sequence according to SEQ ID NO: 9 (5' UUUAUAGAUGUAGUAGAAUUUC 3'), and a sense strand of nucleic acid sequence according to SEQ ID NO: 39 (5' AAUUCUACUACAUCUAUAAA 3') (59.1);

v) an antisense strand of nucleic acid sequence according to SEQ ID NO: 8 (5' UUAUAGAUGUAGUAGAAUUUCU 3'), and a sense strand of nucleic acid sequence according to SEQ ID NO: 38 (5' AAAUUCUACUACAUCUAUAA 3') (66.9);

vi) an antisense strand of nucleic acid sequence according to SEQ ID NO: 26 (5' UUUGUAAUAGGCGUAGACCUUG 3'), and a sense strand of nucleic acid sequence according to SEQ ID NO: 56 (5' AGGUCUACGCCUAUUACAAA 3') (66.8);

vii) an antisense strand of nucleic acid sequence according to SEQ ID NO: 5 (5' UAUGUAGUAGAAUUUCUCUGUA 3'), and a sense strand of nucleic acid sequence according to SEQ ID NO: 35 (5' CAGAGAAAUUCUACUACAUA 3') (60.9);

viii) an antisense strand of nucleic acid sequence according to SEQ ID NO: 17 (5' UAAGUCAAAGUCUUUUAGCUGC 3'), and a sense strand of nucleic acid sequence according to SEQ ID NO: 47 (5' AGCUAAAAGACUUUGACUUA 3') (59.4);

ix) an antisense strand of nucleic acid sequence according to SEQ ID NO: 7 (5' UAUAGAUGUAGUAGAAUUUCUC 3'), and a sense strand of nucleic acid sequence according to SEQ ID NO: 37 (5' GAAAUUCUACUACAUCUAUA 3') (59.1);

x) an antisense strand of nucleic acid sequence according to SEQ ID NO: 18 (5' UAAAGUCAAAGUCUUUUAGCUG 3'), and a sense strand of nucleic acid sequence according to SEQ ID NO: 48 (5' GCUAAAAGACUUUGACUUUA 3') (58.9);

xi) an antisense strand of nucleic acid sequence according to SEQ ID NO: 4 (5' UGUAGUAGAAUUUCUCUGUAGG 3'), and a sense strand of nucleic acid sequence according to SEQ ID NO: 34 (5' UACAGAGAAAUUCUACUACA 3') (57.2);

xii) an antisense strand of nucleic acid sequence according to SEQ ID NO: 28 (5' UCAGAGCUUGUUCAGCUUUCCA 3'), and a sense strand of nucleic acid sequence according to SEQ ID NO: 58 (5' GAAAGCUGAACAAGCUCUGA 3') (56.8);

xiii) an antisense strand of nucleic acid sequence according to SEQ ID NO: 22 (5' UGAGUGUGAGACCUUGUCCAGG 3'), and a sense strand of nucleic acid sequence according to SEQ ID NO: 52 (5' UGGACAAGGUCUCACACUCA 3') (56.2);

xiv) an antisense strand of nucleic acid sequence according to SEQ ID NO: 14 (5' UUUCGAACAACAGAGUAGGGUA 3'), and a sense strand of nucleic acid sequence according to SEQ ID NO: 44 (5' CCCUACUCUGUUGUUCGAAA 3') (56.0);

XV) an antisense strand of nucleic acid sequence according to SEQ ID NO: 23 (5' UCAGAGUGUGAGACCUUGUCCA 3'), and a sense strand of nucleic acid sequence according to SEQ ID NO: 53 (5' GACAAGGUCUCACACUCUGA 3') (55.5);

xvi) an antisense strand of nucleic acid sequence according to SEQ ID NO: 6 (5' UGAUGUAGUAGAAUUUCUCUGU 3'), and a sense strand of nucleic acid sequence according to SEQ ID NO: 36 (5' AGAGAAAUUCUACUACAUCA 3') (55.3);

xvii) an antisense strand of nucleic acid sequence according to SEQ ID NO: 19 (5' UGUUCAUUGAGCCAACGCACGA 3'), and a sense strand of nucleic acid sequence according to SEQ ID NO: 49 (5' GUGCGUUGGCUCAAUGAACA 3') (53.4);

xviii) an antisense strand of nucleic acid sequence according to SEQ ID NO: 20 (5' UAAUUUAUUACAGGUGAGUUGA 3'), and a sense strand of nucleic acid sequence according to SEQ ID NO: 50 (5' AACUCACCUGUAAUAAAUUA 3') (53.4);

xix) an antisense strand of nucleic acid sequence according to SEQ ID NO: 30 (5' UUAUGAAGCAAUUCUCCUCAGC 3'), and a sense strand of nucleic acid sequence according to SEQ ID NO: 60 (5' UGAGGAGAAUUGCUUCAUAA 3') (52.9);

xx) an antisense strand of nucleic acid sequence according to SEQ ID NO: 2 (5' UGAGAAGACAAGGAGUCCUGCU 3'), and a sense strand of nucleic acid sequence according to SEQ ID NO: 32 (5' CAGGACUCCUUGUCUUCUCA 3') (50.9);

xxi) an antisense strand of nucleic acid sequence according to SEQ ID NO: 27 (5' UGUAGAACCGG-GUACAGCUUUC 3'), and a sense strand of nucleic acid sequence according to SEQ ID NO: 57 (5' AAGCUGUACCCGGUUCUACA 3') (50.9); or xxii) an antisense strand of nucleic acid sequence according to SEQ ID NO: 21 (5' UCUG-GUUUUAUGGUGACCUUGA 3'), and a sense strand of nucleic acid sequence according to SEQ ID NO: 51 (5' AAGGUCACCAUAAAACCAGA 3') (50.9).

Embodiment 38. An isolated oligonucleotide comprising a sense strand and an antisense strand, wherein:

the sense strand comprises a nucleotide sequence that is substantially identical to a region comprising 19-25 nucleotides between any one of the nucleotide positions selected from:

a) 33 to 53;
b) 237 to 260;
c) 444 to 480;
d) 583 to 879;
e) 1118 to 1328;
f) 1409 to 1542;
g) 1619 to 1648;
h) 1754 to 1816;
i) 2232 to 2256;
j) 2300 to 2368;
k) 2423 to 2452;
1) 2518 to 2726;
m) 2860 to 2883;
n) 2981 to 3043;
o) 3125 to 3239;
p) 3298 to 3437;
q) 3567 to 3638;
r) 3767 to 3913;
s) 3985 to 4430; and
t) 4490 to 5054, from the 5' end of a C3 mRNA sequence according to SEQ ID NO: 1, and the antisense strand is substantially complementary to the sense strand such that the sense strand and the antisense strand together form a double stranded region.

Embodiment 39. The isolated oligonucleotide of embodiment 38, wherein the isolated oligonucleotide attenuates expression of the C3 mRNA by 20% to 50% at a dose of 0.1 nM.

Embodiment 40. The isolated oligonucleotide of embodiment 39, wherein the double stranded region comprises:

i) an antisense strand of nucleic acid sequence according to SEQ ID NO: 71 (5' UGUAGAUGGUCUU-GUCUGUCUG 3'), and a sense strand of nucleic acid sequence according to SEQ ID NO: 236 (5' GACAGACAAGACCAUCUACA 3') (49.9);

ii) an antisense strand of nucleic acid sequence according to SEQ ID NO: 106 (5' UUGAUGCU-CAAGGGCUUCUGGC 3'), and a sense strand of nucleic acid sequence according to SEQ ID NO: 271 (5' CAGAAGCCCUUGAGCAUCAA 3') (49.2);

iii) an antisense strand of nucleic acid sequence according to SEQ ID NO: 97 (5' UAAGAUGACAAAGGCAGUUCCC 3'), and a sense strand of nucleic acid sequence according to SEQ ID NO: 262 (5' GAACUGCCUUUGUCAUC-UUA 3') (49.1);

iv) an antisense strand of nucleic acid sequence according to SEQ ID NO: 168 (5' UCAAAGUCAAAGU-CUUUUAGCU 3'), and a sense strand of nucleic acid sequence according to SEQ ID NO: 333 (5' CUAAAAGACUUUGACUUUGA 3') (49.1);

v) an antisense strand of nucleic acid sequence according to SEQ ID NO: 115 (5' UGAAGGAAGG-GAUGAAGUCGGU 3'), and a sense strand of nucleic acid sequence according to SEQ ID NO: 280 (5' CGACUUCAUCCCUUCCUUCA 3') (48.8);

vi) an antisense strand of nucleic acid sequence according to SEQ ID NO: 173 (5' UCUUUUG-GUAUUGAGCCAAGGC 3'), and a sense strand of nucleic acid sequence according to SEQ ID NO: 338 (5' CUUGGCUCAAUACCAAAAGA 3') (48.2);

vii) an antisense strand of nucleic acid sequence according to SEQ ID NO: 116 (5' UUUCUGACUGGCCGCUUUUUAC 3'), and a sense strand of nucleic acid sequence according to SEQ ID NO: 281 (5' AAAAAGCGGCCAGU-CAGAAA 3') (47.4);

viii) an antisense strand of nucleic acid sequence according to SEQ ID NO: 169 (5' UCACAAAGU-CAAAGUCUUUUAG 3'), and a sense strand of nucleic acid sequence according to SEQ ID NO: 334 (5' AAAAGACUUUGACUUUGUGA 3') (47.1);

ix) an antisense strand of nucleic acid sequence according to SEQ ID NO: 66 (5' UGUUUUUUGCCUGG-GAAGUCGU 3'), and a sense strand of nucleic acid sequence according to SEQ ID NO: 231 (5' GAC-UUCCCAGGCAAAAAACA 3') (46.5);

x) an antisense strand of nucleic acid sequence according to SEQ ID NO: 153 (5' UUGAAGGCCAGCUGCUGGGUGU 3'), and a sense strand of nucleic acid sequence according to SEQ ID NO: 318 (5' ACCCAGCAGCUGGCCUU-CAA 3') (46.3);

xi) an antisense strand of nucleic acid sequence according to SEQ ID NO: 189 (5' UCUGUUUCCG-GUGCUGGUUUUA 3'), and a sense strand of nucleic acid sequence according to SEQ ID NO: 354 (5' AAACCAGCACCGGAAACAGA 3') (45.6);

xii) an antisense strand of nucleic acid sequence according to SEQ ID NO: 103 (5' UUGUUGAUGCUGAGUUUGGCCA 3'), and a sense strand of nucleic acid sequence according to SEQ ID NO: 268 (5' GCCAAACUCAGCAU-CAACAA 3') (45.1);

xiii) an antisense strand of nucleic acid sequence according to SEQ ID NO: 225 (5' UGUCCAAC-CUGCACCUCAUCCG 3'), and a sense strand of nucleic acid sequence according to SEQ ID NO: 390 (5' GAUGAGGUGCAGGUUGGACA 3') (44.5);

xiv) an antisense strand of nucleic acid sequence according to SEQ ID NO: 117 (5' UAUCUUCAGG-GUCAUCUGCUGC 3'), and a sense strand of nucleic acid sequence according to SEQ ID NO: 282 (5' AGCAGAUGACCCUGAAGAUA 3') (44.5);

xv) an antisense strand of nucleic acid sequence according to SEQ ID NO: 81 (5' UCAUAGUAGG-CUCGGAUCUUCC 3'), and a sense strand of nucleic acid sequence according to SEQ ID NO: 246 (5' AAGAUCCGAGCCUACUAUGA 3') (44.4);

xvi) an antisense strand of nucleic acid sequence according to SEQ ID NO: 133 (5' UGUUUCGAACAACAGAGUAGGG 3'), and a sense strand of nucleic acid sequence according to SEQ ID NO: 298 (5' CUACUCUGUU-GUUCGAAACA 3') (43.9);

xvii) an antisense strand of nucleic acid sequence according to SEQ ID NO: 107 (5' UCAGGUAAUU-GUUGGAGUUGCC 3'), and a sense strand of nucleic acid sequence according to SEQ ID NO: 272 (5' CAACUCCAACAAUUACCUGA 3') (43.0);

xviii) an antisense strand of nucleic acid sequence according to SEQ ID NO: 68 (5' UGUCUGUCUG-GAUGAAGAGGUA 3'), and a sense strand of nucleic acid sequence according to SEQ ID NO: 233 (5' CCUCUUCAUCCAGACAGACA 3') (42.6);

xix) an antisense strand of nucleic acid sequence according to SEQ ID NO: 222 (5' UGUACUCGU-CAAAGUCAUUGGA 3'), and a sense strand of nucleic acid sequence according to SEQ ID NO: 387 (5' CAAUGACUUUGACGAGUACA 3') (42.5);

xx) an antisense strand of nucleic acid sequence according to SEQ ID NO: 139 (5' UGGAUUGUG-GAGUAGUUCCACC 3'), and a sense strand of nucleic acid sequence according to SEQ ID NO: 304 (5' UGGAACUACUCCACAAUCCA 3') (41.8);

xxi) an antisense strand of nucleic acid sequence according to SEQ ID NO: 158 (5' UGGAAGUCUC-CUGCUUUAGUGA 3'), and a sense strand of nucleic acid sequence according to SEQ ID NO: 323 (5' ACUAAAGCAGGAGACUUCCA 3') (40.3);

xxii) an antisense strand of nucleic acid sequence according to SEQ ID NO: 83 (5' UUUUCAU-AGUAGGCUCGGAUCU 3'), and a sense strand of nucleic acid sequence according to SEQ ID NO: 248 (5' AUCCGAGCCUACUAUGAAAA 3') (40.0);

xxiii) an antisense strand of nucleic acid sequence according to SEQ ID NO: 156 (5' UCAG-GAUCAGCCAUUUAACAGC 3'), and a sense strand of nucleic acid sequence according to SEQ ID NO: 321 (5' UGUUAAAUGGCUGAUCCUGA 3') (39.9);

xxiv) an antisense strand of nucleic acid sequence according to SEQ ID NO: 208 (5' UCUUGUCCAG-GUAGAUGAUGAG 3'), and a sense strand of nucleic acid sequence according to SEQ ID NO: 373 (5' CAUCAUCUACCUGGACAAGA 3') (39.4);

xxv) an antisense strand of nucleic acid sequence according to SEQ ID NO: 62 (5' UGACAGUGCAGGGUCAGAGGGA 3'), and a sense strand of nucleic acid sequence according to SEQ ID NO: 227 (5' CCUCUGACCCUGCACU-GUCA 3') (39.3);

xxvi) an antisense strand of nucleic acid sequence according to SEQ ID NO: 202 (5' UCUAUCG-GAGAAGGCUUUGUCC 3'), and a sense strand of nucleic acid sequence according to SEQ ID NO: 367 (5' ACAAAGCCUUCUCCGAUAGA 3') (39.2);

xxvii) an antisense strand of nucleic acid sequence according to SEQ ID NO: 80 (5' UCUUCCA-CUGGCCCAUGUUGAC 3'), and a sense strand of nucleic acid sequence according to SEQ ID NO: 245 (5' CAACAUGGGCCAGUGGAAGA 3') (39.2);

xxviii) an antisense strand of nucleic acid sequence according to SEQ ID NO: 174 (5' UGAUUCCCAGUGGAUACGGUGG 3'), and a sense strand of nucleic acid sequence according to SEQ ID NO: 339 (5' ACCGUAUCCACUGG-GAAUCA 3') (38.5);

xxix) an antisense strand of nucleic acid sequence according to SEQ ID NO: 65 (5' UUUUUUUGC-CUGGGAAGUCGUG 3'), and a sense strand of nucleic acid sequence according to SEQ ID NO: 230 (5' CGACUUCCCAGGCAAAAAAA 3') (38.3);

xxx) an antisense strand of nucleic acid sequence according to SEQ ID NO: 214 (5' UGGUU-GUAAUAGGCGUAGACCU 3'), and a sense strand of nucleic acid sequence according to SEQ ID NO: 379 (5' GUCUACGCCUAUUACAACCA 3') (38.3);

xxxi) an antisense strand of nucleic acid sequence according to SEQ ID NO: 141 (5' UCUGCAGAAGGCUGGAUUGUGG 3'), and a sense strand of nucleic acid sequence according to SEQ ID NO: 306 (5' ACAAUCCAGCC-UUCUGCAGA 3') (37.4);

xxxii) an antisense strand of nucleic acid sequence according to SEQ ID NO: 91 (5' UCUCUGUAGG-CUCCACUAUGAC 3'), and a sense strand of nucleic acid sequence according to SEQ ID NO: 256 (5' CAUAGUGGAGCCUACAGAGA 3') (34.8);

xxxiii) an antisense strand of nucleic acid sequence according to SEQ ID NO: 88 (5' UGAAACUGGGCAGCACGUACUC 3'), and a sense strand of nucleic acid sequence according to SEQ ID NO: 253 (5' GUACGUGCUGCCCAGUUUCA 3') (34.5);

xxxiv) an antisense strand of nucleic acid sequence according to SEQ ID NO: 165 (5' UCUGC-AGUAGGGCCAAGAGGGC 3'), and a sense strand of nucleic acid sequence according to SEQ ID NO: 330 (5' CCUCUUGGCCCUACUGCAGA 3') (33.3);

xxxv) an antisense strand of nucleic acid sequence according to SEQ ID NO: 140 (5' UCUGGAUU-GUGGAGUAGUUCCA 3'), and a sense strand of nucleic acid sequence according to SEQ ID NO: 305 (5' GAACUACUCCACAAUCCAGA 3') (32.2);

xxxvi) an antisense strand of nucleic acid sequence according to SEQ ID NO: 183 (5' UCUUUUCC-UUCAGCUGUGACUG 3'), and a sense strand of nucleic acid sequence according to SEQ ID NO: 348 (5' GUCACAGCUGAAGGAAAAGA 3') (32.0);

xxxvii) an antisense strand of nucleic acid sequence according to SEQ ID NO: 179 (5' UCU-GUGAAACCCUCAUUUUCCU 3'), and a sense strand of nucleic acid sequence according to SEQ ID NO: 344 (5' GAAAAUGAGGGUUUCACAGA 3') (31.6);

xxxviii) an antisense strand of nucleic acid sequence according to SEQ ID NO: 127 (5' UCAUUACU-GUGACCUCGAAGGG 3'), and a sense strand of nucleic acid sequence according to SEQ ID NO: 292 (5' CUUCGAGGUCACAGUAAUGA 3') (31.2);

xxxix) an antisense strand of nucleic acid sequence according to SEQ ID NO: 185 (5' UGAGGU-CGAAUUUAUUACAGGU 3'), and a sense strand of nucleic acid sequence according to SEQ ID NO: 350 (5' CUGUAAUAAAUUCGACCUCA 3') (31.1);

xL) an antisense strand of nucleic acid sequence according to SEQ ID NO: 111 (5' UCAUUCGCAG-GAGGAAGUUGAC 3'), and a sense strand of nucleic acid sequence according to SEQ ID NO: 276 (5' CAACUUCCUCCUGCGAAUGA 3') (30.7);

xLi) an antisense strand of nucleic acid sequence according to SEQ ID NO: 157 (5' UGUAU-CACGGGCGCAUCCUCCU 3'), and a sense strand of nucleic acid sequence according to SEQ ID NO: 322 (5' GAGGAUGCGCCCGUGAUACA 3') (29.7);

xLii) an antisense strand of nucleic acid sequence according to SEQ ID NO: 164 (5' UCAGCAAUGGCCACAGUGUAGG 3'), and a sense strand of nucleic acid sequence according to SEQ ID NO: 329 (5' UACACUGUGGC-CAUUGCUGA 3') (28.3);

xLiii) an antisense strand of nucleic acid sequence according to SEQ ID NO: 90 (5' UCACUAUGAC-CUCGAAACUGGG 3'), and a sense strand of nucleic acid sequence according to SEQ ID NO: 255 (5' CAGUUUCGAGGUCAUAGUGA 3') (27.5);

xLiv) an antisense strand of nucleic acid sequence according to SEQ ID NO: 87 (5' UGUACUCCUU-CACCUCAAACUC 3'), and a sense strand of nucleic acid sequence according to SEQ ID NO: 252 (5' GUUUGAGGUGAAGGAGUACA 3') (26.9);

xLv) an antisense strand of nucleic acid sequence according to SEQ ID NO: 199 (5' UCUCAUAC-UUGGAGAUGUAUCU 3'), and a sense strand of nucleic acid sequence according to SEQ ID NO: 364 (5' AUACAUCUCCAAGUAUGAGA 3') (26.7).

xLvi) an antisense strand of nucleic acid sequence according to SEQ ID NO: 184 (5' UCUUAGCAUG-GUACAUUGUCAC 3'), and a sense strand of nucleic acid sequence according to SEQ ID NO: 349 (5' GACAAUGUACCAUGCUAAGA 3') (26.3);

xLvii) an antisense strand of nucleic acid sequence according to SEQ ID NO: 400 (5' UUGUAGUUGCAGCAGUCCAGGA 3'), and a sense strand of nucleic acid sequence according to SEQ ID NO: 426 (5' CUGGACUGCUGCAACUA-CAA 3') (41.9);

xLiii) an antisense strand of nucleic acid sequence according to SEQ ID NO: 110 (5' UGAG-GAAGUUGACGUUGAGGGU 3'), and a sense strand of nucleic acid sequence according to SEQ ID NO: 275 (5' CCUCAACGUCAACUUCCUCA 3') (23.4);

xLix) an antisense strand of nucleic acid sequence according to SEQ ID NO: 147 (5' UGGCAUCCU-CUGUCAUCUGGGC 3'), and a sense strand of nucleic acid sequence according to SEQ ID NO: 312 (5' CCAGAUGACAGAGGAUGCCA 3') (23.3);

L) an antisense strand of nucleic acid sequence according to SEQ ID NO: 218 (5' UUUUU-GUAUGAAGCAAUUCUCC 3'), and a sense strand of nucleic acid sequence according to SEQ ID NO: 383 (5' AGAAUUGCUUCAUACAAAAA 3') (22.5);

Li) an antisense strand of nucleic acid sequence according to SEQ ID NO: 138 (5' UGAUUGUGG-AGUAGUUCCACCC 3'), and a sense strand of nucleic acid sequence according to SEQ ID NO: 303 (5' GUGGAACUACUCCACAAUCA 3') (22.5);

Lii) an antisense strand of nucleic acid sequence according to SEQ ID NO: 114 (5' UGAUGAAGU-CGGUGGUGAUGGA 3'), and a sense strand of nucleic acid sequence according to SEQ ID NO: 279 (5' CAUCACCACCGACUUCAUCA 3') (21.4);

Liii) an antisense strand of nucleic acid sequence according to SEQ ID NO: 85 (5' UCUCCUUCAC-CUCAAACUCAGU 3'), and a sense strand of nucleic acid sequence according to SEQ ID NO: 250 (5' UGAGUUUGAGGUGAAGGAGA 3') (21.3);

Liv) an antisense strand of nucleic acid sequence according to SEQ ID NO: 152 (5' UCUUC-UUGAUGAGCUCCAAGGC 3'), and a sense strand of nucleic acid sequence according to SEQ ID NO: 317 (5' CUUGGAGCUCAUCAAGAAGA 3') (20.8);

Lv) an antisense strand of nucleic acid sequence according to SEQ ID NO: 402 (5' UCUCAUCCAG-GUUACUCCUGGC 3'), and a sense strand of nucleic acid sequence according to SEQ ID NO: 428 (5' CAGGAGUAACCUGGAUGAGA 3') (40.4);

Lvi) an antisense strand of nucleic acid sequence according to SEQ ID NO: 136 (5' UCUUG-GUUCUGCCGGUAAUUGU 3'), and a sense strand of nucleic acid sequence according to SEQ ID NO: 301 (5' AAUUACCGGCAGAACCAAGA 3') (20.7);

Lvii) an antisense strand of nucleic acid sequence according to SEQ ID NO: 209 (5' UGACCUUGU-CCAGGUAGAUGAU 3'), and a sense strand of nucleic acid sequence according to SEQ ID NO: 374 (5' CAUCUACCUGGACAAGGUCA 3') (20.3); or Lviii) an antisense strand of nucleic acid sequence according to SEQ ID NO: 412 (5' UCUCUGGGAA-CUCACUUCGGGA 3'), and a sense strand of nucleic acid sequence according to SEQ ID NO: 438 (5' CCGAAGUGAGUUCCCAGAGA 3') (30.4).

Embodiment 41. The isolated nucleotide of embodiment 38, wherein the isolated oligonucleotide attenuates expression of the C3 mRNA by at least 50% at a dose of 0.1 nM.

Embodiment 42. The isolated oligonucleotide of embodiment 41, wherein the double stranded region comprises:

i) an antisense strand of nucleic acid sequence according to SEQ ID NO: 94 (5' UUAGAUGUAGUA-GAAUUUCUCU 3'), and a sense strand of nucleic acid sequence according to SEQ ID NO: 259 (5' AGAAAUUCUACUACAUCUAA 3') (89.3);

ii) an antisense strand of nucleic acid sequence according to SEQ ID NO: 74 (5' UGACAAGGAGUC-CUGCUUGACC 3'), and a sense strand of nucleic acid sequence according to SEQ ID NO: 239 (5' UCAAGCAGGACUCCUUGUCA 3') (80.4);

iii) an antisense strand of nucleic acid sequence according to SEQ ID NO: 70 (5' UUAGAUGGUCUUGU-CUGUCUGG 3'), and a sense strand of nucleic acid sequence according to SEQ ID NO: 235 (5' AGACA-GACAAGACCAUCUAA 3') (79.7);

iv) an antisense strand of nucleic acid sequence according to SEQ ID NO: 64 (5' UUUUUUGCCUGG-GAAGUCGUGG 3'), and a sense strand of nucleic acid sequence according to SEQ ID NO: 229 (5' ACGACUUCCCAGGCAAAAAA 3') (78.7);

v) an antisense strand of nucleic acid sequence according to SEQ ID NO: 172 (5' UUAGUAUCUCUGUU-CAUUGAGC 3'), and a sense strand of nucleic acid sequence according to SEQ ID NO: 337 (5' UCAAUGAACAGAGAUACUAA 3') (78.4);

vi) an antisense strand of nucleic acid sequence according to SEQ ID NO: 226 (5' UGU-CAGUUGGGGCACCCAAAGA 3'), and a sense strand of nucleic acid sequence according to SEQ ID NO: 391 (5' UUUGGGUGCCCCAACUGACA 3') (78.3);

vii) an antisense strand of nucleic acid sequence according to SEQ ID NO: 217 (5' UUU- GUAUGAAGCAAUUCUCCUC 3'), and a sense strand of nucleic acid sequence according to SEQ ID NO: 382 (5' GGAGAAUUGCUUCAUACAAA 3') (78.0);

viii) an antisense strand of nucleic acid sequence according to SEQ ID NO: 131 (5' UGAACAACAG-AGUAGGGUAGCC 3'), and a sense strand of nucleic acid sequence according to SEQ ID NO: 296 (5' CUACCCUACUCUGUUGUUCA 3') (77.9);

ix) an antisense strand of nucleic acid sequence according to SEQ ID NO: 113 (5' UAUCAGGUAGGU-GUAGUAGCGG 3'), and a sense strand of nucleic acid sequence according to SEQ ID NO: 278 (5' GCUACUACACCUACCUGAUA 3') (77.8);

x) an antisense strand of nucleic acid sequence according to SEQ ID NO: 126 (5' UAUUACUGUGAC-CUCGAAGGGG 3'), and a sense strand of nucleic acid sequence according to SEQ ID NO: 291 (5' CCUUCGAGGUCACAGUAAUA 3') (77.6);

xi) an antisense strand of nucleic acid sequence according to SEQ ID NO: 146 (5' UGAAUUCUGGU-CUCAGACUCGG 3'), and a sense strand of nucleic acid sequence according to SEQ ID NO: 311 (5' GAGUCUGAGACCAGAAUUCA 3') (77.6);

xii) an antisense strand of nucleic acid sequence according to SEQ ID NO: 170 (5' UGUAUCUCU-GUUCAUUGAGCCA 3'), and a sense strand of nucleic acid sequence according to SEQ ID NO: 335 (5' GCUCAAUGAACAGAGAUACA 3') (76.8);

xiii) an antisense strand of nucleic acid sequence according to SEQ ID NO: 123 (5' UUUU-CAAAAAUAUAUUCAUGAG 3'), and a sense strand of nucleic acid sequence according to SEQ ID NO: 288 (5' CAUGAAUAUAUUUUUGAAAA 3') (76.6);

xiv) an antisense strand of nucleic acid sequence according to SEQ ID NO: 93 (5' UAGUA-GAAUUUCUCUGUAGGCU 3'), and a sense strand of nucleic acid sequence according to SEQ ID NO: 258 (5' CCUACAGAGAAAUUCUACUA 3') (76.5);

XV) an antisense strand of nucleic acid sequence according to SEQ ID NO: 124 (5' UCUUU-CAAAAAUAUAUUCAUGA 3'), and a sense strand of nucleic acid sequence according to SEQ ID NO: 289 (5' AUGAAUAUAUUUUUGAAAGA 3') (76.1);

xvi) an antisense strand of nucleic acid sequence according to SEQ ID NO: 198 (5' UCAUACUUG-GAGAUGUAUCUGU 3'), and a sense strand of nucleic acid sequence according to SEQ ID NO: 363 (5' AGAUACAUCUCCAAGUAUGA 3') (76.0);

xvii) an antisense strand of nucleic acid sequence according to SEQ ID NO: 145 (5' UAAUUCUG-GUCUCAGACUCGGU 3'), and a sense strand of nucleic acid sequence according to SEQ ID NO: 310 (5' CGAGUCUGAGACCAGAAUUA 3') (75.5);

xviii) an antisense strand of nucleic acid sequence according to SEQ ID NO: 188 (5' UGUUUUAUG-GUGACCUUGAGGU 3'), and a sense strand of nucleic acid sequence according to SEQ ID NO: 353 (5' CUCAAGGUCACCAUAAAACA 3') (75.5);

xix) an antisense strand of nucleic acid sequence according to SEQ ID NO: 67 (5' UCUGUCUG-GAUGAAGAGGUACC 3'), and a sense strand of nucleic acid sequence according to SEQ ID NO: 232 (5' UACCUCUUCAUCCAGACAGA 3') (75.1);

xx) an antisense strand of nucleic acid sequence according to SEQ ID NO: 72 (5' UUGUAGAUG-GUCUUGUCUGUCU 3'), and a sense strand of nucleic acid sequence according to SEQ ID NO: 237 (5' ACAGACAAGACCAUCUACAA 3') (75.0);

xxi) an antisense strand of nucleic acid sequence according to SEQ ID NO: 159 (5' UAAGGAAGU-CUCCUGCUUUAGU 3'), and a sense strand of nucleic acid sequence according to SEQ ID NO: 324 (5' UAAAGCAGGAGACUUCCUUA 3') (74.7);

xxii) an antisense strand of nucleic acid sequence according to SEQ ID NO: 181 (5' UUUCC-UUCAGCUGUGACUGUGA 3'), and a sense strand of nucleic acid sequence according to SEQ ID NO: 346 (5' ACAGUCACAGCUGAAGGAAA 3') (74.6);

xxiii) an antisense strand of nucleic acid sequence according to SEQ ID NO: 108 (5' UGAGAUGCAG-GUAAUUGUUGGA 3'), and a sense strand of nucleic acid sequence according to SEQ ID NO: 273 (5' CAACAAUUACCUGCAUCUCA 3') (74.6);

xxiv) an antisense strand of nucleic acid sequence according to SEQ ID NO: 96 (5' UAGAUGACAAAGGCAGUUCCCU 3'), and a sense strand of nucleic acid sequence according to SEQ ID NO: 261 (5' GGAACUGCCUUUGU-CAUCUA 3') (74.0);

xxv) an antisense strand of nucleic acid sequence according to SEQ ID NO: 129 (5' UGAAGAAGU-CCUGCAUUACUGU 3'), and a sense strand of nucleic acid sequence according to SEQ ID NO: 294 (5' AGUAAUGCAGGACUUCUUCA 3') (72.9);

xxvi) an antisense strand of nucleic acid sequence according to SEQ ID NO: 196 (5' UUACUUG-GAGAUGUAUCUGUCA 3'), and a sense strand of nucleic acid sequence according to SEQ ID NO: 361 (5' ACAGAUACAUCUCCAAGUAA 3') (72.5);

xxvii) an antisense strand of nucleic acid sequence according to SEQ ID NO: 122 (5' UUU-CAAAAAUAUAUUCAUGAGC 3'), and a sense strand of nucleic acid sequence according to SEQ ID NO: 287 (5' UCAUGAAUAUAUUUUUGAAA 3') (72.4);

xxviii) an antisense strand of nucleic acid sequence according to SEQ ID NO: 160 (5' UUUCAU-GUAGUUGGCUUCAAGG 3'), and a sense strand of nucleic acid sequence according to SEQ ID NO: 325 (5' UUGAAGCCAACUACAUGAAA 3') (72.2);

xxix) an antisense strand of nucleic acid sequence according to SEQ ID NO: 162 (5' UAUCUCU-GUAGGUUCAUGUAGU 3'), and a sense strand of nucleic acid sequence according to SEQ ID NO: 327 (5' UACAUGAACCUACAGAGAUA 3') (71.9);

xxx) an antisense strand of nucleic acid sequence according to SEQ ID NO: 104 (5' UGU-GUUGAUGCUGAGUUUGGCC 3'), and a sense strand of nucleic acid sequence according to SEQ ID NO: 269 (5' CCAAACUCAGCAUCAACACA 3') (71.7);

xxxi) an antisense strand of nucleic acid sequence according to SEQ ID NO: 201 (5' UCUUUGU-CCAGCUCAUACUUGG 3'), and a sense strand of nucleic acid sequence according to SEQ ID NO: 366 (5' AAGUAUGAGCUGGACAAAGA 3') (71.3);

xxxii) an antisense strand of nucleic acid sequence according to SEQ ID NO: 63 (5' UUUUUGCCUGG- GAAGUCGUGGA 3'), and a sense strand of nucleic acid sequence according to SEQ ID NO: 228 (5' CACGACUUCCCAGGCAAAAA 3') (71.1);

xxxiii) an antisense strand of nucleic acid sequence according to SEQ ID NO: 178 (5' UCAUUUUCC-UUGGUCUCUUCUG 3'), and a sense strand of nucleic acid sequence according to SEQ ID NO: 343 (5' GAAGAGACCAAGGAAAAUGA 3') (71.0);

xxxiv) an antisense strand of nucleic acid sequence according to SEQ ID NO: 203 (5' UUUCCUAUCG-GAGAAGGCUUUG 3'), and a sense strand of nucleic acid sequence according to SEQ ID NO: 368 (5' AAGCCUUCUCCGAUAGGAAA 3') (70.9);

xxxv) an antisense strand of nucleic acid sequence according to SEQ ID NO: 216 (5' UGAAGCAAUU-CUCCUCAGCACA 3'), and a sense strand of nucleic acid sequence according to SEQ ID NO: 381 (5' UGCUGAGGAGAAUUGCUUCA 3') (70.9);

xxxvi) an antisense strand of nucleic acid sequence according to SEQ ID NO: 220 (5' UGUACACAUA-GUCCACUCCUGG 3'), and a sense strand of nucleic acid sequence according to SEQ ID NO: 385 (5' AGGAGUGGACUAUGUGUACA 3') (70.5);

xxxvii) an antisense strand of nucleic acid sequence according to SEQ ID NO: 118 (5' UUAUC-UUCAGGGUCAUCUGCUG 3'), and a sense strand of nucleic acid sequence according to SEQ ID NO: 283 (5' GCAGAUGACCCUGAAGAUAA 3') (70.4);

xxxviii) an antisense strand of nucleic acid sequence according to SEQ ID NO: 194 (5' UUAGA-CAUAGUGGCAUCCUGGU 3'), and a sense strand of nucleic acid sequence according to SEQ ID NO: 359 (5' CAGGAUGCCACUAUGUCUAA 3') (70.3);

xxxix) an antisense strand of nucleic acid sequence according to SEQ ID NO: 219 (5' UUACACAUA-GUCCACUCCUGGC 3'), and a sense strand of nucleic acid sequence according to SEQ ID NO: 384 (5' CAGGAGUGGACUAUGUGUAA 3') (69.8);

xL) an antisense strand of nucleic acid sequence according to SEQ ID NO: 99 (5' UGUCUUG-GUGAAGUGGAUCUGG 3'), and a sense strand of nucleic acid sequence according to SEQ ID NO: 264 (5' AGAUCCACUUCACCAAGACA 3') (69.0);

xLi) an antisense strand of nucleic acid sequence according to SEQ ID NO: 154 (5' UAAGACC-UUGACCACGUAGGCG 3'), and a sense strand of nucleic acid sequence according to SEQ ID NO: 319 (5' CCUACGUGGUCAAGGUCUUA 3') (68.7);

xLii) an antisense strand of nucleic acid sequence according to SEQ ID NO: 171 (5' UAGUAUCUCU-GUUCAUUGAGCC 3'), and a sense strand of nucleic acid sequence according to SEQ ID NO: 336 (5' CUCAAUGAACAGAGAUACUA 3') (68.7);

xLiii) an antisense strand of nucleic acid sequence according to SEQ ID NO: 195 (5' UCAGUCAU-CAUGGAUAUGUCCA 3'), and a sense strand of nucleic acid sequence according to SEQ ID NO: 360 (5' GACAUAUCCAUGAUGACUGA 3') (68.7);

xLiv) an antisense strand of nucleic acid sequence according to SEQ ID NO: 73 (5' UGUGUAGAUG-GUCUUGUCUGUC 3'), and a sense strand of nucleic acid sequence according to SEQ ID NO: 238 (5' CAGACAAGACCAUCUACACA 3') (68.3);

xLv) an antisense strand of nucleic acid sequence according to SEQ ID NO: 180 (5' UUUCAGCU-GUGACUGUGAAACC 3'), and a sense strand of nucleic acid sequence according to SEQ ID NO: 345 (5' UUUCACAGUCACAGCUGAAA 3') (68.3).

xLvi) an antisense strand of nucleic acid sequence according to SEQ ID NO: 92 (5' UUUCUCU-GUAGGCUCCACUAUG 3'), and a sense strand of nucleic acid sequence according to SEQ ID NO: 257 (5' UAGUGGAGCCUACAGAGAAA 3') (67.8);

xLvii) an antisense strand of nucleic acid sequence according to SEQ ID NO: 75 (5' UAA-GACAAGGAGUCCUGCUUGA 3'), and a sense strand of nucleic acid sequence according to SEQ ID NO: 240 (5' AAGCAGGACUCCUUGUCUUA 3') (67.3);

xLviii) an antisense strand of nucleic acid sequence according to SEQ ID NO: 137 (5' UGUAGUUC-CACCCUCACCUUGA 3'), and a sense strand of nucleic acid sequence according to SEQ ID NO: 302 (5' AAGGUGAGGGUGGAACUACA 3') (66.3);

xLix) an antisense strand of nucleic acid sequence according to SEQ ID NO: 89 (5' UCUAUGAC-CUCGAAACUGGGCA 3'), and a sense strand of nucleic acid sequence according to SEQ ID NO: 254 (5' CCCAGUUUCGAGGUCAUAGA 3') (66.2);

L) an antisense strand of nucleic acid sequence according to SEQ ID NO: 130 (5' UGAUGAAGAAGUC-CUGCAUUAC 3'), and a sense strand of nucleic acid sequence according to SEQ ID NO: 295 (5' AAUGCAGGACUUCUUCAUCA 3') (66.1);

Li) an antisense strand of nucleic acid sequence according to SEQ ID NO: 69 (5' UUUGUCUGUCUG-GAUGAAGAGG 3'), and a sense strand of nucleic acid sequence according to SEQ ID NO: 234 (5' UCUUCAUCCAGACAGACAAA 3') (66.1);

Lii) an antisense strand of nucleic acid sequence according to SEQ ID NO: 176 (5' UUUUUCCUUG-GUCUCUUCUGAU 3'), and a sense strand of nucleic acid sequence according to SEQ ID NO: 341 (5' CAGAAGAGACCAAGGAAAAA 3') (65.9);

Liii) an antisense strand of nucleic acid sequence according to SEQ ID NO: 100 (5' UGAGGU-CAAAGGGCAUUCCUGG 3'), and a sense strand of nucleic acid sequence according to SEQ ID NO: 265 (5' AGGAAUGCCCUUUGACCUCA 3') (65.7);

Liv) an antisense strand of nucleic acid sequence according to SEQ ID NO: 82 (5' UUUCAU-AGUAGGCUCGGAUCUU 3'), and a sense strand of nucleic acid sequence according to SEQ ID NO: 247 (5' GAUCCGAGCCUACUAUGAAA 3') (65.6);

Lv) an antisense strand of nucleic acid sequence according to SEQ ID NO: 212 (5' UGUAAUAGGCGUAGACCUUGAC 3'), and a sense strand of nucleic acid sequence according to SEQ ID NO: 377 (5' CAAGGUCUACGCC-UAUUACA 3') (65.6);

Lvi) an antisense strand of nucleic acid sequence according to SEQ ID NO: 191 (5' UAUCAUAGU-GUUCUUGGCAUCC 3'), and a sense strand of nucleic acid sequence according to SEQ ID NO: 356 (5' AUGCCAAGAACACUAUGAUA 3') (65.4);

Lvii) an antisense strand of nucleic acid sequence according to SEQ ID NO: 161 (5' UUGUAGGUU-CAUGUAGUUGGCU 3'), and a sense strand of nucleic acid sequence according to SEQ ID NO: 326 (5' CCAACUACAUGAACCUACAA 3') (65.4);

Lviii) an antisense strand of nucleic acid sequence according to SEQ ID NO: 112 (5' UGUGU-AGUAGCGGAUCUUGGCC 3'), and a sense strand of nucleic acid sequence according to SEQ ID NO: 277 (5' CCAAGAUCCGCUACUACACA 3') (65.2);

Lix) an antisense strand of nucleic acid sequence according to SEQ ID NO: 151 (5' UUUC-UUGAUGAGCUCCAAGGCC 3'), and a sense strand of nucleic acid sequence according to SEQ ID NO: 316 (5' CCUUGGAGCUCAUCAAGAAA 3') (65.0);

Lx) an antisense strand of nucleic acid sequence according to SEQ ID NO: 213 (5' UGUU-GUAAUAGGCGUAGACCUU 3'), and a sense strand of nucleic acid sequence according to SEQ ID NO: 378 (5' GGUCUACGCCUAUUACAACA 3') (64.9);

Lxi) an antisense strand of nucleic acid sequence according to SEQ ID NO: 206 (5' UGAUGAUGAGGGUGUUCCUAUC 3'), and a sense strand of nucleic acid sequence according to SEQ ID NO: 371 (5' UAGGAACACCCUCAU-CAUCA 3') (63.8);

Lxii) an antisense strand of nucleic acid sequence according to SEQ ID NO: 155 (5' UGAGAGAA-GACCUUGACCACGU 3'), and a sense strand of nucleic acid sequence according to SEQ ID NO: 320 (5' GUGGUCAAGGUCUUCUCUCA 3') (63.5);

Lxiii) an antisense strand of nucleic acid sequence according to SEQ ID NO: 143 (5' UUUGUU-CAUUCUGAUUCCUUCC 3'), and a sense strand of nucleic acid sequence according to SEQ ID NO: 308 (5' AAGGAAUCAGAAUGAACAAA 3') (63.1);

Lxiv) an antisense strand of nucleic acid sequence according to SEQ ID NO: 193 (5' UCAAGGAU-CAUAGUGUUCUUGG 3'), and a sense strand of nucleic acid sequence according to SEQ ID NO: 358 (5' AAGAACACUAUGAUCCUUGA 3') (63.0);

Lxv) an antisense strand of nucleic acid sequence according to SEQ ID NO: 163 (5' UCAGUGUAG-GAUCUCUGUAGGU 3'), and a sense strand of nucleic acid sequence according to SEQ ID NO: 328 (5' CUACAGAGAUCCUACACUGA 3') (62.8);

Lxvi) an antisense strand of nucleic acid sequence according to SEQ ID NO: 149 (5' UUUCAUCCAG-GUAAUGCACAGC 3'), and a sense strand of nucleic acid sequence according to SEQ ID NO: 314 (5' UGUGCAUUACCUGGAUGAAA 3') (62.4);

Lxvii) an antisense strand of nucleic acid sequence according to SEQ ID NO: 200 (5' UUUUGUCCAG-CUCAUACUUGGA 3'), and a sense strand of nucleic acid sequence according to SEQ ID NO: 365 (5' CAAGUAUGAGCUGGACAAAA 3') (61.6);

Lxviii) an antisense strand of nucleic acid sequence according to SEQ ID NO: 210 (5' UCUCAGAGU-GUGAGACCUUGUC 3'), and a sense strand of nucleic acid sequence according to SEQ ID NO: 375 (5' CAAGGUCUCACACUCUGAGA 3') (61.5);

Lxix) an antisense strand of nucleic acid sequence according to SEQ ID NO: 215 (5' UUGUUCAGC-UUUCCAUCCUCCU 3'), and a sense strand of nucleic acid sequence according to SEQ ID NO: 380 (5' GAGGAUGGAAAGCUGAACAA 3') (61.4);

Lxx) an antisense strand of nucleic acid sequence according to SEQ ID NO: 98 (5' UCUUG-GUGAAGUGGAUCUGGUA 3'), and a sense strand of nucleic acid sequence according to SEQ ID NO: 263 (5' CCAGAUCCACUUCACCAAGA 3') (61.3);

Lxxi) an antisense strand of nucleic acid sequence according to SEQ ID NO: 182 (5' UUUUUCC-UUCAGCUGUGACUGU 3'), and a sense strand of nucleic acid sequence according to SEQ ID NO: 347 (5' AGUCACAGCUGAAGGAAAAA 3') (61.0);

Lxxii) an antisense strand of nucleic acid sequence according to SEQ ID NO: 150 (5' UGUUU-CAUCCAGGUAAUGCACA 3'), and a sense strand of nucleic acid sequence according to SEQ ID NO: 315 (5' UGCAUUACCUGGAUGAAACA 3') (61.0);

Lxxiii) an antisense strand of nucleic acid sequence according to SEQ ID NO: 223 (5' UAUGAUGUA-CUCGUCAAAGUCA 3'), and a sense strand of nucleic acid sequence according to SEQ ID NO: 388 (5' ACUUUGACGAGUACAUCAUA 3') (60.9);

Lxxiv) an antisense strand of nucleic acid sequence according to SEQ ID NO: 177 (5' UAUUUUCC-UUGGUCUCUUCUGA 3'), and a sense strand of nucleic acid sequence according to SEQ ID NO: 342 (5' AGAAGAGACCAAGGAAAAUA 3') (60.7);

Lxxv) an antisense strand of nucleic acid sequence according to SEQ ID NO: 128 (5' UGAAGUCCUG-CAUUACUGUGAC 3'), and a sense strand of nucleic acid sequence according to SEQ ID NO: 293 (5' CACAGUAAUGCAGGACUUCA 3') (60.4);

Lxxvi) an antisense strand of nucleic acid sequence according to SEQ ID NO: 224 (5' UCU-CAUCCGAGCCUGACUUGAU 3'), and a sense strand of nucleic acid sequence according to SEQ ID NO: 389 (5' CAAGUCAGGCUCGGAUGAGA 3') (59.9);

Lxxvii) an antisense strand of nucleic acid sequence according to SEQ ID NO: 205 (5' UAUGAUGAGG-GUGUUCCUAUCG 3'), and a sense strand of nucleic acid sequence according to SEQ ID NO: 370 (5' AUAGGAACACCCUCAUCAUA 3') (59.9);

Lxxviii) an antisense strand of nucleic acid sequence according to SEQ ID NO: 186 (5' UUUUAUG-GUGACCUUGAGGUCG 3'), and a sense strand of nucleic acid sequence according to SEQ ID NO: 351 (5' ACCUCAAGGUCACCAUAAAA 3') (59.3);

Lxxix) an antisense strand of nucleic acid sequence according to SEQ ID NO: 77 (5' UGACGAGUUCCGGAAUGUCCCA 3'), and a sense strand of nucleic acid sequence according to SEQ ID NO: 242 (5' GGACAUUCCGGAACUC-GUCA 3') (59.1);

Lxxx) an antisense strand of nucleic acid sequence according to SEQ ID NO: 197 (5' UAUACUUG-GAGAUGUAUCUGUC 3'), and a sense strand of nucleic acid sequence according to SEQ ID NO: 362 (5' CAGAUACAUCUCCAAGUAUA 3') (59.1);

Lxxxi) an antisense strand of nucleic acid sequence according to SEQ ID NO: 95 (5' UGUUAUAGAU-GUAGUAGAAUUU 3'), and a sense strand of nucleic acid sequence according to SEQ ID NO: 260 (5' AUUCUACUACAUCUAUAACA 3') (57.9);

Lxxxii) an antisense strand of nucleic acid sequence according to SEQ ID NO: 78 (5' UUUGACGAGUUCCGGAAUGUCC 3'), and a sense strand of nucleic acid sequence according to SEQ ID NO: 243 (5' ACAUUCCGGAACUCGU-CAAA 3') (56.6);

Lxxxiii) an antisense strand of nucleic acid sequence according to SEQ ID NO: 101 (5' UAACACCAUGAGGUCAAAGGGC 3'), and a sense strand of nucleic acid sequence according to SEQ ID NO: 266 (5' CCUUUGACCUCAUGGUGUUA 3') (56.2);

Lxxxiv) an antisense strand of nucleic acid sequence according to SEQ ID NO: 79 (5' UGUUGACGAGUUCCGGAAUGUC 3'), and a sense strand of nucleic acid sequence according to SEQ ID NO: 244 (5' CAUUCCGGAACUCGUCAACA 3') (56.2);

Lxxxv) an antisense strand of nucleic acid sequence according to SEQ ID NO: 221 (5' UGUCUUGUACACAUAGUCCACU 3'), and a sense strand of nucleic acid sequence according to SEQ ID NO: 386 (5' UGGACUAUGUGUACAAGACA 3') (55.7);

Lxxxvi) an antisense strand of nucleic acid sequence according to SEQ ID NO: 167 (5' UGUCUUUUAGCUGCAGUAGGGC 3'), and a sense strand of nucleic acid sequence according to SEQ ID NO: 332 (5' CCUACUGCAGCUAAAAGACA 3') (55.7);

Lxxxvii) an antisense strand of nucleic acid sequence according to SEQ ID NO: 84 (5' UCAAACUCAGUGGAGAAGACCU 3'), and a sense strand of nucleic acid sequence according to SEQ ID NO: 249 (5' GUCUUCUCCACUGAGUUUGA 3') (55.3);

Lxxxviii) an antisense strand of nucleic acid sequence according to SEQ ID NO: 144 (5' UGUUUUGUUCAUUCUGAUUCCU 3'), and a sense strand of nucleic acid sequence according to SEQ ID NO: 309 (5' GAAUCAGAAUGAACAAAACA 3') (55.1);

Lxxxix) an antisense strand of nucleic acid sequence according to SEQ ID NO: 166 (5' UUCUUUUAGCUGCAGUAGGGCC 3'), and a sense strand of nucleic acid sequence according to SEQ ID NO: 331 (5' CCCUACUGCAGCUAAAAGAA 3') (54.9);

xc) an antisense strand of nucleic acid sequence according to SEQ ID NO: 76 (5' UUUCUGAGAAGACAAGGAGUCC 3'), and a sense strand of nucleic acid sequence according to SEQ ID NO: 241 (5' ACUCCUUGUCUUCUCAGAAA 3') (54.9);

xci) an antisense strand of nucleic acid sequence according to SEQ ID NO: 204 (5' UGUGUUCCUAUCGGAGAAGGCU 3'), and a sense strand of nucleic acid sequence according to SEQ ID NO: 369 (5' CCUUCUCCGAUAGGAACACA 3') (54.9);

xcii) an antisense strand of nucleic acid sequence according to SEQ ID NO: 211 (5' UCAUCCUCAGAGUGUGAGACCU 3'), and a sense strand of nucleic acid sequence according to SEQ ID NO: 376 (5' GUCUCACACUCUGAGGAUGA 3') (54.7);

xciii) an antisense strand of nucleic acid sequence according to SEQ ID NO: 132 (5' UUUUCGAACAACAGAGUAGGGU 3'), and a sense strand of nucleic acid sequence according to SEQ ID NO: 297 (5' CCUACUCUGUUGUUCGAAAA 3') (54.3);

xciv) an antisense strand of nucleic acid sequence according to SEQ ID NO: 142 (5' UGGAUGGUUACGGUCUGCUGGU 3'), and a sense strand of nucleic acid sequence according to SEQ ID NO: 307 (5' CAGCAGACCGUAACCAUCCA 3') (53.9);

xCV) an antisense strand of nucleic acid sequence according to SEQ ID NO: 148 (5' UCAGGUAAUGCACAGCGAUGAC 3'), and a sense strand of nucleic acid sequence according to SEQ ID NO: 313 (5' CAUCGCUGUGCAUUACCUGA 3') (53.9);

xcvi) an antisense strand of nucleic acid sequence according to SEQ ID NO: 207 (5' UGUAGAUGAUGAGGGUGUUCCU 3'), and a sense strand of nucleic acid sequence according to SEQ ID NO: 372 (5' GAACACCCUCAUCAUCUACA 3') (53.5);

xcvii) an antisense strand of nucleic acid sequence according to SEQ ID NO: 86 (5' UUACUCCUUCACCUCAAACUCA 3'), and a sense strand of nucleic acid sequence according to SEQ ID NO: 251 (5' AGUUUGAGGUGAAGGAGUAA 3') (53.2);

xcviii) an antisense strand of nucleic acid sequence according to SEQ ID NO: 192 (5' UAAGGAUCAUAGUGUUCUUGGC 3'), and a sense strand of nucleic acid sequence according to SEQ ID NO: 357 (5' CAAGAACACUAUGAUCCUUA 3') (52.6);

xcix) an antisense strand of nucleic acid sequence according to SEQ ID NO: 175 (5' UCAGAUUCCCAGUGGAUACGGU 3'), and a sense strand of nucleic acid sequence according to SEQ ID NO: 340 (5' CGUAUCCACUGGGAAUCUGA 3') (52.4);

c) an antisense strand of nucleic acid sequence according to SEQ ID NO: 187 (5' UUUUUAUGGUGACCUUGAGGUC 3'), and a sense strand of nucleic acid sequence according to SEQ ID NO: 352 (5' CCUCAAGGUCACCAUAAAAA 3') (52.4);

ci) an antisense strand of nucleic acid sequence according to SEQ ID NO: 109 (5' UCUGAGAGAUGCAGGUAAUUGU 3'), and a sense strand of nucleic acid sequence according to SEQ ID NO: 274 (5' AAUUACCUGCAUCUCUCAGA 3') (52.2);

cii) an antisense strand of nucleic acid sequence according to SEQ ID NO: 102 (5' UGACUCGGUAGGCUGGAGAGCC 3'), and a sense strand of nucleic acid sequence according to SEQ ID NO: 267 (5' CUCUCCAGCCUACCGAGUCA 3') (51.9).

ciii) an antisense strand of nucleic acid sequence according to SEQ ID NO: 121 (5' UCAAAAAUAUAUUCAUGAGCUU 3'), and a sense strand of nucleic acid sequence according to SEQ ID NO: 286 (5' GCUCAUGAAUAUAUUUUUGA 3') (51.8);

civ) an antisense strand of nucleic acid sequence according to SEQ ID NO: 134 (5' UGAUUUCCACCUGCUCGUUUCG 3'), and a sense strand of nucleic acid sequence according to SEQ ID NO: 299 (5' AAACGAGCAGGUGGAAAUCA 3') (51.4);

cv) an antisense strand of nucleic acid sequence according to SEQ ID NO: 135 (5' UUUGGUUCUGCCGGUAAUUGUA 3'), and a sense strand of nucleic acid sequence according to SEQ ID NO: 300 (5' CAAUUACCGGCAGAACCAAA 3') (51.0);

cvi) an antisense strand of nucleic acid sequence according to SEQ ID NO: 105 (5' UGAUGCUCAAGGGCUUCUGGCU 3'), and a sense strand of nucleic acid sequence according to SEQ ID NO: 270 (5' CCAGAAGCCCUUGAGCAUCA 3') (50.7);

cvii) an antisense strand of nucleic acid sequence according to SEQ ID NO: 125 (5' UGUCUUUCAAAAAUAUAUUCAU 3'), and a sense strand of nucleic acid sequence according to SEQ ID NO: 290 (5' GAAUAUAUUUUUGAAAGACA 3') (50.3);

cviii) an antisense strand of nucleic acid sequence according to SEQ ID NO: 190 (5' UGUGUUCUUGGCAUCCUGAGGC 3'), and a sense strand of nucleic acid sequence according to SEQ ID NO: 355 (5' CUCAGGAUGCCAAGAACACA 3') (50.2);

cix) an antisense strand of nucleic acid sequence according to SEQ ID NO: 119 (5' UAUGUAGUUGCAGCAGUCCAGG 3'), and a sense strand of nucleic acid sequence according to SEQ ID NO: 284 (5' UGGACUGCUGCAACUACAUA 3') (70.4);

cx) an antisense strand of nucleic acid sequence according to SEQ ID NO: 120 (5' UGUGAUGUAGUUGCAGCAGUCC 3'), and a sense strand of nucleic acid sequence according to SEQ ID NO: 285 (5' ACUGCUGCAACUACAUCACA 3') (67.2); or cxi) an antisense strand of nucleic acid sequence according to SEQ ID NO: 394 (5' UAAAUAUAUUCAUGAGCUUCGU 3'), and a sense strand of nucleic acid sequence according to SEQ ID NO: 420 (5' GAAGCUCAUGAAUAUAUUUA 3') (50.6).

Embodiment 43. The isolated oligonucleotide of any one of embodiments 38-42, wherein the isolated oligonucleotide attenuates expression of the C3 mRNA by 20% to 50% at a dose of 0.01 nM.

Embodiment 44. The isolated oligonucleotide of embodiment 43, wherein the double stranded region comprises:

i) an antisense strand of nucleic acid sequence according to SEQ ID NO: 96 (5' UAGAUGACAAAGGCAGUUCCCU 3'), and a sense strand of nucleic acid sequence according to SEQ ID NO: 261 (5' GGAACUGCCUUUGUCAUCUA 3') (45.5);

ii) an antisense strand of nucleic acid sequence according to SEQ ID NO: 217 (5' UUUGUAUGAAGCAAUUCUCCUC 3'), and a sense strand of nucleic acid sequence according to SEQ ID NO: 382 (5' GGAGAAUUGCUUCAUACAAA 3') (45.3);

iii) an antisense strand of nucleic acid sequence according to SEQ ID NO: 70 (5' UUAGAUGGUCUUGUCUGUCUGG 3'), and a sense strand of nucleic acid sequence according to SEQ ID NO: 235 (5' AGACAGACAAGACCAUCUAA 3') (44.9);

iv) an antisense strand of nucleic acid sequence according to SEQ ID NO: 198 (5' UCAUACUUGGAGAUGUAUCUGU 3'), and a sense strand of nucleic acid sequence according to SEQ ID NO: 363 (5' AGAUACAUCUCCAAGUAUGA 3') (44.7);

v) an antisense strand of nucleic acid sequence according to SEQ ID NO: 113 (5' UAUCAGGUAGGUGUAGUAGCGG 3'), and a sense strand of nucleic acid sequence according to SEQ ID NO: 278 (5' GCUACUACACCUACCUGAUA 3') (42.9);

vi) an antisense strand of nucleic acid sequence according to SEQ ID NO: 126 (5' UAUUACUGUGACCUCGAAGGGG 3'), and a sense strand of nucleic acid sequence according to SEQ ID NO: 291 (5' CCUUCGAGGUCACAGUAAUA 3') (42.3);

vii) an antisense strand of nucleic acid sequence according to SEQ ID NO: 170 (5' UGUAUCUCUGUUCAUUGAGCCA 3'), and a sense strand of nucleic acid sequence according to SEQ ID NO: 335 (5' GCUCAAUGAACAGAGAUACA 3') (42.0);

viii) an antisense strand of nucleic acid sequence according to SEQ ID NO: 123 (5' UUUUCAAAAAUAUAUUCAUGAG 3'), and a sense strand of nucleic acid sequence according to SEQ ID NO: 288 (5' CAUGAAUAUAUUUUUGAAAA 3') (41.7);

ix) an antisense strand of nucleic acid sequence according to SEQ ID NO: 226 (5' UGUCAGUUGGGGCACCCAAAGA 3'), and a sense strand of nucleic acid sequence according to SEQ ID NO: 391 (5' UUUGGGUGCCCCAACUGACA 3') (41.5);

x) an antisense strand of nucleic acid sequence according to SEQ ID NO: 67 (5' UCUGUCUGGAUGAAGAGGUACC 3'), and a sense strand of nucleic acid sequence according to SEQ ID NO: 232 (5' UACCUCUUCAUCCAGACAGA 3') (41.1);

xi) an antisense strand of nucleic acid sequence according to SEQ ID NO: 172 (5' UUAGUAUCUCUGUUCAUUGAGC 3'), and a sense strand of nucleic acid sequence according to SEQ ID NO: 337 (5' UCAAUGAACAGAGAUACUAA 3') (41.0);

xii) an antisense strand of nucleic acid sequence according to SEQ ID NO: 74 (5' UGACAAGGAGUCCUGCUUGACC 3'), and a sense strand of nucleic acid sequence according to SEQ ID NO: 239 (5' UCAAGCAGGACUCCUUGUCA 3') (40.6);

xiii) an antisense strand of nucleic acid sequence according to SEQ ID NO: 64 (5' UUUUUUGCCUGGGAAGUCGUGG 3'), and a sense strand of nucleic acid sequence according to SEQ ID NO: 229 (5' ACGACUUCCCAGGCAAAAAA 3') (39.5);

xiv) an antisense strand of nucleic acid sequence according to SEQ ID NO: 181 (5' UUUCCUUCAGCUGUGACUGUGA 3'), and a sense strand of nucleic acid sequence according to SEQ ID NO: 346 (5' ACAGUCACAGCUGAAGGAAA 3') (39.2);

xv) an antisense strand of nucleic acid sequence according to SEQ ID NO: 131 (5' UGAACAACAGAGUAGGGUAGCC 3'), and a sense strand of nucleic acid sequence according to SEQ ID NO: 296 (5' CUACCCUACUCUGUUGUUCA 3') (39.1);

xvi) an antisense strand of nucleic acid sequence according to SEQ ID NO: 196 (5' UUACUUGGAGAUGUAUCUGUCA 3'), and a sense strand of nucleic acid sequence according to SEQ ID NO: 361 (5' ACAGAUACAUCUCCAAGUAA 3') (38.8);

xvii) an antisense strand of nucleic acid sequence according to SEQ ID NO: 129 (5' UGAAGAAGUCCUGCAUUACUGU 3'), and a sense strand of nucleic acid sequence according to SEQ ID NO: 294 (5' AGUAAUGCAGGACUUCUUCA 3') (38.5);

xviii) an antisense strand of nucleic acid sequence according to SEQ ID NO: 212 (5' UGUAAUAGGCGUAGACCUUGAC 3'), and a sense strand of nucleic acid sequence according to SEQ ID NO: 377 (5' CAAGGUCUACGCCUAUUACA 3') (37.7);

xix) an antisense strand of nucleic acid sequence according to SEQ ID NO: 93 (5' UAGUAGAAUUUCUCUGUAGGCU 3'), and a sense strand of nucleic acid sequence according to SEQ ID NO: 258 (5' CCUACAGAGAAAUUCUACUA 3') (37.2);

xx) an antisense strand of nucleic acid sequence according to SEQ ID NO: 194 (5' UUAGA-CAUAGUGGCAUCCUGGU 3'), and a sense strand of nucleic acid sequence according to SEQ ID NO: 359 (5' CAGGAUGCCACUAUGUCUAA 3') (37.1);

xxi) an antisense strand of nucleic acid sequence according to SEQ ID NO: 154 (5' UAAGACC-UUGACCACGUAGGCG 3'), and a sense strand of nucleic acid sequence according to SEQ ID NO: 319 (5' CCUACGUGGUCAAGGUCUUA 3') (36.6);

xxii) an antisense strand of nucleic acid sequence according to SEQ ID NO: 108 (5' UGAGAUGCAG-GUAAUUGUUGGA 3'), and a sense strand of nucleic acid sequence according to SEQ ID NO: 273 (5' CAACAAUUACCUGCAUCUCA 3') (36.6);

xxiii) an antisense strand of nucleic acid sequence according to SEQ ID NO: 72 (5' UUGUAGAUG-GUCUUGUCUGUCU 3'), and a sense strand of nucleic acid sequence according to SEQ ID NO: 237 (5' ACAGACAAGACCAUCUACAA 3') (36.4);

xxiv) an antisense strand of nucleic acid sequence according to SEQ ID NO: 78 (5' UUUGACGAGUUCCGGAAUGUCC 3'), and a sense strand of nucleic acid sequence according to SEQ ID NO: 243 (5' ACAUUCCGGAACUCGU-CAAA 3') (36.3);

XXV) an antisense strand of nucleic acid sequence according to SEQ ID NO: 211 (5' UCAUC-CUCAGAGUGUGAGACCU 3'), and a sense strand of nucleic acid sequence according to SEQ ID NO: 376 (5' GUCUCACACUCUGAGGAUGA 3') (35.6);

xxvi) an antisense strand of nucleic acid sequence according to SEQ ID NO: 188 (5' UGUUUUAUG-GUGACCUUGAGGU 3'), and a sense strand of nucleic acid sequence according to SEQ ID NO: 353 (5' CUCAAGGUCACCAUAAAACA 3') (35.6);

xxvii) an antisense strand of nucleic acid sequence according to SEQ ID NO: 124 (5' UCUUU-CAAAAAUAUAUUCAUGA 3'), and a sense strand of nucleic acid sequence according to SEQ ID NO: 289 (5' AUGAAUAUAUUUUUGAAAGA 3') (35.5);

xxviii) an antisense strand of nucleic acid sequence according to SEQ ID NO: 159 (5' UAAGGAAGU-CUCCUGCUUUAGU 3'), and a sense strand of nucleic acid sequence according to SEQ ID NO: 324 (5' UAAAGCAGGAGACUUCCUUA 3') (35.5);

xxix) an antisense strand of nucleic acid sequence according to SEQ ID NO: 208 (5' UCUUGUCCAG-GUAGAUGAUGAG 3'), and a sense strand of nucleic acid sequence according to SEQ ID NO: 373 (5' CAUCAUCUACCUGGACAAGA 3') (33.9);

xxx) an antisense strand of nucleic acid sequence according to SEQ ID NO: 137 (5' UGUAGUUC-CACCCUCACCUUGA 3'), and a sense strand of nucleic acid sequence according to SEQ ID NO: 302 (5' AAGGUGAGGGUGGAACUACA 3') (33.6);

xxxi) an antisense strand of nucleic acid sequence according to SEQ ID NO: 122 (5' UUU-CAAAAAUAUAUUCAUGAGC 3'), and a sense strand of nucleic acid sequence according to SEQ ID NO: 287 (5' UCAUGAAUAUAUUUUUGAAA 3') (33.4);

xxxii) an antisense strand of nucleic acid sequence according to SEQ ID NO: 63 (5' UUUUUGCCUGG-GAAGUCGUGGA 3'), and a sense strand of nucleic acid sequence according to SEQ ID NO: 228 (5' CACGACUUCCCAGGCAAAAA 3') (33.2);

xxxiii) an antisense strand of nucleic acid sequence according to SEQ ID NO: 219 (5' UUACACAUA-GUCCACUCCUGGC 3'), and a sense strand of nucleic acid sequence according to SEQ ID NO: 384 (5' CAGGAGUGGACUAUGUGUAA 3') (32.9);

xxxiv) an antisense strand of nucleic acid sequence according to SEQ ID NO: 195 (5' UCAGUCAU-CAUGGAUAUGUCCA 3'), and a sense strand of nucleic acid sequence according to SEQ ID NO: 360 (5' GACAUAUCCAUGAUGACUGA 3') (32.5);

xxxv) an antisense strand of nucleic acid sequence according to SEQ ID NO: 95 (5' UGUUAUAGAU-GUAGUAGAAUUU 3'), and a sense strand of nucleic acid sequence according to SEQ ID NO: 260 (5' AUUCUACUACAUCUAUAACA 3') (32.3);

xxxvi) an antisense strand of nucleic acid sequence according to SEQ ID NO: 146 (5' UGAAUUCUG-GUCUCAGACUCGG 3'), and a sense strand of nucleic acid sequence according to SEQ ID NO: 311 (5' GAGUCUGAGACCAGAAUUCA 3') (32.2);

xxxvii) an antisense strand of nucleic acid sequence according to SEQ ID NO: 220 (5' UGUACACAUA-GUCCACUCCUGG 3'), and a sense strand of nucleic acid sequence according to SEQ ID NO: 385 (5' AGGAGUGGACUAUGUGUACA 3') (32.1);

xxxviii) an antisense strand of nucleic acid sequence according to SEQ ID NO: 151 (5' UUUC-UUGAUGAGCUCCAAGGCC 3'), and a sense strand of nucleic acid sequence according to SEQ ID NO: 316 (5' CCUUGGAGCUCAUCAAGAAA 3') (31.9);

xxxix) an antisense strand of nucleic acid sequence according to SEQ ID NO: 118 (5' UUAUC-UUCAGGGUCAUCUGCUG 3'), and a sense strand of nucleic acid sequence according to SEQ ID NO: 283 (5' GCAGAUGACCCUGAAGAUAA 3') (31.9);

xL) an antisense strand of nucleic acid sequence according to SEQ ID NO: 180 (5' UUUCAGCU-GUGACUGUGAAACC 3'), and a sense strand of nucleic acid sequence according to SEQ ID NO: 345 (5' UUUCACAGUCACAGCUGAAA 3') (31.8);

xLi) an antisense strand of nucleic acid sequence according to SEQ ID NO: 210 (5' UCUCAGAGU-GUGAGACCUUGUC 3'), and a sense strand of nucleic acid sequence according to SEQ ID NO: 375 (5' CAAGGUCUCACACUCUGAGA 3') (31.7);

xLii) an antisense strand of nucleic acid sequence according to SEQ ID NO: 187 (5' UUUUUAUG-GUGACCUUGAGGUC 3'), and a sense strand of nucleic acid sequence according to SEQ ID NO: 352 (5' CCUCAAGGUCACCAUAAAAA 3') (31.7);

xLiii) an antisense strand of nucleic acid sequence according to SEQ ID NO: 162 (5' UAUCUCU-GUAGGUUCAUGUAGU 3'), and a sense strand of nucleic acid sequence according to SEQ ID NO: 327 (5' UACAUGAACCUACAGAGAUA 3') (31.3);

xLiv) an antisense strand of nucleic acid sequence according to SEQ ID NO: 145 (5' UAAUUCUG-GUCUCAGACUCGGU 3'), and a sense strand of nucleic acid sequence according to SEQ ID NO: 310 (5' CGAGUCUGAGACCAGAAUUA 3') (30.9);

xLv) an antisense strand of nucleic acid sequence according to SEQ ID NO: 201 (5' UCUUUGU- CCAGCUCAUACUUGG 3'), and a sense strand of nucleic acid sequence according to SEQ ID NO: 366 (5' AAGUAUGAGCUGGACAAAGA 3') (30.3);

xLvi) an antisense strand of nucleic acid sequence according to SEQ ID NO: 81 (5' UCAUAGUAGG-CUCGGAUCUUCC 3'), and a sense strand of nucleic acid sequence according to SEQ ID NO: 246 (5' AAGAUCCGAGCCUACUAUGA 3') (29.9);

xLvii) an antisense strand of nucleic acid sequence according to SEQ ID NO: 206 (5' UGAUGAUGAGGGUGUUCCUAUC 3'), and a sense strand of nucleic acid sequence according to SEQ ID NO: 371 (5' UAGGAACACCCUCAU-CAUCA 3') (29.7);

xLviii) an antisense strand of nucleic acid sequence according to SEQ ID NO: 215 (5' UUGUUCAGC-UUUCCAUCCUCCU 3'), and a sense strand of nucleic acid sequence according to SEQ ID NO: 380 (5' GAGGAUGGAAAGCUGAACAA 3') (29.5);

xLix) an antisense strand of nucleic acid sequence according to SEQ ID NO: 213 (5' UGUU-GUAAUAGGCGUAGACCUU 3'), and a sense strand of nucleic acid sequence according to SEQ ID NO: 378 (5' GGUCUACGCCUAUUACAACA 3') (29.3);

L) an antisense strand of nucleic acid sequence according to SEQ ID NO: 189 (5' UCUGUUUCCG-GUGCUGGUUUUA 3'), and a sense strand of nucleic acid sequence according to SEQ ID NO: 354 (5' AAACCAGCACCGGAAACAGA 3') (28.9);

Li) an antisense strand of nucleic acid sequence according to SEQ ID NO: 207 (5' UGUA-GAUGAUGAGGGUGUUCCU 3'), and a sense strand of nucleic acid sequence according to SEQ ID NO: 372 (5' GAACACCCUCAUCAUCUACA 3') (28.3);

Lii) an antisense strand of nucleic acid sequence according to SEQ ID NO: 139 (5' UGGAUUGUG-GAGUAGUUCCACC 3'), and a sense strand of nucleic acid sequence according to SEQ ID NO: 304 (5' UGGAACUACUCCACAAUCCA 3') (27.5);

Liii) an antisense strand of nucleic acid sequence according to SEQ ID NO: 143 (5' UUUGUU-CAUUCUGAUUCCUUCC 3'), and a sense strand of nucleic acid sequence according to SEQ ID NO: 308 (5' AAGGAAUCAGAAUGAACAAA 3') (27.4);

Liv) an antisense strand of nucleic acid sequence according to SEQ ID NO: 178 (5' UCAUUUUCC-UUGGUCUCUUCUG 3'), and a sense strand of nucleic acid sequence according to SEQ ID NO: 343 (5' GAAGAGACCAAGGAAAAUGA 3') (27.4);

Lv) an antisense strand of nucleic acid sequence according to SEQ ID NO: 128 (5' UGAAGUCCUG-CAUUACUGUGAC 3'), and a sense strand of nucleic acid sequence according to SEQ ID NO: 293 (5' CACAGUAAUGCAGGACUUCA 3') (27.3);

Lvi) an antisense strand of nucleic acid sequence according to SEQ ID NO: 160 (5' UUUCAU-GUAGUUGGCUUCAAGG 3'), and a sense strand of nucleic acid sequence according to SEQ ID NO: 325 (5' UUGAAGCCAACUACAUGAAA 3') (27.3);

Lvii) an antisense strand of nucleic acid sequence according to SEQ ID NO: 176 (5' UUUUUCCUUG-GUCUCUUCUGAU 3'), and a sense strand of nucleic acid sequence according to SEQ ID NO: 341 (5' CAGAAGAGACCAAGGAAAAA 3') (27.2);

Lviii) an antisense strand of nucleic acid sequence according to SEQ ID NO: 80 (5' UCUUCCA-CUGGCCCAUGUUGAC 3'), and a sense strand of nucleic acid sequence according to SEQ ID NO: 245 (5' CAACAUGGGCCAGUGGAAGA 3') (27.0);

Lix) an antisense strand of nucleic acid sequence according to SEQ ID NO: 203 (5' UUUCCUAUCG-GAGAAGGCUUUG 3'), and a sense strand of nucleic acid sequence according to SEQ ID NO: 368 (5' AAGCCUUCUCCGAUAGGAAA 3') (26.9);

Lx) an antisense strand of nucleic acid sequence according to SEQ ID NO: 87 (5' UGUACUCCUU-CACCUCAAACUC 3'), and a sense strand of nucleic acid sequence according to SEQ ID NO: 252 (5' GUUUGAGGUGAAGGAGUACA 3') (26.3);

Lxi) an antisense strand of nucleic acid sequence according to SEQ ID NO: 104 (5' UGU-GUUGAUGCUGAGUUUGGCC 3'), and a sense strand of nucleic acid sequence according to SEQ ID NO: 269 (5' CCAAACUCAGCAUCAACACA 3') (26.1);

Lxii) an antisense strand of nucleic acid sequence according to SEQ ID NO: 69 (5' UUUGUCUGU-CUGGAUGAAGAGG 3'), and a sense strand of nucleic acid sequence according to SEQ ID NO: 234 (5' UCUUCAUCCAGACAGACAAA 3') (25.9);

Lxiii) an antisense strand of nucleic acid sequence according to SEQ ID NO: 197 (5' UAUACUUG-GAGAUGUAUCUGUC 3'), and a sense strand of nucleic acid sequence according to SEQ ID NO: 362 (5' CAGAUACAUCUCCAAGUAUA 3') (25.9);

Lxiv) an antisense strand of nucleic acid sequence according to SEQ ID NO: 223 (5' UAUGAUGUA-CUCGUCAAAGUCA 3'), and a sense strand of nucleic acid sequence according to SEQ ID NO: 388 (5' ACUUUGACGAGUACAUCAUA 3') (25.8);

Lxv) an antisense strand of nucleic acid sequence according to SEQ ID NO: 142 (5' UGGAUG-GUUACGGUCUGCUGGU 3'), and a sense strand of nucleic acid sequence according to SEQ ID NO: 307 (5' CAGCAGACCGUAACCAUCCA 3') (25.5);

Lxvi) an antisense strand of nucleic acid sequence according to SEQ ID NO: 138 (5' UGAUUGUGG-AGUAGUUCCACCC 3'), and a sense strand of nucleic acid sequence according to SEQ ID NO: 303 (5' GUGGAACUACUCCACAAUCA 3') (25.4);

Lxvii) an antisense strand of nucleic acid sequence according to SEQ ID NO: 75 (5' UAA-GACAAGGAGUCCUGCUUGA 3'), and a sense strand of nucleic acid sequence according to SEQ ID NO: 240 (5' AAGCAGGACUCCUUGUCUUA 3') (25.2);

Lxviii) an antisense strand of nucleic acid sequence according to SEQ ID NO: 163 (5' UCAGUGUAG-GAUCUCUGUAGGU 3'), and a sense strand of nucleic acid sequence according to SEQ ID NO: 328 (5' CUACAGAGAUCCUACACUGA 3') (24.6);

Lxix) an antisense strand of nucleic acid sequence according to SEQ ID NO: 116 (5' UUUCUGACUGGCCGCUUUUUAC 3'), and a sense strand of nucleic acid sequence according to SEQ ID NO: 281 (5' AAAAAGCGGCCAGU-CAGAAA 3') (24.6);

Lxx) an antisense strand of nucleic acid sequence according to SEQ ID NO: 112 (5' UGUGU- AGUAGCGGAUCUUGGCC 3'), and a sense strand of nucleic acid sequence according to SEQ ID NO: 277 (5' CCAAGAUCCGCUACUACACA 3') (24.4);

Lxxi) an antisense strand of nucleic acid sequence according to SEQ ID NO: 204 (5' UGUGUUCC-UAUCGGAGAAGGCU 3'), and a sense strand of nucleic acid sequence according to SEQ ID NO: 369 (5' CCUUCUCCGAUAGGAACACA 3') (24.4);

Lxxii) an antisense strand of nucleic acid sequence according to SEQ ID NO: 169 (5' UCACAAAGU-CAAAGUCUUUUAG 3'), and a sense strand of nucleic acid sequence according to SEQ ID NO: 334 (5' AAAAGACUUUGACUUUGUGA 3') (24.4);

Lxxiii) an antisense strand of nucleic acid sequence according to SEQ ID NO: 99 (5' UGUCUUG-GUGAAGUGGAUCUGG 3'), and a sense strand of nucleic acid sequence according to SEQ ID NO: 264 (5' AGAUCCACUUCACCAAGACA 3') (24.4);

Lxxiv) an antisense strand of nucleic acid sequence according to SEQ ID NO: 140 (5' UCUGGAUU-GUGGAGUAGUUCCA 3'), and a sense strand of nucleic acid sequence according to SEQ ID NO: 305 (5' GAACUACUCCACAAUCCAGA 3') (24.4);

Lxxv) an antisense strand of nucleic acid sequence according to SEQ ID NO: 130 (5' UGAUGAAGAA-GUCCUGCAUUAC 3'), and a sense strand of nucleic acid sequence according to SEQ ID NO: 295 (5' AAUGCAGGACUUCUUCAUCA 3') (24.3);

Lxxvi) an antisense strand of nucleic acid sequence according to SEQ ID NO: 68 (5' UGUCUGUCUG-GAUGAAGAGGUA 3'), and a sense strand of nucleic acid sequence according to SEQ ID NO: 233 (5' CCUCUUCAUCCAGACAGACA 3') (24.2);

Lxxvii) an antisense strand of nucleic acid sequence according to SEQ ID NO: 73 (5' UGUGUAGAUG-GUCUUGUCUGUC 3'), and a sense strand of nucleic acid sequence according to SEQ ID NO: 238 (5' CAGACAAGACCAUCUACACA 3') (23.9);

Lxxviii) an antisense strand of nucleic acid sequence according to SEQ ID NO: 100 (5' UGAGGU-CAAAGGGCAUUCCUGG 3'), and a sense strand of nucleic acid sequence according to SEQ ID NO: 265 (5' AGGAAUGCCCUUUGACCUCA 3') (23.9);

Lxxix) an antisense strand of nucleic acid sequence according to SEQ ID NO: 205 (5' UAUGAUGAGG-GUGUUCCUAUCG 3'), and a sense strand of nucleic acid sequence according to SEQ ID NO: 370 (5' AUAGGAACACCCUCAUCAUA 3') (23.9);

Lxxx) an antisense strand of nucleic acid sequence according to SEQ ID NO: 119 (5' UAU-GUAGUUGCAGCAGUCCAGG 3'), and a sense strand of nucleic acid sequence according to SEQ ID NO: 284 (5' UGGACUGCUGCAACUACAUA 3') (23.8);

Lxxxi) an antisense strand of nucleic acid sequence according to SEQ ID NO: 82 (5' UUUCAU-AGUAGGCUCGGAUCUU 3'), and a sense strand of nucleic acid sequence according to SEQ ID NO: 247 (5' GAUCCGAGCCUACUAUGAAA 3') (23.5);

Lxxxii) an antisense strand of nucleic acid sequence according to SEQ ID NO: 79 (5' UGUUGACGAGUUCCGGAAUGUC 3'), and a sense strand of nucleic acid sequence according to SEQ ID NO: 244 (5' CAUUCCGGAACUCGU-CAACA 3') (23.2);

Lxxxiii) an antisense strand of nucleic acid sequence according to SEQ ID NO: 171 (5' UAGUAUCUCU-GUUCAUUGAGCC 3'), and a sense strand of nucleic acid sequence according to SEQ ID NO: 336 (5' CUCAAUGAACAGAGAUACUA 3') (23.1);

Lxxxiv) an antisense strand of nucleic acid sequence according to SEQ ID NO: 182 (5' UUUUUCC-UUCAGCUGUGACUGU 3'), and a sense strand of nucleic acid sequence according to SEQ ID NO: 347 (5' AGUCACAGCUGAAGGAAAAA 3') (23.1);

Lxxxv) an antisense strand of nucleic acid sequence according to SEQ ID NO: 153 (5' UUGAAGGCCAGCUGCUGGGUGU 3'), and a sense strand of nucleic acid sequence according to SEQ ID NO: 318 (5' ACCCAGCAGCUGGCCUU-CAA 3') (22.9);

Lxxxvi) an antisense strand of nucleic acid sequence according to SEQ ID NO: 186 (5' UUUUAUG-GUGACCUUGAGGUCG 3'), and a sense strand of nucleic acid sequence according to SEQ ID NO: 351 (5' ACCUCAAGGUCACCAUAAAA 3') (22.9);

Lxxxvii) an antisense strand of nucleic acid sequence according to SEQ ID NO: 191 (5' UAUCAUAGU-GUUCUUGGCAUCC 3'), and a sense strand of nucleic acid sequence according to SEQ ID NO: 356 (5' AUGCCAAGAACACUAUGAUA 3') (22.4);

Lxxxviii) an antisense strand of nucleic acid sequence according to SEQ ID NO: 141 (5' UCUGCAGAAGGCUGGAUUGUGG 3'), and a sense strand of nucleic acid sequence according to SEQ ID NO: 306 (5' ACAAUCCAGCC-UUCUGCAGA 3') (21.7);

Lxxxix) an antisense strand of nucleic acid sequence according to SEQ ID NO: 144 (5' UGUUUUGUU-CAUUCUGAUUCCU 3'), and a sense strand of nucleic acid sequence according to SEQ ID NO: 309 (5' GAAUCAGAAUGAACAAAACA 3') (21.5);

XC) an antisense strand of nucleic acid sequence according to SEQ ID NO: 200 (5' UUUUGUCCAG-CUCAUACUUGGA 3'), and a sense strand of nucleic acid sequence according to SEQ ID NO: 365 (5' CAAGUAUGAGCUGGACAAAA 3') (21.1);

XCi) an antisense strand of nucleic acid sequence according to SEQ ID NO: 89 (5' UCUAUGAC-CUCGAAACUGGGCA 3'), and a sense strand of nucleic acid sequence according to SEQ ID NO: 254 (5' CCCAGUUUCGAGGUCAUAGA 3') (20.8);

XCii) an antisense strand of nucleic acid sequence according to SEQ ID NO: 120 (5' UGUGAU-GUAGUUGCAGCAGUCC 3'), and a sense strand of nucleic acid sequence according to SEQ ID NO: 285 (5' ACUGCUGCAACUACAUCACA 3') (20.8);

XCiii) an antisense strand of nucleic acid sequence according to SEQ ID NO: 86 (5' UUACUCCUU-CACCUCAAACUCA 3'), and a sense strand of nucleic acid sequence according to SEQ ID NO: 251 (5' AGUUUGAGGUGAAGGAGUAA 3') (20.8);

XCiv) an antisense strand of nucleic acid sequence according to SEQ ID NO: 166 (5' UUC-UUUUAGCUGCAGUAGGGCC 3'), and a sense strand of nucleic acid sequence according to SEQ ID NO: 331 (5' CCCUACUGCAGCUAAAAGAA 3') (20.6);

XCv) an antisense strand of nucleic acid sequence according to SEQ ID NO: 101 (5' UAACAC-CAUGAGGUCAAAGGGC 3'), and a sense strand of nucleic acid sequence according to SEQ ID NO: 266 (5' CCUUUGACCUCAUGGUGUUA 3') (20.6);

XCvi) an antisense strand of nucleic acid sequence according to SEQ ID NO: 161 (5' UUGUAGGUUCAUGUAGUUGGCU 3'), and a sense strand of nucleic acid sequence according to SEQ ID NO: 326 (5' CCAACUACAUGAACCUACAA 3') (20.4);

XCvii) an antisense strand of nucleic acid sequence according to SEQ ID NO: 175 (5' UCAGAUUCCCAGUGGAUACGGU 3'), and a sense strand of nucleic acid sequence according to SEQ ID NO: 340 (5' CGUAUCCACUGGGAAUCUGA 3') (20.3);

XCviii) an antisense strand of nucleic acid sequence according to SEQ ID NO: 149 (5' UUUCAUCCAGGUAAUGCACAGC 3'), and a sense strand of nucleic acid sequence according to SEQ ID NO: 314 (5' UGUGCAUUACCUGGAUGAAA 3') (20.2);

XCix) an antisense strand of nucleic acid sequence according to SEQ ID NO: 214 (5' UGGUUGUAAUAGGCGUAGACCU 3'), and a sense strand of nucleic acid sequence according to SEQ ID NO: 379 (5' GUCUACGCCUAUUACAACCA 3') (20.2); or C) an antisense strand of nucleic acid sequence according to SEQ ID NO: 62 (5' UGACAGUGCAGGGUCAGAGGGA 3'), and a sense strand of nucleic acid sequence according to SEQ ID NO: 227 (5' CCUCUGACCCUGCACUGUCA 3') (19.9).

Embodiment 45. The isolated oligonucleotide of any one of embodiments 38-42, wherein the isolated oligonucleotide attenuates expression of the C3 mRNA by at least 50% at a dose of 0.01 nM.

Embodiment 46. The isolated oligonucleotide of embodiment 45, wherein the double stranded region comprises:

i) an antisense strand of nucleic acid sequence according to SEQ ID NO: 94 (5' UUAGAUGUAGUAGAAUUUCUCU 3'), and a sense strand of nucleic acid sequence according to SEQ ID NO: 259 (5' AGAAAUUCUACUACAUCUAA 3') (79.3); or ii) an antisense strand of nucleic acid sequence according to SEQ ID NO: 216 (5' UGAAGCAAUUCUCCUCAGCACA 3'), and a sense strand of nucleic acid sequence according to SEQ ID NO: 381 (5' UGCUGAGGAGAAUUGCUUCA 3') (51.6).

Embodiment 47. The isolated oligonucleotide of any one of embodiments 1-46, wherein the sense strand or the antisense strand or both comprise one or more modified nucleotide(s).

Embodiment 48. A vector encoding the isolated oligonucleotide of any one of embodiments 1-47.

Embodiment 49. A delivery system comprising the isolated oligonucleotide of any one of embodiments 1-47 or the vector of embodiment 48.

Embodiment 50. A pharmaceutical composition comprising at least one isolated oligonucleotide of any one of embodiments 1-47, the vector of embodiment 48, the delivery system of embodiment 49, and a pharmaceutically acceptable carrier, diluent or excipient.

Embodiment 51. A kit comprising at least one isolated oligonucleotide of any one of embodiments 1-47, the vector of embodiment 48, the delivery system of embodiment 49, or the pharmaceutical composition of embodiment 50.

Embodiment 52. A method of inhibiting or downregulating the expression or level of C3 in a subject in need thereof, wherein the method comprises administering to the subject an effective amount of at least one isolated oligonucleotide of any one of embodiments 1-47, the vector of embodiment 48, the delivery system of embodiment 49, or the pharmaceutical composition of embodiment 50.

Embodiment 53. A method of treating or preventing a disease or disorder associated with aberrant or increased expression or activity of C3 or a disease or disorder where C3 plays a role in a subject in need thereof, wherein the method comprises administering to the subject an effective amount of at least one isolated oligonucleotide of any one of embodiments 1-47, the vector of embodiment 48, the delivery system of embodiment 49, or the pharmaceutical composition of embodiment 50.

What is claimed is:

1. An isolated oligonucleotide comprising:

an antisense strand comprising the nucleic acid sequence 5' [mUs][fUs][fA][mG][fU][mA][fG][mA][mA][fU][mU][mU][mC][fU][mC][fU][mG][mU][mA][mGs][mGs][mC] 3' (SEQ ID NO: 451), and a sense strand comprising the nucleic acid sequence 5' [mCs][mUs][mA][mC][mA][fG][mA][fG][fA][fA][fA][mU][mU][mC][mU][mA][mC][mUs][mAs][mA][G1b][G1b][G1b] 3' (SEQ ID NO: 444), wherein "m" is a 2'-O-methyl modification, "f" is a 2'-F modification, "s" is a phosphorothioate internucleotide linkage, and "G1b" is a GalNAc G1b moiety.

2. A delivery system comprising the isolated oligonucleotide of claim 1, wherein the delivery system is a liposome, a nanoparticle, a polymer-based delivery system, a ligand-conjugate delivery system, or a combination thereof.

3. A pharmaceutical composition comprising the isolated oligonucleotide of claim 1, and a pharmaceutically acceptable carrier, diluent or excipient.

4. An isolated oligonucleotide comprising an antisense strand and a sense strand:

the antisense strand consisting of the nucleic acid sequence 5' [mUs][fUs][fA][mG][fU][mA][fG][mA][mA][fU][mU][mU][mC][fU][mC][fU][mG][mU][mA][mGs][mGs][mC] 3' (SEQ ID NO: 451), and the sense strand consisting of the nucleic acid sequence 5' [mCs][mUs][mA][mC][mA][fG][mA][fG][fA][fA][fA][mU][mU][mC][mU][mA][mC][mUs][mAs][mA][G1b][G1b][G1b] 3' (SEQ ID NO: 444), wherein "m" is a 2'-O-methyl modification, "f" is a 2'-F modification, "s" is a phosphorothioate internucleotide linkage, and "G1b" is a GalNAc G1b moiety.

5. A delivery system comprising the isolated oligonucleotide of claim 4, wherein the delivery system is a liposome, a nanoparticle, a polymer-based delivery system, a ligand-conjugate delivery system, or a combination thereof.

6. A pharmaceutical composition comprising the isolated oligonucleotide of claim 4, and a pharmaceutically acceptable carrier, diluent or excipient.

7. An isolated oligonucleotide consisting of an antisense strand and a sense strand:

the antisense strand consisting of the nucleic acid sequence 5' [mUs][fUs][fA][mG][fU][mA][fG][mA][mA][fU][mU][mU][mC][fU][mC][fU][mG][mU][mA][mGs][mGs][mC] 3' (SEQ ID NO: 451), and the sense strand consisting of the nucleic acid sequence 5' [mCs][mUs][mA][mC][mA][fG][mA][fG][fA][fA][fA][mU][mU][mC][mU][mA][mC][mUs][mAs][mA][G1b][G1b][G1b] 3' (SEQ ID NO: 444), wherein "m" is a 2'-O-methyl modification, "f" is a 2'-F modification, "s" is a phosphorothioate internucleotide linkage, and "G1b" is a GalNAc G1b moiety.

8. A delivery system comprising the isolated oligonucleotide of claim 7, wherein the delivery system is a liposome, a nanoparticle, a polymer-based delivery system, a ligand-conjugate delivery system, or a combination thereof.

9. A pharmaceutical composition comprising the isolated oligonucleotide of claim 7, and a pharmaceutically acceptable carrier, diluent or excipient.

* * * * *